United States Patent
Nodu et al.

(10) Patent No.: US 11,198,695 B2
(45) Date of Patent: Dec. 14, 2021

(54) FUSED RING DERIVATIVE HAVING MGAT-2 INHIBITORY ACTIVITY

(71) Applicant: Shionogi & Co., Ltd., Osaka (JP)

(72) Inventors: Kouhei Nodu, Osaka (JP); Yusuke Tateno, Osaka (JP); Kengo Masuda, Osaka (JP); Yuji Nishiura, Osaka (JP); Yoshikazu Sasaki, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 27 days.

(21) Appl. No.: 16/628,753

(22) PCT Filed: Jul. 13, 2018

(86) PCT No.: PCT/JP2018/026417
§ 371 (c)(1),
(2) Date: Jan. 6, 2020

(87) PCT Pub. No.: WO2019/013311
PCT Pub. Date: Jan. 17, 2019

(65) Prior Publication Data
US 2020/0291025 A1 Sep. 17, 2020

(30) Foreign Application Priority Data
Jul. 14, 2017 (JP) .............................. JP2017-137678

(51) Int. Cl.
| C07D 471/20 | (2006.01) |
| C07D 471/10 | (2006.01) |
| C07D 487/10 | (2006.01) |
| C07D 491/20 | (2006.01) |
| C07D 519/00 | (2006.01) |

(52) U.S. Cl.
CPC ......... C07D 471/20 (2013.01); C07D 471/10 (2013.01); C07D 487/10 (2013.01); C07D 491/20 (2013.01); C07D 519/00 (2013.01)

(58) Field of Classification Search
CPC .. C07D 471/20; C07D 487/10; C07D 491/20; C07D 519/00
See application file for complete search history.

(56) References Cited

U.S. PATENT DOCUMENTS

2015/0368242 A1   12/2015   Suzuki et al.

FOREIGN PATENT DOCUMENTS

| CN | 103012397 | 3/2017 |
| CN | 104109160 | 12/2017 |
| EP | 2 078 719 | 7/2009 |
| EP | 2 687 507 | 1/2014 |
| EP | 3 112 369 | 1/2017 |
| JP | 2013-67595 | 4/2013 |
| JP | 2014-5245 | 1/2014 |
| JP | 2014-9165 | 1/2014 |
| JP | 2016-164154 | 9/2016 |
| KR | 10-2010-0097077 | 9/2010 |
| WO | 2004/058176 | 7/2004 |
| WO | 2004/058762 | 7/2004 |
| WO | 2008/085509 | 7/2008 |
| WO | 2009/126584 | 10/2009 |
| WO | 2010/095767 | 8/2010 |
| WO | 2011/079051 | 6/2011 |
| WO | 2012/091010 | 7/2012 |
| WO | 2012/117027 | 9/2012 |
| WO | 2013/045400 | 4/2013 |
| WO | 2013/082345 | 6/2013 |

(Continued)

OTHER PUBLICATIONS

International Search Report (ISR) dated Oct. 16, 2018 in International (PCT) Application No. PCT/JP2018/026417.
Jingsong Cao et al., "A Predominant Role of Acyl-CoA:monoacylglycerol Acyltransferase-2 in Dietary Fat Absorption Implicated by Tissue Distribution, Subcellular Localization, and Up-Regulation by High Fat Diet", Journal of Biological Chemistry, vol. 279, No. 18, p. 18878-18886, 2004.

(Continued)

*Primary Examiner* — Alicia L Otton
(74) *Attorney, Agent, or Firm* — Wenderoth, Lind & Ponack, L.L.P.

(57) ABSTRACT

The present invention provides the compound represented by the following formula (I):

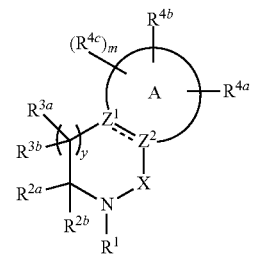

(I)

wherein a moiety represented by formula:

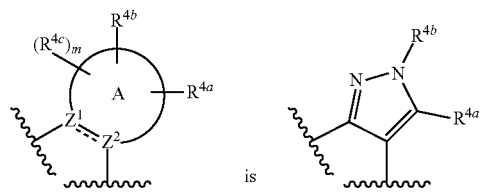

is or the like. The symbols are defined in the specification. The compounds of the present invention have MGAT2 inhibitory activity, and are useful as a medicine for treatment of MGAT2-associated diseases including obesity, metabolic syndrome, hyperlipidemia, hypertriglyceridemia, hyper-VLDL-triglyceridemia, hyperfattyacidemia, diabetes mellitus, and arteriosclerosis.

13 Claims, No Drawings

(56) References Cited

FOREIGN PATENT DOCUMENTS

| WO | 2013/112323 | 8/2013 |
|---|---|---|
| WO | 2013/116065 | 8/2013 |
| WO | 2013/116075 | 8/2013 |
| WO | 2013/130660 | 9/2013 |
| WO | 2013/175417 | 11/2013 |
| WO | 2014/054053 | 4/2014 |
| WO | 2014/074365 | 5/2014 |
| WO | 2014/133134 | 9/2014 |
| WO | 2014/140065 | 9/2014 |
| WO | 2014/154586 | 10/2014 |
| WO | 2014/193884 | 12/2014 |
| WO | 2015/073763 | 5/2015 |
| WO | 2015/073767 | 5/2015 |
| WO | 2015/112465 | 7/2015 |
| WO | 2015/112754 | 7/2015 |
| WO | 2015/129845 | 9/2015 |
| WO | 2015/134699 | 9/2015 |
| WO | 2015/134701 | 9/2015 |
| WO | 2015/144799 | 10/2015 |
| WO | 2015/191681 | 12/2015 |
| WO | 2016/024598 | 2/2016 |
| WO | 2016/044120 | 3/2016 |
| WO | 2016/090382 | 6/2016 |
| WO | 2016/106009 | 6/2016 |
| WO | 2016/121782 | 8/2016 |
| WO | 2017/069224 | 4/2017 |

OTHER PUBLICATIONS

Chi-Liang Eric Yen et al., "Deficiency of the intestinal enzyme acyl CoA:monoacylglycerol acyltransferase-2 protects mice from metabolic disorders induced by high-fat feeding", Nature Medicine, vol. 15, No. 4, pp. 442-446, Apr. 2009.
Jonas G. Barlind et al., "Identification and design of a novel series of MGAT2 inhibitors", Bioorganic & Medicinal Chemistry Letters, vol. 23, pp. 2721-2726, 2013.
James S. Scott, et al., "Achieving improved permeability by hydrogen bond donor modulation in a series of MGAT2 inhibitors", Med. Chem. Comm., vol. 4, pp. 1305-1311, 2013.
Tsuyoshi Busujima et al., "Identification of 2-[2-(4-tert-butylphenyl)ethyl]-N-(4-fluorophenyl)-1,2,3,4-tetrahydroisoquinoline-6-sulfonamide (29) as an orally available MGAT2 inhibitor", Bioorganic & Medicinal Chemistry, vol. 23, pp. 5922-5931, 2015.
Kenjiro Sato et al., "Optimization of a novel series of N-phenylindoline-5-sulfonamide based acyl CoA:monoacylglycerol acyltransferase-2 inhibitors: Mitigation of CYP3A4 time-dependent inhibition and phototoxic liabilities", Bioorganic & Medicinal Chemistry, vol. 23, pp. 4544-4560, 2015.
Joelle M. Onorato et al., "Cell-based assay of MGAT2-driven diacylglycerol synthesis for profiling inhibitors: use of a stable isotopelabeled substrate and high-resolution LC/MS", Journal of Lipid Research, vol. 56, pp. 747-753, 2015.
Chihiro Okuma et al., "JTP-103237, a novel monoacylglycerol acyltransferase inhibitor, modulates fat absorption and prevents diet-induced obesity", European Journal of Pharmacology, vol. 758, pp. 72-81, 2015.
Kenjiro Sato, et al., "Discovery of a Novel Series of N-Phenylindoline-5-sulfonamide Derivatives as Potent, Selective, and Orally Bioavailable Acyl CoA:Monoacylglycerol Acyltransferase-2 Inhibitors", Journal of Medicinal Chemistry, vol. 58, pp. 3892-3909, 2015.
Tsuyoshi Busujima et al., "An Efficient and Convenient Synthesis of Acyl CoA:Monoacylglycerol Acyltransferase 2 Inhibitor, 2-[2-(4-tert-Butylphenyl)Ethyl]-N-[4-(3-Cyclopentylpropyl)-2-Fluorophenyl]-1,2,3,4-Tetrahydroisoquinoline-6-Sulfonamide", Heterocycles, vol. 92, No. 3, pp. 470-484, 2016.
Tsuyoshi Busujima et al., "Identification of 2-[2-(4-tert-Butylphenyl)ethyl]-N-[4-(3-cyclopentylpropyl)-2-fluorophenyl]-1,2,3,4-tetrahydroisoquinoline-6-sulfonamide as an Orally Active MGAT2 Inhibitor", Chemical and Pharmaceutical Bulletin, vol. 64, pp. 228-238, 2016.
Ryutaro Adachi et al., "Pharmacological characterization of a series of aryl-sulfonamide derivatives that potently and selectively inhibit monoacylglycerol acyltransferase 2", European Journal of Pharmacology, vol. 791, pp. 569-577, 2016.
Zhengping Ma et al., "Characterization of monoacylglycerol acyltransferase 2 inhibitors by a novel probe in binding assays", Analytical Biochemistry, vol. 501, pp. 48-55, 2016.
Pratik Devasthale et al., "Monoacylglycerol Acyltransferase 2 (MGAT2) Inhibitors for the Treatment of Metabolic Diseases and Nonalcoholic Steatohepatitis (NASH)", Journal of Medicinal Chemistry, vol. 61, pp. 9879-9888, 2018.
International Preliminary Report On Patentability dated Jan. 23, 2020 in International (PCT) Application No. PCT/JP2018/026417.
Pettus et al. "Discovery and Optimization of Quinazolinone-pyrrolopyrrolones as Potent and Orally Bioavailable Pan-Pim Kinase Inhibitors", Journal of Medicinal Chemistry, 2016, vol. 59, pp. 6407-6430.
Zhang et al., "Facile Synthesis of Isoindolinones via Rh(III)-Catalyzed One-Pot Reaction of Benzamides, Ketones, and Hydrazines", Organic Letters, 2015, vol. 17, pp. 2494-2497.
Stanetty et al., "New Benzo- and Thieno-fused Spirolactams", Acta Chim. Slov., 2009, vol. 56, pp. 513-520.
Gunawan et al., "Bifunctional building blocks in the Ugi-azide condensation reaction: a general strategy toward exploration of new molecular diversity", Organic & Biomolecular Chemistry, 2013, vol. 11, pp. 6036-6046.

FUSED RING DERIVATIVE HAVING MGAT-2 INHIBITORY ACTIVITY

TECHNICAL FIELD

The present invention relates to a compound having monoacylglycerol acyltransferase 2 (hereinafter, also referred to as "MGAT2") inhibitory activity or its pharmaceutically acceptable salt, and a pharmaceutical composition including thereof.

BACKGROUND ART

Obesity is defined as an excessively high amount of body fat or adipose tissue in relation to lean body mass and recognized as a major risk factor for health problems. Body mass index (BMI) is a simple index of weight-for-height that is commonly used in classifying overweight and obesity in adult (age 15 and over) populations and individuals. It is defined as the weight in kilograms divided by the square of the height in meters ($kg/m^2$). World Health Organization defines "overweight" as a BMI of 25 $kg/m^2$ or greater and "obesity" as a BMI of 30 $kg/m^2$ or greater. On the other hand, Japan Society for the Study of Obesity defines "obesity" as a BMI of 25 $kg/m^2$ or greater. This is because the number of obesity-related disorders including diabetes and dislipidemia increases in accordance with BMI, and the mean number of obesity-related disorders is 1.0 or greater at a BMI of 25 $kg/m^2$. World Health Organization reported that about 1600 million and at least 400 million people were classified as overweight and obesity around the world in 2005, respectively. Obesity is mainly caused by taking in more calories than using up in physical activity and daily life. The number of obese people has been increasing by taking in more food including high fat and/or sugar, and it is estimated that 700 million people or more would be diagnosed as obesity around the world in 2015. Diet therapy, exercise therapy, drug therapy, and so on are performed for treatment of obesity. In the drug therapy, drugs including orlistat, mazindol, and sibutramine are used. However, they are not satisfactory in both aspects of efficacy and side effects.

One of the causes for obesity is excessive intake of neutral fat. Neutral fat (triglycerol) taken in meals is decomposed into 2-monoacylglycerol and free fatty acids by the action of pancreatic lipase in the digestive tract, and they are absorbed by small intestinal epithelial cells. An acyl group is transferred from the free fatty acids to the 2-monoacylglycerol by the action of monoacylglycerol acyltransferase (MGAT). The diacylglycerol formed is further converted into neutral fat by the action of diacylglycerol acyltransferase (DGAT).

Three isoforms of MGAT, namely, MGAT1, MGAT2, and MGAT3 have been identified. Among them, MGAT2 and MGAT3 are highly expressed in the small intestine, and believed to be involved in fat absorption in the small intestine.

It has been reported that an experiment with MGAT2 knock-out mice has demonstrated that high-fat diet promotes expression of MGAT2 in the small intestine to increase the MGAT activity (Non-patent Document 1). In addition, reduction of weight gain caused by high-fat diet, suppression of induction of insulin resistance, reduction of increase of blood cholesterol, prevention of fatty liver formation or the like, and promotion of energy consumption have been found for MGAT2 knock-out mice (Non-patent Document 2).

Although compounds having MGAT2 inhibitory activity have been previously reported (Patent Documents 1 to 19, Non-patent Documents 3 to 13), compounds of the present invention as described below have not been disclosed.

PRIOR ART REFERENCES

Patent Documents

[Patent Document 1] International Publication WO 2010/095767 A
[Patent Document 2] International Publication WO 2012/091010 A
[Patent Document 3] International Publication WO 2012/124744 A
[Patent Document 4] International Publication WO 2013/082345 A
[Patent Document 5] International Publication WO 2013/112323 A
[Patent Document 6] International Publication WO 2013/116065 A
[Patent Document 7] International Publication WO 2013/116075 A
[Patent Document 8] International Publication WO 2014/074365 A
[Patent Document 9] International Publication WO 2014/133134 A
[Patent Document 10] International Publication WO 2014/193884 A
[Patent Document 11] JP 2014-5245 A
[Patent Document 12] JP 2014-9165 A
[Patent Document 13] International Publication WO 2015/112465 A
[Patent Document 14] International Publication WO 2015/129845 A
[Patent Document 15] International Publication WO 2015/134699 A
[Patent Document 16] International Publication WO 2015/134701 A
[Patent Document 17] International Publication WO 2015/191681 A
[Patent Document 18] International Publication WO 2016/121782 A
[Patent Document 19] International Publication WO 2017/069224 A

Non-Patent Document

[Non-patent Document 1] Journal of Biological Chemistry (2004), 279, 18878-18886
[Non-patent Document 2] Nature Medicine (2009), 15, (4), 442-446
[Non-patent Document 3] Bioorganic & Medicinal Chemistry Letter (2013), 23, 2721-2726
[Non-patent Document 4] Med. Chem. Commun (2013), 4, 1305-1311
[Non-patent Document 5] Bioorganic & Medicinal Chemistry Letter (2015), 23, 5922-5931
[Non-patent Document 6] Bioorganic & Medicinal Chemistry Letter (2015), 23, 4544-4560
[Non-patent Document 7] Journal of Lipid Research 2015, 56, 747-753
[Non-patent Document 8] European Journal of Pharmacology, 2015, 758, 72-81
[Non-patent Document 9] Journal of Medicinal Chemistry (2015), 58, 3892-3909

[Non-patent Document 10] HETEROCYCLES 2016, 92, 470-484
[Non-patent Document 11] Chemical and Pharmaceutical Bulletin, 2016, 64, 228-238
[Non-patent Document 12] European Journal of Pharmacology, 2016, 791, 569-577
[Non-patent Document 13] Analytical Biochemistry, 2016, 501, 48-55

SUMMARY OF THE INVENTION

Problems to be Solved by the Invention

An object of the present invention is to provide a compound having MGAT2 inhibitory activity or its pharmaceutically acceptable salt, and a pharmaceutical composition including thereof.

Means for Solving the Problem

The present inventors have diligently studied, and succeeded in synthesizing superior compounds having MGAT2 inhibitory activity. This invention includes the followings.

[1] A compound represented by formula (I);

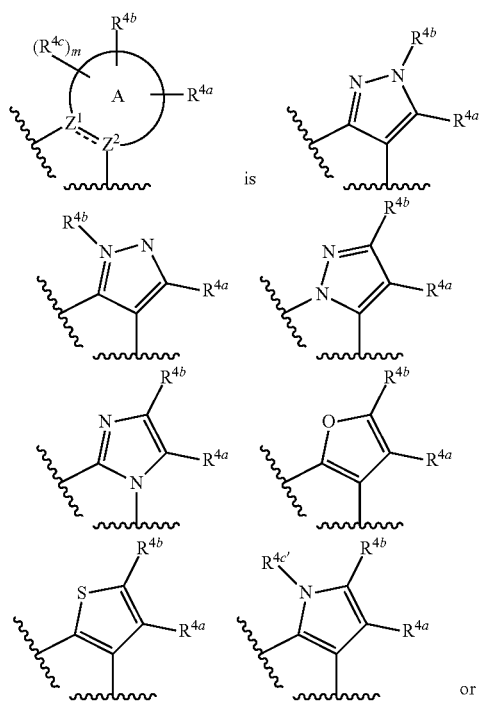

wherein a moiety represented by formula;

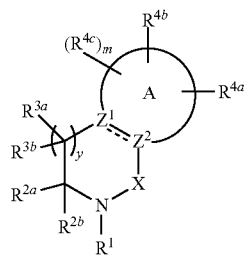

is

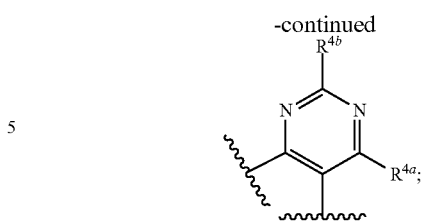

y is 0 or 1;
X is C(=O), C(=S), or SO$_2$;
m is 0 or 1;
R$^1$ is hydrogen, hydroxy, substituted or unsubstituted carbamoyl, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, provided that R$^1$ is not represented by formula:

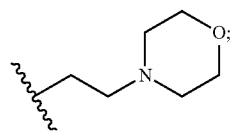 [SMILES: *CCN1CCOCC1]

R$^{2a}$ is represented by formula:

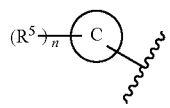

wherein ring C is an aromatic carbocycle, an aromatic heterocycle, a non-aromatic carbocycle, or a non-aromatic heterocycle;
R$^5$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)—$R^{S1}$, or a group represented by formula: —S(=N—$R^N$)$_2$—$R^{S1}$, and n is an integer of 1 to 5), $R^{2b}$ is cyano, substituted or unsubstituted carbamoyl, substituted or unsubstituted alkyl, substituted or unsubstituted alkenyl, substituted or unsubstituted alkynyl, or substituted or unsubstituted alkylsulfonyl, or optionally, $R^{2a}$ and $R^{2b}$ are taken together with an adjacent carbon atom to form ring B, ring B is a substituted or unsubstituted non-aromatic carbocycle or a substituted or unsubstituted non-aromatic heterocycle;

$R^{3a}$ is hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl, $R^{3b}$ is hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl, optionally, $R^{3a}$ and $R^{3b}$ are taken together with an adjacent carbon atom to form a substituted or unsubstituted non-aromatic carbocycle or a substituted or unsubstituted non-aromatic heterocycle, or optionally, $R^{2b}$ and $R^{3b}$ are taken together with adjacent carbon atoms to form a substituted or unsubstituted non-aromatic carbocycle or a substituted or unsubstituted non-aromatic heterocycle;

$R^{4a}$ is represented by formula:

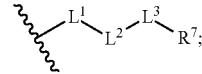

$L^1$ is a single bond or substituted or unsubstituted alkylene, $L^2$ is a single bond, —C(=O)—, —C(=O)—O—, —O—C(=O)—, —N(H)—, —C(O)—N(H)—, —N(H)—C(=O)—, —N(H)—C(=O)—N(H)—, —C(=O)—N(H)—S(=O)$_2$—, —N(H)—S(=O)$_2$—, —S(=O)$_2$—N(H)—, —N(H)—S(=O)$_2$—N(H)—, or —S(=O)$_2$—N(H)—C(=O)—, $L^3$ is a single bond or substituted or unsubstituted alkylene, $R^7$ is hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, provided that when $L^1$, $L^2$, and $L^3$ are single bonds, $R^7$ is not hydrogen or halogen, $R^{4b}$ is halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{4c'}$ is hydrogen, halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, L is each independently a single bond, alkylene, or C(=O), $R^{S1}$ and $R^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or optionally, $R^{S1}$ and $R^{S2}$ attached to an identical sulfur atom are taken together with the identical sulfur atom to form a substituted or unsubstituted non-aromatic heterocycle;

$R^N$ is each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl, provided that compounds below are excluded:

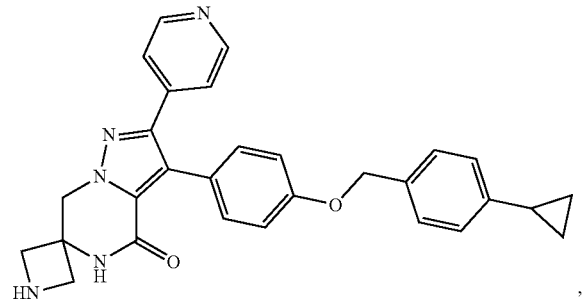 [SMILES: O=C1NC2(CNC2)Cn2nc(-c3ccncc3)c(-c3ccc(OCc4ccc(C5CC5)cc4)cc3)c21]

or its pharmaceutically acceptable salt.

[2] The compound or its pharmaceutically acceptable salt according to [1], wherein ring B is represented by any one of formulas:

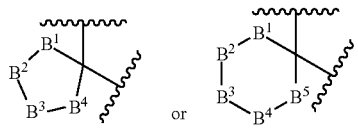

wherein
$B^1$ is $CR^{11a}R^{11b}$, $NR^{11c}$, O or S,
$B^2$ is $CR^{12a}R^{12b}$, $NR^{12c}$, O, or S,
$B^3$ is $CR^{13a}R^{13b}$, $NR^{13c}$, O, or S,
$B^4$ is $CR^{14a}R^{14b}$, $NR^{14c}$, O, or S, and
$B^5$ is $CR^{15a}R^{15b}$, $NR^{15c}$, O, or S, $R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(—N—$R^N$)(—$R^{S1}$)—$R^{S2}$, or a group represented by formula: —S(=N—$R^N$)$_2$—$R^{S1}$, $R^{11b}$, $R^{12b}$, $R^{13b}$, $R^{14b}$, and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, a group represented by formula: -L-N=S(=O)(—$R^{S1}$)—$R^{S2}$, a group represented by formula: -L-S(=O)(=N—$R^{N}$)—$R^{S1}$, a group represented by formula: —N=S(=N—$R^{N}$)(—$R^{S1}$)—$R^{S2}$, or a group represented by formula: —S(=N—$R^{N}$)$_2$—$R^{S1}$, $R^{11c}$, $R^{12c}$, $R^{13c}$, $R^{14c}$, and $R^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or optionally $R^{11a}$ and $R^{12a}$, $R^{12a}$, and $R^{13a}$, $R^{13a}$, and $R^{14a}$ and/or $R^{14a}$ and $R^{15a}$ are taken together with adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, and/or optionally $R^{11c}$ and $R^{12a}$, $R^{11c}$ and $R^{12c}$, $R^{12c}$ and $R^{11a}$, $R^{12c}$ and $R^{13a}$, $R^{12c}$ and $R^{13c}$, $R^{13c}$ and $R^{12a}$, $R^{13c}$ and $R^{14a}$, $R^{13c}$ and $R^{14c}$, $R^{14c}$ and $R^{13a}$, $R^{14c}$ and $R^{15a}$, $R^{14c}$ and $R^{15c}$, and/or $R^{15c}$ and $R^{14a}$ are taken together with adjacent atoms to form a substituted or unsubstituted aromatic heterocycle or a substituted or unsubstituted non-aromatic heterocycle, and/or optionally $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{15a}$, $R^{11a}$ and $R^{15c}$, $R^{11c}$ and $R^{13a}$, $R^{11c}$ and $R^{13c}$, $R^{11c}$ and $R^{14a}$, $R^{11c}$ and $R^{14c}$, $R^{11c}$ and $R^{15a}$, $R^{11c}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{12c}$ and $R^{14a}$, $R^{12c}$ and $R^{14c}$, $R^{12c}$ and $R^{15a}$, $R^{12c}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$, are taken together to form a C2-C4 bridge optionally containing a heteroatom, and/or optionally $R^{11b}$ and $R^{12b}$, $R^{11b}$ and $R^{12c}$, $R^{11c}$ and $R^{12b}$, $R^{11c}$ and $R^{12c}$, $R^{12b}$ and $R^{13b}$, $R^{12b}$ and $R^{13c}$, $R^{12c}$ and $R^{13b}$, $R^{12c}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ are taken together to form a bond, and other symbols are as described in [1].

[3] The compound or its pharmaceutically acceptable salt according to [1] or [2], wherein ring B is represented by any one of formulas:

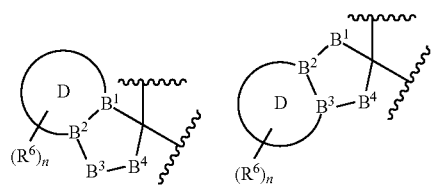

-continued

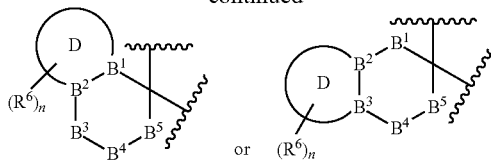

wherein
B¹ is C, $CR^{11a}R^{11b}$, $NR^{11c}$, O or S,
B² is C, $CR^{12a}$ or N,
B³ is C, $CR^{13a}$, $CR^{13a}R^{13b}$, $NR^{13c}$, N, O, or S,
B⁴ is $CR^{14a}R^{14b}$, $NR^{14c}$, O, or S,
B⁵ is $CR^{15a}R^{15b}$, $NR^{15c}$, O, or S,
provided that when B¹ and B³ are member atoms of ring D, B¹ is C, $CR^{11a}$ or N, B³ is C, $CR^{13a}$ or N, $R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{11b}$, $R^{12b}$, $R^{13b}$, $R^{14b}$, and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{11c}$, $R^{12c}$, $R^{13c}$, $R^{14c}$, and $R^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or optionally $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{15a}$, $R^{11a}$ and $R^{15c}$, $R^{11c}$ and $R^{13a}$, $R^{11c}$ and $R^{13c}$, $R^{11c}$ and $R^{14a}$, $R^{11c}$ and $R^{14c}$, $R^{11c}$ and $R^{15a}$, $R^{11c}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{12c}$ and $R^{14a}$, $R^{12c}$ and $R^{14c}$, $R^{12c}$ and $R^{15a}$, $R^{12c}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$, are taken together to form a C2-C4 bridge optionally containing a heteroatom, and/or optionally $R^{11b}$ and $R^{12b}$, $R^{11b}$ and $R^{12c}$, $R^{11c}$ and $R^{12b}$, $R^{11c}$ and $R^{12c}$, $R^{12b}$ and $R^{13b}$, $R^{12b}$ and $R^{13c}$, $R^{12c}$ and $R^{13b}$, $R^{12c}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ are taken together to form a bond, and ring D is an aromatic carbocycle, a non-aromatic carbocycle, an aromatic heterocycle, or a non-aromatic heterocycle, $R^6$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, n is an integer of 1 to 4, and other symbols are as described in [1].

[4] The compound or its pharmaceutically acceptable salt according to any one of [1] to [3], wherein ring B is represented by any one of formulas:

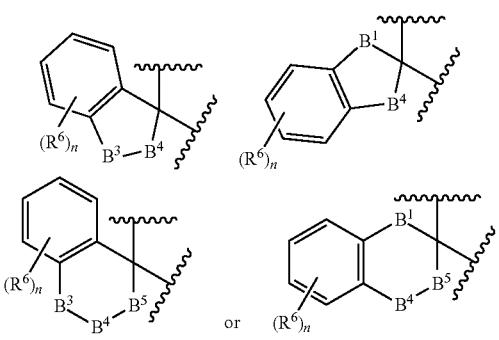

wherein $B^1$, $B^3$, $B^4$, $B^5$, $R^6$ and n are as described in [3].

[5] The compound or its pharmaceutically acceptable salt according to [3] or [4], wherein $R^6$ is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl.

[6] The compound or its pharmaceutically acceptable salt according to [1], wherein ring C is an aromatic carbocycle or an aromatic heterocycle.

[7] The compound or its pharmaceutically acceptable salt according to [1] or [6], wherein $R^5$ is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl, and
n is 1 to 3.

[8] The compound or its pharmaceutically acceptable salt according to any one of [1], [6] and [7], wherein $R^{2b}$ is substituted or unsubstituted alkyl.

[9] The compound or its pharmaceutically acceptable salt according to any one of [1] to [8], wherein $R^{4a}$ is a group represented by formula:

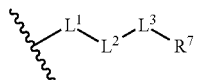

wherein
$L^1$ is a single bond or substituted or unsubstituted alkylene,
$L^2$ is —N(H)—, —C(=O)—, —C(=O)—O—, —O—C(=O)—, —C(=O)—N(H)—, —N(H)—C(=O)—, —C(=O)—N(H)—S(=O)$_2$—, or —N(H)—S(=O)$_2$—,
$L^3$ is a single bond or substituted or unsubstituted alkylene,
$R^7$ is hydrogen, halogen, hydroxy, cyano, substituted or unsubstituted amino, substituted or unsubstituted carbamoyl, substituted or unsubstituted sulfamoyl, substituted or unsubstituted alkyloxy, substituted or unsubstituted alkylsulfanyl, substituted or unsubstituted alkylsulfinyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, a group represented by formula: =N=S(=O)(—R$^{21}$)—R$^{S2}$, or a group represented by formula: —S(=O)(=N—R$^N$)—R$^{S1}$, and
other symbols are as described in [1].

[10] The compound or its pharmaceutically acceptable salt according to any one of [1] to [9], wherein $R^{4b}$ is substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

[11] The compound or its pharmaceutically acceptable salt according to any one of [1] to [10], wherein $R^{3a}$ and $R^{3b}$ are each hydrogen.

[12] The compound or its pharmaceutically acceptable salt according to [1], wherein the compound is selected from the group consisting of Compounds I-8, I-10, I-12, I-23, I-24, I-34, I-67, I-170, I-190, I-212, I-236, I-253, I-275, I-276, II-93, II-94, II-103, II-121, II-151, II-168, II-174, II-203, II-225, II-233, II-270, II-276, and II-295.

[12-1] The compound or its pharmaceutically acceptable salt according to [1], wherein the compound is selected from the group consisting of Compounds I-9, I-72, I-97, I-100, I-104, I-110, I-122, I-131, I-133, I-163, I-167, I-168, I-186, I-193, I-200, I-242, I-280, I-284, II-67, II-72, II-87, II-137, II-147, II-201, II-202, II-214, II-238, II-262, II-273 and II-274.

[13] A compound represented by formula (I):

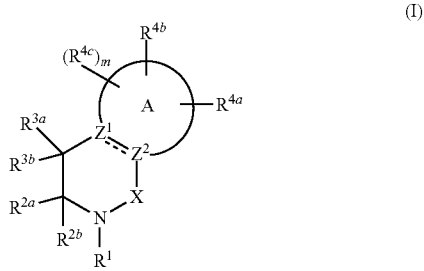

wherein
the moiety represented by the formula:

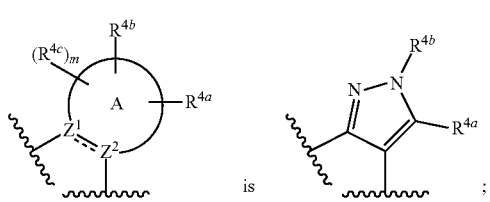

wherein X is C(=O);
$R^1$ is hydrogen;
$R^{2a}$ is represented by formula:

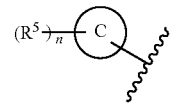

wherein ring C is benzene or pyridine;
$R^5$ is each independently halogen, haloalkyl, haloalkyloxy, non-aromatic carbocyclyl optionally substituted with halogen or haloalkyl, or non-aromatic heterocyclyl optionally substituted with halogen or haloalkyl, and n is an integer of 1 to 3, $R^{2b}$ is alkyl or haloalkyl, or optionally, $R^{2a}$ and $R^{2b}$ are taken together with an adjacent carbon atom to form ring B, ring B is represented by formula:

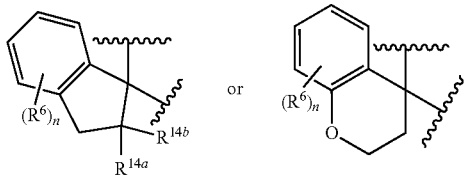

wherein $R^6$ is each independently halogen, haloalkyl, haloalkyloxy, non-aromatic carbocyclyl optionally substituted with halogen or haloalkyl, or non-aromatic heterocyclyl optionally substituted with halogen or haloalkyl, $R^{14a}$ and $R^{14b}$ are each independently hydrogen or halogen, and n is an integer of 1 to 3;

$R^{3a}$ is hydrogen, $R^{3b}$ is hydrogen;

$R^{4a}$ is carboxy or represented by formula;

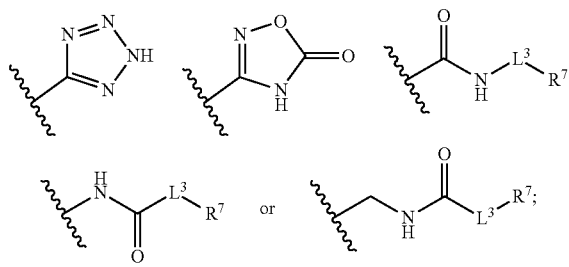

$L^3$ is a single bond or alkylene, $R^7$ is hydrogen, halogen, alkylsulfonyl, non-aromatic heterocyclyl optionally substituted with oxo, or non-aromatic carbocyclylsulfonyl optionally substituted with alkyl, or is represented by formula; —S(=O)(=N—H)—$R^{S1}$, $R^{4b}$ is alkyl optionally substituted with a substituent group α, aromatic carbocyclyl optionally substituted with a substituent group β, or aromatic heterocyclyl optionally substituted with the substituent group β, $R^{S1}$ is alkyl, the substituent group α is halogen, haloalkyloxy, and non-aromatic carbocyclyl, and the substituent group β is halogen, cyano, alkyl, haloalkyl, and alkyloxy, or its pharmaceutically acceptable salt.

[14] A pharmaceutical composition comprising the compound or its pharmaceutically acceptable salt according to any one of [1] to [13] or [12-1].

[15] The pharmaceutical composition according to [14], having MGAT2 inhibitory activity.

[16] The pharmaceutical composition according to [14] or [15], for use in treating or preventing an MGAT2-associated disease.

[17] The pharmaceutical composition according to [16], for use in treating or preventing obesity, metabolic syndrome, hyperlipidemia, hypertriglyceridemia, hyper-VLDL-triglyceridemia, hyperfattyacidemia, diabetes mellitus, or arteriosclerosis.

[18] A method for treating or preventing an MGAT2-associated disease, comprising administering the compound or its pharmaceutically acceptable salt according to any one of [1] to [13] or [12-1].

[19] The compound or its pharmaceutically acceptable salt according to any one of [1] to [13] or [12-1] for treating or preventing an MGAT2-associated disease.

[20] A use of the compound according to any one of [1] to [13] or [12-1], or its pharmaceutically acceptable salt, for treating or preventing an MGAT2-associated disease.

[1'] A compound represented by formula (I');

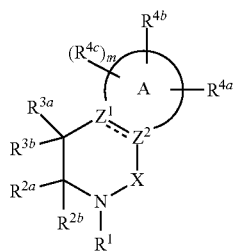

wherein ring A is a benzene ring or a 5- or 6-membered aromatic heterocycle, $Z^1$ is C or N, $Z^2$ is C or N, a broken line represents the presence or absence of a bond, when the bond is present, $Z^1$ is C, $Z^2$ is C, X is C(=O), C(=S), or SO$_2$, $R^1$ is hydrogen, hydroxy, substituted or unsubstituted carbamoyl, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, provided that $R^1$ is not represented by formula:

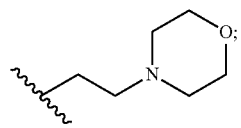 [SMILES: *CCN1CCOCC1]

$R^{2a}$ and $R^{2b}$ are taken together with an adjacent carbon atom to form ring B, ring B is a substituted or unsubstituted non-aromatic carbocycle or a substituted or unsubstituted non-aromatic heterocycle, provided that when ring A is a 5-membered aromatic heterocycle, $R^{2a}$ is optionally represented by formula:

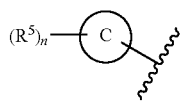

optionally $R^{2b}$ is hydrogen, cyano, substituted or unsubstituted carbamoyl, substituted or unsubstituted alkyl, substituted or unsubstituted alkenyl, substituted or unsubstituted alkynyl, or substituted or unsubstituted alkylsulfonyl, ring C is an aromatic carbocycle, an aromatic heterocycle, a non-aromatic heterocycle, or a C4 to C16 non-aromatic carbocycle, $R^5$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)($R^{S1}$)—$R^{S2}$, or a group represented by formula: —S(=N—$R^N$)$_2$—$R^{S1}$, n is an integer from 1 to 5;

$R^{3a}$ is hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl, $R^{3b}$ is hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl, or optionally, $R^{3a}$ and $R^{4b}$ are taken together with an adjacent carbon atom to form a substituted or unsubstituted non-aromatic carbocycle or a substituted or unsubstituted non-aromatic heterocycle;

$R^{4a}$ is represented by formula:

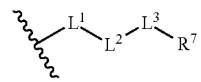

$L^1$ is a single bond or substituted or unsubstituted alkylene, $L^2$ is a single bond, —C(=O)—, —C(=O)—O—, —O—C(=O)—, —C(=O)—N(H)—, —N(H)—(=O)—, —C(=O)—N(H)—S(=O)$_2$—, —N(H)—S(=O)$_2$—, —S(=O)$_2$—N(H)—, or —S(=O)$_2$—N(H)—C(=O)—, $L^3$ is a single bond or substituted or unsubstituted alkylene, $R^7$ is hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^{N}$)—$R^{S1}$, a group represented by formula: —N=S(=N—$R^{N}$)(—$R^{S1}$)—$R^{S2}$, or a group represented by formula: —S(=N—$R^{N}$)$_2$—$R^{S1}$, provided that when $L^1$, $L^2$, and $L^3$ are single bonds, $R^7$ is not hydrogen or hydroxy, $R^{4b}$ is halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^{N}$)—$R^{S1}$, a group represented by formula: —N=S(=N—$R^{N}$)(—$R^{S1}$)—$R^{S2}$, or a group represented by formula: —S(=N—$R^{N}$)$_2$—$R^{S1}$, $R^{4c}$ is each independently halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, provided that $R^{4a}$, $R^{4b}$ and $R^{4c}$ are not benzyloxy, methoxy and methylsulfanyl;

m is an integer of 0 to 3,

L is each independently a single bond, alkylene, or C(=O), $R^{S1}$ and $R^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or optionally, $R^{S1}$ and $R^{S2}$ attached to an identical sulfur atom are taken together with the identical sulfur atom to form a substituted or unsubstituted non-aromatic heterocycle;

$R^N$ is each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl, provided that compounds below are excluded:

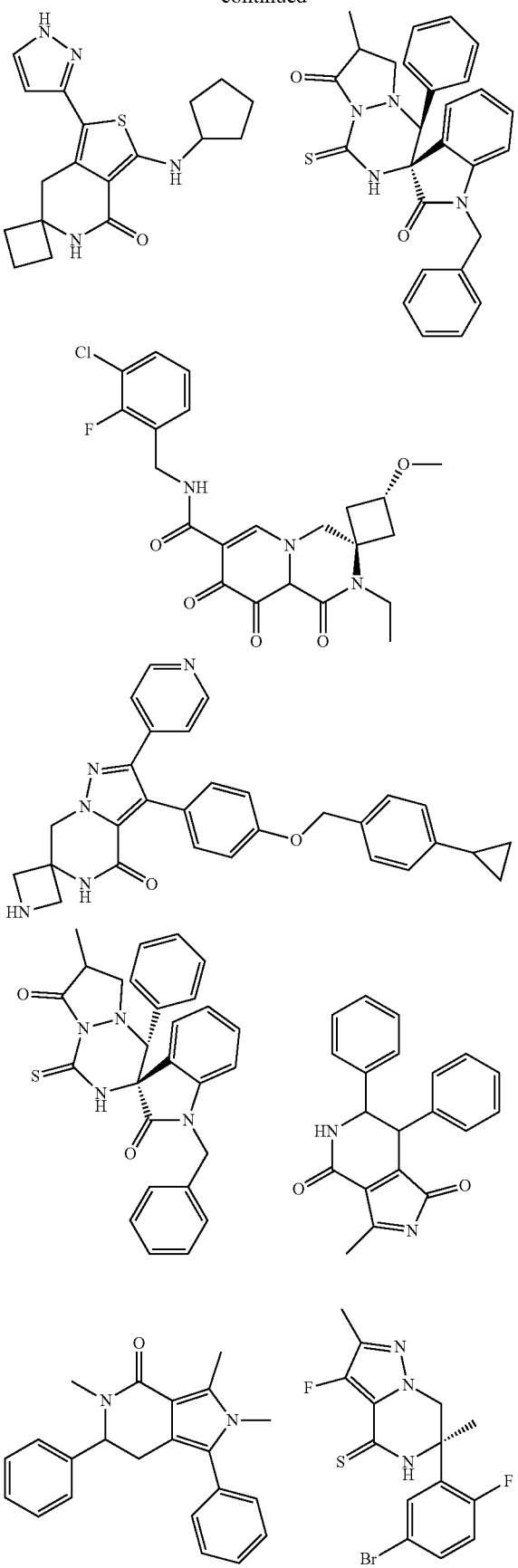

-continued

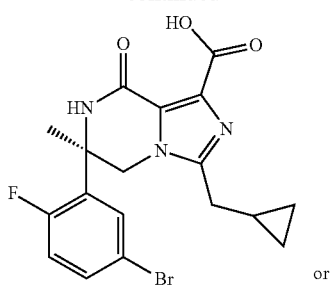

or

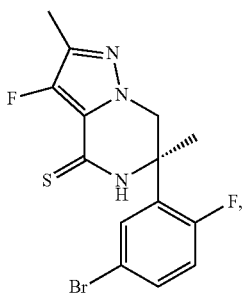

or its pharmaceutically acceptable salt.

[2'] The compound or its pharmaceutically acceptable salt according to [1'], wherein a moiety represented by formula:

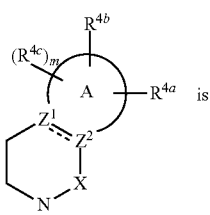 is

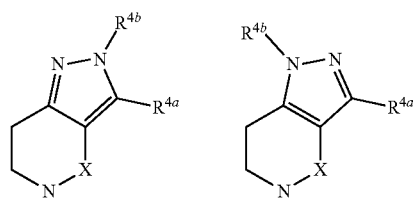

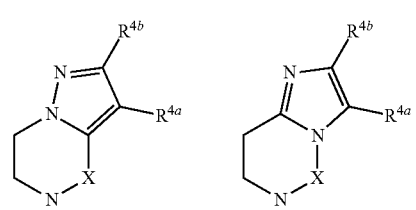

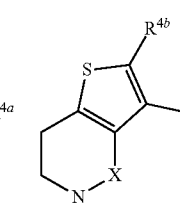

-continued

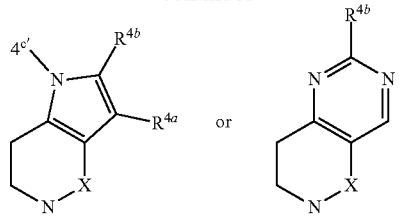 or 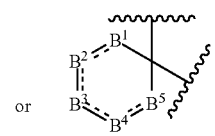

wherein $R^{4c'}$ is hydrogen, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted non-aromatic carbocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, other symbols are as described in [1'].

[3'] The compound or its pharmaceutically acceptable salt according to [1'] or [2'], wherein ring B is represented by any one of formulas:

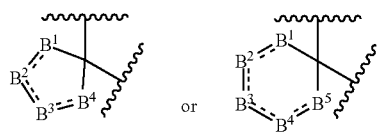

wherein $B^1$ is $CR^{11a}R^{11b}$, $NR^{11c}$, O or S,
$B^2$ is $CR^{12a}R^{12b}$, $NR^{12c}$, O, or S,
$B^3$ is $CR^{13a}R^{13b}$, $NR^{13c}$, O, or S,
$B^4$ is $CR^{14a}R^{14b}$, $NR^{14c}$, O, or S, and
$B^5$ is $CR^{15a}R^{15b}$, $NR^{15c}$, O, or S, $R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{11b}$, $R^{12b}$, $R^{13b}$, $R^{14b}$, and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{11c}$, $R^{12c}$, $R^{13c}$, $R^{14c}$, and $R^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or optionally $R^{11a}$ and $R^{12a}$, $R^{12a}$, and $R^{13a}$, $R^{13a}$, and $R^{14a}$ and/or $R^{14a}$ and $R^{15a}$ are taken together with adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, and/or optionally $R^{11c}$ and $R^{12a}$, $R^{11c}$ and $R^{12c}$, $R^{12c}$ and $R^{11a}$, $R^{12c}$ and $R^{13a}$, $R^{12c}$ and $R^{13c}$, $R^{13c}$ and $R^{12a}$, $R^{13c}$ and $R^{14a}$, $R^{13c}$ and $R^{14c}$, $R^{14c}$ and $R^{13a}$, $R^{14c}$ and $R^{15a}$, $R^{14c}$ and $R^{15c}$, and/or $R^{15c}$ and $R^{14a}$ are taken together with adjacent atoms to form a substituted or unsubstituted aromatic heterocycle or a substituted or unsubstituted non-aromatic heterocycle, and/or optionally $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{15a}$, $R^{11a}$ and $R^{15c}$, $R^{11c}$ and $R^{13a}$, $R^{11c}$ and $R^{13c}$, $R^{11c}$ and $R^{14a}$, $R^{11c}$ and $R^{14c}$, $R^{11c}$ and $R^{15a}$, $R^{11c}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{12c}$ and $R^{14a}$, $R^{12c}$ and $R^{14c}$, $R^{12c}$ and $R^{15a}$, $R^{12c}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$, are taken together to form a C2-C4 bridge optionally containing a heteroatom, and/or optionally $R^{11b}$ and $R^{12b}$, $R^{11b}$ and $R^{12c}$, $R^{11c}$ and $R^{12b}$, $R^{11c}$ and $R^{12c}$, $R^{12b}$ and $R^{13b}$, $R^{12b}$ and $R^{13c}$, $R^{12c}$ and $R^{13b}$, $R^{12c}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ are taken together to form a bond, and a dashed line represents a presence or absence of a bond, and other symbols are as described in [1'].

[4'] The compound or its pharmaceutically acceptable salt according to any one of [1'] to [3'], wherein ring B is represented by any one of formulas:

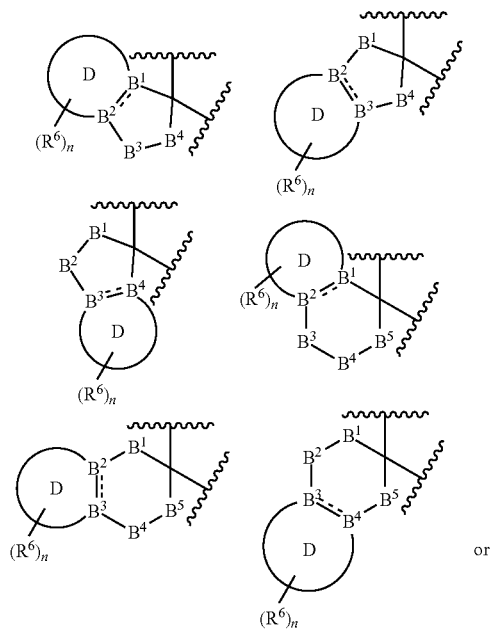

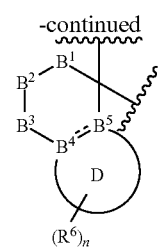

wherein ring D is an aromatic carbocycle, a non-aromatic carbocycle, an aromatic heterocycle, or a non-aromatic heterocycle, $R^6$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula:

-L-N=S(=O)(—R^{S1})—R^{S2}, a group represented by formula: -L-S(=O)(=N—R^N)—R^{S1}, a group represented by formula: —N=S(=N—R^N)(—R^{S1})—R^{S2}, or a group represented by formula: —S(=N—R^N)$_2$—R^{S1}, n is an integer of 0 to 4, $B^1$, $B^2$, $B^3$, $B^4$ and $B^5$ are as described in [3'], and other symbols are as described in [1'].

[5'] The compound or its pharmaceutically acceptable salt according to any one of [1'] to [4'], wherein ring B is represented by any one of formulas:

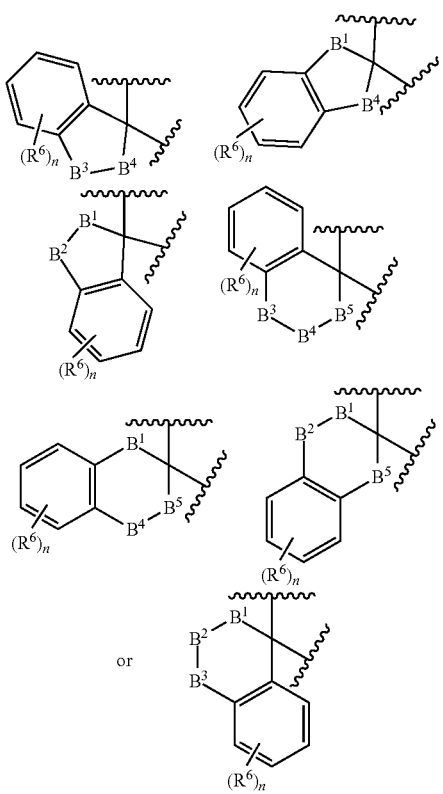

wherein $R^6$ and n are as described in [4'], $B^1$, $B^2$, $B^3$, $B^4$ and $B^5$ are as described in [3'], and other symbols are as described in [1'].

[6'] The compound or its pharmaceutically acceptable salt according to [4'] or [5'], wherein $R^6$ is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl.

[7'] The compound or its pharmaceutically acceptable salt according to [1'] or [2'], wherein ring C is an aromatic carbocycle or an aromatic heterocycle.

[8'] The compound or its pharmaceutically acceptable salt according to any one of [1'], [2'], or [7'], wherein $R^5$ is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl, and n is 1 to 3.

[9'] The compound or its pharmaceutically acceptable salt according to any one of [1'], [2'], [7'] or [8'], wherein $R^{2b}$ is hydrogen, or substituted or unsubstituted alkyl.

[10'] The compound or its pharmaceutically acceptable salt according to any one of [1'] to [9'], wherein $R^{4a}$ is a group represented by formula:

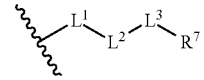

wherein $L^1$ is a single bond or substituted or unsubstituted alkylene, $L^2$ is a single bond, —C(=O)—, —C(=O)—O—, —O—C(=O)—, —C(=O)—N(H)—, —N(H)—C(=O)—, —C(=O)—N(H)—S(=O)$_2$—, or —N(H)—S(=O)$_2$—, $L^3$ is a single bond or substituted or unsubstituted alkylene, $R^7$ is hydrogen, halogen, hydroxy, cyano, substituted or unsubstituted amino, substituted or unsubstituted alkyl, substituted or unsubstituted alkyloxy, substituted or unsubstituted alkylsulfonyl, substituted or unsubstituted alkylaminosulfonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, provided that when $L^1$, $L^2$, and $L^3$ are single bonds, $R^7$ is not hydrogen or hydroxy.

[11'] The compound or its pharmaceutically acceptable salt according to any one of [1'] to [10'], wherein Rob is substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

[12'] The compound or its pharmaceutically acceptable salt according to any one of [1'] to [11'], wherein $R^{3a}$ is hydrogen, halogen, or substituted or unsubstituted alkyl, and $R^{3b}$ is hydrogen, halogen, or substituted or unsubstituted alkyl.

[13'] A pharmaceutical composition comprising the compound or its pharmaceutically acceptable salt according to any one of [1'] to [12'].

[14'] The pharmaceutical composition according to [13'], having MGAT2 inhibitory activity.

[15'] The pharmaceutical composition according to [13'] or [14'], for use in treating or preventing an MGAT2-associated disease.

[16'] The pharmaceutical composition according to [15'], for use in treating or preventing obesity, metabolic syndrome, hyperlipidemia, hypertriglyceridemia, hyper-VLDL-triglyceridemia, hyperfattyacidemia, diabetes mellitus, or arteriosclerosis.

[17'] A method for treating or preventing an MGAT2-associated disease, comprising administering the compound or its pharmaceutically acceptable salt according to any one of [1'] to [12'].

[18'] A use of the compound according to any one of [1'] to [12'], or its pharmaceutically acceptable salt, for producing a therapeutic agent or prophylactic agent for an MGAT2-associated disease.

[19'] The compound or its pharmaceutically acceptable salt according to any one of [1'] to [12'], for treating or preventing an MGAT2-associated disease.

Effect of the Invention

The compound according to the present invention has MGAT2 inhibitory activity, and are useful as a prophylactic agent and/or therapeutic agent for, for example, obesity, metabolic syndrome, hyperlipidemia, hypertriglyceridemia, hyper-VLDL-triglyceridemia, hyperfattyacidemia, diabetes mellitus, or arteriosclerosis.

MODE FOR CARRYING OUT THE INVENTION

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

The term "halogen" includes a fluorine atom, a chlorine atom, a bromine atom and an iodine atom. In particular, a fluorine atom and a chlorine atom are preferable.

The term "alkyl" includes a C1 to C15, preferably a C1 to C10, more preferably a C1 to C6, and further preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6, and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

A preferred embodiment of "alkenyl" is vinyl, allyl, propenyl, isopropenyl or butenyl.

The term "alkynyl" includes a C2 to C10, preferably a C2 to C8, more preferably a C2 to C6, and further preferably a C2 to C4 linear or branched hydrocarbon group having one or more triple bond(s) at any position(s). Furthermore, it may have double bond(s) at any position(s). For example, it includes ethynyl, propynyl, butynyl, pentynyl, hexynyl, heptynyl, octynyl, nonynyl, decynyl and the like.

A preferred embodiment of "alkynyl" is ethynyl, propynyl, butynyl or pentynyl.

The term "alkylene" includes a C1 to C15, preferably a C1 to C10, more preferably a C1 to C6, and further preferably a C1 to C4 liner or branched divalent hydrocarbon group. Examples include methylene, ethylene, propylene, tetramethylene, pentamethylene, and hexamethylene.

The term "aromatic carbocyclyl" means a cyclic aromatic hydrocarbon group which is monocyclic or polycyclic having two or more rings. Examples include phenyl, naphthyl, anthryl, and phenanthryl.

A preferred embodiment of "aromatic carbocyclyl" is phenyl.

The term "non-aromatic carbocyclyl" means a cyclic saturated hydrocarbon group or a cyclic unsaturated non-aromatic hydrocarbon group, which is monocyclic or polycyclic having two or more rings. The "non-aromatic carbocyclyl" which is polycyclic having two or more rings includes a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

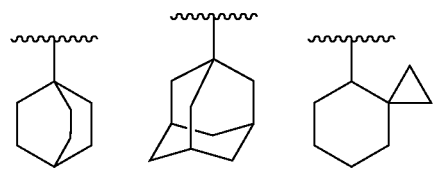 [SMILES: *C12CCC(CC1)CC2 ; *C12CC3CC(CC(C3)C1)C2 ; *C1CCCCC12CC2]

The non-aromatic carbocyclyl which is monocyclic is preferably C3 to C16 carbocyclyl, more preferably C3 to C12 carbocyclyl, and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

A non-aromatic carbocyclyl which is polycyclic having two or more rings is preferably C8 to C20 carbocyclyl, and more preferably C8 to C16 carbocyclyl. Examples include indanyl, indenyl, acenaphthyl, tetrahydronaphthyl, and fluorenyl.

The term "aromatic carbocycle" includes a cyclic aromatic hydrocarbon which is monocyclic or polycyclic having two or more rings. Examples include a benzene ring, a naphthalene ring, an anthracene ring, and a phenanthrene ring.

An embodiment of "aromatic carbocycle" is a benzene ring and a naphthalene ring. Another embodiment thereof includes a benzene ring.

The term "non-aromatic carbocycle" includes a cyclic saturated hydrocarbon or a cyclic unsaturated non-aromatic hydrocarbon, which is monocyclic or polycyclic having two or more rings. The "non-aromatic carbocycle", which is polycyclic having two or more rings, includes a fused ring wherein the non-aromatic carbocycle, which is monocyclic or polycyclic having two or more rings, is fused with a ring of the above "aromatic carbocycle".

In addition, examples of the "non-aromatic carbocycle" also include a ring having a bridge or a ring to form a spiro ring as follows:

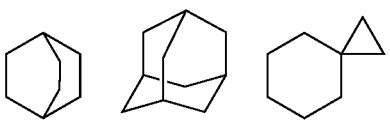

The non-aromatic carbocycle which is monocyclic is preferably a C3 to C16 carbocycle, more preferably a C3 to C12 carbocycle, and further preferably a C3 to C8 carbocycle. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, and cyclohexadiene.

A non-aromatic carbocycle which is polycyclic having two or more rings is preferably a C8 to C20 carbocycle, and more preferably a C8 to C16 carbocycle. Examples include indane, indene, acenaphthene, tetrahydronaphthalene, and fluorene.

The term "aromatic heterocyclyl" means an aromatic cyclyl, which is monocyclic or polycyclic having two or more rings, containing one or more, same or different heteroatom(s) selected independently from O, S and N. The "aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered ring, and more preferably a 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

An aromatic heterocyclyl which is bicyclic is preferably an 8- to 10-membered ring, and more preferably a 9- or 10-membered ring. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

Examples of aromatic heterocyclyl, which is polycyclic having three or more rings, include carbazolyl, acridinyl, xanthenyl, phenothiazinyl, phenoxathiinyl, phenoxazinyl, and dibenzofuryl.

The term "non-aromatic heterocyclyl" means a non-aromatic cyclyl, which is monocyclic or polycyclic having two or more rings, containing one or more, same or different heteroatom(s) selected independently from O, S and N. "Non-aromatic heterocyclyl", which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl", and includes a fused ring group wherein a ring of the above "aromatic heterocyclyl" is fused with the above "non-aromatic carbocyclyl", which is monocyclic or polycyclic having two or more ring(s).

In addition, examples of the "non-aromatic heterocyclyl" also include a group having a bridge or a group to form a spiro ring as follows:

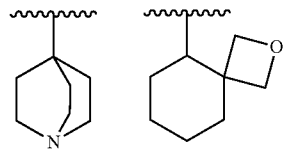

The non-aromatic heterocyclyl, which is monocyclic, is preferably a 3- to 8-membered, and more preferably a 5- to 6-membered. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolynyl, oxepanyl, thiolanyl, thiinyl, and thiazinyl.

A non-aromatic heterocyclyl which is polycyclic having two or more rings is preferably an 8- to 20-membered, and more preferably an 8- to 10-membered. Examples include indolinyl, isoindolinyl, chromanyl, and isochromanyl.

The term "aromatic heterocycle" includes an aromatic ring, which is monocyclic or polycyclic having two or more rings, containing one or more, same or different heteroatom(s) selected independently from O, S and N.

The "aromatic heterocycle", which is polycyclic having two or more rings, includes a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered ring, and more preferably a 5- or 6-membered ring. Examples include pyrrole, imidazole, pyrazole, pyridine, pyridazine, pyrimidine, pyrazine, triazole, triazine, tetrazole, furan, thiophen, isoxazole, oxazole, oxadiazole, isothiazole, thiazole, and thiadiazole.

The aromatic heterocycle, which is bicyclic, is preferably an 8- to 10-membered, and more preferably a 9- or 10-membered. Examples include indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, and thiazolopyridine.

The aromatic heterocycle, which is polycyclic having three or more rings, is preferably a 11- to 26-membered ring, and more preferably a 13- or 14-membered ring. Examples include carbazole, acridine, xanthene, phenothiazine, phenoxathiine, phenoxazine, and dibenzofuran.

The term "non-aromatic heterocycle" includes a cyclic non-aromatic ring, which is monocyclic or polycyclic having two or more rings, containing one or more, same or different heteroatom(s) selected independently from an oxygen atom, a sulfur atom, and a nitrogen atom.

The "non-aromatic heterocycle", which is polycyclic having two or more rings, includes a fused ring wherein a non-aromatic heterocycle, which is monocyclic or polycyclic having two or more ring(s), is fused with a ring of the above "aromatic carbocycle", "non-aromatic carbocycle" and/or "aromatic heterocycle".

In addition, the "non-aromatic heterocycle" also includes a ring having a bridge or a ring to form a spiro ring as follows:

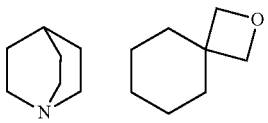

The non-aromatic heterocycle which is monocyclic is preferably a 3 to 8-membered ring, and more preferably a 5 or 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyrane, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxole, oxepane, thiolane, thiine, and thiazine.

A non-aromatic heterocycle which is polycyclic having two or more rings is preferably an 8- to 20-membered ring, and is an 8- to 10-membered ring. Examples include indoline, isoindoline, chroman, and isochroman.

The substituents of "substituted carbamoyl", "substituted thiocarbamoyl", "substituted amidino", "substituted amino", "substituted ureido", "substituted guanidino", "substituted sulfamoyl", "substituted alkyl", "substituted alkenyl", "substituted alkynyl", "substituted alkylene", "substituted alkyloxy", "substituted alkenyloxy", "substituted alkylcarbonyloxy", "substituted alkenylcarbonyloxy", "substituted alkylcarbonyl", "substituted alkenylcarbonyl", "substituted alkyloxycarbonyl", "substituted alkenyloxycarbonyl", "substituted alkylsulfanyl", "substituted alkenylsulfanyl", "substituted alkylsulfinyl", "substituted alkenylsulfinyl", "substituted alkylsulfonyl", and "substituted alkenylsulfonyl" include the substituents given below. A carbon atom or nitrogen atom at any position(s) may be bonded to one or more group(s) selected from the following substituents.

Substituent group: halogen, hydroxy, cyano, formyl, formyl oxy, thioformyl, carboxy, thiocarboxy, dithiocarboxy, carbamoyl thiocarbamoyl, amidino, amino, hydroxyamino, azido, hydradino, ureido, guanidino, pentafluorothio, thiol, sulfino, sulfo, sulfamoyl, trialkylsilyl, alkyl, alkenyl, alkynyl, haloalkyl, haloalkenyl, haloalkynyl, alkyloxy, alkenyloxy, alkynyloxy, haloalkyloxy, haloalkyloxyalkyl, alkylcarbonyloxy, alkenylcarbonyloxy, alkynylcarbonyloxy, alkylcarbonyl, alkenylcarbonyl, alkynylcarbonyl, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylsulfonyl, alkenylsulfonyl, alkynylsulfonyl, monoalkylaminosulfonyl, monoalkenylaminosulfonyl, monoalkynylaminosulfonyl, dialkylaminosulfonyl, dialkenylaminosulfonyl, dialkynylaminosulfonyl, monoalkylamino, monoalkenylamino, monoalkynylamino, dialkylamino, dialkenylamino, dialkynylamino, monoalkylcarbonylamino, monoalkenylcarbonylamino, monoalkynylcarbonylamino, dialkenylcarbonylamino, dialkynylcarbonylamino, monoalkyloxycarbonylamino, monoalkenyloxycarbonylamino, monoalkynyloxycarbonylamino, dialkyloxycarbonylamino, dialkenyloxycarbonylamino, dialkynyloxycarbonylamino, monoalkylsulfonylamino, monoalkenylsulfonylamino, monoalkynylsulfonylamino, dialkylsulfonylamino, dialkenylsulfonylamino, dialkynylsulfonylamino, monoalkylcarbamoyl, monoalkenylcarbamoyl, monoalkynylcarbamoyl, dialkylcarbamoyl, dialkenylcarbamoyl, dialkynylcarbamoyl, monoalkyloxycarbamoyl, monoalkenyloxycarbamoyl, monoalkynyloxycarbamoyl, dialkyloxycarbamoyl, dialkenyloxycarbamoyl, dialkynyloxycarbamoyl, monoalkylcarbonylcarbamoyl, monoalkenylcarbonylcarbamoyl, monoalkynylcarbonylcarbamoyl, monoalkyloxycarbonylcarbamoyl, monoalkenyloxycarbonylcarbamoyl, monoalkynyloxycarbonylcarbamoyl, monoalkylsulfonylcarbamoyl, monoalkenylsulfonylcarbamoyl, monoalkynylsulfonylcarbamoyl, monoalkylsulfamoyl, monoalkenylsulfamoyl, monoalkynylsulfamoyl, dialkylsulfamoyl, dialkenylsulfamoyl, dialkynylsulfamoyl, monoalkyloxysulfamoyl, monoalkenyloxysulfamoyl, monoalkynyloxysulfamoyl, dialkyloxysulfamoyl, dialkenyloxysulfamoyl, dialkynyloxysulfamoyl, monoalkylcarbonylsulfamoyl, monoalkenylcarbonylsulfamoyl, monoalkynylcarbonylsulfamoyl, monoalkyloxycarbonylsulfamoyl, monoalkenyloxycarbonylsulfamoyl, monoalkynyloxycarbonylsulfamoyl, monoalkylsulfonylsulfamoyl, monoalkenylsulfonylsulfamoyl, monoalkynylsulfonylsulfamoyl, aromatic carbocyclyl optionally substituted with Substituent Group A, non-aromatic carbocyclyl optionally substituted with Substituent Group A, aromatic heterocyclyl optionally substituted with Substituent Group A, non-aromatic heterocyclyl optionally substituted with Substituent Group A, aromatic carbocyclyloxy optionally substituted with Substituent Group A, non-aromatic carbocyclyloxy optionally substituted with Substituent Group A, aromatic heterocyclyloxy optionally substituted with Substituent Group A, non-aromatic heterocyclyloxy optionally substituted with Substituent Group A, aromatic carbocyclylcarbonyloxy optionally substituted with Substituent Group A, non-aromatic carbocyclylcarbonyloxy optionally substituted with Substituent Group A, aromatic heterocyclylcarbonyloxy optionally substituted with Substituent Group A, non-aromatic heterocyclylcarbonyloxy optionally substituted with Substituent Group A, aromatic carbocyclylcarbonyl optionally substituted with Substituent Group A, non-aromatic carbocyclylcarbonyl optionally substituted with Substituent Group A, aromatic heterocyclylcarbonyl optionally substituted with Substituent Group A, non-aromatic heterocyclylcarbonyl optionally substituted with Substituent Group A, aromatic carbocyclyloxycarbonyl optionally substituted with Substituent Group A, non-aromatic carbocyclyloxycarbonyl optionally substituted with Substituent Group A, aromatic heterocyclyloxycarbonyl optionally substituted with Substituent Group A, non-aromatic heterocyclyloxycarbonyl optionally substituted with Substituent Group A, aromatic carbocyclylsulfanyl optionally substituted with Substituent Group A, non-aromatic carbocyclylsulfanyl optionally substituted with Substituent Group A, aromatic heterocyclylsulfanyl optionally substituted with Substituent Group A, non-aromatic heterocyclylsulfanyl optionally substituted with Substituent Group A, aromatic carbocyclylsulfinyl optionally substituted with Substituent Group A, non-aromatic carbocyclylsulfinyl optionally substituted with Substituent Group A, aromatic heterocyclylsulfinyl optionally substituted with Substituent Group A, non-aromatic heterocyclylsulfinyl optionally substituted with Substituent Group A, aromatic carbocyclylsulfonyl optionally substituted with Substituent Group A, non-aromatic carbocyclylsulfonyl optionally substituted with Substituent Group A, aromatic heterocyclylsulfonyl optionally substituted with Substituent Group A, non-aromatic heterocyclylsulfonyl optionally substituted with Substituent Group A, aromatic carbocyclylalkyl optionally substituted with Substituent Group A, non-aromatic carbocyclylalkyl optionally substituted with Substituent Group A, aromatic heterocyclylalkyl optionally substituted with Substituent Group A, non-aromatic heterocyclylalkyl optionally substituted with Substituent Group A, aromatic carbocyclylalkyloxy optionally substituted with Substituent Group A, non-aromatic carbocyclylalkyloxy optionally substituted with Substituent Group A, aromatic heterocyclylalkyloxy optionally substituted with Substituent Group A, non-aromatic heterocyclylalkyloxy optionally substituted with Substituent Group A, aromatic carbocyclylalkylcarbonyl optionally substituted with Substituent Group A, non-aromatic carbocyclylalkylcarbonyl optionally substituted with Substituent Group A, aromatic heterocyclylalkylcarbonyl optionally substituted with Substituent Group A, non-aromatic heterocyclylalkylcarbonyl optionally substituted with Substituent Group A, aromatic carbocyclylalkyloxycarbonyl optionally substituted with Substituent Group A, non-aromatic carbocyclylalkyloxycarbonyl, aromatic heterocyclylalkyloxycarbonyl optionally substituted with Substituent Group A, non-aromatic heterocyclylalkyloxycarbonyl optionally substituted with Substituent Group A, aromatic carbocyclylalkylsulfanyl optionally substituted with Substituent Group A, non-aromatic carbocyclylalkylsulfanyl optionally substituted with Substituent Group A, aromatic heterocyclylalkylsulfanyl optionally substituted with Substituent Group A, non-aromatic heterocyclylalkylsulfanyl optionally substituted with Substituent Group A, aromatic carbocyclylalkylsulfinyl optionally substituted with Substituent Group A, non-aromatic carbocyclylalkylsulfinyl optionally substituted with Substituent Group A, aromatic heterocyclylalkylsulfinyl optionally substituted with Substituent Group A, non-aromatic heterocyclylalkylsulfinyl optionally substituted with Substituent Group A, aromatic carbocyclylalkylsulfonyl optionally substituted with Substituent Group A, non-aromatic carbocyclylalkylsulfonyl optionally substituted with Substituent Group A, aromatic heterocyclylalkylsulfonyl optionally substituted with Substituent Group A, non-aromatic heterocyclylalkylsulfonyl optionally substituted with Substituent Group A, aromatic carbocyclylalkylamino optionally substituted with Substituent Group A, non-aromatic carbocyclylalkylamino optionally substituted with Substituent Group A, aromatic heterocyclylalkylamino optionally substituted with Substituent Group A, non-aromatic heterocyclylalkylamino optionally substituted with Substituent Group A, aromatic carbocyclylalkylcarbonylamino optionally substituted with Substituent Group A, non-aromatic carbocyclylalkylcarbonylamino optionally substituted with Substituent Group A, aromatic heterocyclylalkylcarbonylamino optionally substituted with Substituent Group A, non-aromatic heterocyclylalkylcarbonylamino optionally substituted with Substituent Group A, aromatic carbocyclylalkyloxycarbonylamino optionally substituted with Substituent Group A, non-aromatic carbocyclylalkyloxycarbonylamino optionally substituted with Substituent Group A, aromatic heterocyclylalkyloxycarbonylamino optionally substituted with Substituent Group A, non-aromatic heterocyclylalkyloxycarbonylamino optionally substituted with Substituent Group A, aromatic carbocyclylalkylsulfonylamino optionally substituted with Substituent Group A, non-aromatic carbocyclylalkylsulfonylamino optionally substituted with Substituent Group A, aromatic heterocyclylalkylsulfonylamino optionally substituted with Substituent Group A, non-aromatic heterocyclylalkylsulfonylamino optionally substituted with Substituent Group A, aromatic carbocyclyloxyalkylamino optionally substituted with Substituent Group A, non-aromatic carbocyclyloxyalkylamino optionally substituted with Substituent Group A, aromatic heterocyclyloxyalkylamino optionally substituted with Substituent Group A, and non-aromatic heterocyclyloxyalkylamino optionally substituted with Substituent Group A.

The term "optionally substituted with Substituent Group A" means that a carbon atom, nitrogen atom or sulfur atom at any position may be bonded to one or more groups selected from Substituent Group A.

Substituent Group A: oxo, halogen, hydroxy, alkyl, haloalkyl, hydroxyalkyl, alkyloxy, haloalkyloxy, alkyloxycarbonylalkyl, monoalkylamino, dialkylamino, aromatic carbocyclyl, aromatic heterocyclyl, and aromatic carbocyclyloxy.

Hereinafter, the same applies to the term "optionally substituted with Substituent Group B".

Substituent Group B: halogen, alkyl, and haloalkyl.

The substituents on the ring of "aromatic carbocycle", "non-aromatic carbocycle", "aromatic heterocycle", or "non-aromatic heterocycle" of "substituted non-aromatic carbocycle", "substituted non-aromatic heterocycle", "substituted aromatic carbocyclyl", "substituted non-aromatic carbocyclyl", "substituted aromatic heterocyclyl", "substituted non-aromatic heterocyclyl", "substituted aromatic carbocyclyloxy", "substituted non-aromatic carbocyclyloxy", "substituted aromatic heterocyclyloxy", "substituted non-aromatic heterocyclyloxy", "substituted aromatic carbocyclylcarbonyloxy", "substituted non-aromatic carbocyclylcarbonyloxy", "substituted aromatic heterocyclylcarbonyloxy", "substituted non-aromatic heterocyclylcarbonyloxy", "substituted aromatic carbocyclylcarbonyl", "substituted non-aromatic carbocyclylcarbonyl", "substituted aromatic heterocyclylcarbonyl", "substituted non-aromatic heterocyclylcarbonyl", "substituted aromatic carbocyclyloxycarbonyl", "substituted non-aromatic carbocyclyloxycarbonyl", "substituted aromatic heterocyclyloxycarbonyl", "substituted non-aromatic heterocyclyloxycarbonyl", "substituted aromatic carbocyclylsulfanyl", "substituted non-aromatic carbocyclylsulfanyl", "substituted aromatic heterocyclylsulfanyl", "substituted non-aromatic heterocyclylsulfanyl", "substituted aromatic carbocyclylsulfinyl", "substituted non-aromatic carbocyclylsulfinyl", "substituted aromatic heterocyclylsulfinyl", "substituted non-aromatic heterocyclylsulfinyl", "substituted aromatic carbocyclylsulfonyl", "substituted non-aromatic carbocyclylsulfonyl", "substituted aromatic heterocyclylsulfonyl", and "substituted non-aromatic heterocyclylsulfonyl" include the substituents given below. An atom at any position(s) on the ring may be bonded to one or more group(s) selected from the following substituents.

Substituents: oxo, halogen, hydroxy, cyano, formyl, formyloxy, thioformyl, carboxy, thiocarboxy, dithiocarboxy, carbamoyl, thiocarbamoyl, amidino, amino, hydroxyamino, imino, hydroxyimino, azide, hydrazino, ureido, guanidino, pentafluorothio, thiol, sulfino, sulfo, sulfamoyl, trialkylsilyl, alkyl, alkenyl, alkynyl, haloalkyl, alkyloxy, alkenyloxy, alkynyloxy, haloalkyloxy, haloalkenyloxy, haloalkynyloxy, haloalkyloxyalkyloxy, hydroxyalkyl, alkylcarbonyloxy, alkenylcarbonyloxy, alkynylcarbonyloxy, alkylcarbonyl, alkenylcarbonyl, alkynylcarbonyl, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylsulfonyl, alkenylsulfonyl, alkynylsulfonyl, monoalkylaminosulfonyl, monoalkenylaminosulfonyl, monoalkynylaminosulfonyl, dialkylaminosulfonyl, dialkenylaminosulfonyl, dialkynylaminosulfonyl, monoalkylamino, monoalkenylamino, monoalkynylamino, monohaloalkylamino, dialkylamino, dialkenylamino, dialkynylamino, monoalkylcarbonylamino, monoalkenylcarbonylamino, monoalkynylcarbonylamino, monohaloalkylcarbonylamino, dialkylcarbonylamino, dialkenylcarbonylamino, dialkynylcarbonylamino, monoalkyloxycarbonylamino, monoalkenyloxycarbonylamino, monoalkynyloxycarbonylamino, dialkyloxycarbonylamino, dialkenyloxycarbonylamino, dialkynyloxycarbonylamino, monoalkylsulfonylamino, monoalkenylsulfonylamino, monoalkynylsulfonylamino, dialkylsulfonylamino, dialkenylsulfonylamino, dialkynylsulfonylamino, alkylimino, alkenylimino, alkynylimino, alkyloxyimino, alkenyloxyimino, alkynyloxyimino, monoalkylcarbamoyl, monoalkenylcarbamoyl, monoalkynylcarbamoyl, dialkylcarbamoyl, dialkenylcarbamoyl, dialkynylcarbamoyl, monoalkyloxycarbamoyl, monoalkenyloxycarbamoyl, monoalkynyloxycarbamoyl, dialkyloxycarbamoyl, dialkenyloxycarbamoyl, dialkynyloxycarbamoyl, monoalkylcarbonylcarbamoyl, monoalkenylcarbonylcarbamoyl, monoalkynylcarbonylcarbamoyl, monoalkyloxycarbonylcarbamoyl, monoalkenyloxycarbonylcarbamoyl, monoalkynyloxycarbonylcarbamoyl, monoalkylsulfonylcarbamoyl, monoalkenylsulfonylcarbamoyl, monoalkynylsulfonylcarbamoyl, monoalkylsulfamoyl, monoalkenylsulfamoyl, monoalkynylsulfamoyl, dialkylsulfamoyl, dialkenylsulfamoyl, dialkynylsulfamoyl, monoalkyloxysulfamoyl, monoalkenyloxysulfamoyl, monoalkynyloxysulfamoyl, dialkyloxysulfamoyl, dialkenyloxysulfamoyl, dialkynyloxysulfamoyl, monoalkylcarbonylsulfamoyl, monoalkenylcarbonylsulfamoyl, monoalkynylcarbonylsulfamoyl, monoalkyloxycarbonylsulfamoyl, monoalkenyloxycarbonylsulfamoyl, monoalkynyloxycarbonylsulfamoyl, monoalkylsulfonylsulfamoyl, monoalkenylsulfonylsulfamoyl, monoalkynylsulfonylsulfamoyl, aromatic carbocyclyl optionally substituted with Substituent Group A, non-aromatic carbocyclyl optionally substituted with Substituent Group A, aromatic heterocyclyl optionally substituted with Substituent Group A, non-aromatic heterocyclyl optionally substituted with Substituent Group A, aromatic carbocyclyloxy optionally substituted with Substituent Group A, non-aromatic carbocyclyloxy optionally substituted with Substituent Group A, aromatic heterocyclyloxy optionally substituted with Substituent Group A, non-aromatic heterocyclyloxy optionally substituted with Substituent Group A, aromatic carbocyclylcarbonyloxy optionally substituted with Substituent Group A, non-aromatic carbocyclylcarbonyloxy optionally substituted with Substituent Group A, aromatic heterocyclylcarbonyloxy optionally substituted with Substituent Group A, non-aromatic heterocyclylcarbonyloxy optionally substituted with Substituent Group A, aromatic carbocyclylcarbonyl optionally substituted with Substituent Group A, non-aromatic carbocyclylcarbonyl optionally substituted with Substituent Group A, aromatic heterocyclylcarbonyl optionally substituted with Substituent Group A, non-aromatic heterocyclylcarbonyl optionally substituted with Substituent Group A, aromatic carbocyclyloxycarbonyl optionally substituted with Substituent Group A, non-aromatic carbocyclyloxycarbonyl optionally substituted with Substituent Group A, aromatic heterocyclyloxycarbonyl optionally substituted with Substituent Group A, non-aromatic heterocyclyloxycarbonyl optionally substituted with Substituent Group A, aromatic carbocyclylsulfanyl optionally substituted with Substituent Group A, non-aromatic carbocyclylsulfanyl optionally substituted with Substituent Group A, aromatic heterocyclylsulfanyl optionally substituted with Substituent Group A, non-aromatic heterocyclylsulfanyl optionally substituted with Substituent Group A, aromatic carbocyclylsulfinyl optionally substituted with Substituent Group A, non-aromatic carbocyclylsulfinyl optionally substituted with Substituent Group A, aromatic heterocyclylsulfinyl optionally substituted with Substituent Group A, non-aromatic heterocyclylsulfinyl optionally substituted with Substituent Group A, aromatic carbocyclylsulfonyl optionally substituted with Substituent Group A, non-aromatic carbocyclylsulfonyl optionally substituted with Substituent Group A, aromatic heterocyclylsulfonyl optionally substituted with Substituent Group A, non-aromatic heterocyclylsulfonyl optionally substituted with Substituent Group A, aromatic carbocyclylamino optionally substituted with Substituent Group A, non-aromatic carbocyclylamino optionally substituted with Substituent Group A, aromatic heterocyclylamino optionally substituted with Substituent Group A, non-aromatic heterocyclylamino optionally substituted with Substituent Group A, aromatic carbocyclylalkyl optionally substituted with Substituent Group A, non-aromatic carbocyclylalkyl optionally substituted with Substituent Group A, aromatic heterocyclylalkyl optionally substituted with Substituent Group A, non-aromatic heterocyclylalkyl optionally substituted with Substituent Group A, aromatic carbocyclylalkyloxy optionally substituted with Substituent Group A, non-aromatic carbocyclylalkyloxy optionally substituted with Substituent Group A, aromatic heterocyclylalkyloxy optionally substituted with Substituent Group A, non-aromatic heterocyclylalkyloxy optionally substituted with Substituent Group A, aromatic carbocyclylalkylcarbonyl optionally substituted with Substituent Group A, non-aromatic carbocyclylalkylcarbonyl optionally substituted with Substituent Group A, aromatic heterocyclylalkylcarbonyl optionally substituted with Substituent Group A, non-aromatic heterocyclylalkylcarbonyl optionally substituted with Substituent Group A, aromatic carbocyclylalkyloxycarbonyl optionally substituted with Substituent Group A, non-aromatic carbocyclylalkyloxycarbonyl, aromatic heterocyclylalkyloxycarbonyl optionally substituted with Substituent Group A, non-aromatic heterocyclylalkyloxycarbonyl optionally substituted with Substituent Group A, aromatic carbocyclylalkylsulfanyl optionally substituted with Substituent Group A, non-aromatic carbocyclylalkylsulfanyl optionally substituted with Substituent Group A, aromatic heterocyclylalkylsulfanyl optionally substituted with Substituent Group A, non-aromatic heterocyclylalkylsulfanyl optionally substituted with Substituent Group A, aromatic carbocyclylalkylsulfinyl optionally substituted with Substituent Group A, non-aromatic carbocyclylalkylsulfinyl optionally substituted with Substituent Group A, aromatic heterocyclylalkylsulfinyl optionally substituted with Substituent Group A, non-aromatic heterocyclylalkylsulfinyl optionally substituted with Substituent Group A, aromatic carbocyclylalkylsulfonyl optionally substituted with Substituent Group A, non-aromatic carbocyclylalkylsulfonyl optionally substituted with Substituent Group A, aromatic heterocyclylalkylsulfonyl optionally substituted with Substituent Group A, non-aromatic heterocyclylalkylsulfonyl optionally substituted with Substituent Group A, aromatic carbocyclylalkylamino optionally substituted with Substituent Group A, non-aromatic carbocyclylalkylamino optionally substituted with Substituent Group A, aromatic heterocyclylalkylamino optionally substituted with Substituent Group A, non-aromatic heterocyclylalkylamino optionally substituted with Substituent Group A, aromatic carbocyclylalkylcarbonylamino optionally substituted with Substituent Group A, non-aromatic carbocyclylalkylcarbonylamino optionally substituted with Substituent Group A, aromatic heterocyclylalkylcarbonylamino optionally substituted with Substituent Group A, non-aromatic heterocyclylalkylcarbonylamino optionally substituted with Substituent Group A, aromatic carbocyclylalkyloxycarbonylamino optionally substituted with Substituent Group A, non-aromatic carbocyclylalkyloxycarbonylamino optionally substituted with Substituent Group A, aromatic heterocyclylalkyloxycarbonylamino optionally substituted with Substituent Group A, non-aromatic heterocyclylalkyloxycarbonylamino optionally substituted with Substituent Group A, aromatic carbocyclylalkylsulfonylamino optionally substituted with Substituent Group A, non-aromatic carbocyclylalkylsulfonylamino optionally substituted with Substituent Group A, aromatic heterocyclylalkylsulfonylamino optionally substituted with Substituent Group A, non-aromatic heterocyclylalkylsulfonylamino optionally substituted with Substituent Group A, aromatic carbocyclyloxyalkylamino optionally substituted with Substituent Group A, non-aromatic carbocyclyloxyalkylamino optionally substituted with Substituent Group A, aromatic heterocyclyloxyalkylamino optionally substituted with Substituent Group A, and non-aromatic heterocyclyloxyalkylamino optionally substituted with Substituent Group A.

Embodiments and preferred embodiments of each substituent in the compound represented by Formula (I) or (I') are shown below. The following compounds having possible combination of the embodiments of each substituent are preferable.

A preferred embodiment of a moiety represented by Formula

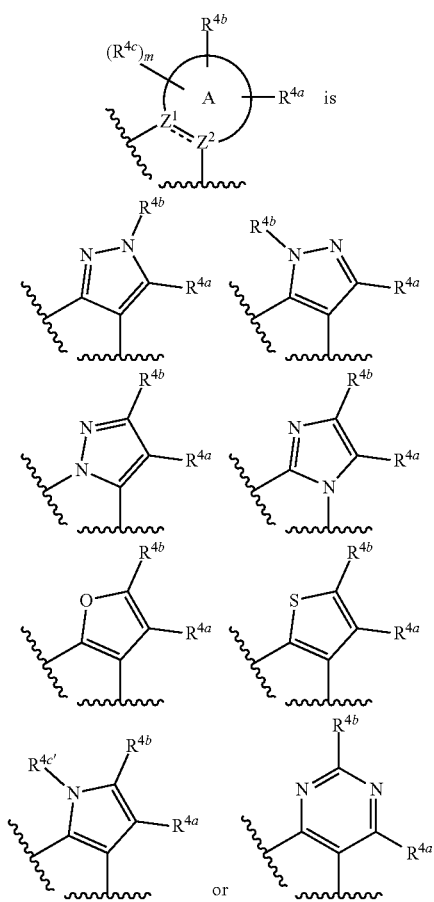

a more preferred embodiment is

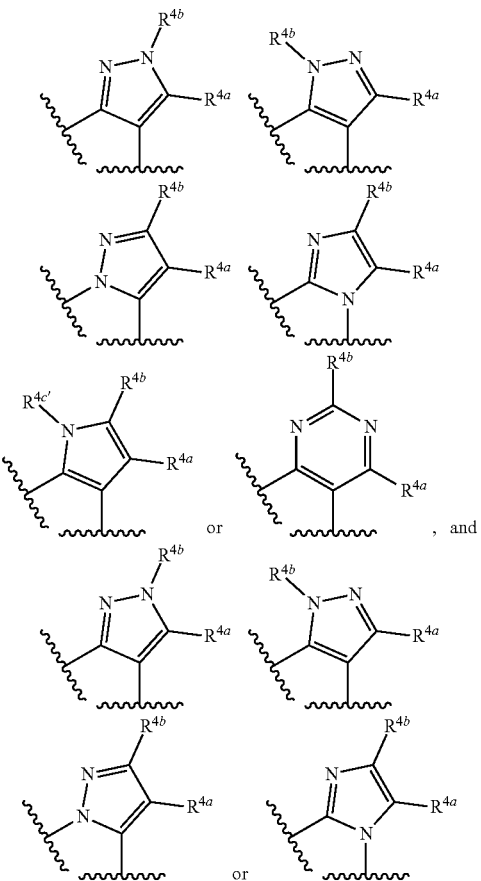

is particularly preferable.

X includes C(=O), C(=S), and SO$_2$.

A preferred embodiment of X is C(=O) or C(=S).

A more preferred embodiment of X is C(=O).

$R^1$ includes hydrogen, hydroxy, substituted or unsubstituted alkyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, and substituted or unsubstituted non-aromatic heterocyclylsulfonyl.

A preferred embodiment of $R^1$ is hydrogen or hydroxy.

A more preferred embodiment of $R^1$ is hydrogen.

Examples of the substituent in the case that $R^1$ is substituted include halogen, hydroxy, amino, alkyl, monoalkylamino, dialkylamino, aromatic carbocyclyl, non-aromatic carbocyclyl, aromatic heterocyclyl, or non-aromatic heterocyclyl.

In a preferred embodiment, $R^{2a}$ and $R^{2b}$ are taken together with an adjacent carbon atom to form ring B.

As another embodiment of $R^{2a}$ and $R^{2b}$, the following embodiments are also preferable, $R^{2a}$ is represented by formula:

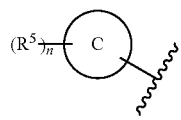

$R^{2b}$ is hydrogen, cyano, substituted or unsubstituted carbamoyl, substituted or unsubstituted alkyl, substituted or unsubstituted alkenyl, substituted or unsubstituted alkynyl, or substituted or unsubstituted alkylsulfonyl.

In this case, a more preferred embodiment of $R^{2b}$ is hydrogen or substituted or unsubstituted alkyl, and alkyl and haloalkyl are particularly preferable.

Examples of the substituent in the case that $R^{2b}$ is substituted include halogen.

A preferred embodiment of ring B is represented by formula:

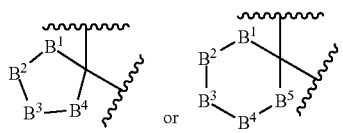

A more preferred embodiment of ring B is represented by formula:

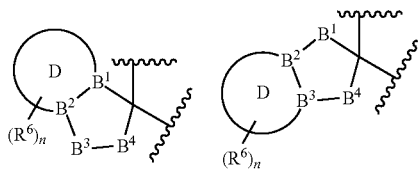

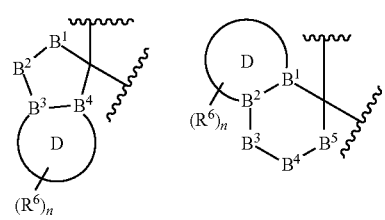

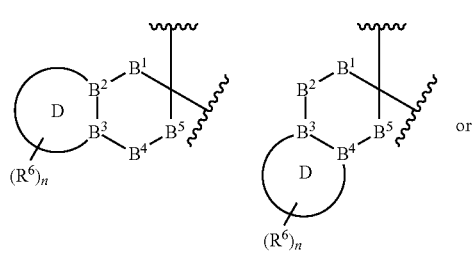

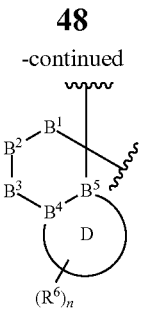

A particularly preferred embodiment of ring B is represented by formula:

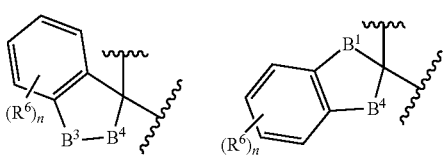

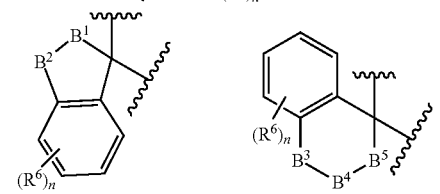

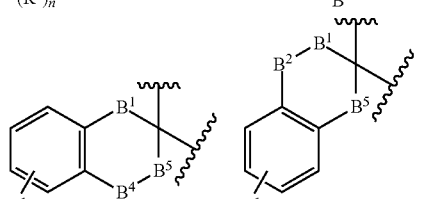

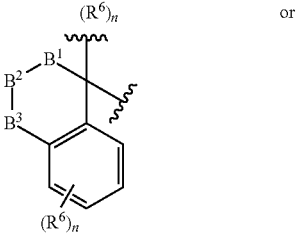

Another preferred embodiment of ring B is represented by formula:

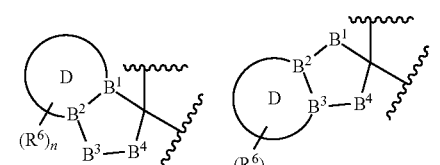

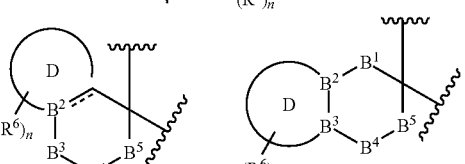

and, more preferred embodiment is represented by formula:

Another particularly preferred embodiment of ring B is represented by formula:

Specific preferred embodiment of ring B is represented by formula:

Another specific preferred embodiment of ring B is represented by formula:

Yet another embodiment of ring B is represented by formula:

A preferred embodiment of $B^1$ is $CR^{11a}R^{11b}$.
A more preferred embodiment of $B^1$ is C, $CR^{11a}$, $CR^{11a}R^{11b}$, $NR^{11c}$ or N.
$B^2$ includes $CR^{12a}R^{12b}$, $NR^{12c}$, O, or S.
A preferred embodiment of $B^2$ is $CR^{12a}R^{12b}$, $NR^{12c}$ or O.
A more preferred embodiment of $B^2$ is C, $CR^{12a}$ or N.
A more preferred embodiment of $B^2$ is C.
$B^3$ includes $CR^{13a}R^{13b}$, $NR^{13c}$, O, or S.

A preferred embodiment of $B^3$ is $CR^{13a}R^{13b}$, $NR^{13c}$ or O.
A more preferred embodiment of $B^3$ is C, $CR^{13a}$, $CR^{13a}R^{13b}$, or O.
Specific preferred embodiment of $B^3$ include, for example, $CH_2$, NMe, and O.
$B^4$ includes $CR^{14a}R^{14b}$, $NR^{14c}$, O, or S.
A preferred embodiment of $B^4$ is $CR^{14a}R^{14b}$, $NR^{14c}$ or O.
A more preferred embodiment of $B^4$ is $CR^{14a}R^{14b}$.
A specific preferred embodiment of $B^4$ is $CH_2$, $CF_2$, C(=O), or O.
A preferred embodiment of $B^5$ is $CR^{15a}R^{15b}$.
Provided, three or more same atoms in any one of N, O, and S in —$B^1$—$B^2$—$B^3$—$B^4$— or —$B^1$—$B^2$—$B^3$—$B^4$—$B^5$— are not continuously connected like —O—O—O—O—, —S—S—S—S—, or the like.

$R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—R$^{S1}$)—R$^{S2}$, a group represented by formula: -L-S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$.

Here, the group represented by formula: -L-N=S(=O)(—R$^{S1}$)—R$^{S2}$, the group represented by formula: -L-S(=O)(=N—R$^N$)—R$^{S1}$, the group represented by formula: —N=S(=N—R$^N$)(—R$^{S1}$)—R$^{S2}$, and the group represented by formula: —S(=N—R$^N$)$_2$—R$^{S1}$ each have the following chemical structures:

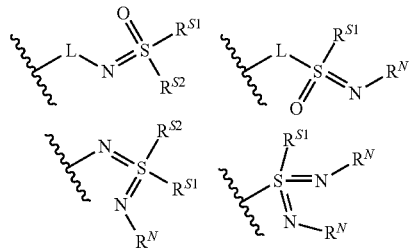

A preferred embodiment of R$^{11a}$, R$^{12a}$, R$^{13a}$, R$^{14a}$, and R$^{15a}$ is each independently hydrogen, halogen, or substituted or unsubstituted alkyl.

A more preferred embodiment of R$^{11a}$, R$^{12a}$, R$^{13a}$, R$^{14a}$, and R$^{15a}$ is each independently hydrogen or halogen.

The substituent in the case that R$^{11a}$, R$^{12a}$, R$^{13a}$, R$^{14a}$, and R$^{15a}$ are substituted is each independently halogen, hydroxy, amino, alkyl, monoalkylamino, dialkylamino, aromatic carbocyclyl, non-aromatic carbocyclyl, aromatic heterocyclyl, or non-aromatic heterocyclyl.

R$^{11b}$, R$^{12b}$, R$^{13b}$, R$^{14b}$ and R$^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—R$^{S1}$)—R$^{S2}$, a group represented by formula: -L-S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$.

A preferred embodiment of R$^{11b}$, R$^{12b}$, R$^{13b}$, R$^{14b}$, and R$^{15b}$ is each independently hydrogen or halogen.

The substituent in the case that R$^{11b}$, R$^{12b}$, R$^{13b}$, R$^{14b}$, and R$^{15b}$ are substituted is each independently halogen, hydroxy, amino, alkyl, monoalkylamino, dialkylamino, aromatic carbocyclyl, non-aromatic carbocyclyl, aromatic heterocyclyl, or non-aromatic heterocyclyl.

R$^{11c}$, R$^{12c}$, R$^{13c}$, R$^{14c}$, and R$^{15c}$ are each independently hydrogen, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl.

A preferred embodiment of $R^{11c}$, $R^{12c}$, $R^{13c}$, $R^{14c}$, and $R^{15c}$ is each independently hydrogen, halogen, or substituted or unsubstituted alkyl.

A more preferred embodiment of $R^{11c}$, $R^{12c}$, $R^{13c}$, $R^{14c}$, and $R^{15c}$ is hydrogen.

The substituent in the case that $R^{11c}$, $R^{12c}$, $R^{13c}$, $R^{14c}$, and $R^{15c}$ are substituted is each independently halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{S1}$ and $R^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or, optionally, $R^{S1}$ and $R^{S2}$ bonding to the same sulfur atom are taken together with the sulfur atom to form a substituted or unsubstituted non-aromatic heterocycle.

A preferred embodiment of $R^{S1}$ and $R^{S2}$ is each independently hydrogen or substituted or unsubstituted alkyl.

A more preferred embodiment of $R^{S1}$ and $R^{S2}$ is hydrogen.

Examples of the substituent in the case that $R^{S1}$ and $R^{S2}$ are substituted include each independently halogen, hydroxy, amino, alkyl, alkyloxy, monoalkylamino, dialkylamino, aromatic carbocyclyl, non-aromatic carbocyclyl, aromatic heterocyclyl, or non-aromatic heterocyclyl.

$R^N$ includes each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl.

A preferred embodiment of $R^N$ is each independently hydrogen or substituted or unsubstituted alkyl.

A more preferred embodiment of $R^N$ is each independently substituted or unsubstituted alkyl.

Examples of the substituent in the case that $R^N$ is substituted each independently include halogen, hydroxy, amino, alkyl, alkyloxy, monoalkylamino, dialkylamino, aromatic carbocyclyl, non-aromatic carbocyclyl, aromatic heterocyclyl, or non-aromatic heterocyclyl.

The groups L include each independently a single bond, alkylene, or C(=O).

A preferred embodiment of L is each independently a single bond or alkylene.

A more preferred embodiment of L is a single bond.

n is an integer of 0 to 5.

A preferred embodiment of n is an integer of 0 to 3.

A more preferred embodiment of n is an integer of 0 to 2.

A more preferred embodiment of n is an integer of 1 to 2.

Ring C includes an aromatic carbocycle, a C4 to C20 non-aromatic carbocycle, an aromatic heterocycle, or a non-aromatic heterocycle.

A preferred embodiment of ring C is an aromatic carbocycle or an aromatic heterocycle.

A more preferred embodiment of ring C is benzene, naphthalene, indane, pyridine, pyrimidine, pyrazole, piperidine, piperazine, benzodioxole, benzothiophene, or thiazole.

A more preferred embodiment of ring C is benzene or pyridine.

A particularly preferred embodiment of ring C is benzene.

$R^5$ includes each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$.

A preferred embodiment of $R^5$ is each independently halogen, cyano, substituted or unsubstituted carbamoyl, substituted or unsubstituted amino, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

A more preferred embodiment of $R^5$ is each independently halogen, cyano, substituted or unsubstituted amino, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

A still more preferred embodiment of $R^5$ is each independently halogen, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

A particularly preferred embodiment of $R^5$ is halogen, substituted or unsubstituted alkyl, substituted or unsubstituted alkyloxy, substituted or unsubstituted non-aromatic carbocyclyl, or substituted or unsubstituted non-aromatic heterocyclyl.

Examples of the substituent in the case that $R^5$ is substituted include halogen, alkyl, haloalkyl, cyanoalkyl, alkyloxyalkyl, haloalkylcarbonyl, non-aromatic carbocyclyl, non-aromatic heterocyclyl, non-aromatic carbocyclylalkyl, aromatic heterocyclylalkyl, or non-aromatic heterocyclylalkyl.

$R^{3a}$ includes hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl.

A preferred embodiment of $R^{3a}$ is hydrogen.

Examples of the substituent in the case that $R^{3a}$ is substituted include halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{3b}$ includes hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl.

A preferred embodiment of $R^{3b}$ is hydrogen.

Examples of the substituent in the case that $R^{3b}$ is substituted include halogen, hydroxy, amino, alkyl, monoalkylamino, dialkylamino, aromatic carbocyclyl, non-aromatic carbocyclyl, aromatic heterocyclyl, or non-aromatic heterocyclyl.

A preferred embodiment of $R^{4a}$ is represented by formula:

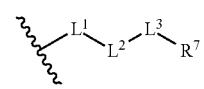

Another preferred embodiment of $R^{4a}$ is cyano,

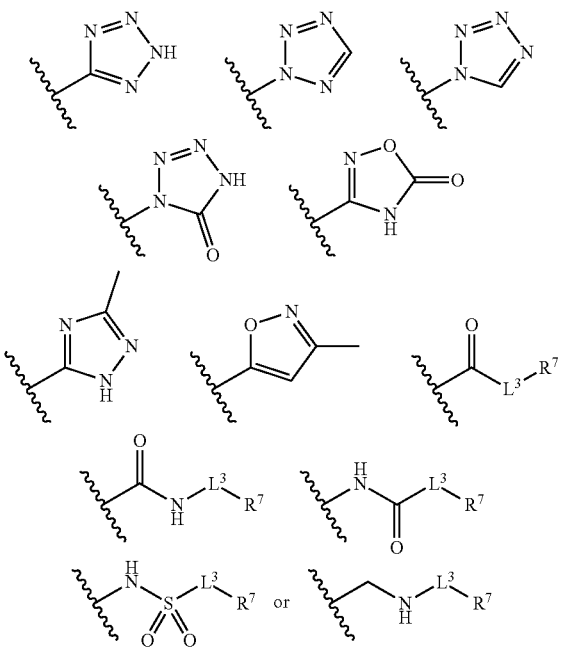

A more preferred embodiment of $R^{4a}$ is

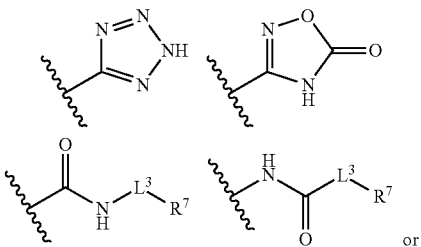

or

-continued

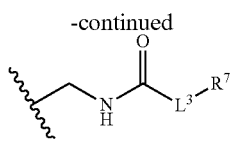

A more preferred embodiment of R$^{4a}$ is

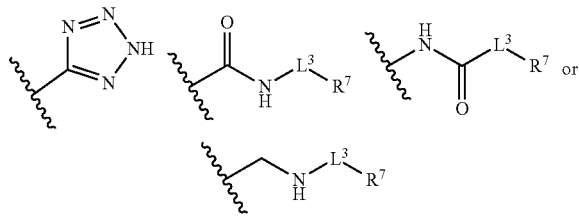

A preferred embodiment of R$^{4b}$ is substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

Examples of the substituent in the case that R$^{4b}$ is substituted include halogen, hydroxy, cyano, alkyl, alkenyl, haloalkyl, hydroxyalkyl, alkyloxy, haloalkyloxy, alkylsulfonyl, dialkylamino, an aromatic carbocycle optionally substituted with Substituent Group B, a non-aromatic carbocycle optionally substituted with Substituent Group B, an aromatic heterocycle optionally substituted with Substituent Group B, and a non-aromatic heterocycle optionally substituted with Substituent Group B.

A preferred substituent in the case that R$^{4b}$ is substituted includes halogen, cyano, alkyl, haloalkyl, alkyloxy, haloalkyloxy, an aromatic carbocycle optionally substituted with Substituent Group B, a non-aromatic carbocycle optionally substituted with Substituent Group B, an aromatic heterocycle optionally substituted with Substituent Group B, and a non-aromatic heterocycle optionally substituted with Substituent Group B.

A preferred embodiment of R$^{4c}$ is substituted or unsubstituted alkyl.

A preferred embodiment of R$^{4c'}$ is hydrogen or substituted or unsubstituted alkyl.

The substituent in the case that R$^{4c}$ or R$^{4c'}$ is substituted includes halogen.

m is an integer of 0 to 3.

A preferred embodiment of m is 0 or 1.

A preferred embodiment of L$^1$ is a single bond or alkylene.

A more preferred embodiment of L$^1$ is a single bond or methylene.

A preferred embodiment of L$^2$ is a single bond, —C(=O)—O—, —N(H)—, —C(=O)—N(H)—, —N(H)—C(=O)—, —N(H)—C(=O)—N(H)—, —C(=O)—N(H)—S(=O)$_2$—, N(H)—S(=O)$_2$—, or —N(H)—S(=O)$_2$—N(H)—.

A more preferred embodiment of L$^2$ is a single bond, —C(=O)—, —C(=O)—N(H)—, —N(H)—C(=O)—, —C(=O)—N(H)—S(=O)$_2$—, or —N(H)—S(=O)$_2$—.

A more preferred embodiment of L$^2$ is —N(H)—, —C(O)—N(H)—, —N(H)—C(=O)—, or C(=O)—N(H)—S(=O)$_2$—.

A preferred embodiment of L$^3$ is a single bond, or alkylene which may be substituted with halogen or hydroxy.

Specific preferred embodiment of L$^3$ include a single bond, methylene, ethylene and propylene.

R$^7$ includes hydrogen, halogen, hydroxy, cyano, substituted or unsubstituted amino, substituted or unsubstituted alkyl, substituted or unsubstituted alkyloxy, substituted or unsubstituted alkylsulfonyl, substituted or unsubstituted alkylaminosulfonyl, substituted or unsubstituted aromatic carbocyclyl, substituted or unsubstituted non-aromatic carbocyclyl, substituted or unsubstituted aromatic heterocyclyl, and substituted or unsubstituted non-aromatic heterocyclyl.

A preferred embodiment of R$^7$ is hydrogen, halogen, hydroxy, cyano, substituted or unsubstituted amino, substituted or unsubstituted carbamoyl, substituted or unsubstituted sulfamoyl, substituted or unsubstituted alkyloxy, substituted or unsubstituted alkylsulfanyl, substituted or unsubstituted alkylsulfinyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclylsulfonyl, a group represented by formula: —N=S(=O)(—R$^{S1}$)—R$^{S2}$, or a group represented by formula: —S(=O)(=N—R$^N$)—R$^{S1}$.

A more preferred embodiment of R$^7$ is hydrogen, halogen, substituted or unsubstituted alkylsulfonyl, substituted or unsubstituted non-aromatic carbocyclyl, substituted or unsubstituted non-aromatic heterocyclyl, substituted or unsubstituted non-aromatic carbocyclylsulfonyl, or a group represented by formula: —S(=O)(=N—R$^N$)—R$^{S1}$.

Examples of the substituent in the case that R$^7$ is substituted include oxo, halogen, cyano, hydroxy, alkyl, haloalkyl, alkyloxy, haloalkyloxy, hydroxyalkyl, alkylcarbonyl, or alkylsulfonyl.

A preferred embodiment of R$^6$ is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl.

A more preferred embodiment of R$^6$ is each independently halogen, cyano, substituted or unsubstituted amino, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy.

A more preferred embodiment of R$^6$ is each independently halogen, haloalkyl, haloalkyloxy, a non-aromatic carbocyclyl optionally substituted with halogen or haloalkyl, or a non-aromatic heterocyclyl optionally substituted with halogen or haloalkyl.

Examples of the substituent in the case that R$^6$ is substituted include halogen, alkyl, haloalkyl, cyanoalkyl, hydroxyalkyl, alkyloxy, haloalkyloxy, alkyloxyalkyl, haloalkylcarbonyl, alkyloxycarbonylalkyl, aromatic carbocyclyl optionally substituted with Substituent Group B, non-aromatic carbocyclyl optionally substituted with Substituent Group B, aromatic heterocyclyl optionally substituted with Substituent Group B, non-aromatic heterocyclyl optionally substituted with Substituent Group B, aromatic carbocyclyloxy optionally substituted with Substituent Group B, non-aromatic carbocyclyloxy optionally substituted with Substituent Group B, aromatic heterocyclyloxy optionally substituted with Substituent Group B, and non-aromatic heterocyclyloxy optionally substituted with Substituent Group B.

$R^{16}$ includes each independently hydrogen, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, or the like.

A preferred embodiment of $R^{16}$ is substituted or unsubstituted alkyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl.

A preferred embodiment of $R^{16}$ is substituted or unsubstituted alkyl, aromatic carbocyclyl optionally substituted with Substituent Group B, non-aromatic carbocyclyl optionally substituted with Substituent Group B, aromatic heterocyclyl optionally substituted with Substituent Group B, non-aromatic heterocyclyl optionally substituted with Substituent Group B, aromatic carbocyclylcarbonyl optionally substituted with Substituent Group B, non-aromatic carbocyclylcarbonyl optionally substituted with Substituent Group B, aromatic heterocyclylcarbonyl optionally substituted with Substituent Group B, or non-aromatic heterocyclylcarbonyl optionally substituted with Substituent Group B.

Examples of the substituent in the case that $R^{16}$ is substituted include halogen, alkyl, haloalkyl, aromatic carbocyclyl optionally substituted with Substituent Group B, non-aromatic carbocyclyl optionally substituted with Substituent Group B, aromatic heterocyclyl optionally substituted with Substituent Group B, and non-aromatic heterocyclyl optionally substituted with Substituent Group B.

A feature of the compound according to the present invention is that it has MGAT2 inhibitory activity by condensing ring A to a monocycle such as dihydropyridone of formula (I) or (I'). Another feature is that the ring A is condensed to a monocycle such as dihydropyridone, whereby an enone structure can be avoided and toxicity can be suppressed.

The compounds represented by formula (I) or (I') are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atoms in the compounds represented by formula (I) or (I') may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by formula (I) or (I') include the compounds replaced with these isotopes. The compounds replaced with the above isotopes are useful as medicines and include all of radiolabeled compounds of the compound represented by formula (I) or (I'). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds represented by formula (I) or (I') can be prepared using well-known methods in the art. For example, a tritium-labeled compound represented by formula (I) or (I') can be prepared by introducing a tritium to a certain compound represented by formula (I) or (I'), through a catalytic dehalogenation reaction using a tritium. This method comprises reacting an appropriately-halogenated precursor of the compound represented by formula (I) or (I') with tritium gas in the presence of an appropriate catalyst, such as Pd/C, and in the presence or absence of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by formula (I) or (I') include, for example, salts of the compounds represented by formula (I) with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by formula (I) or (I') or pharmaceutically acceptable salts thereof according to the present invention may form solvates (e.g., hydrates or the like), cocrystals and/or crystal polymorphs. The present invention encompasses those various solvates, cocrystals and crystal polymorphs. "Solvates" may be those wherein any numbers of solvent molecules (e.g., water molecules or the like) are coordinated with the compounds represented by formula (I) or (I'). When the compounds represented by formula (I) or pharmaceutically acceptable salts thereof are allowed to stand in the atmosphere, the compounds may absorb water, resulting in attachment of adsorbed water or formation of hydrates. Recrystallization of the compounds represented by formula (I) or (I') or pharmaceutically acceptable salts thereof may produce crystal polymorphs. "Cocrystal" means that the compound represented by formula (I) or (I') or salt thereof and a counter molecule are present in the same crystal lattice, and a cocrystal with any number of counter molecules may be formed.

The compounds represented by formula (I) or (I') or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by formula (I) or (I') through enzymatic oxidation, reduction, hydrolysis or the like under physiological conditions and in vivo, compounds that are converted to the compounds represented by formula (I) or (I') through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds represented by formula (I) or (I') or pharmaceutically acceptable salts thereof have hydroxy group(s), prodrugs include acyloxy derivatives and sulfonyloxy derivatives that are prepared by, for example, reacting compounds having hydroxy group(s) with suitable acyl halide, suitable acid anhydride, suitable sulfonyl chloride, suitable sulfonyl anhydride and mixed anhydride, or with a condensing agent. Examples include $CH_3COO—$, $C_2H_5COO—$, tert-BuCOO—, $C_{15}H_{31}CO—$, PhCOO—, (m-NaOOCPh)COO—, $NaOOCCH_2CH_2COO—$, $CH_3CH$ $(NH_2)COO—$, $CH_2N(CH_3)_2COO—$, $CH_3SO_3—$, $CH_3CH_2SO_3—$, $CF_3SO_3—$, $CH_2FSO_3—$, $CF_3CH_2SO_3—$, p-$CH_3O$-PhSO_3—, PhSO_3— and p-$CH_3$PhSO_3—.

(Production Method for Compound of the Present Invention)

For example, the compounds represented by formula (I) or (I') of the present invention can be prepared by the general procedures described below. In extraction, purification, and other operations, any process commonly performed therefor in organic chemistry experiments can be employed.

The compound of the present invention can be synthesized in accordance with a method known in the art.
(General Synthetic Procedure 1)

The compound of the present invention which is represented by formula (I) or (I') (a5 below) can be produced, for example, through the following production method.

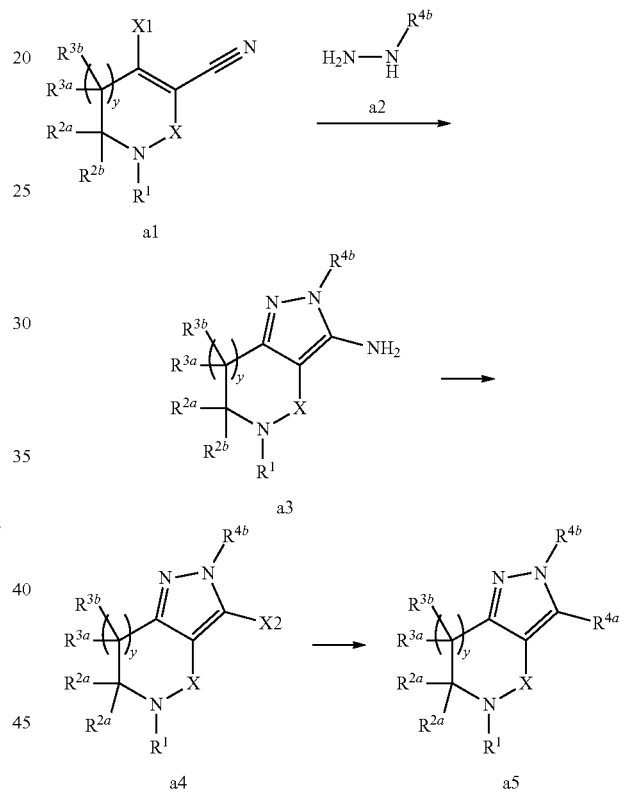

wherein X1 is chlorine, bromine, iodine, or trifluoromethanesulfonate; X2 is chlorine, bromine, or iodine; and each of other symbols is as described above.
Step 1

Compound a3 can be obtained by reacting Compound a2 and a base with Compound a1.

As the base, triethylamine, diisopropylethylamine, sodium bicarbonate, cesium carbonate, and potassium bicarbonate are exemplified.

The reaction temperature is 0° C. to 100° C.

The reaction time is 1 hour to 10 hours.

As the reaction solvent, methanol, ethanol, and tetrahydrofuran are exemplified.
Step 2

Compound a4 can be obtained by reacting Compound a3 with a halogenating agent such as copper chloride or copper bromide, an acid and an aqueous solution of sodium nitrite or the like.

As the acid, hydrochloric acid and acetic acid are exemplified.

The reaction temperature is 0° C. to 100° C.

The reaction time is 1 hour to 10 hours.

Step 3

Compound a5 can be obtained by reacting Compound a4 with boronic acid, boronate ester, trialkylstannane, or the like in the presence of a metal catalyst and a base.

As the metal catalyst, palladium acetate, bis(dibenzylideneacetone)palladium, tetrakis(triphenylphosphine)palladium, bis(triphenylphosphine)palladium (II) dichloride, bis(tri-tert-butylphosphine)palladium, and the like are exemplified, and 0.001 to 0.5 molar equivalents of the metal catalyst with respect to Compound a4 can be used.

As the base, lithium hydroxide, sodium hydroxide, potassium hydroxide, potassium tert-butoxide, sodium tert-butoxide, sodium carbonate, potassium bicarbonate, sodium bicarbonate, sodium phosphate, sodium hydrogen phosphate, potassium phosphate, potassium hydrogen phosphate and the like are exemplified, and 1 to 10 molar equivalents of the base with respect to Compound a4 can be used.

1 to 10 molar equivalents of boronic acid, boronic ester, trialkylstannane or the like with respect to Compound a4 can be used.

The reaction temperature may be 20° C. to reflux temperature of solvent, and if necessary, by a microwave irradiation.

The reaction time is 0.1 to 48 hours, preferably 0.5 to 12 hours.

As the reaction solvent, tetrahydrofuran, toluene, DMF, dioxane, and water are exemplified, and one of or a mixture of these can be used.

Compound a5 having an amine, imine, cyan, or the like in $R^{4a}$ can be synthesized by reacting Compound a4 with an amine, imine, potassium cyanide, or the like.

When $R^{4a}$ is carbonylamino, sulfonylamino or the like, synthesis can be performed by adding various functional groups to Compound a3.

(Alternative Method)

Compound a3 described above can be produced, for example, by the following production method.

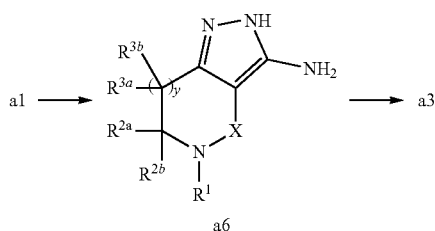

wherein each symbol is as described in above.

Step 1

Compound a6 can be obtained by reacting hydrazine hydrate with Compound a1.

The reaction temperature is 0° C. to 100° C.

The reaction time is 1 hour to 20 hours.

As the reaction solvent, methanol, ethanol, and tetrahydrofuran are exemplified.

Step 2

Compound a3 can be obtained by reacting a base, halide, etc. with Compound a6.

As the base, sodium bicarbonate, sodium carbonate, potassium carbonate, cesium carbonate, triethylamine, diisopropylethylamine, and sodium hydride are exemplified.

The reaction temperature is 0° C. to 100° C.

The reaction time is 1 hour to 10 hours.

As the reaction solvent, tetrahydrofuran, dichloromethane, and dimethylformamide are exemplified.

(General Procedure 2)

The compound of the present invention which is represented by formula (I) or (I') (b3 below) can be produced, for example, through the following production method.

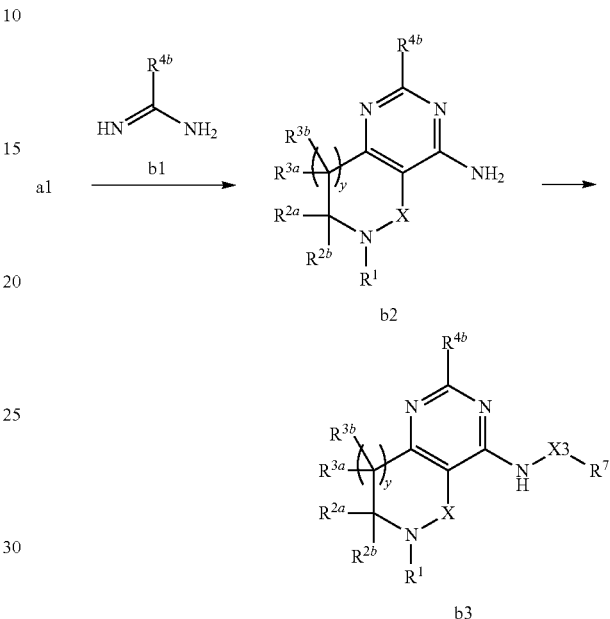

wherein X3 is C(=O), C(=S), or SO$_2$; and each of other symbols is as described above.

Step 1

Compound b2 can be obtained by reacting Compound b1 and a base with Compound a1.

As the base, DBU, triethylamine, diisopropylethylamine, and sodium bicarbonate are exemplified.

The reaction temperature is 0° C. to 150° C.

The reaction time is 30 minutes to 10 hours.

As the reaction solvent, methanol, ethanol, and tetrahydrofuran are exemplified.

Step 2

Compound b3 can be obtained by reacting Compound b2 and a carboxylic acid chloride, sulfonic acid chloride, thiocarboxylic acid chloride or the like in the presence of a base.

As the base, pyridine, DIEA, potassium carbonate, sodium bicarbonate, sodium hydride, and sodium hydroxide are exemplified.

The reaction temperature is 0° C. to 150° C., and preferably 20° C. to 100° C.

The reaction time is 0.5 hour to 120 hours, and preferably 1 hour to 72 hours.

As the reaction solvent, acetonitrile, tetrahydrofuran, toluene, and dichloromethane are exemplified.

Step 2' can be employed as an alternative method to Step 2.

Step 2'

Compound b3 can be obtained by reacting Compound b2 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4- methylmorpholinium chloride, and HATU are exemplified. 1 to 5 molar equivalents of the condensing agent with respect to Compound a3 can be used.

As the base, triethylamine and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

(General Procedure 3)

The compound of the present invention which is represented by formula (I) or (c8 below) can be produced, for example, through the following production method.

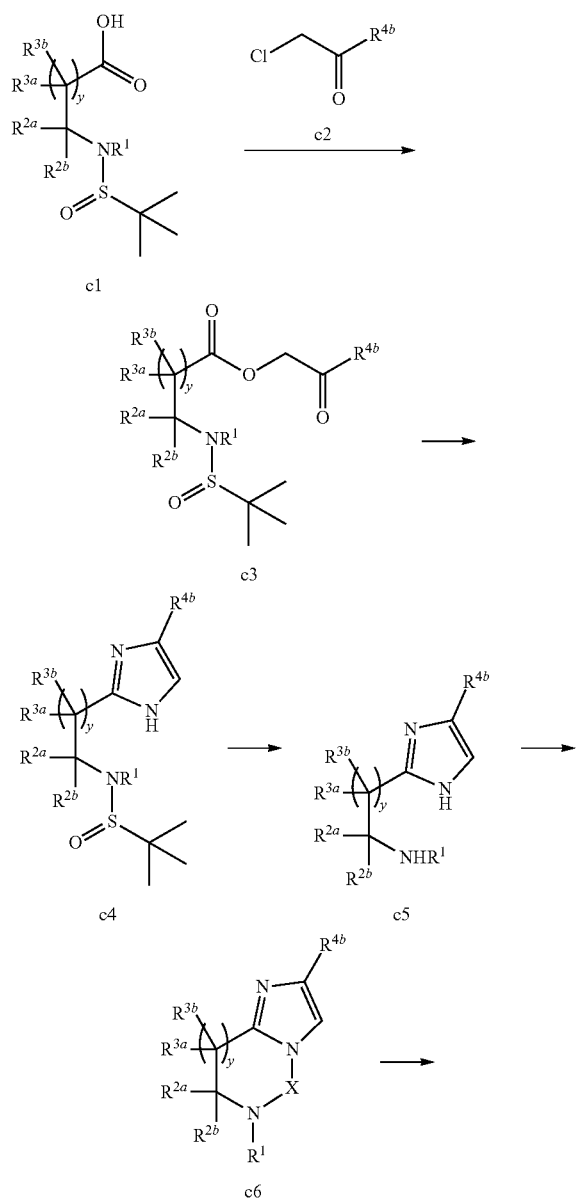

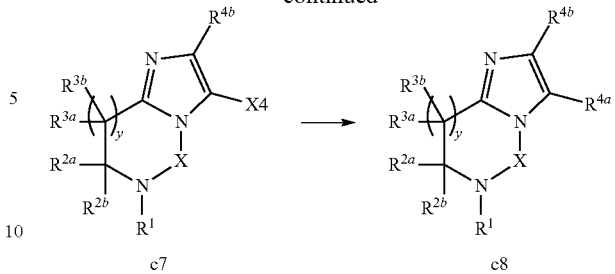

wherein X4 is chlorine, bromine, or iodine; and each of other symbols is as described above.

Step 1

Compound c3 can be obtained by reacting Compound c2 and a base with Compound c1.

As the base, DBU, triethylamine, diisopropylethylamine, sodium bicarbonate, and cesium carbonate are exemplified.

The reaction temperature is 0° C. to 150° C.

The reaction time is 30 minutes to 10 hours.

As the reaction solvent, methanol, ethanol, tetrahydrofuran, and acetonitrile are exemplified.

Step 2

Compound c4 can be obtained by reacting ammonium acetate or the like with Compound c3.

The reaction temperature is 0° C. to 150° C.

The reaction time is 30 minutes to 10 hours.

As the reaction solvent, toluene is exemplified.

Step 3

Compound a5 can be obtained by reacting Compound c4 and an acid or Lewis acid.

As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3$·$(Et_2O)$ are exemplified. 1 to 10 molar equivalents of the acid or Lewis acid with respect to Compound c4 can be used.

The reaction temperature is 0° C. to 60° C., and preferably 0° C. to 20° C.

The reaction time is 0.5 hour to 12 hours, and preferably 1 hour to 6 hours.

As the reaction solvent, methanol, ethanol, water, acetone, acetonitrile, and DMF are exemplified, and these reaction solvents can be used alone or in combination.

Step 4

Compound c6 can be obtained by reacting Compound c5 with 4-nitrophenyl chloroformate, CDI, TCDI or the like in the presence of a base.

As the base, pyridine, DIEA and triethylamine are exemplified.

The reaction temperature is 0° C. to 150° C., and preferably 20° C. to 100° C.

The reaction time is 0.5 hour to 120 hours, and preferably 1 hour to 72 hours.

As the reaction solvent, acetonitrile, tetrahydrofuran, toluene, and dichloromethane are exemplified.

Step 5

Compound c7 can be obtained by reacting Compound c6 with a halogenating agent such as N-bromosuccinimide or N-iodosuccinimide.

As the acid, hydrochloric acid and acetic acid are exemplified.

The reaction temperature is 0° C. to 100° C.

The reaction time is 1 hour to 10 hours.

As the reaction solvent, dichloromethane and dimethylformamide are exemplified.

Step 6

Compound c8 can be obtained by reacting Compound c7 with boronic acid, boronate ester, trialkylstannane, or the like in the presence of a metal catalyst and a base.

As the metal catalyst, palladium acetate, bis(dibenzylideneacetone)palladium, tetrakis(triphenylphosphine)palladium, bis(triphenylphosphine)palladium (II) dichloride, bis(tri-tert-butylphosphine)palladium, and the like are exemplified, and 0.001 to 0.5 molar equivalents of the metal catalyst with respect to Compound c7 can be used.

As the base, lithium hydroxide, sodium hydroxide, potassium hydroxide, potassium tert-butoxide, sodium tert-butoxide, sodium carbonate, potassium bicarbonate, sodium bicarbonate, sodium phosphate, sodium hydrogen phosphate, potassium phosphate, potassium hydrogen phosphate and the like are exemplified, and 1 to 10 molar equivalents of the base with respect to Compound c7 can be used.

1 to 10 molar equivalents of boronic acid, boronic ester, trialkylstannane or the like with respect to Compound c7 can be used.

The reaction temperature may be 20° C. to reflux temperature of solvent, and if necessary, by a microwave irradiation.

The reaction time is 0.1 to 48 hours, preferably 0.5 to 12 hours.

As the reaction solvent, tetrahydrofuran, toluene, DMF, dioxane, and water are exemplified, and one of or a mixture of these can be used.

Compound c8 having an amine, imine, cyan, or the like in $R^{4a}$ can be synthesized by reacting Compound c7 with an amine, imine, potassium cyanide, or the like.

(General Procedure 4)

The compound of the present invention which is represented by formula (I) or (I') (d10 below) can be produced, for example, through the following production method.

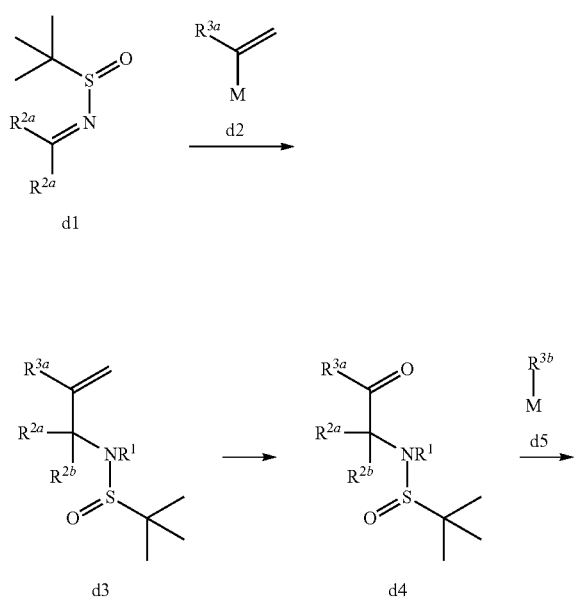

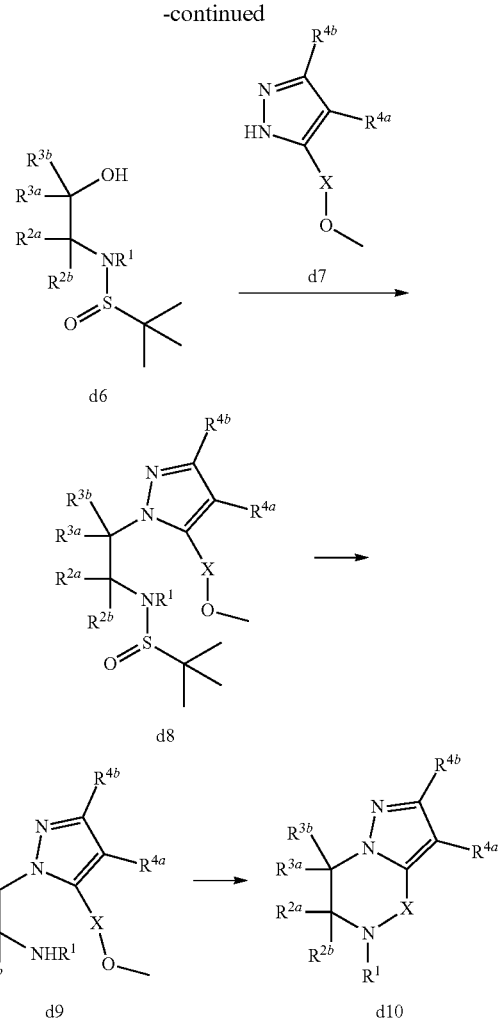

wherein M is lithium, magnesium chloride, magnesium bromide, magnesium iodide, etc.; each of other symbols is as described above.

Step 1

Compound d3 can be obtained by reacting Compound d1 with a nucleophile d2.

Examples of the nucleophile d2 includes lithium reagent such as methyllithium, ethyllithium, etc., Grignard reagent such as methylmagnesium bromide, methylmagnesium chloride, methylmagnesium iodide, ethylmagnesium bromide, ethylmagnesium chloride, ethylmagnesium iodide, etc., and its mixed reagent of metallic salt thereof, and 1 to 5 molar equivalents with respect to Compound a1 can be used.

The reaction temperature −78° C. to the reflux temperature of the solvent, preferably −45° C. to 0° C.

The reaction time is 0.5 to 24 hours, preferably 1 hour to 6 hours.

As the reaction solvent, tetrahydrofuran, hexane, diethylether, methyl tert-butyl ether, toluene, and dichloromethane are exemplified, and these reaction solvents can be used alone or in combination.

The nucleophile d2 can be prepared by lithiation of a halide with an alkyl lithium such as n-butyllithium.

The reaction solvent is not particularly limited as long as it is not a solvent such as tetrahydrofuran and dioxane not reacting with alkyllithium. The lithiation temperature is preferably about −78° C. to 0° C.

A compound in which $R^1$ is alkyl or the like can be synthesized by sequentially performing a reaction of alkylation or the like.

Step 2

Compound d4 can be obtained by introducing ozone gas into a solvent containing Compound d3 and reacting, followed by oxidative treatment or reductive treatment.

The reaction temperature −78° C. to −15° C., and preferably −78° C. to −40° C.

As the reaction time, the reaction may be performed until the color of the reaction solution becomes blue.

As the oxidative treatment, hydrogen peroxide, chromic acid-sulfuric acid or the like can be used.

As the reductive treatment, Zn-acetic acid, $(EtO)_3P$, catalytic hydrogenation, dimethyl sulfide, or the like can be used.

As the reaction solvent, dichloromethane, methanol, ethanol, and ethyl acetate are exemplified.

Step 3

Compound d6 can be obtained by reacting Compound d4 with a nucleophile d5.

Examples of the nucleophile d5 includes lithium reagent such as methyllithium, ethyllithium, etc., Grignard reagent such as methylmagnesium bromide, methylmagnesium chloride, methylmagnesium iodide, ethylmagnesium bromide, ethylmagunesium chloride, ethylmagnesium iodide, etc., and its mixed reagent of metallic salt thereof, and 1 to 5 molar equivalents with respect to Compound d4 can be used.

The reaction temperature −78° C. to the reflux temperature of the solvent, preferably −45° C. to 0° C.

The reaction time is 0.5 to 24 hours, preferably 1 hour to 6 hours.

As the reaction solvent, tetrahydrofuran, hexane, diethylether, methyl tert-butyl ether, toluene, and dichloromethane are exemplified, and these reaction solvents can be used alone or in combination.

The nucleophile d5 can be prepared by lithiation of a halide with an alkyl lithium such as n-butyllithium.

The reaction solvent is not particularly limited as long as it is not a solvent such as tetrahydrofuran and dioxane not reacting with alkyllithium. The lithiation temperature is preferably about −78° C. to 0° C.

A compound in which $R^{3b}$ is hydrogen can be obtained by allowing a reducing agent, such as sodium borohydride, lithium borohydride, or lithium aluminum hydride, to act instead of the nucleophile d5.

Step 4

Compound d8 can be obtained by reacting Compound d6 and Compound d7 in the presence of triphenylphosphine and a condensing agent.

As the condensing agent, DEAD and DIAD are exemplified. 1 to 5 molar equivalents of the condensing agent with respect to Compound d6 can be used.

The reaction temperature is 0° C. to 60° C., and preferably 10° C. to 40° C.

The reaction time is 0.1 hour to 12 hours, and preferably 0.2 hour to 6 hours.

As the reaction solvent, tetrahydrofuran, dioxane, ethyl acetate, toluene, and acetonitrile are exemplified, and these reaction solvents can be used alone or in combination.

Step 5

Compound d9 can be obtained by reacting Compound d8 and an acid or Lewis acid.

As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3 \cdot (Et_2O)$ are exemplified. 1 to 10 molar equivalents of the acid or Lewis acid with respect to Compound d8 can be used.

The reaction temperature is 0° C. to 60° C., and preferably 0° C. to 20° C.

The reaction time is 0.5 hour to 12 hours, and preferably 1 hour to 6 hours.

As the reaction solvent, methanol, ethanol, water, acetone, acetonitrile, and DMF are exemplified, and these reaction solvents can be used alone or in combination.

Step 6

Compound d10 can be obtained by heating Compound d9.

The reaction time is 0.5 hour to 12 hours, and preferably 1 hour to 6 hours.

The reaction temperature is 50° C. to 120° C., and preferably 60° C. to 90° C.

Examples of the reaction solvent include methanol, ethanol, DMF, and tetrahydrofuran, and one of or a mixture of these can be used.

(General Procedure 5)

The compound of the present invention which is represented by formula (I) or (I') (e7 below) can be produced, for example, through the following production method.

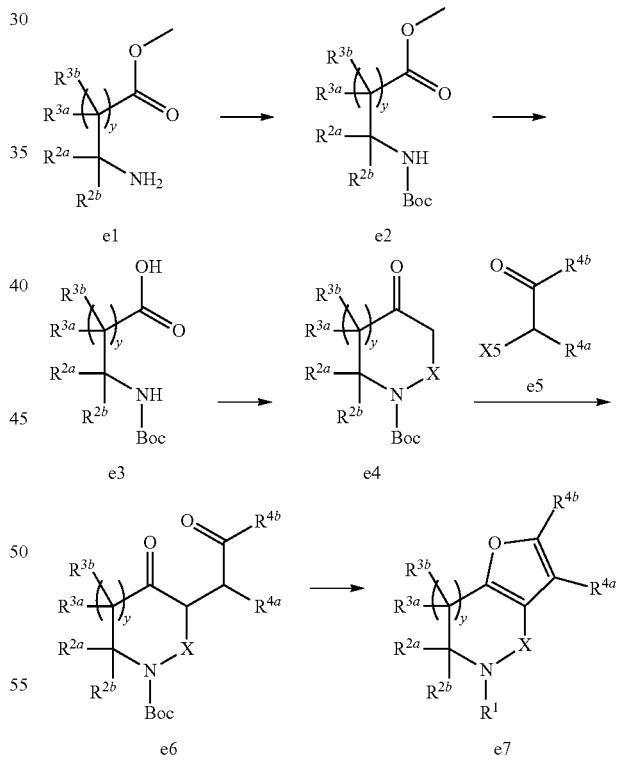

wherein X5 is fluorine, chlorine, bromine, or iodine; and each of other symbols is as described above.

Step 1

Compound e2 can be obtained by reacting Compound e1 with $Boc_2O$ in the presence or absence of a base.

As the base, sodium hydroxide, sodium carbonate, sodium bicarbonate, potassium carbonate, calcium carbonate, cesium carbonate, pyridine, and triethylamine are exemplified, and 1 to 5 molar equivalents of the base with respect to Compound a4 can be used.

The reaction temperature −10° C. to 80° C., and preferably 10° C. to 60° C.

The reaction time is 0.5 to 24 hours, preferably 1 to 12 hours.

As the reaction solvent, tetrahydrofuran, dioxane, acetonitrile, and water are exemplified, and one of or a mixture of these can be used.

As protecting groups other than Boc, other protecting groups such as Bn group, Alloc group, Fmoc group, Cbz group, Ac group, Troc group, methoxycarbonyl group, and trifluoroacetyl group can be used.

Step 2

Compound e3 can be obtained by reacting Compound e2 with a basic aqueous solution.

The reaction temperature is 0° C. to 40° C., preferably 0° C. to 20° C.

The reaction time is 0.5 hour to 12 hours, and preferably 1 hour to 6 hours.

As the base, sodium carbonate, potassium carbonate, cesium carbonate, lithium hydroxide, sodium hydroxide, and potassium hydroxide are exemplified.

As the reaction solvent, methanol, ethanol, water, acetone, acetonitrile, and tetrahydrofuran are exemplified, and these reaction solvents can be used alone or in combination.

Step 3

Compound e4 can be obtained by reacting Compound e3 with Meldrum's acid in the presence of a condensing agent, under the action of a base, as necessary and then heating.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound e3 can be used.

As the base, triethylamine, diisopropylethylamine, and paradimethylaminopyridine are exemplified.

The reaction temperature is −20° C. to 60° C., preferably 0° C. to 30° C. for the condensation reaction, and 50° C. to 80° C. for the subsequent heating reaction.

The reaction time is 0.1 to 24 hours, preferably 1 to 12 hours for the condensation reaction, and 2 to 5 hours for the subsequent heating reaction.

As the reaction solvent, DMF, DMA, NMP, tetrahydrofuran, dioxane, dichloromethane, acetonitrile and ethyl acetate are exemplified, and these reaction solvents can be used alone or in combination.

Step 4

Compound e6 can be obtained by reacting a base and a halide e5 with Compound e4.

As the base, sodium bicarbonate, sodium carbonate, potassium carbonate, cesium carbonate, triethylamine, diisopropylethylamine, and sodium hydride are exemplified.

The reaction temperature is 0° C. to 100° C.

The reaction time is 1 hour to 10 hours.

As the reaction solvent, tetrahydrofuran, dichloromethane, and dimethylformamide are exemplified.

Step 5

Compound e7 can be obtained by reacting Compound e6 with an acid.

As the acid, hydrochloric acid, sulfuric acid, methanesulfonic acid, trifluoroacetic acid and the like are exemplified.

The reaction temperature is 0° C. to 60° C., and preferably 0° C. to 20° C.

The reaction time is 0.5 hour to 12 hours, and preferably 1 hour to 6 hours.

As the reaction solvent, methanol, ethanol, water, acetone, acetonitrile, DMF, and dichloromethane are exemplified, and these reaction solvents can be used alone or in combination.

A compound in which $R^1$ is alkyl or the like can be synthesized by sequentially performing a reaction of alkylation or the like.

(General Procedure 6)

The compound of the present invention which is represented by formula (I) or (I') (f2 below) can be produced, for example, through the following production method.

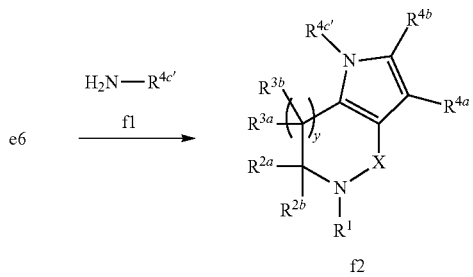

wherein each symbol is as described in above.

Compound f2 can be obtained by reacting Compound e6 with an amine f1 and an acid.

As the acid, hydrochloric acid, sulfuric acid, methanesulfonic acid, acetic acid, trifluoroacetic acid and the like are exemplified.

The reaction temperature is 0° C. to 120° C., preferably 50° C. to 100° C.

The reaction time is 0.5 hour to 12 hours, and preferably 1 hour to 6 hours.

As the reaction solvent, toluene, benzene, and tetrahydrofuran are exemplified, and one of or a mixture of these can be used.

A compound in which $R^1$ is alkyl or the like can be synthesized by sequentially performing a reaction of alkylation or the like.

(General Procedure 7)

The compound of the present invention which is represented by formula (I) or (I') (g1 below) can be produced, for example, through the following production method.

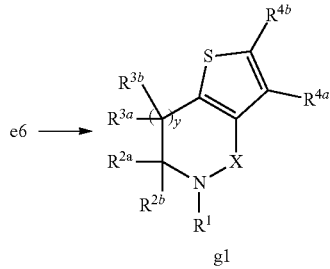

wherein each symbol is as described in above.

Compound g1 can be obtained by reacting Compound e6 with a sulfurizing reagent.

As the sulfurizing reagent, phosphorous pentasulfide and 2,4-bis(4-methoxyphenyl)-1,3,2,4-dithiadiphosphetane-2,4-disulfide are exemplified.

The reaction temperature is 0° C. to 120° C., preferably 50° C. to 100° C.

The reaction time is 0.5 hour to 12 hours, and preferably 1 hour to 6 hours.

As the reaction solvent, toluene, benzene, and tetrahydrofuran are exemplified, and one of or a mixture of these can be used.

A compound in which $R^1$ is alkyl or the like can be synthesized by sequentially performing a reaction of alkylation or the like.

(General Procedure 8)

The compound of the present invention which is represented by formula (I) (h15 below) can be produced, for example, through the following production method.

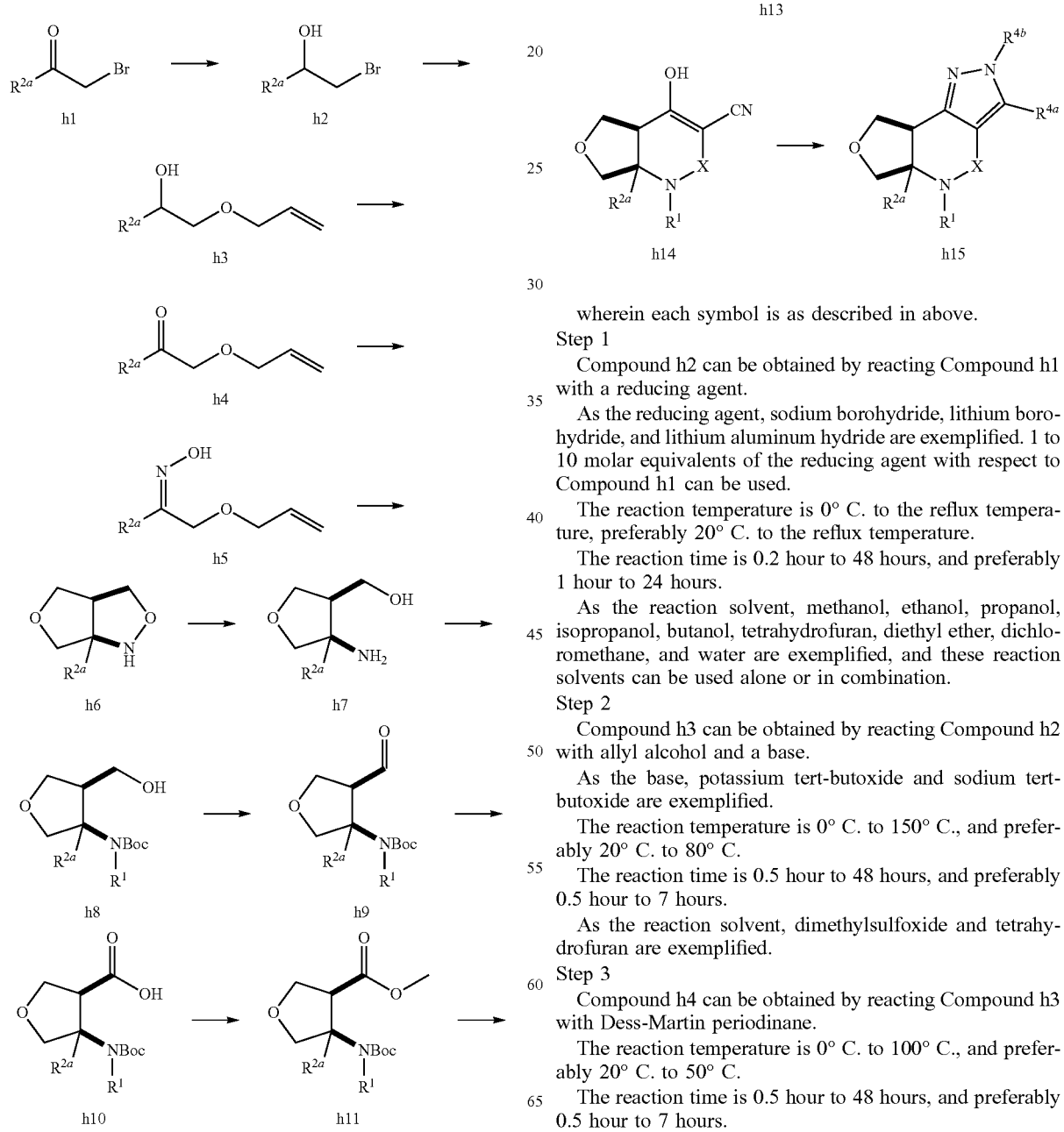

wherein each symbol is as described in above.

Step 1

Compound h2 can be obtained by reacting Compound h1 with a reducing agent.

As the reducing agent, sodium borohydride, lithium borohydride, and lithium aluminum hydride are exemplified. 1 to 10 molar equivalents of the reducing agent with respect to Compound h1 can be used.

The reaction temperature is 0° C. to the reflux temperature, preferably 20° C. to the reflux temperature.

The reaction time is 0.2 hour to 48 hours, and preferably 1 hour to 24 hours.

As the reaction solvent, methanol, ethanol, propanol, isopropanol, butanol, tetrahydrofuran, diethyl ether, dichloromethane, and water are exemplified, and these reaction solvents can be used alone or in combination.

Step 2

Compound h3 can be obtained by reacting Compound h2 with allyl alcohol and a base.

As the base, potassium tert-butoxide and sodium tert-butoxide are exemplified.

The reaction temperature is 0° C. to 150° C., and preferably 20° C. to 80° C.

The reaction time is 0.5 hour to 48 hours, and preferably 0.5 hour to 7 hours.

As the reaction solvent, dimethylsulfoxide and tetrahydrofuran are exemplified.

Step 3

Compound h4 can be obtained by reacting Compound h3 with Dess-Martin periodinane.

The reaction temperature is 0° C. to 100° C., and preferably 20° C. to 50° C.

The reaction time is 0.5 hour to 48 hours, and preferably 0.5 hour to 7 hours.

As the reaction solvent, dichloromethane is exemplified.

Step 4
Compound h5 can be obtained by reacting Compound h4 with hydroxylamine and sodium acetate.

The reaction temperature is 0° C. to 150° C., and preferably 50° C. to 100° C.

The reaction time is 0.5 hour to 48 hours, and preferably 0.5 hour to 7 hours.

As the reaction solvent, ethanol and methanol are exemplified.

Step 5
Compound h6 can be obtained by reacting Compound h5 and hydroquinone.

The reaction temperature is 0° C. to 150° C., and preferably 50° C. to 100° C.

The reaction time is 0.5 hour to 48 hours, and preferably 10 hours to 24 hours.

As the reaction solvent, toluene is exemplified.

Step 6
Compound h7 can be obtained by reacting compound h6 with hydrogen gas in the presence of a metal catalyst.

Examples of the metal catalyst include palladium-carbon and rhodium-carbon, and the metal catalyst can be used in an amount of 0.01 to 100% by weight with respect to Compound h6.

The hydrogen pressure can be 1 to 50 atm.

The reaction temperature is 0° C. to the reflux temperature of the solvent, preferably 20° C. to 40° C.

The reaction time is 0.5 to 72 hours, preferably 1 to 12 hours.

As the reaction solvent, methanol, ethanol, propanol, isopropanol, butanol, tetrahydrofuran, diethyl ether, toluene, ethyl acetate, acetic acid, and water are exemplified, and these reaction solvents can be used alone or in combination.

Step 7
Compound h8 can be obtained by reacting Compound h7 with $Boc_2O$ in the presence or absence of a base.

As the base, sodium hydroxide, sodium carbonate, sodium bicarbonate, potassium carbonate, calcium carbonate, cesium carbonate, pyridine, and triethylamine are exemplified, and 1 to 5 molar equivalents of the base with respect to Compound 11 can be used.

The reaction temperature −10° C. to 80° C., and preferably 10° C. to 60° C.

The reaction time is 0.5 to 24 hours, preferably 1 to 12 hours.

As the reaction solvent, tetrahydrofuran, dioxane, acetonitrile, and water are exemplified, and one of or a mixture of these can be used.

A compound in which $R^1$ is alkyl or the like can be synthesized by sequentially performing a reaction of alkylation or the like.

Step 8
Compound h9 can be obtained by reacting Compound h8 with Dess-Martin periodinane.

The reaction temperature is 0° C. to 100° C., and preferably 20° C. to 50° C.

The reaction time is 0.5 hour to 48 hours, and preferably 0.5 hour to 7 hours.

As the reaction solvent, dichloromethane is exemplified.

Step 9
Compound h10 can be obtained by reacting Compound h9 with 2-methyl-2-butene, sodium dihydrogen phosphate and sodium chlorite.

The reaction temperature is 0° C. to 100° C., and preferably 20° C. to 50° C.

The reaction time is 0.5 hour to 48 hours, and preferably 0.5 hour to 7 hours.

As the reaction solvent, tert-butanol is exemplified.

Step 10
Compound h11 can be obtained by reacting Compound h10 with methyl iodide and a base.

As the base, potassium carbonate, cesium carbonate, sodium carbonate, and sodium bicarbonate are exemplified.

The reaction temperature is 0° C. to 100° C., and preferably 20° C. to 50° C.

The reaction time is 0.5 hour to 48 hours, and preferably 0.5 hour to 10 hours.

As the reaction solvent, dimethylsulfoxide, tetrahydrofuran, acetone, DMF, DMA, and NMP are exemplified.

Step 11
Compound h12 can be obtained by reacting Compound h11 and an acid or Lewis acid.

As the acid, hydrochloric acid-ethyl acetate, hydrochloric acid-methanol, hydrochloric acid-dioxane, sulfuric acid, formic acid, concentrated hydrochloric acid, and trifluoroacetic acid are exemplified. As the Lewis acid, trimethylsilyl iodide, $BBr_3$, $AlCl_3$, and $BF_3.(Et_2O)$ are exemplified. 1 to 10 molar equivalents of the acid or Lewis acid with respect to Compound h11 can be used.

The reaction temperature is 0° C. to 100° C., and preferably 20° C. to 50° C.

The reaction time is 0.5 hour to 150 hours, and preferably 10 hours to 100 hours.

As the reaction solvent, methanol, ethanol, water, acetone, acetonitrile, and DMF are exemplified, and these reaction solvents can be used alone or in combination.

Step 12
Compound h13 can be obtained by reacting Compound h12 with carboxylic acid chloride, sulfonic acid chloride, thiocarboxylic acid chloride or the like in the presence or absence of a base.

As the base, pyridine, DIEA, potassium carbonate, sodium bicarbonate, sodium hydride, and sodium hydroxide are exemplified.

The reaction temperature is 0° C. to 150° C., and preferably 20° C. to 100° C.

The reaction time is 0.5 hour to 48 hours, and preferably 1 hour to 24 hours.

As the reaction solvent, acetonitrile, tetrahydrofuran, toluene, dichloromethane, dimethylacetamide, and dimethylformamide are exemplified.

Step 12' can be employed as an alternative method to Step 12.

Step 12'
Compound a13 can be obtained by reacting Compound h12 with a condensing agent, carboxylic acid, and the like in the presence or absence of a base.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound h12 can be used.

As the base, triethylamine and diisopropylethylamine are exemplified.

The reaction temperature −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

Step 13

Compound h14 can be obtained by reacting Compound h13 and a base.

As the base, piperidine, pyrrolidine, triethylamine, diisopropylethylamine, sodium methoxide, and sodium ethoxide are exemplified.

The reaction temperature is 0° C. to 100° C.

The reaction time is 1 hour to 10 hours.

As the reaction solvent, methanol, ethanol, and tetrahydrofuran are exemplified.

Step 14

Compound h15 can be obtained by reacting Compound h14 in accordance with the method described in the General Synthetic Procedure 1.

(General Procedure 9)

The compound of the present invention which is represented by formula (I) or (I') (j6 below) can be produced, for example, through the following production method.

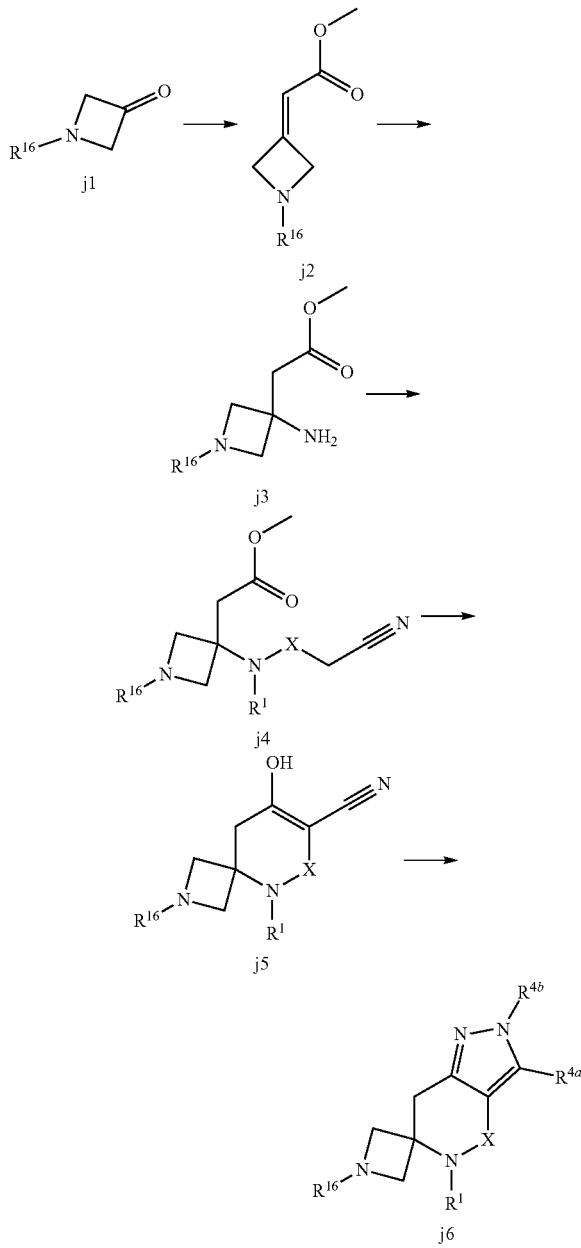

wherein each symbol is as described in above.

Step 1

Compound j2 can be obtained by reacting Compound j1 with methyl (triphenylphosphoranylidene)acetate.

The reaction temperature is 0° C. to 200° C., and preferably 20° C. to 150° C.

The reaction time is 0.5 hour to 48 hours, and preferably 0.5 hour to 12 hours.

As the reaction solvent, toluene, dimethylsulfoxide, and tetrahydrofuran are exemplified.

Step 2

Compound j3 can be obtained by reacting Compound j2 and ammonia.

The reaction temperature is 0° C. to 150° C., and preferably 20° C. to 80° C.

The reaction time is 0.5 hour to 48 hours, and preferably 0.5 hour to 7 hours.

As the reaction solvent, dimethylsulfoxide, tetrahydrofuran, diethyl ether, and toluene are exemplified.

Step 3

Compound j5 can be obtained by reacting Compound j3 and a carboxylic acid chloride, sulfonic acid chloride, thiocarboxylic acid chloride or the like, under the action of a base, as necessary.

As the base, pyridine, DIEA, potassium carbonate, sodium bicarbonate, sodium hydride, and sodium hydroxide are exemplified.

The reaction temperature is 0° C. to 150° C., and preferably 20° C. to 100° C.

The reaction time is 0.5 hour to 48 hours, and preferably 1 hour to 24 hours.

As the reaction solvent, acetonitrile, tetrahydrofuran, toluene, dichloromethane, dimethylacetamide, and dimethylformamide are exemplified.

Step 3' can be employed as an alternative method to Step 3.

Step 3'

Compound j4 can be obtained by reacting Compound j3 with a condensing agent, carboxylic acid, and the like in the presence or absence of a base.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified, and 1 to 5 molar equivalents of the condensing agent with respect to Compound j3 can be used.

As the base, triethylamine and diisopropylethylamine are exemplified.

The reaction temperature -20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

Step 4

Compound j5 can be obtained by reacting Compound j4 and a base.

As the base, piperidine, pyrrolidine, triethylamine, diisopropylethylamine, sodium methoxide, and sodium ethoxide are exemplified.

The reaction temperature is 0° C. to 100° C.

The reaction time is 1 hour to 10 hours.

As the reaction solvent, methanol, ethanol, and tetrahydrofuran are exemplified.

Step 5

Compound j6 can be obtained by reacting Compound j5 in accordance with the method described in the General Synthetic Procedure 1.

The compounds of the present invention have MGAT2 inhibitory activity, and are useful as a prophylactic agent and/or therapeutic agent for, for example, obesity, metabolic syndrome, hyperlipidemia, hypertriglyceridemia, hyper-VLDL-triglyceridemia, hyperfattyacidemia, diabetes mellitus, or arteriosclerosis.

The compounds of the present invention have not only MGAT2 inhibitory activity but also usefulness as a medicine, and have any or all of the following superior features:
a) having high metabolic stability,
b) exhibiting high solubility,
c) having less risk of phototoxicity,
d) having less risk of hepatotoxicity,
e) having less risk of kidney toxicity,
f) having less risk of cardiovascular toxicity,
g) having less risk of gastrointestinal disorders,
h) having less risk of drug interaction,
i) having high oral absorbability,
j) having small clearance,
k) having high distribution to a targeted tissue,
l) having intense enzymatic activity,
m) causing less induction of drug-metabolizing enzyme,
n) having intense efficacy,
o) having high selectivity of MGAT2 inhibitory activity, and
p) having high chemical stability.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, and inner ear or vaginal administration.

In the case of oral administration, any forms, which are usually used, such as oral solid formulations (e.g., tablets, powders, granules, capsules, pills, or films), and oral liquid formulations (e.g., suspension, emulsion, elixir, syrup, lemonade, spirit, aromatic water, extract, decoction, or tincture) may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, and external preparations (e.g., ophthalmic drops, nasal drops, ear drops, aerosols, inhalations, lotion, infusion, liniment, mouthwash, enema, ointment, plaster, jelly, cream, patch, cataplasm, external powder, or suppository) can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for formulation, such as excipients, binders, disintegrants, lubricants, and diluents. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of the pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered in one to several divisions per day.

The dose for co-administered drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

The pharmaceutical composition of the present invention is also effective for obesity (however, only when there are both type 2 diabetes and dyslipidemia and BMI is 25 kg/m$^2$ or greater even if diet therapy/exercise therapy is performed).

The pharmaceutical composition of the present invention is also effective for severe obesity for which the effect of diet therapy and exercise therapy applied in advance is insufficient.

The pharmaceutical composition of the present invention can be used in combination with other anti-obesity agent(s) (the pharmaceutical composition comprising compounds having anti-obesity effect, or the medicinal agent for obesity or for the weight management for obesity). For example, a combination treatment with a pharmaceutical composition comprising a compound having an anti-obesity effect and the compound of the present invention can be used for the prevention and/or treatment of obesity or the weight management for obesity. A combination treatment with the pharmaceutical composition comprising the compound of the present invention and a pharmaceutical composition(s) comprising a compound having an anti-obesity effect can be used for the prevention and/or treatment of obesity or the weight management for obesity. Furthermore, a method of treatment by administering the pharmaceutical composition of the invention can be used in combination of the diet therapy, drug therapy, exercise and the like.

In this description, meanings of each abbreviation are as follows:
Ac: Acetyl
Alloc: Allyloxycarbonyl
Bn: Benzyl
Boc: tert-butoxycarbonyl
Cbz: Benzyloxycarbonyl
CDI: Carbonyldiimidazole
DBU: Diazabicycloundecene
DEAD: Diethyl azodicarboxylate
DIAD: Diisopropyl dicarboxylate
DIEA: N,N-diisopropylethylamine
DMA: Dimethylacetamide
DMF: N,N-dimethylformamide
DMSO: Dimethylsulfoxide EDC: 1-ethyl-3-(3-dimethylaminopropyl)-carbodiimide
Et: Ethyl
Fmoc: 9-fluorenylmethyloxycarbonyl
HATU: O-(7-Azabenzotriazol-1-yl)-1,1,3,3-tetramethyluronium hexafluorophosphate
NMP: N-methylpyrrolidone
TCDI: 1,1'-thiocarbonyldiimidazole
Troc: 2,2,2-trichloroethoxycarbonyl

EXAMPLES

The present invention will be described in more detail with reference to, but not limited to, the following Examples and Test Examples.

Example 1

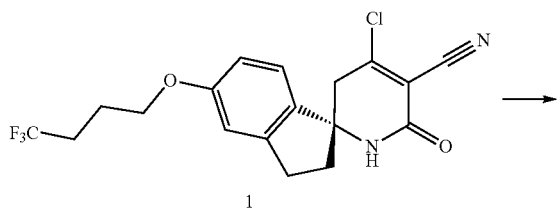

1

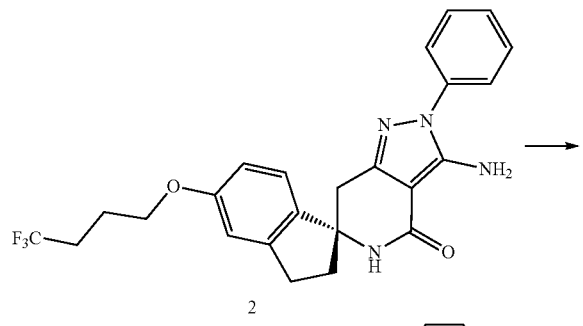

2

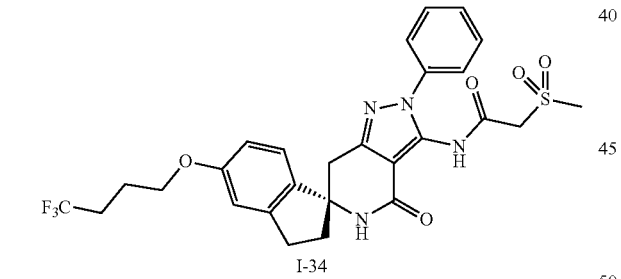

I-34

Step 1

The known compound 1 (WO2017069224A1) (54.7 mg, 0.142 mmol) was dissolved in tetrahydrofuran (1.1 mL), and phenylhydrazine (28 μL, 0.28 mmol) was added under ice cooling, and the mixture was stirred for 20 minutes. DIEA (50 μL, 0.28 mmol) was added to the reaction solution under ice cooling, and the mixture was stirred at room temperature for 3 hours, and further stirred at 70° C. for 1 hour. The solvent of the reaction solution was evaporated under reduced pressure. The obtained residue was purified by column chromatography (chloroform-methanol) to give Compound 2 (59.4 mg, yield 92%).

1H-NMR (CDCl3) δ: 2.01-2.10 (2H, m), 2.17 (1H, dt, J=12.8, 8.3 Hz), 2.24-2.39 (2H, m), 2.49 (1H, ddd, J=12.8, 7.4, 3.8 Hz), 2.83-3.01 (2H, m), 2.93 (1H, d, J=15.9 Hz), 3.06 (1H, d, J=15.9 Hz), 4.02 (2H, t, J=6.0 Hz), 5.12 (2H, s), 5.37 (1H, s), 6.78 (1H, s), 6.79 (1H, d, J=7.5 Hz), 7.29 (1H, d, J=7.5 Hz), 7.39 (1H, t, J=7.3 Hz), 7.51 (2H, t, J=7.8 Hz), 7.57 (2H, d, J=7.5 Hz).

Step 2

Compound 2 (44.9 mg, 98.4 μmol), 2-methanesulfonylacetic acid (54 mg, 0.40 mmol), and N,N-dicyclohexylcarbodiimide (82 mg, 0.40 mmol) were suspended in dichloromethane (2 mL) and stirred at room temperature for 25 hours. N,N-dimethylamino-4-pyridine (2.4 mg, 20 μmol) was added to the reaction solution, and the mixture was further stirred at room temperature for 4 hours. 2-methanesulfonylacetic acid (27 mg, 0.20 mmol) and N,N-dicyclohexylcarbodiimide (41 mg, 0.20 mmol) were added to the reaction solution, and the mixture was further stirred at room temperature for 24 hours. The reaction solution was filtered, and the solvent of the filtrate was evaporated under reduced pressure. The obtained residue was purified by silica gel chromatography (chloroform-methanol). Further, the obtained solid was washed with diisopropyl ether to give Compound I-34 (36.3 mg, yield 64%).

1H-NMR (CDCl3) δ: 1.95-2.06 (2H, m), 2.19-2.32 (3H, m), 2.44-2.54 (1H, m), 2.90 (3H, S), 2.91-3.04 (2H, m), 3.09 (1H, d, J=15.8 Hz), 3.18 (1H, d, J=15.8 Hz), 3.88-3.97 (2H, m), 4.02 (1H, d, J=14.3 Hz), 4.22 (1H, d, J=14.3 Hz), 6.12 (1H, S), 6.66-6.72 (1H, m), 6.76-6.79 (1H, m), 7.18 (1H, d, J=8.3 Hz), 7.35-7.52 (5H, m), 9.66 (1H, s).

Example 2

1 ⟶

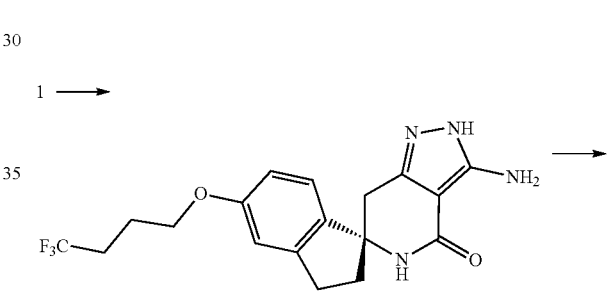

3

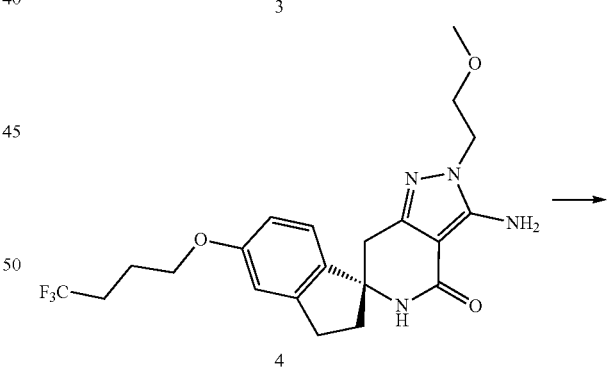

4

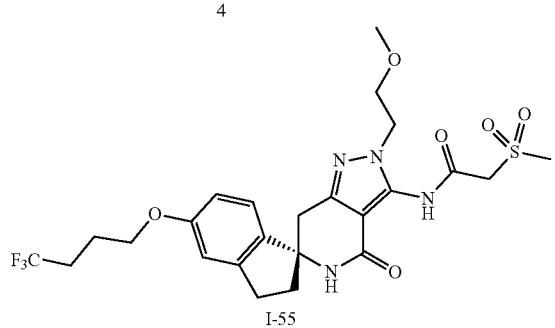

I-55

Step 1

Compound 1 (1.0 g, 2.60 mmol) was dissolved in ethanol (15 mL), and hydrazine monohydrate (0.65 mL, 13.0 mmol) was added. The mixture was stirred from room temperature to 80° C. for 18 hours. At room temperature, sodium bicarbonate water was added to the reaction solution, followed by the extraction with chloroform, and the resultant was dried over sodium sulfate. The solvent was evaporated under reduced pressure, and purified by suspending (ethyl acetate/hexane) to give Compound 3 (890 mg, yield 90%).

1H-NMR (CDCl3) δ: 2.01-2.18 (m, 3H), 2.25-2.42 (m, 3H), 2.81-3.02 (m, 4H), 4.00 (t, J=5.9 Hz, 2H), 5.49 (s, 1H), 6.75-6.77 (m, 2H), 7.22 (d, J=9.0 Hz, 1H).

Step 2

Compound 3 (100 mg, 0.24 mmol) was dissolved in dichloromethane (1.0 mL), and 1-bromo-2-methoxyethane (66.7 mg, 0.48 mmol) and cesium carbonate (313 mg, 0.96 mmol) were added and stirred 90° C. for 2 hours. At room temperature, water was added to the reaction solution, followed by the extraction with ethyl acetate, and the resultant was dried over sodium sulfate. The solvent was evaporated under reduced pressure to give Compound 4 as a crude product.

Step 3

The crude product of Compound 4 (0.24 mmol) was dissolved in toluene (1 mL), and 2-methanesulfonylaceticacid (66.2 mg, 0.48 mmol) and N,N'-dicyclohexylcarbodiimide (99.0 mg, 0.48 mmol) were added at room temperature and stirred for 1 hour. At room temperature, water was added to the reaction solution, followed by the extraction with ethyl acetate, and the resultant was dried over sodium sulfate. The solvent was evaporated under reduced pressure, and the obtained residue was purified by silica gel column chromatography (hexane-ethyl acetate) and reverse phase chromatography to give Compound I-55 (30.0 mg, yield in two steps 22%).

1H-NMR (CDCl3) δ: 2.01-2.20 (m, 3H), 2.25-2.44 (m, 3H), 2.85-2.97 (m, 3H), 3.09 (d, J=15.8 Hz, 1H), 3.30 (br-s, 3H), 3.39 (s, 3H), 3.72 (t, J=5.0 Hz, 2H), 3.99 (t, J=5.9 Hz, 2H), 4.13 (br-s, 2H), 4.28 (br-s, 2H), 5.68 (s, 1H), 6.77 (br-s, 2H), 7.20-7.22 (m, 1H).

Example 3

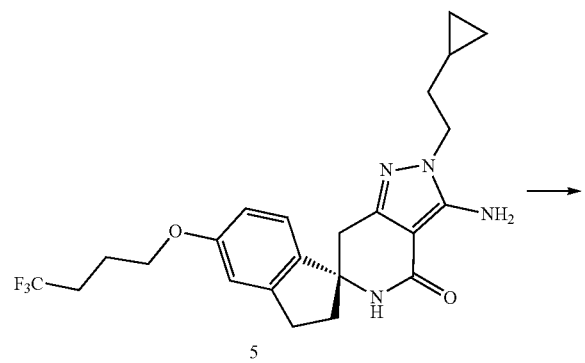

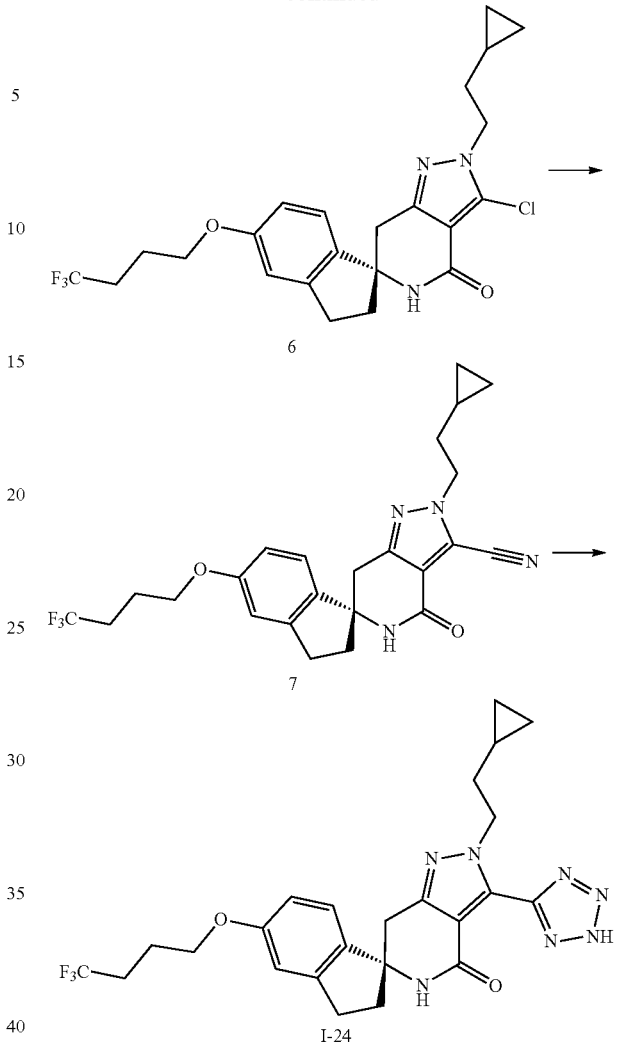

Step 1

Compound 3 (719 mg, 1.89 mmol) was dissolved in DMF (7 mL), and 2-cyclopropylethyl methanesulfonate (466 mg, 2.84 mmol) and potassium carbonate (1.31 g, 9.45 mmol) were added. The mixture was stirred at 80° C. for 5 hours. At room temperature, water was added to the reaction solution, followed by the extraction with chloroform, and the resultant was dried over sodium sulfate. The solvent was evaporated under reduced pressure, and the obtained residue was purified by column chromatography (ethyl acetate) to give Compound 5 (358 mg, yield 42%).

1H-NMR (CDCl3) δ: 0.06-0.10 (m, 2H), 0.46-0.51 (m, 2H), 0.63-0.72 (m, 1H), 1.69-1.75 (m, 2H), 2.03-2.15 (dt, J=30.7, 9.3 Hz, 3H), 2.28-2.43 (m, 3H), 2.82-3.00 (m, 4H), 3.93-4.02 (m, 4H), 4.78 (br-s, 2H), 5.23 (s, 1H), 6.76-9.78 (m, 2H), 7.23-7.25 (m, 1H).

Step 2

Compound 5 (2.30 g, 5.13 mmol) and copper dichloride (1.38 g, 10.3 mmol) were dissolved in acetic acid (7 mL) and concentrated hydrochloric acid (11 mL), and an aqueous solution (1 mL) of sodium nitrite (460 mg, 6.67 mmol) was added dropwise under ice cooling and stirred for 45 minutes under ice cooling. The reaction solution was extracted with chloroform, and an organic layer was washed with a saturated aqueous ammonium chloride solution and a 2M aqueous sodium carbonate solution, and then dried over sodium sulfate. The solvent was evaporated under reduced pressure, and the obtained residue was purified by column chromatography (chloroform-ethyl acetate) to give Compound 6 (1.24 g, yield 52%).

1H-NMR (CDCl3) δ: −0.04-0.05 (2H, m), 0.40-0.51 (2H, m), 0.61-0.72 (1H, m), 1.69-1.82 (2H, m), 2.01-2.10 (2H, m), 2.14 (1H, dt, J=13.1, 8.3 Hz), 2.25-2.42 (3H, m), 2.82-3.00 (2H, m), 2.94 (1H, d, J=15.8 Hz), 3.08 (1H, d, J=15.8 Hz), 4.01 (2H, t, J=5.9 Hz), 4.24 (2H, t, J=7.0 Hz), 5.59 (1H, s), 6.76-6.80 (2H, m), 7.22 (1H, d, J=9.0 Hz).

Step 3

Compound 6 (1.57 g, 3.36 mmol) was dissolved in DMA (16 ml), potassium cyanide (678 mg, 10.4 mmol) was added, and the mixture was stirred at 200° C. for 3 hours under microwave irradiation. After the resultant reaction solution was allowed to cool to room temperature, a saturated sodium bicarbonate aqueous solution and water were added thereto, followed by the extraction of an aqueous layer with hexane-ethyl acetate (2:1). The organic layer was washed with water and saturated saline, and then dried over sodium sulfate. The solvent was evaporated under reduced pressure to give a crude product of Compound 7 (1.46 g).

Step 4

The crude product of Compound 7 (212 mg), sodium azide (150 mg, 2.31 mmol) and ammonium chloride (124 mg, 2.31 mmol) were suspended in DMF (4.2 mL) and water (0.4 mL) and stirred at 140° C. for 3 hours. After the resultant reaction solution was allowed to cool to room temperature, an aqueous solution of citric acid was added thereto, followed by the extraction of an aqueous layer with ethyl acetate. The organic layer was dried over sodium sulfate, and the solvent was evaporated under reduced pressure. The obtained residue was purified by silica gel column chromatography (chloroform-methanol) to give Compound I-24 (162 mg, yield in two steps 66%).

1H-NMR (CDCl3) δ: 0.01-0.06 (2H, m), 0.36-0.42 (2H, m), 0.73-0.82 (1H, m), 1.88 (2H, q, J=7.1 Hz), 2.02-2.11 (2H, m), 2.18 (1H, s), 2.20 (1H, dt, J=13.3, 8.2 Hz), 2.26-2.39 (2H, m), 2.45 (1H, ddd, J=13.0, 7.7, 4.5 Hz), 2.88-3.06 (2H, m), 3.12 (1H, d, J=15.9 Hz), 3.22 (1H, d, J=15.9 Hz), 4.03 (2H, t, J=6.0 Hz), 4.99-5.13 (2H, m), 5.97 (1H, s), 6.79-6.83 (2H, m), 7.24 (1H, d, J=9.3 Hz).

Example 4

7 ⟶

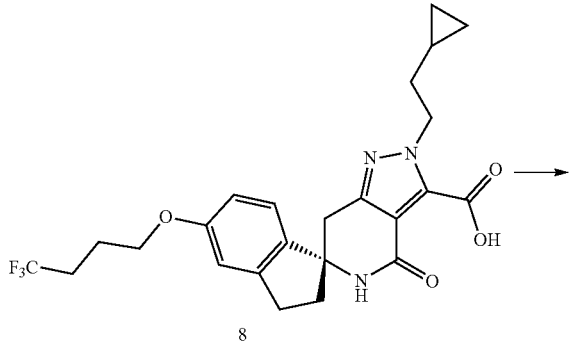

8

⟶

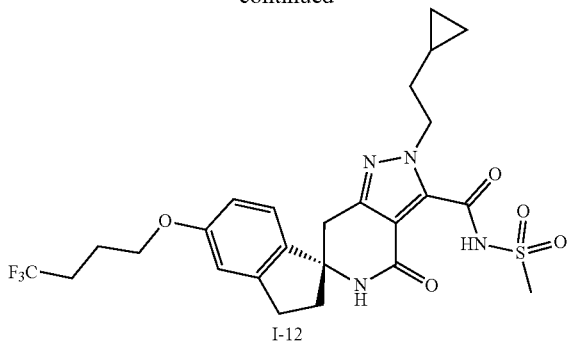

I-12

Step 1

Compound 7 (1.46 g, 3.18 mmol) was dissolved in tetrahydrofuran (6 mL) and methanol (6 mL), and a 5N aqueous sodium hydroxide solution (6.4 mL, 3.2 mmol) was added. The mixture was stirred at 120° C. for 75 minutes under microwave irradiation. After the resultant reaction solution was allowed to cool to room temperature, 2N hydrochloric acid (30 mL) was added, followed by the extraction of an aqueous layer with chloroform, and an organic layer was dried over sodium sulfate. The solvent was evaporated under reduced pressure. The obtained residue was purified by silica gel column chromatography (chloroform-methanol) to give the compound 2 (1.12 g, yield 73%).

1H-NMR (CDCl3) δ: −0.02-0.02 (2H, m), 0.39-0.45 (2H, m), 0.69-0.77 (1H, m), 1.78 (2H, q, J=7.2 Hz), 2.02-2.11 (2H, m), 2.21 (1H, dt, J=13.2, 8.2 Hz), 2.26-2.39 (2H, m), 2.45 (1H, ddd, J=13.0, 7.7, 4.5 Hz), 2.93 (1H, dt, J=16.2, 7.7 Hz), 3.01 (1H, ddd, J=16.5, 8.6, 4.3 Hz), 3.09 (1H, d, J=16.2 Hz), 3.19 (1H, d, J=16.1 Hz), 4.03 (2H, t, J=6.0 Hz), 4.76-4.89 (2H, m), 6.01 (1H, s), 6.79-6.84 (2H, m), 7.19-7.23 (1H, m), 15.66 (1H, s).

Step 2

Compound 2 (486 mg, 1.02 mmol) and carbonyldiimidazole (495 mg, 3.05 mmol) were dissolved in tetrahydrofuran (5 mL) and stirred at 70° C. for 100 minutes. After the resultant reaction solution was allowed to cool to room temperature, methanesulfonic acid amide (484 mg, 5.09 mmol) and diazabicycloundecene (0.77 mL, 5.1 mmol) were added, and the mixture was stirred at room temperature for 14 hours. After the solvent was evaporated under reduced pressure, 2N hydrochloric acid (20 mL) was added to the residue, followed by the extraction of the aqueous layer with chloroform, and the organic layer was dried over sodium sulfate. The solvent was evaporated under reduced pressure, and the obtained residue was purified by solidification (diisopropyl ether-chloroform) to give Compound I-12 (281 mg, yield 50%).

1H-NMR (CDCl3) δ: 0.00-0.04 (2H, m), 0.41-0.47 (2H, m), 0.67-0.76 (1H, m), 1.78 (2H, qd, J=7.2, 1.4 Hz), 2.02-2.11 (2H, m), 2.18 (1H, dt, J=13.2, 8.2 Hz), 2.26-2.36 (2H, m), 2.40 (1H, ddd, J=13.1, 7.7, 4.4 Hz), 2.91 (1H, dt, J=16.4, 8.1 Hz), 2.99 (1H, ddd, J=16.5, 8.6, 4.5 Hz), 3.07 (1H, d, J=15.8 Hz), 3.18 (1H, d, J=15.8 Hz), 3.38 (3H, s), 4.02 (2H, t, J=6.0 Hz), 4.75-4.87 (2H, m), 5.95 (1H, s), 6.79-6.83 (2H, m), 7.20-7.23 (1H, m), 14.99 (1H, s).

Example 5

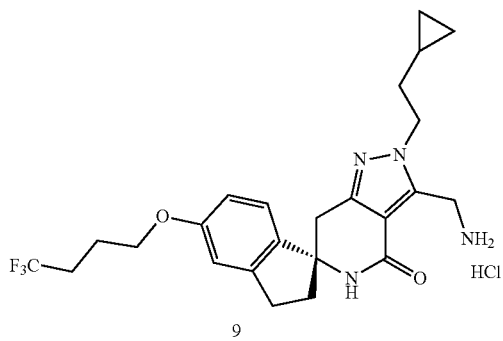

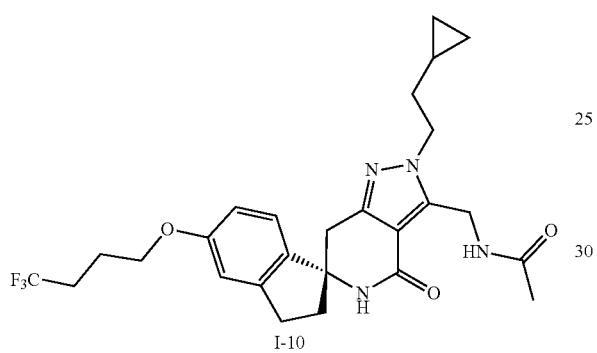

Step 1

Compound 7 (23.1 mg, 50.4 μmol) and 5% palladium carbon (23 mg) were suspended in methanol (1.5 mL) and concentrated hydrochloric acid (0.2 mL), and stirred at room temperature for 4 hours under a hydrogen atmosphere. After the reaction solution was filtered, the solvent was evaporated under reduced pressure to give Compound 9 (24.9 mg, yield 99%).

1H-NMR (DMSO-D6) δ: −0.08-0.04 (2H, m), 0.34-0.41 (2H, m), 0.58-0.67 (1H, m), 1.59-1.67 (2H, m), 1.91 (2H, dt, J=15.6, 6.4 Hz), 2.14-2.28 (2H, m), 2.36-2.45 (2H, m), 2.90 (2H, t, J=6.7 Hz), 2.94 (1H, d, J=15.8 Hz), 3.01 (1H, d, J=15.8 Hz), 4.01 (2H, t, J=6.1 Hz), 4.22 (2H, t, J=6.7 Hz), 4.38 (1H, d, J=15.2 Hz), 4.43 (1H, d, J=15.2 Hz), 6.68 (1H, dd, J=8.4, 2.3 Hz), 6.85 (1H, d, J=2.3 Hz), 7.01 (1H, d, J=8.4 Hz), 8.42 (1H, s), 8.73 (3H, s).

Step 2

Compound 9 (6.0 mg, 12 μmol) was suspended in tetrahydrofuran (0.7 mL), acetic anhydride (6 μL, 0.06 mmol) and triethylamine (17 μL, 0.12 mmol) were added, and the mixture was stirred at room temperature for 20 minutes. After methanol (2 mL) was added, the solvent was evaporated under reduced pressure. The obtained residue was purified by silica gel column chromatography (chloroform-methanol) to give the compound I-10 (4.6 mg, yield 76%).

1H-NMR (CDCl3) δ: −0.05-0.05 (2H, m), 0.39-0.48 (2H, m), 0.60-0.72 (1H, m), 1.75 (2H, q, J=7.0 Hz), 2.02 (3H, s), 2.03-2.10 (2H, m), 2.14 (1H, dt, J=13.1, 8.0 Hz), 2.25-2.36 (2H, m), 2.40 (1H, ddd, J=12.9, 7.7, 4.2 Hz), 2.83-2.97 (2H, m), 2.96 (1H, d, J=15.8 Hz), 3.07 (1H, d, J=15.8 Hz), 4.02 (2H, t, J=6.0 Hz), 4.27 (2H, t, J=7.2 Hz), 4.55 (1H, dd, J=16.1, 4.8 Hz), 4.76 (1H, dd, J=16.1, 6.0 Hz), 5.73 (1H, s), 6.76-6.81 (2H, m), 7.19-7.24 (1H, m), 8.65-8.72 (1H, m).

Example 6

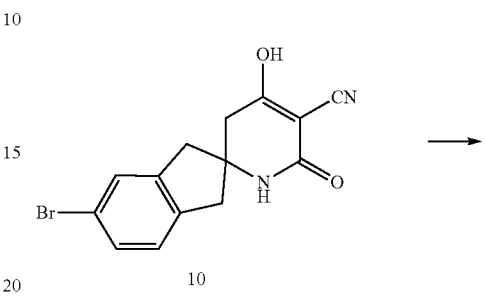

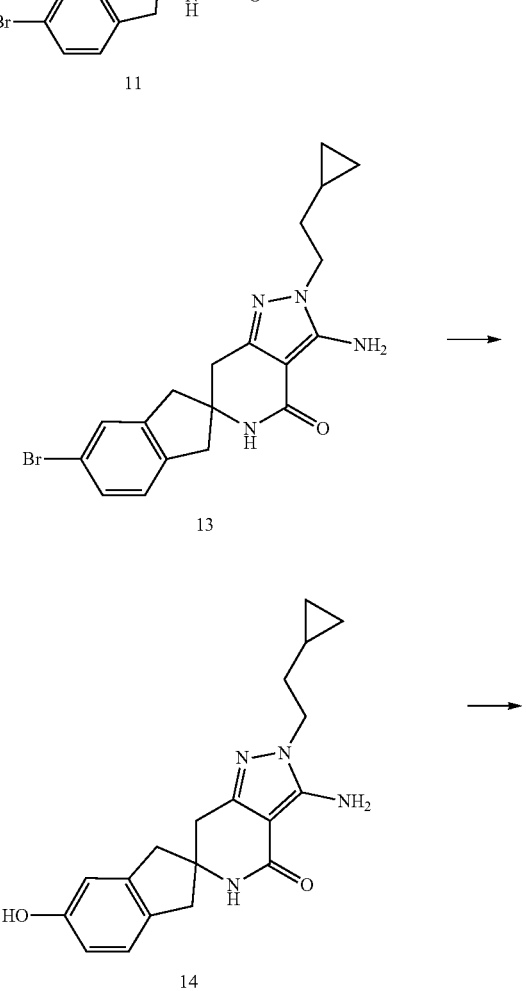

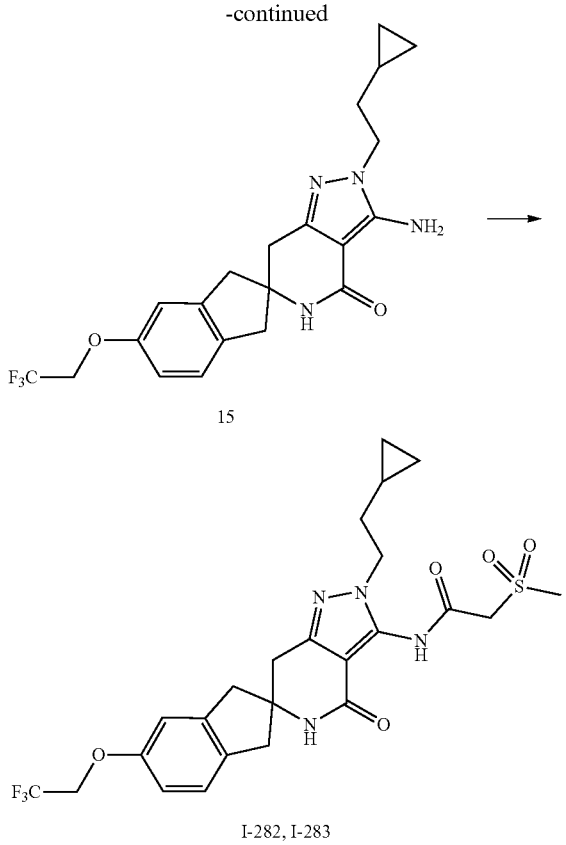

15

I-282, I-283

Step 1

The known compound 10 (WO2017069224A1) (1000 mg, 3.13 mmol) was dissolved in dichloroethane (10 mL), and a dichloroethane solution (2.5 mL) of phosphoryl chloride (0.524 mL, 5.64 mmol) was added, and the mixture was stirred for 20 min. DMF (0.434 mL, 5.64 mmol) was added to the reaction solution and stirred for 3 hours. The aqueous solution of sodium bicarbonate was added to the reaction solution, followed by the extraction with ethyl acetate. The organic layer was washed with water, and then dried over sodium sulfate. The solvent was evaporated under reduced pressure, and the obtained residue was purified by suspending (hexane-ethyl acetate) to give Compound 11 (720 mg, yield 68%).

[M+H]=336.90, measurement condition C

Step 2

Compound 11 (350 mg, 1.04 mmol) was dissolved in isopropanol (3.5 mL), Compound 12 (270 mg, 1.35 mmol) and sodium bicarbonate (131 mg, 1.55 mmol) were added, and the mixture was stirred at 90° C. for 6 hours. The solution was filtered, and the solvent was evaporated under reduced pressure. 10 wt % hydrochloric acid-methanol (3.55 g, 5.18 mmol) was added to the obtained residue and stirred for 14 hours. The aqueous solution of sodium bicarbonate was added to the reaction solution, followed by the extraction with ethyl acetate. The organic layer was washed with water, and then dried over sodium sulfate. The solvent was evaporated under reduced pressure. The obtained residue was purified by silica gel column chromatography (chloroform-methanol) to give the compound 13 (360 mg, yield 87%).

[M+H]=401.00, measurement condition C

Step 3

Compound 13 (100 mg, 0.249 mmol) was dissolved in dioxane (3 mL), and 4,4,4',4',5,5,5',5'-octamethyl-2,2'-bi-1,3,2-dioxaborolane (82 mg, 0.324 mmol), [1,1'-bis(diphenylphosphino)ferrocene]palladium (II) dichloride dichloromethane adduct (20 mg, 0.025 mmol) and potassium acetate (68 mg, 0.698 mmol) were added. The mixture was stirred at 95° C. for 1 hour. A 30% aqueous hydrogen peroxide solution (283 mL, 2.49 mmol) was added to the reaction solution under ice cooling and stirred at room temperature for 2 hours. A sodium thiosulfate aqueous solution was added to the reaction solution, followed by the extraction with ethyl acetate, and the organic layer was washed with water and then dried over anhydrous sodium sulfate. The solvent was evaporated under reduced pressure. The obtained residue was purified by silica gel column chromatography (chloroform-methanol) to give the compound 14 (75 mg, yield 89%).

[M+H]=339.05, measurement condition C

Step 4

Compound 14 (75 mg, 0.222 mmol) was dissolved in DMF (1 mL), and potassium carbonate (306 mg, 2.216 mmol) and 2,2,2-trifluoroethyl trifluoromethanesulfonate (0.096 mL, 0.665 mmol) were added. The mixture was stirred for 3 hours. Water was added to the reaction solution, followed by the extraction with ethyl acetate, and the organic layer was washed with water and then dried over anhydrous sodium sulfate. The solvent was evaporated under reduced pressure, and the obtained residue was purified by the silica gel column chromatography (hexane-ethyl acetate) to give Compound 15 (93 mg, yield 100%).

[M+H]=421.10, measurement condition C

Step 5

Compound 15 (93 mg, 0.221 mmol) was dissolved in dichloromethane (1 mL), and 2-methylsulfonylacetic acid (61 mg, 0.442 mmol) and dicyclohexylcarbodiimide (91 mg, 0.442 mmol) were added. The mixture was stirred for 1 hour. Water was added to the reaction solution, followed by the extraction with ethyl acetate, and the organic layer was washed with water and then dried over anhydrous sodium sulfate. The solvent was evaporated under reduced pressure, and the obtained residue was purified by silica gel column chromatography (hexane-ethyl acetate) and optically resolved by supercritical chromatography (ethanol) to give Compounds I-282 and I-283 (21 mg, yield 35%).

Condition

<SFC30 System from Waters Corporation>

Column: CHIRALPAK IB/SFC (5 μm, i.d. 250×4.6 mm) (DAICEL)

Flow rate: 2.0 mL/min; UV detection wavelength: 220 nm

Back pressure: 15 Mpa

Mobile phase: [A] liquefied carbonic acid, [B] ethanol

70% solvent [B] was maintained for 15 minutes.

Dissolution time: I-283 4.1 minutes, I-282 4.7 minutes

I-282: [M+H]=541, measurement condition B, retention time 1.94 min

I-283: $^1$H-NMR (CDCl$_3$) δ: 0.01-0.02 (m, 2H), 0.39-0.44 (m, 2H), 1.77 (q, J=7.2 Hz, 2H), 3.02-3.10 (m, 6H), 3.23 (s, 3H), 4.08 (t, J=7.3 Hz, 2H), 4.27-4.31 (m, 4H), 6.19 (s, 1H), 6.73-6.76 (m, 2H), 7.11 (d, J=8.2 Hz, 1H), 9.67 (s, 1H).

Although Compounds I-282 and I-283 are optically active substances, the steric configuration is not determined.

Example 7

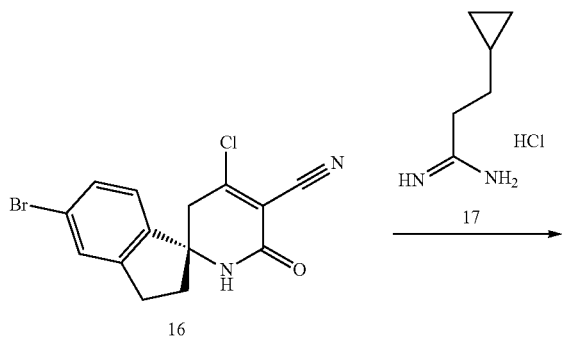

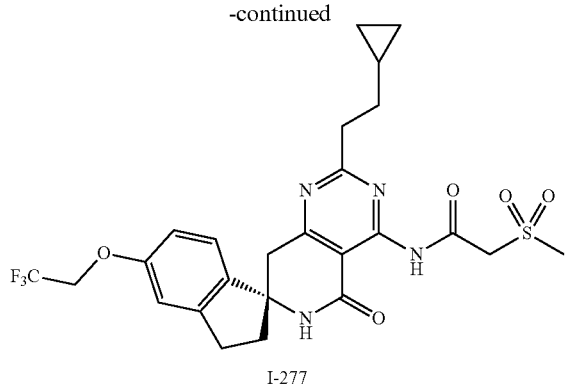

Step 1

Compound 16 (150 mg, 0.44 mmol) was dissolved in ethanol (1 mL), and Compound 17 (132 mg, 0.89 mmol) and DBU (0.67 mL, 4.44 mmol) were added at room temperature. The mixture was stirred at 100° C. for 30 minutes. The solvent was distilled off under reduced pressure, and the obtained residue was purified by the silica gel column chromatography (hexane-ethyl acetate) to give Compound 18 (60 mg, yield 33%).

$^1$H-NMR (CDCl3) δ: 0.04-0.08 (m, 2H), 0.39-0.44 (m, 2H), 0.72-0.81 (m, 1H), 1.67 (dd, J=15.4, 7.2 Hz, 2H), 2.05-2.17 (m, 1H), 2.39-2.45 (m, 1H), 2.78-2.82 (m, 2H), 2.93-3.00 (m, 3H), 3.14 (d, J=16.3 Hz, 1H), 5.57 (s, 1H), 5.79 (s, 1H), 7.16 (d, J=8.3 Hz, 1H), 7.34-7.42 (m, 2H), 8.43 (s, 1H).

Step 2

Compound 19 (45 mg, 92%) was obtained according to Step 3 of Example 6.

[M+H]=351.05, measurement condition C

Step 3

A crude product of Compound 20 was obtained according to Step 4 of Example 6.

Step 4

The crude product of Compound 5 (0.053 mmol) was dissolved in dichloromethane (1 mL), and 2-(methanesulfonyl)acetyl chloride (0.48 mmol) and pyridine (0.063 mL, 0.81 mmol) were added at 0° C. The mixture was stirred for 3 hours. At room temperature, water was added, followed by the extraction with ethyl acetate, and the resultant was dried over sodium sulfate. The solvent was evaporated under reduced pressure, and the obtained residue was purified by silica gel column chromatography (hexane-ethyl acetate), reverse phase chromatography and preparative TLC to give Compound I-277 (2.2 mg, yield in two steps 8%).

$^1$H-NMR (CDCl3) δ: 0.05-0.09 (m, 2H), 0.41-0.46 (m, 2H), 0.72-0.81 (m, 1H), 1.74 (dd, J=15.2, 7.2 Hz, 2H), 2.16-2.23 (m, 1H), 2.37-2.43 (m, 1H), 2.92-3.04 (m, 4H), 3.11 (d, J=17.7 Hz, 1H), 3.30 (d, J=16.8 Hz, 1H), 4.33-4.39 (m, 2H), 4.93 (d, J=14.3 Hz, 1H), 5.10 (d, J=14.3 Hz, 1H), 6.30 (s, 1H), 6.85-6.87 (m, 2H), 7.21-7.23 (m, 1H), 12.11 (s, 1H).

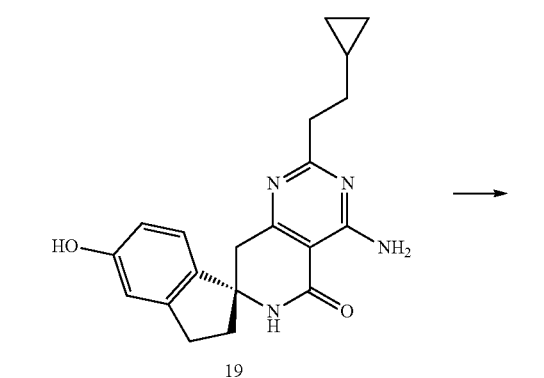

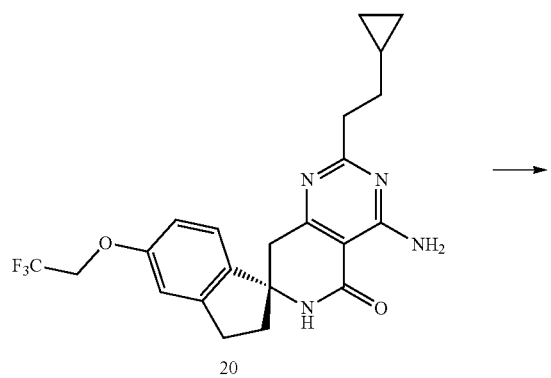

Example 8
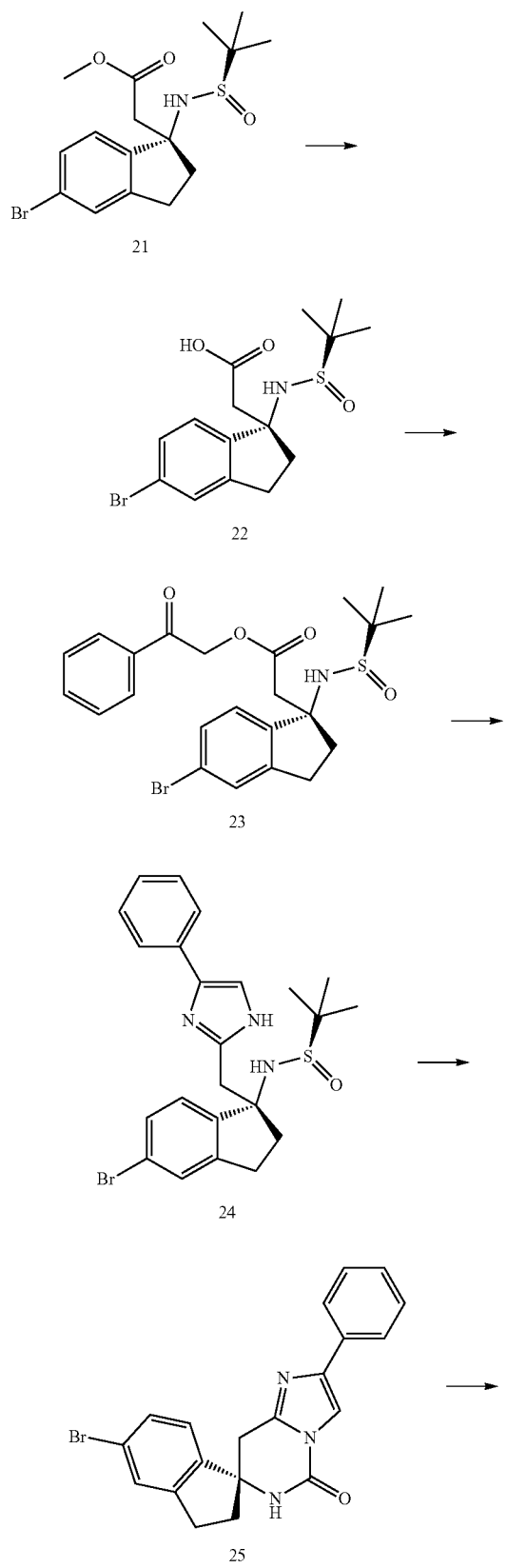
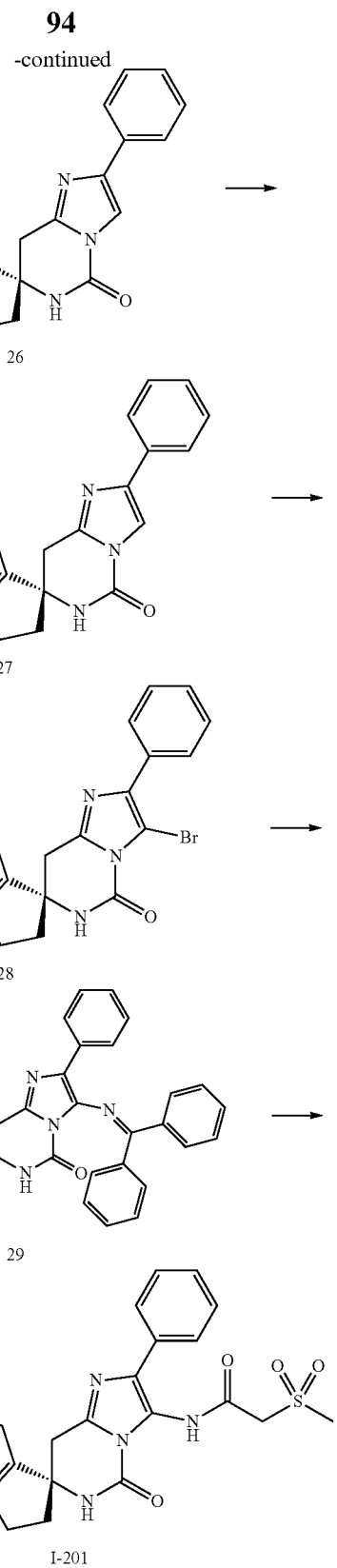
Step 1
The known compound 21 (WO2017069224A1) (3.0 g, 7.73 mmol) was dissolved in a mixed solvent of tetrahydrofuran (20 mL) and methanol (10 mL), and a 2N aqueous sodium hydroxide solution (4.64 mL, 9.27 mmol) was added. The mixture was stirred for 2 hours. A 1N aqueous solution of hydrochloric acid was added to the reaction solution, followed by the extraction with ethyl acetate. The organic layer was washed with water, and then dried over sodium sulfate. The solvent was evaporated under reduced pressure, and the obtained residue was purified by solidification (hexane-ethyl acetate) to give Compound 22 (2.7 g, yield 93%).

[M+H]=374.00, measurement condition C

Step 2

Compound 22 (500 mg, 1.34 mmol) was dissolved in acetonitrile (5 mL), and 2-chloroacetophenone (217 mg, 1.40 mmol) and cesium carbonate (653 mg, 2.00 mmol) were added. The mixture was stirred for 1 hour. Water was added to the reaction solution, followed by the extraction with ethyl acetate. The organic layer was washed with water, and then dried over sodium sulfate. The solvent was evaporated under reduced pressure, and the obtained residue was purified by solidification (hexane-ethyl acetate) to give Compound 23 (330 mg, yield 50%).

[M+H]=492.00, measurement condition C

Step 3

Compound 23 (330 mg, 0.670 mmol) was dissolved in toluene (5 mL), and ammonium acetate (517 mg, 6.70 mmol) was added. The mixture was stirred at 120° C. for 4 hours. Water was added to the reaction solution, followed by the extraction with ethyl acetate. The organic layer was washed with water, and then dried over sodium sulfate. The solvent was evaporated under reduced pressure. The obtained residue was purified by silica gel column chromatography (chloroform-methanol) to give the compound 24 (220 mg, yield 70%).

$^1$H-NMR (DMSO-D$_6$) δ: 1.17 (s, 9H), 2.14-2.17 (m, 1H), 2.35-2.41 (m, 1H), 2.82-2.88 (m, 2H), 2.96-3.00 (m, 1H), 3.12 (d, J=14.4 Hz, 1H), 6.71 (s, 1H), 7.13-7.21 (m, 2H), 7.33-7.42 (m, 4H), 7.48 (s, 1H), 7.57 (s, 2H), 7.76 (d, J=7.7 Hz, 2H). [M+H]=472.05, measurement condition C Step 4

Compound 24 (100 mg, 0.212 mmol) was dissolved in methanol (1 mL), 4N hydrochloric acid-dioxane solution (159 mL, 0.635 mmol) was added, and the mixture was stirred for 1 hour. The solvent was evaporated under reduced pressure. The obtained residue was dissolved in dichloromethane (1 mL), and pyridine (0.085 mL, 1.06 mmol) and 4-nitrophenyl chloroformate (58.9 mg, 0.317 mmol) were added. The mixture was stirred for 30 minutes. Triethylamine (0.293 mL, 2.12 mmol) was added to the reaction solution and stirred for 2 hours. Thereafter, water was added, followed by the extraction with ethyl acetate. The organic layer was washed with water, and then dried over sodium sulfate. The solvent was evaporated under reduced pressure, and the obtained residue was purified by the silica gel column chromatography (hexane-ethyl acetate) to give Compound 25 (65 mg, yield 78%).

$^1$H-NMR (DMSO-D$_6$) δ: 2.23-2.28 (m, 2H), 2.99 (t, J=6.9 Hz, 2H), 3.26 (q, J=14.3 Hz, 2H), 6.92 (d, J=8.3 Hz, 1H), 7.26 (t, J=7.4 Hz, 1H), 7.38 (t, J=7.5 Hz, 3H), 7.52 (s, 1H), 7.86 (d, J=7.0 Hz, 2H), 8.08 (s, 1H), 8.82 (s, 1H).

Step 5

A mixture (80 mg) of Compound 26 and impurities was obtained according to Step 3 of Example 6.

[M+H]=332.05, measurement condition C

Step 6

Compound 27 (40 mg, yield in two steps 61%) was obtained according to Step 4 of Example 6.

$^1$H-NMR (CDCl3) δ: 2.23-2.27 (m, 1H), 2.45-2.49 (m, 1H), 2.90-3.01 (m, 2H), 3.20-3.31 (m, 2H), 4.36 (q, J=8.1 Hz, 2H), 5.89 (s, 1H), 6.83-7.21 (m, 3H), 7.36-8.00 (m, 5H).

Step 7

Compound 27 (40 mg, 0.097 mmol) was dissolved in dichloromethane (3 mL), N-bromosuccinimide (34 mg, 0.194 mmol) was added under ice cooling, and the mixture was stirred at room temperature for 1 hour. A sodium thiosulfate aqueous solution was added to the reaction solution, followed by the extraction with ethyl acetate, and the organic layer was washed with water and then dried over anhydrous sodium sulfate. The solvent was evaporated under reduced pressure, and the obtained residue was purified by the silica gel column chromatography (hexane-ethyl acetate) to give Compound 28 (12 mg, 25%).

$^1$H-NMR (CDCl3) δ: 2.23-2.27 (m, 1H), 2.45-2.49 (m, 1H), 2.90-3.01 (m, 2H), 3.20-3.31 (m, 2H), 4.36 (q, J=8.1 Hz, 2H), 5.89 (s, 1H), 6.83-7.21 (m, 3H), 7.36-8.00 (m, 5H).

Step 8

Compound 28 (5.0 mg, 0.010 mmol) was dissolved in dioxane (0.5 mL), and diphenylmethanimine (9.2 mg, 0.051 mmol), chloro[(4,5-bis(diphenylphosphino)-9,9-dimethylxanthene)-2-(2'-amino-1,1'biphenyl)]palladium (II) (3.5 mg, 0.010 mmol) and sodium t-butoxy (2.7 mg, 0.028 mmol) were added. The mixture was stirred at 140° C. for 30 minutes under microwave irradiation. Water was added to the reaction solution, followed by the extraction with ethyl acetate, and the organic layer was washed with water and then dried over anhydrous sodium sulfate. The solvent was evaporated under reduced pressure, and the obtained residue was purified by the silica gel column chromatography (hexane-ethyl acetate) to give Compound 29 (4.0 mg, 67%).

[M+H]=593.15, measurement condition C

Step 9

Compound 29 (4.0 mg, 0.007 mmol) was dissolved in tetrahydrofuran (0.5 mL), a 2N aqueous solution of hydrochloric acid (0.10 mL, 0.202 mmol) was added, and the mixture was stirred for 3 hours. The solvent was evaporated under reduced pressure, and the obtained residue was dissolved in toluene (0.5 mL). Subsequently, 2-methylsulfonylacetic acid (4.8 mg, 0.035 mmol) and dicyclohexylcarbodiimide (7.2 mg, 0.035 mmol) were added and stirred for 30 minutes. Water was added to the reaction solution, followed by the extraction with ethyl acetate, and the organic layer was washed with water and then dried over anhydrous sodium sulfate. The solvent was evaporated under reduced pressure, and the obtained residue was purified by reverse phase column chromatography to give Compound I-201 (1.0 mg, yield in two steps 26%).

$^1$H-NMR (CDCl3) δ: 2.26-2.27 (m, 1H), 2.44-2.51 (m, 1H), 2.93-3.07 (m, 2H), 3.15 (s, 2H), 3.18-3.32 (m, 2H), 3.93-4.18 (m, 2H), 4.30-4.37 (m, 2H), 5.59-5.87 (m, 1H), 6.83-6.89 (m, 2H), 7.19-7.20 (m, 1H), 7.30-7.32 (m, 1H), 7.38-7.43 (m, 3H), 7.76 (d, J=7.8 Hz, 1H), 8.19-8.79 (m, 1H).

Example 9

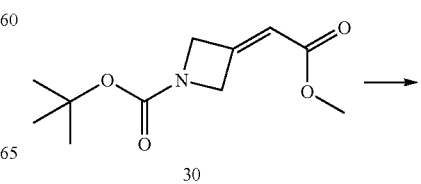

30

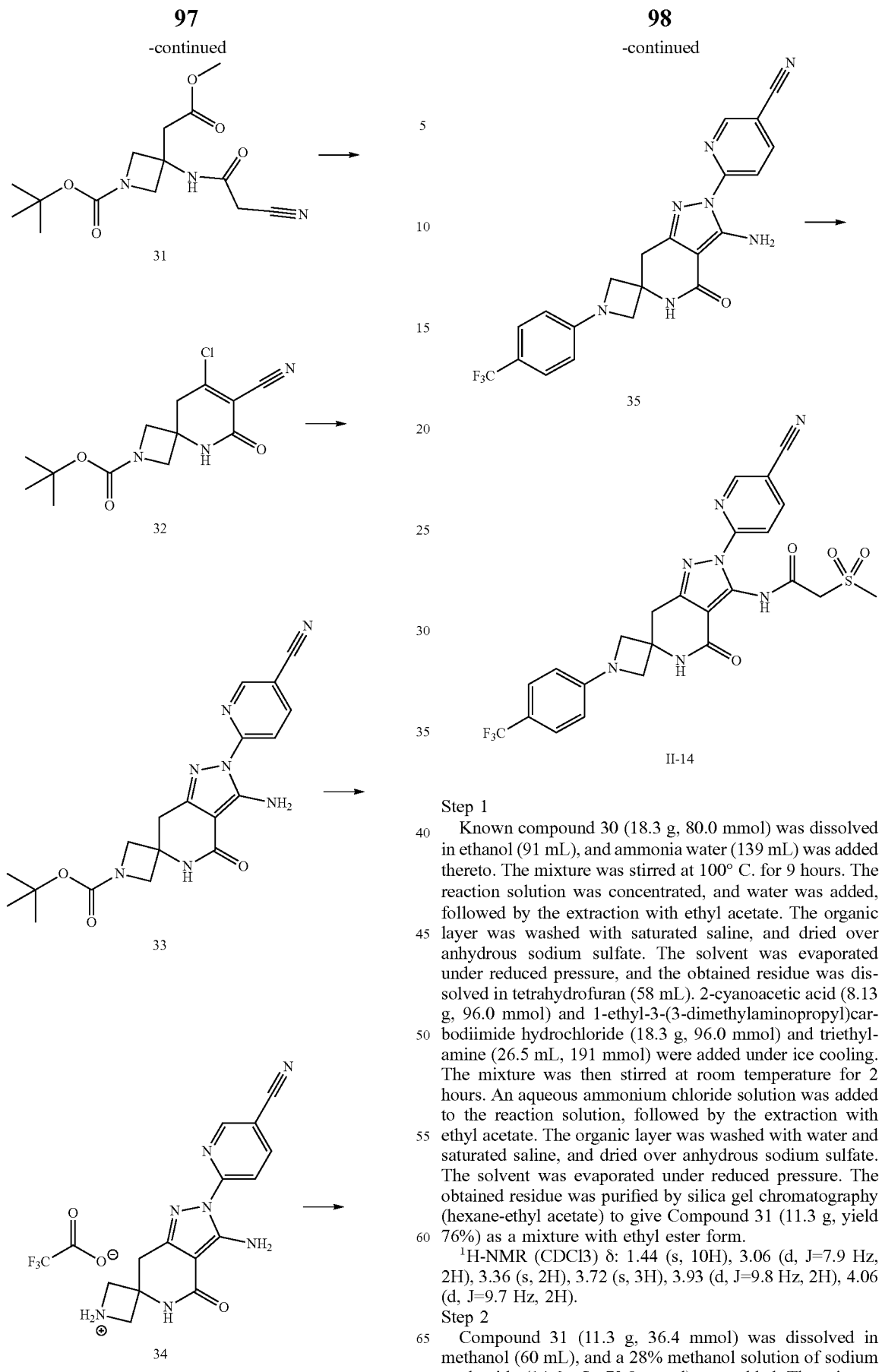

Step 1

Known compound 30 (18.3 g, 80.0 mmol) was dissolved in ethanol (91 mL), and ammonia water (139 mL) was added thereto. The mixture was stirred at 100° C. for 9 hours. The reaction solution was concentrated, and water was added, followed by the extraction with ethyl acetate. The organic layer was washed with saturated saline, and dried over anhydrous sodium sulfate. The solvent was evaporated under reduced pressure, and the obtained residue was dissolved in tetrahydrofuran (58 mL). 2-cyanoacetic acid (8.13 g, 96.0 mmol) and 1-ethyl-3-(3-dimethylaminopropyl)carbodiimide hydrochloride (18.3 g, 96.0 mmol) and triethylamine (26.5 mL, 191 mmol) were added under ice cooling. The mixture was then stirred at room temperature for 2 hours. An aqueous ammonium chloride solution was added to the reaction solution, followed by the extraction with ethyl acetate. The organic layer was washed with water and saturated saline, and dried over anhydrous sodium sulfate. The solvent was evaporated under reduced pressure. The obtained residue was purified by silica gel chromatography (hexane-ethyl acetate) to give Compound 31 (11.3 g, yield 76%) as a mixture with ethyl ester form.

$^1$H-NMR (CDCl3) δ: 1.44 (s, 10H), 3.06 (d, J=7.9 Hz, 2H), 3.36 (s, 2H), 3.72 (s, 3H), 3.93 (d, J=9.8 Hz, 2H), 4.06 (d, J=9.7 Hz, 2H).

Step 2

Compound 31 (11.3 g, 36.4 mmol) was dissolved in methanol (60 mL), and a 28% methanol solution of sodium methoxide (14.6 mL, 72.8 mmol) was added. The mixture was stirred at room temperature for 1 hour. The reaction solution was poured into a 1 mol/L aqueous solution of hydrochloric acid (36.4 mL), and water was added, followed by the extraction with ethyl acetate. The organic layer was washed with water, and then dried over anhydrous magnesium sulfate. The solvent was evaporated under reduced pressure. The obtained residue was dissolved in dichloroethane (142 mL), and DMF (0.27.8 mL, 357 mmol) was added. Subsequently, phosphoryl chloride (4.98 mL, 53.6 mmol) was added under ice cooling, and the mixture was warmed to room temperature and stirred for 2 hours. Saturated sodium bicarbonate water was added to the reaction solution, followed by the extraction with ethyl acetate, and the organic layer was dried over anhydrous sodium sulfate. The solvent was evaporated under reduced pressure, and the obtained residue was purified by the silica gel column chromatography (hexane-ethyl acetate) to give Compound 32 (6.60 g, 61%).

$^1$H-NMR (CDCl3) δ: 1.45 (s, 9H), 3.22 (s, 2H), 3.94-4.00 (m, 4H), 6.32 (s, 1H).

Step 3

6-hydrazinylnicotinonitrile (991 mg, 7.39 mmol) and sodium bicarbonate (734 mg, 8.73 mmol) were added to a solution of ethanol (20 mL) of Compound 32 (2.00 g, 6.72 mmol), and the mixture was stirred at 80° C. for 3 hours. The precipitated solid was collected by filtration and washed with ethanol and water to give Compound 33 (1.73 g, yield 65%).

$^1$H-NMR (CDCl3) δ: 1.44 (s, 9H), 3.12 (s, 2H), 3.91 (d, J=9.0 Hz, 2H), 4.01 (d, J=9.0 Hz, 2H), 5.63 (s, 1H), 7.19 (br-s, 2H), 8.01-8.07 (m, 2H), 8.66 (s, 1H).

Step 4

Trifluoroacetic acid (1.0 mL, 13.0 mmol) was added to a solution of dichloromethane (2 mL) of Compound 33 (103 mg, 0.26 mmol), and the mixture was stirred at room temperature for 1 hour. After concentration, methanol was added, and the precipitated solid was collected by filtration to give Compound 34 (82 mg, yield 77%).

$^1$H-NMR (DMSO-D$_6$) δ: 3.24 (s, 2H), 3.90 (d, J=11.4 Hz, 2H), 4.07 (d, J=11.4 Hz, 2H), 7.58 (s, 2H), 7.95 (d, J=8.9 Hz, 1H), 8.07 (s, 1H), 8.42 (dd, J=8.8, 2.3 Hz, 1H), 8.92-9.01 (m, 2H).

Step 5

Phenol (20.2 mg, 0.22 mmol) was dissolved in dioxane (1 mL), potassium tertiary butoxide (23.0 mg, 0.21 mmol) was added, and the mixture was stirred at room temperature for 10 minutes. Compound 34 (40 mg, 0.098 mmol), 5-[di(1-adamantyl)phosphino]-1',3',5'-triphenyl-1'H-[1,4]bipyrazole (13.0 mg, 0.020 mmol), allyl palladium chloride dimer (1.8 mg, 0.005 mmol) and 1-bromo-4-(trifluoromethyl)benzene (26.4 mg, 0.12 mmol) were added to the reaction solution, and the mixture was stirred at 90° C. for 2 hours. The solvent was evaporated under reduced pressure, and the obtained residue was purified by the silica gel column chromatography (hexane-ethyl acetate) to give Compound 35 (30.4 mg, 47%).

$^1$H-NMR (DMSO-D$_6$) δ: 3.17 (s, 2H), 3.86 (d, J=7.8 Hz, 2H), 4.00 (d, J=7.8 Hz, 2H), 6.57 (d, J=8.5 Hz, 2H), 7.47-7.54 (m, 4H), 7.95 (d, J=8.8 Hz, 1H), 8.00 (s, 1H), 8.40-8.42 (m, 1H), 8.93 (s, 1H).

Step 6

To a solution of dichloromethane (0.6 mL) of Compound 35 (30.4 mg, 0.053 mmol), 2-(methanesulfonyl)acetyl chloride (0.28 mmol) and pyridine (0.022 mL, 0.28 mmol) were added at 0° C., and the mixture was stirred for 1 hour. At room temperature, water was added, followed by the extraction with ethyl acetate, and the resultant was dried over sodium sulfate. The solvent was evaporated under reduced pressure, and the obtained residue was purified by silica gel column chromatography (chloroform-methanol) to give Compound II-14 (18.2 mg, 47%).

$^1$H-NMR (DMSO-D$_6$) δ: 3.13 (s, 3H), 3.31 (s, 2H), 3.90 (d, J=7.8 Hz, 2H), 4.05 (d, J=7.8 Hz, 2H), 4.37 (s, 2H), 6.58 (d, J=8.5 Hz, 2H), 7.49 (d, J=8.8 Hz, 2H), 7.96 (d, J=8.5 Hz, 1H), 8.49 (dd, J=8.8, 2.3 Hz, 1H), 8.55 (s, 1H), 8.88 (d, J=1.8 Hz, 1H), 11.16 (s, 1H).

Example 10

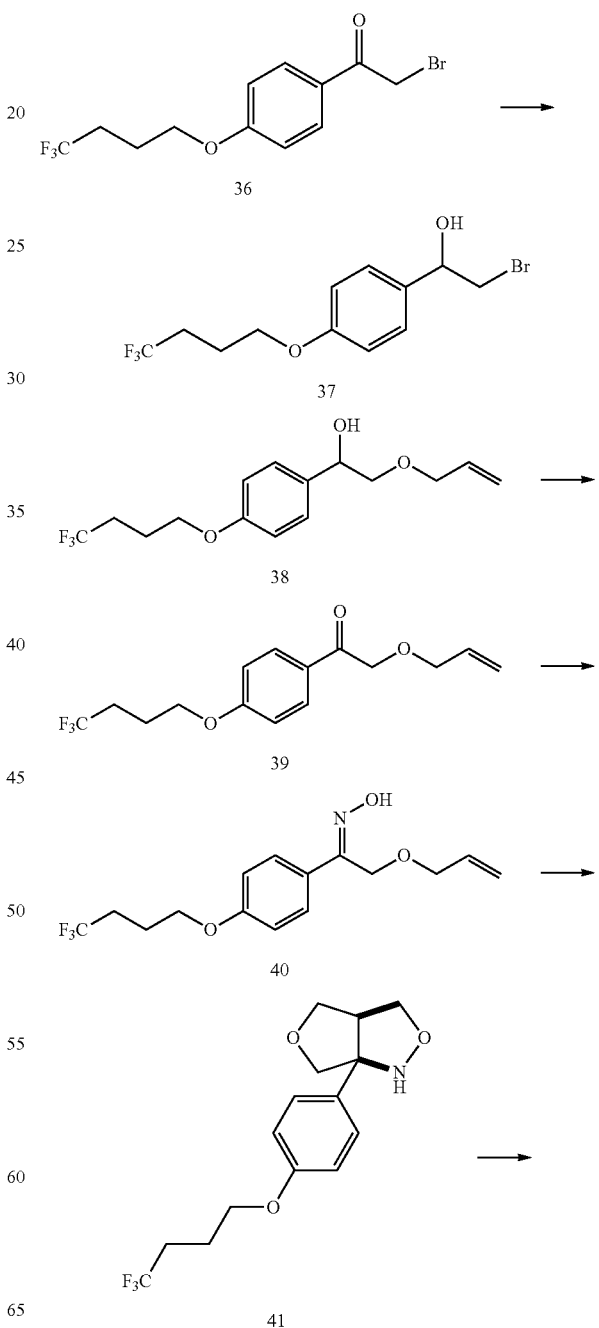

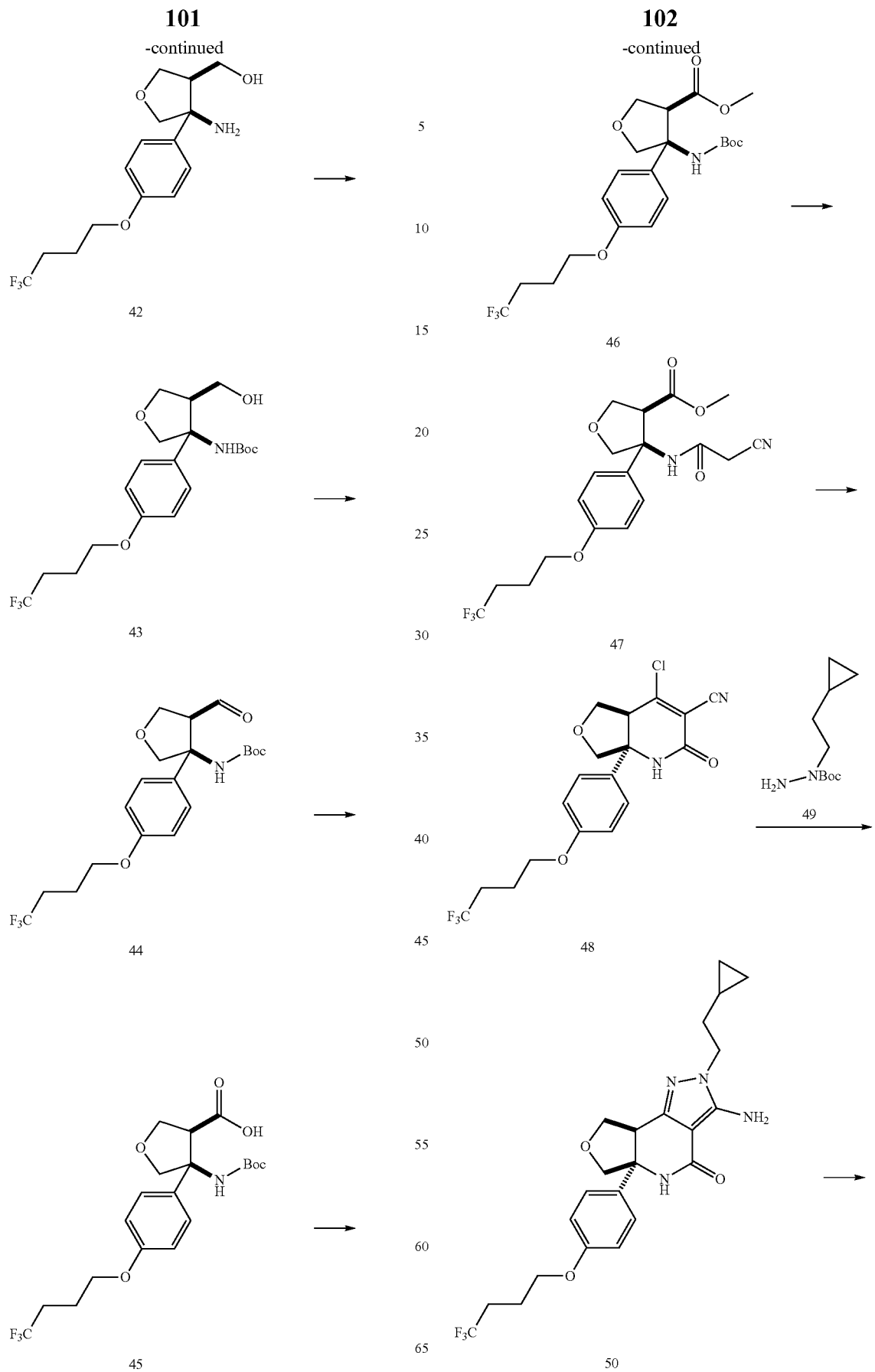

-continued

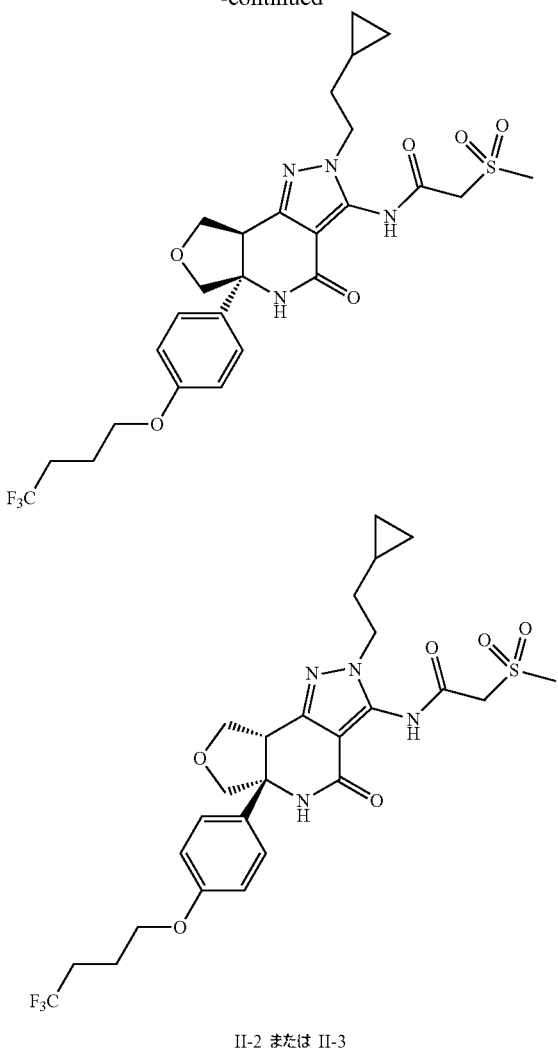

II-2 または II-3

Step 1

Sodium borohydride (408 mg, 10.80 mmol) under ice cooling was added to a solution of methanol (30 mL) of Compound 36 (4.5 g (purity 78%), 11.11 mmol), and the mixture was stirred at 0° C. for 1 hour. A saturated aqueous ammonium chloride solution was added to the reaction solution under ice cooling, followed by the extraction with ethyl acetate. The organic layer was washed with water and saturated saline, and dried over anhydrous sodium sulfate. The solvent was evaporated reduced pressure, and the obtained residue was purified by the silica gel column chromatography (hexane-ethyl acetate) to give Compound 37 (4.66 g (purity 78%), yield 103%).

Step 2

Potassium tertiary butoxide (8.79 g, 78 mmol) was slowly added to a solution of dimethyl sulfoxide (40 mL) of allyl alcohol (4.84 mL, 71.2 mmol), and the mixture was stirred at room temperature for 30 minutes. A solution of dimethyl sulfoxide (5 mL) of Compound 37 (4.5 g (purity 78%), 11.11 mmol) was added to the reaction solution, and the mixture was further stirred at room temperature for 1 hour. A 2 mol/L aqueous solution of hydrochloric acid was added to the reaction solution under ice cooling, and the mixture was stirred, followed by the extraction with ethyl acetate. The organic layer was washed with water and saturated saline, and dried over anhydrous sodium sulfate. The solvent was evaporated under reduced pressure, and the obtained residue was purified by the silica gel column chromatography (hexane-ethyl acetate) to give Compound 38 (1.65 g, yield 49%).

$^1$H-NMR (CDCl3) δ: 2.01-2.08 (m, 2H), 2.31 (ddt, J=23.8, 13.1, 4.0 Hz, 2H), 2.75 (s, 1H), 3.44 (t, J=9.4 Hz, 1H), 3.57 (dd, J=9.7, 3.2 Hz, 1H), 4.01 (t, J=6.0 Hz, 2H), 4.07 (dd, J=4.5, 1.2 Hz, 2H), 4.86 (dd, J=9.0, 3.0 Hz, 1H), 5.21 (dd, J=10.6, 1.6 Hz, 1H), 5.29 (dd, J=17.3, 1.6 Hz, 1H), 5.93 (ddd, J=22.6, 10.6, 5.5 Hz, 1H), 6.87 (d, J=8.5 Hz, 2H), 7.31 (d, J=8.5 Hz, 2H).

Step 3

A Dess-Martin reagent (2.53 g, 5.96 mmol) under ice cooling was added to a solution of dichloromethane (15 mL) of Compound 38 (1.65 g, 5.42 mmol), and the mixture was stirred at room temperature for 1.5 hours. Saturated sodium bicarbonate water was added to the reaction solution, followed by the extraction with ethyl acetate. The organic layer was washed with a 10% sodium thiosulfate aqueous solution and saturated saline, and then dried over anhydrous sodium sulfate. The solvent was evaporated under reduced pressure, and the obtained residue was purified by the silica gel column chromatography (hexane-ethyl acetate) to give Compound 39 (760 mg, 46%).

$^1$H-NMR (CDCl3) δ: 2.04-2.13 (m, 2H), 2.26-2.40 (m, 2H), 4.09 (t, J=6.0 Hz, 2H), 4.13-4.16 (m, 2H), 4.70 (s, 2H), 5.24 (dd, J=10.4, 1.5 Hz, 1H), 5.33 (dq, J=17.3, 1.5 Hz, 1H), 5.91-6.01 (m, 1H), 6.93 (dt, J=9.5, 2.3 Hz, 2H), 7.94 (dt, J=9.5, 2.3 Hz, 2H).

Step 4

Hydroxylamine hydrochloride (349 mg, 5.03 mmol) and sodium acetate (412 mg, 5.03 mmol) were added to a solution of ethanol (10 mL) of Compound 39 (760 mg, 2.51 mmol), and the mixture was stirred for 4 hours with heating under reflux. The solvent was evaporated under reduced pressure, and the obtained residue was purified by silica gel column chromatography (hexane-ethyl acetate) to give Compound 40 (567 mg, 71%).

$^1$H-NMR (CDCl3) δ: 2.02-2.11 (m, 3H), 2.25-2.39 (m, 2H), 4.00 (dt, J=5.7, 1.3 Hz, 2H), 4.04 (t, J=6.0 Hz, 2H), 4.70 (s, 2H), 5.19 (dd, J=10.4, 1.4 Hz, 1H), 5.27 (dq, J=17.2, 1.5 Hz, 1H), 5.84-5.93 (m, 1H), 6.88 (dt, J=9.5, 2.4 Hz, 2H), 7.63-7.68 (m, 3H).

Step 5

Compound 40 (729 mg, 2.30 mmol) was dissolved in toluene (5 ml), and hydroquinone (759 mg, 6.89 mmol) was added. The mixture was stirred with heating under reflux for 24 hours. After insoluble matter was filtered, the solvent was evaporated under reduced pressure, and the obtained residue was purified by silica gel column chromatography (hexane-ethyl acetate) to give Compound 41 (680 mg, 93%).

$^1$H-NMR (CDCl3) δ: 2.01-2.08 (m, 2H), 2.24-2.38 (m, 2H), 3.28-3.33 (m, 1H), 3.78-4.54 (m, 8H), 5.16 (s, 1H), 6.88 (dt, J=9.5, 2.5 Hz, 2H), 7.42 (s, 2H).

Step 6

2.5% rhodium-carbon (438 mg, 0.106 mmol) was added to a solution of ethanol (7 mL) of Compound 41 (675 mg, 2.13 mmol), and the mixture was stirred at room temperature for 6 hours under a hydrogen atmosphere. After filtration through celite, the reaction solution was concentrated to give Compound 42 (642 mg, 95%).

$^1$H-NMR (CDCl3) δ: 2.02-2.09 (m, 2H), 2.26-2.38 (m, 2H), 2.45-2.55 (m, 1H), 3.68-3.76 (m, 2H), 3.84-3.91 (m, 1H), 3.99-4.07 (m, 3H), 4.10-4.16 (m, 2H), 6.90 (d, J=7.8 Hz, 2H), 7.43 (d, J=7.8 Hz, 2H).

Step 7

Di-tert-butyl dicarbonate (607 mg, 2.78 mmol) was added to a solution of tetrahydrofuran (3 mL) of Compound 42 (296 mg, 0.93 mmol), and the mixture was stirred at room temperature for 24 hours. The solvent was evaporated under reduced pressure, and the obtained residue was purified by the silica gel column chromatography (hexane-ethyl acetate) to give Compound 43 (292 mg, 75%).

$^1$H-NMR (CDCl3) δ: 1.40 (s, 9H), 1.99-2.08 (m, 2H), 2.24-2.38 (m, 2H), 3.19 (s, 1H), 3.45 (s, 1H), 3.61 (t, J=8.5 Hz, 1H), 3.73-3.84 (m, 3H), 3.94 (d, J=9.5 Hz, 1H), 4.00 (t, J=5.9 Hz, 2H), 4.12 (t, J=8.6 Hz, 1H), 5.77 (s, 1H), 6.85 (d, J=8.7 Hz, 2H), 7.45 (d, J=8.7 Hz, 2H).

Step 8

A Dess-Martin reagent (323 mg, 0.761 mmol) under ice cooling was added to a solution of dichloromethane (3 mL) of Compound 43 (290 mg, 0.69 mmol), and the mixture was stirred at room temperature for 1 hour. Saturated sodium bicarbonate water was added to the reaction solution, followed by the extraction with ethyl acetate. The organic layer was washed with a 10% sodium thiosulfate aqueous solution and saturated saline, and then dried over anhydrous sodium sulfate. The solvent was evaporated under reduced pressure, and the obtained residue was purified by the silica gel column chromatography (hexane-ethyl acetate) to give Compound 44 (248 mg, 86%).

$^1$H-NMR (CDCl3) δ: 1.32 (brs, 9H), 2.01-2.08 (m, 3H), 2.24-2.39 (m, 2H), 3.64 (t, J=6.5 Hz, 1H), 3.96-4.21 (m, 4H), 4.41 (dd, J=9.2, 7.4 Hz, 1H), 5.50 (s, 1H), 6.89 (dt, J=9.6, 2.7 Hz, 2H), 7.37 (dt, J=9.6, 2.7 Hz, 2H), 9.82 (d, J=2.4 Hz, 1H).

Step 9

To a tert-butanol (3 mL) solution of Compound 44 (245 mg, 0.59 mmol) and 2-methyl-2-butene (622 mL, 5.9 mmol), an aqueous solution (0.5 mL) of sodium dihydrogen phosphate (352 mg, 2.93 mmol) and sodium chlorite (159 mg, 1.76 mmol) aqueous solution (0.5 mL) were sequentially added, and the mixture was stirred at room temperature for 2 hours. A 10% aqueous solution of citric acid was added to the reaction solution, followed by the extraction with chloroform. After drying over anhydrous sodium sulfate, the solvent was evaporated under reduced pressure to give Compound 45 (254 mg, 99%) as a crude product.

Step 10

Dimethylformamide (1 mL), potassium carbonate (176 mg, 1.26 mmol) and methyl iodide (0.08 mL, 1.26 mmol) were added to a solution of acetone (4 mL) of Compound 45 (250 mg, 0.58 mmol), and the mixture was stirred for 7 hours. Water was added to the reaction solution, followed by the extraction with ethyl acetate. The organic layer was washed with water and saturated saline, and then dried over anhydrous sodium sulfate. The solvent was evaporated under reduced pressure, and the obtained residue was purified by the silica gel column chromatography (hexane-ethyl acetate) to give Compound 46 (200 mg, 78%).

$^1$H-NMR (CDCl3) δ: 1.38 (s, 9H), 1.99-2.08 (m, 2H), 2.24-2.38 (m, 2H), 3.32 (s, 1H), 3.71 (s, 3H), 4.00 (t, J=6.0 Hz, 2H), 4.10-4.45 (m, 4H), 6.25 (s, 1H), 6.85 (dt, J=9.6, 2.6 Hz, 2H), 7.32 (dt, J=9.6, 2.6 Hz, 2H).

Step 11

A 4 mol/L hydrochloric acid-ethyl acetate solution (2 mL, 8 mmol) was added to Compound 46 (190 mg, 0.425 mmol), and the mixture was stirred at room temperature for 2 hours. After the solvent was evaporated under reduced pressure, tetrahydrofuran (2 mL) was added, and HATU (206 mg, 0.54 mmol), 2-cyanoacetic acid (46.1 mg, 0.54 mmol) and triethylamine (0.17 mL, 1.25 mmol) were added. The mixture was stirred at room temperature for 10 hours. A 10% aqueous solution of citric acid was added to the reaction solution, followed by the extraction with ethyl acetate. The organic layer was washed with a 10% aqueous citric acid solution, saturated sodium bicarbonate water, and saturated saline, and then dried over anhydrous sodium sulfate. The solvent was evaporated under reduced pressure, and the obtained residue was purified by the silica gel column chromatography (hexane-ethyl acetate) to give Compound 47 (135 mg, 78%).

$^1$H-NMR (CDCl3) δ: 2.01-2.08 (m, 2H), 2.23-2.37 (m, 2H), 3.31-3.44 (m, 3H), 3.79 (s, 3H), 4.00 (t, J=6.0 Hz, 2H), 4.08-4.15 (m, 1H), 4.29-4.38 (m, 2H), 4.66 (d, J=9.7 Hz, 1H), 6.86 (dt, J=9.6, 2.6 Hz, 2H), 7.26 (dt, J=9.6, 2.6 Hz, 2H), 8.48 (s, 1H).

Step 12

A 1 mol/L sodium methoxide-methanol solution (0.94 mL, 0.94 mmol) under ice cooling was added to a solution of methanol (1 mL) of Compound 47 (130 mg, 0.31 mmol), and the mixture was stirred at room temperature for 1 hour. After the reaction solution was diluted with water, the resulting solution was adjusted to a pH of about 4 with a 1 mol/L aqueous solution of hydrochloric acid, followed by the extraction with ethyl acetate. The organic layer was washed with a 0.1 mol/L aqueous solution of hydrochloric acid and saturated saline, and then dried over anhydrous sodium sulfate. After the solvent was evaporated under reduced pressure, 1,2-dichloroethane (2 mL), phosphorus oxychloride (0.041 mL, 0.52 mmol) and 2,6-lutidine (0.02 mL, 0.17 mmol) were added, and the mixture was stirred at room temperature for 14 hours. A 0.1 mol/L aqueous solution of hydrochloric acid was added to the reaction solution, followed by the extraction with ethyl acetate. The organic layer was washed with a 0.1 mol/L aqueous solution of hydrochloric acid and saturated saline, and then dried over anhydrous sodium sulfate. The solvent was evaporated under reduced pressure, and the obtained residue was purified by the silica gel column chromatography (hexane-ethyl acetate) to give Compound 48 (101 mg, 80%).

Step 13

Compound 49 (71.2 mg, 0.36 mmol) and sodium bicarbonate (30 mg, 0.36 mmol) were added to a solution of 2-propanol (2 mL) of Compound 48 (95 mg, 0.24 mmol), and the mixture was stirred at 80° C. for 18 hours. After filtration through celite, the solvent was evaporated under reduced pressure, and 2 mol/L hydrochloric acid-methanol solution (6 mL, 12 mmol) was added to the residue. The mixture was stirred at 50° C. for 2 hours. After the solvent was evaporated under reduced pressure, saturated sodium bicarbonate water was added, followed by the extraction with ethyl acetate. The organic layer was washed with saturated sodium bicarbonate water and saturated saline, and then dried over anhydrous sodium sulfate. The solvent was evaporated under reduced pressure, and the obtained residue was purified by the silica gel column chromatography (hexane-ethyl acetate) to give Compound 50 (76.4 mg, 69%).

$^1$H-NMR (CDCl3) δ: −0.04-0.05 (m, 2H), 0.40-0.48 (m, 2H), 0.57-0.69 (m, 1H), 1.67 (q, J=7.0 Hz, 2H), 1.98-2.08 (m, 2H), 2.23-2.35 (m, 2H), 3.66 (t, J=8.2 Hz, 1H), 3.89 (t, J=6.8 Hz, 2H), 3.99 (t, J=6.0 Hz, 2H), 4.07 (t, J=8.2 Hz, 2H), 4.29 (d, J=9.4 Hz, 1H), 4.40 (t, J=8.2 Hz, 1H), 4.79 (s, 2H), 5.35 (s, 1H), 6.85 (d, J=8.8 Hz, 2H), 7.33 (d, J=8.8 Hz, 2H).

Step 14

Compound 50 (75 mg, 0.16 mmol) was suspended in toluene (2 mL), dicyclohexylcarbodiimide (100 mg, 0.48 mmol) and 2-methylsulfonylacetic acid (67 mg, 0.48 mmol)

were added, and the mixture was stirred at room temperature for 18 hours. After insoluble matter was filtered, the solvent was evaporated under reduced pressure, and the residue was purified by amino silica gel column chromatography (chloroform-methanol). The obtained compound was optically resolved by SFC (ID column (manufactured by Daicel Corporation), MeOH 30%).

Compound II-2 or II-3

$^1$H-NMR (CDCl3) δ: −0.07-0.01 (m, 2H), 0.35-0.41 (m, 2H), 0.54-0.66 (m, 1H), 1.74 (q, J=7.2 Hz, 2H), 1.98-2.07 (m, 2H), 2.21-2.35 (m, 2H), 3.22 (s, 3H), 3.79 (t, J=8.2 Hz, 1H), 3.95 (t, J=5.9 Hz, 2H), 4.01-4.09 (m, 3H), 4.14 (d, J=9.7 Hz, 1H), 4.19-4.37 (m, 3H), 4.45 (t, J=8.4 Hz, 1H), 6.40 (s, 1H), 6.79 (d, J=8.8 Hz, 2H), 7.26 (d, J=8.8 Hz, 2H), 9.74 (s, 1H).

Compound II-2 or II-3

$^1$H-NMR (CDCl3) δ: −0.07-0.01 (m, 2H), 0.35-0.41 (m, 2H), 0.54-0.66 (m, 1H), 1.74 (q, J=7.2 Hz, 2H), 1.98-2.07 (m, 2H), 2.21-2.35 (m, 2H), 3.22 (s, 3H), 3.79 (t, J=8.2 Hz, 1H), 3.95 (t, J=5.9 Hz, 2H), 4.01-4.09 (m, 3H), 4.14 (d, J=9.7 Hz, 1H), 4.19-4.37 (m, 3H), 4.45 (t, J=8.4 Hz, 1H), 6.40 (s, 1H), 6.79 (d, J=8.8 Hz, 2H), 7.26 (d, J=8.8 Hz, 2H), 9.74 (s, 1H).

Example 11

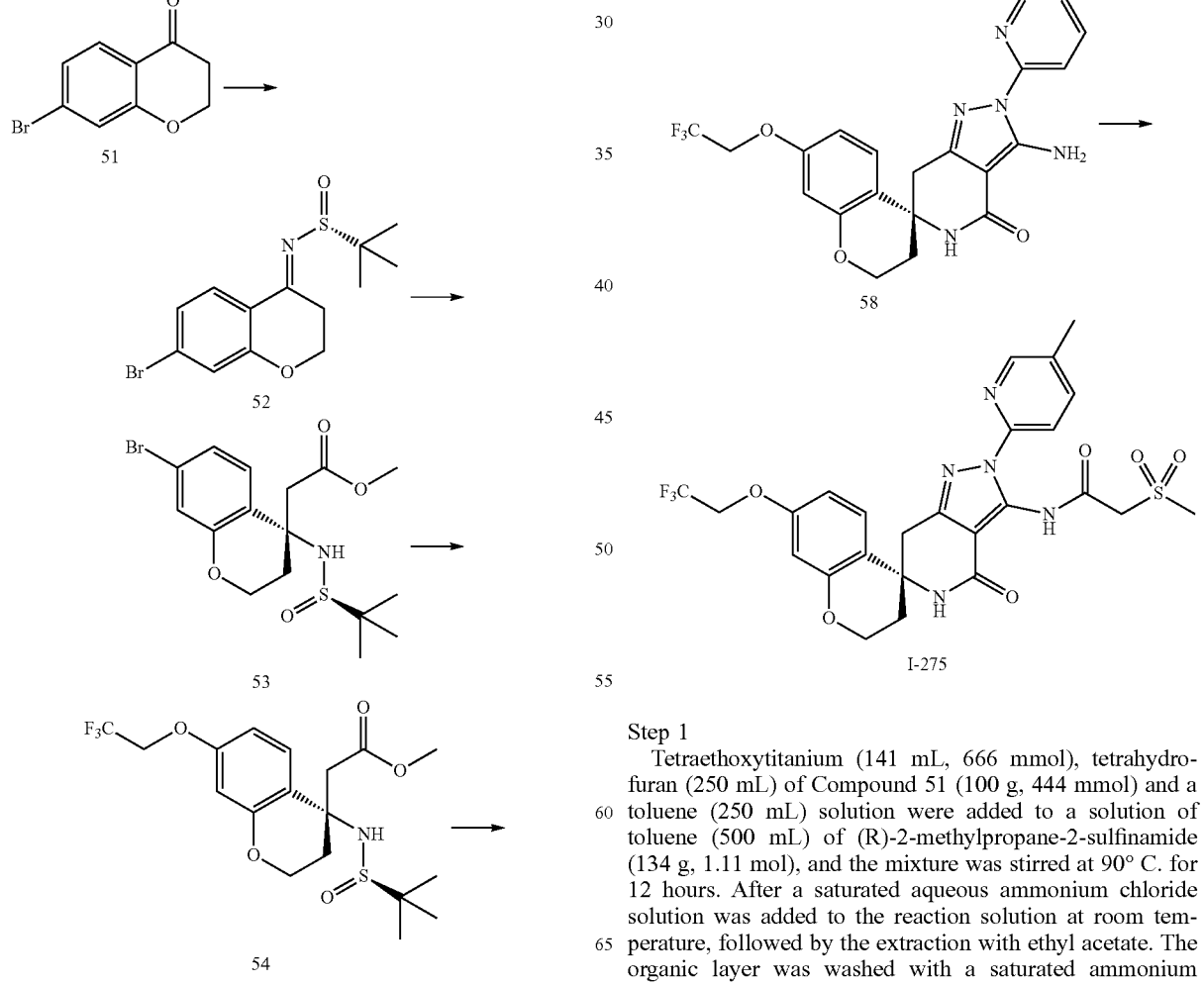

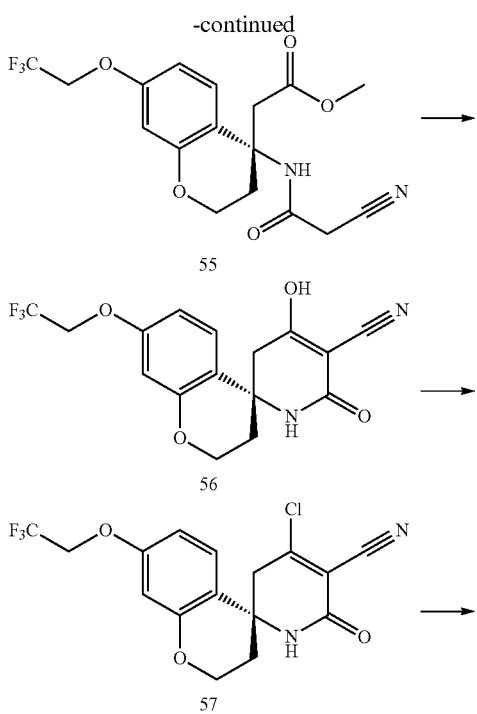

Step 1

Tetraethoxytitanium (141 mL, 666 mmol), tetrahydrofuran (250 mL) of Compound 51 (100 g, 444 mmol) and a toluene (250 mL) solution were added to a solution of toluene (500 mL) of (R)-2-methylpropane-2-sulfinamide (134 g, 1.11 mol), and the mixture was stirred at 90° C. for 12 hours. After a saturated aqueous ammonium chloride solution was added to the reaction solution at room temperature, followed by the extraction with ethyl acetate. The organic layer was washed with a saturated ammonium chloride solution, and then dried over anhydrous sodium sulfate. The solvent was evaporated under reduced pressure, and the obtained residue was purified by the silica gel column chromatography (hexane-ethyl acetate) to give Compound 52 (82 g, yield 56%).

$^1$H-NMR (CDCl3) δ: 1.32 (s, 9H), 3.24-3.31 (m, 1H), 3.45-3.53 (m, 1H), 4.27-4.41 (m, 2H), 7.09-7.12 (m, 2H), 7.83 (d, 1H, J=8.31 Hz).

Step 2

To a 1 mol/L lithium hexamethyldisilazide/tetrahydrofuran solution (334 mL, 333 mmol), methyl acetate (26.5 mL, 333 mmol) was added at −78° C., and the mixture was stirred for 1 hour. To the reaction solution, a solution of tetrahydrofuran (250 mL) of titanium chloride triisopropoxide (110 g, 424 mmol) was added dropwise at −78° C., and the mixture was stirred for 2 hours. A solution of tetrahydrofuran (250 mL) of Compound 52 (50.0 g, 151 mmol) was added dropwise to the reaction solution at −78° C., and the mixture was stirred for 30 minutes. A saturated ammonium chloride solution and Rochelle salt were added, and the mixture was warmed to room temperature and stirred for 12 hours. Thereafter, extraction was performed with ethyl acetate, and the organic layer was washed with water and then dried over anhydrous sodium sulfate. The solvent was evaporated under reduced pressure, and the obtained residue was purified by the silica gel column chromatography (hexane-ethyl acetate) to give Compound 53 (35 g, yield 57%).

$^1$H-NMR (400 MHz, DMSO-$d_6$) δ: 1.09 (s, 9H), 2.26-2.36 (m, 2H), 3.04 (q, 2H, J=5.6 Hz), 3.53 (s, 3H), 4.22-4.26 (m, 1H), 4.34-4.37 (m, 1H), 5.45 (s, 1H), 7.01-7.07 (m, 2H), 7.28 (d, 1H, J=8.56 Hz).

Step 3

Bis(pinacolato)diboron (1.32 g, 5.19 mmol), [1,1'-bis(diphenylphosphino)ferrocene]palladium (II) dichloride dichloromethane complex (1:1) (0.141 g, 0.17 mmol) and potassium acetate (1.02 g, 10.4 mmol) were added to a solution of dioxane (15 mL) of Compound 53 (1.4 g, 3.46 mmol), and the mixture was stirred at 100° C. for 4 hours. To the reaction solution, 30% aqueous hydrogen peroxide (1.96 mL, 17.3 mmol) was added at room temperature, and the mixture was stirred for 2 hours. Water was added to the reaction solution, followed by the extraction with ethyl acetate, the organic layer was washed with a 10% sodium thiosulfate aqueous solution and then dried over anhydrous sodium sulfate, and the solvent was evaporated under reduced pressure. The obtained residue was dissolved in DMF (10 mL), and cesium carbonate (1.69 g, 5.19 mmol) and trifluoromethanesulfonic acid 2,2,2-trifluoroethyl ester (597 mL, 4.16 mmmol) were added. The mixture was stirred at room temperature for 12 hours. A 10% aqueous citric acid solution was added to the reaction solution, followed by the extraction with ethyl acetate. After washing with saturated sodium bicarbonate water and saturated aqueous sodium chloride solution, drying was performed over anhydrous sodium sulfate, and the solvent was evaporated under reduced pressure. The obtained residue was purified by the silica gel column chromatography (hexane-ethyl acetate) to give Compound 54 (1.23 g, yield 84%).

$^1$H-NMR (CDCl3) δ: 1.22 (s, 9H), 2.21-2.28 (m, 1H), 2.52-2.57 (m, 1H), 2.77 (d, J=15.7 Hz, 1H), 2.96 (d, J=15.7 Hz, 1H), 3.71 (s, 3H), 4.19-4.25 (m, 1H), 4.31 (q, J=8.1 Hz, 2H), 4.45-4.51 (m, 1H), 5.13 (s, 1H), 6.40 (d, J=2.6 Hz, 1H), 6.56 (dd, J=8.8, 2.6 Hz, 1H), 7.17 (d, J=8.8 Hz, 1H).

Step 4

A 4 mol/L dioxane hydrochloride solution (0.64 mL, 2.57 mmol) was added to a solution of methanol (1.1 mL) of Compound 54 (545 mg, 1.29 mmol), and the mixture was stirred at room temperature for 1 hour. After the solvent of the reaction solution was evaporated under reduced pressure, the obtained residue was dissolved in tetrahydrofuran (4.5 ml), and 2-cyanoacetic acid (219 mg, 2.57 mmol), 1-ethyl-3-(3-dimethylaminopropyl)carbodiimide hydrochloride (493 mg, 2.57 mmol) and triethylamine (0.71 mL, 5.15 mmol) were added. The mixture was stirred at room temperature for 3 hours. Water was added to the reaction solution, followed by the extraction with ethyl acetate. After washing with saturated sodium bicarbonate water and saturated aqueous sodium chloride solution, drying was performed over anhydrous sodium sulfate, and the solvent was evaporated under reduced pressure to give Compound 55 (483 mg, yield 97%).

$^1$H-NMR (CDCl3) δ: 2.14-2.20 (m, 1H), 2.81-2.88 (m, 1H), 3.02 (d, J=15.1 Hz, 1H), 3.17 (d, J=15.1 Hz, 1H), 3.33 (dd, J=20.2, 18.9 Hz, 2H), 3.70 (s, 3H), 4.19-4.32 (m, 4H), 6.40 (d, J=2.8 Hz, 1H), 6.54 (dd, J=8.8, 2.8 Hz, 1H), 7.15 (s, 1H), 7.20 (d, J=8.8 Hz, 1H).

Step 5

A 28% sodium methoxide methanol solution (993 mg, 5.15 mmol) was added to a solution of methanol (2.5 mL) of Compound 55 (497 mg, 1.29 mmol), and the mixture was stirred at room temperature for 1 hour. A 2 mol/L aqueous solution of hydrochloric acid (6 mL) and water were added to the reaction solution, followed by the extraction with ethyl acetate. The organic layer was washed with water, and then dried over anhydrous magnesium sulfate. After concentration, the obtained residue was dissolved in ethyl acetate and back extracted with saturated sodium bicarbonate water. Thereafter, concentrated hydrochloric acid was added to an aqueous layer under ice cooling, and the precipitated solid was collected by filtration to give Compound 56 (340 mg, 75%).

$^1$H-NMR (DMSO-$D_6$) δ: 1.99-2.15 (m, 2H), 2.67 (d, J=17.3 Hz, 1H), 3.21 (d, J=17.3 Hz, 1H), 4.09-4.15 (m, 1H), 4.20-4.25 (m, 1H), 4.72 (q, J=8.9 Hz, 2H), 6.49 (d, J=2.6 Hz, 1H), 6.64 (dd, J=8.8, 2.6 Hz, 1H), 7.41 (d, J=8.8 Hz, 1H), 7.89 (s, 1H).

Step 6

A dichloroethane (5 mL) solution of phosphoryl chloride (0.152 mL, 1.69 mmol) and DMF (0.136 mL, 1.70 mmol) was added to a dichloroethane (5 ml) solution of Compound 56 (500 mg, 1.41 mmol), and the mixture was stirred at room temperature for 75 hours. Water was added to the reaction solution, followed by the extraction with ethyl acetate. After washing with saturated sodium bicarbonate water and saturated aqueous sodium chloride solution, drying was performed over anhydrous magnesium sulfate, and the solvent was evaporated under reduced pressure to give Compound 57 (486 mg, yield 92%).

$^1$H-NMR (CDCl3) δ: 2.24-2.27 (m, 2H), 3.00 (d, J=18.8 Hz, 1H), 3.43 (d, J=18.8 Hz, 1H), 4.17-4.35 (m, 4H), 5.92 (s, 1H), 6.42 (d, J=2.5 Hz, 1H), 6.63 (dd, J=8.8, 2.5 Hz, 1H), 7.33 (d, J=8.8 Hz, 1H).

Step 7

2-hydrazinyl-5-methylpyridine hydrochloride (51.4 mg, 0.32 mmol) and sodium bicarbonate (56.3 mg, 0.67 mmol) were added to a solution of ethanol (2 mL) of Compound 57 (100 mg, 0.27 mmol), and the mixture was stirred at 70° C. for 7 hours. Then, water was added, followed by the extraction with chloroform. After washing with saturated aqueous sodium chloride solution, drying was performed over anhydrous magnesium sulfate, and the solvent was evaporated under reduced pressure. The obtained residue was purified by the silica gel column chromatography (chloroform-methanol) to give Compound 58 (77.6 mg, yield 63%).

¹H-NMR (CDCl3) δ: 2.15-2.26 (m, 2H), 2.36 (s, 3H), 3.01 (d, J=16.2 Hz, 1H), 3.27 (d, J=16.2 Hz, 1H), 4.21-4.24 (m, 2H), 4.32 (q, J=8.1 Hz, 2H), 5.20 (s, 1H), 6.42 (d, J=2.6 Hz, 1H), 6.61 (dd, J=8.8, 2.6 Hz, 1H), 7.18 (s, 2H), 7.50 (d, J=8.8 Hz, 1H), 7.63 (dd, J=8.6, 2.2 Hz, 1H), 7.77 (d, J=8.4 Hz, 1H), 8.19 (s, 1H).

Step 8

To a solution of dichloromethane (5 mL) of Compound 58 (430 mg, 0.94 mmol), a solution of dichloromethane (3 ml) of 2-(methanesulfonyl)acetyl chloride (3.74 mmol) and pyridine (0.303 ml, 3.74 mmol) were added at 0° C., and the mixture was stirred for 1.5 hours. At room temperature, water was added, followed by the extraction with ethyl acetate, and the resultant was dried over magnesium sulfate. The solvent was evaporated under reduced pressure. The obtained residue was purified by silica gel column chromatography (chloroform-methanol, amino silica gel), and powdered with hexane-ethyl acetate to give Compound I-275 (320 mg, 59%).

¹H-NMR (CDCl3) δ: 2.19-2.31 (m, 2H), 2.40 (s, 3H), 3.11 (d, J=16.3 Hz, 1H), 3.22 (s, 3H), 3.41 (d, J=16.3 Hz, 1H), 4.14 (s, 2H), 4.23-4.25 (m, 2H), 4.33 (q, J=8.0 Hz, 2H), 5.59 (s, 1H), 6.44 (d, J=2.6 Hz, 1H), 6.62 (dd, J=8.8, 2.6 Hz, 1H), 7.49 (d, J=8.8 Hz, 1H), 7.69-7.72 (m, 1H), 7.81 (d, J=8.3 Hz, 1H), 8.30 (br-s, 1H), 11.19 (s, 1H).

Example 12

51 →

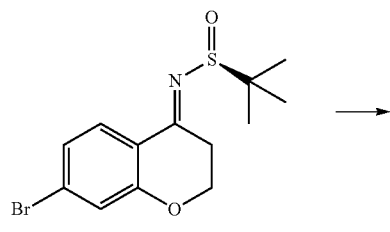
59

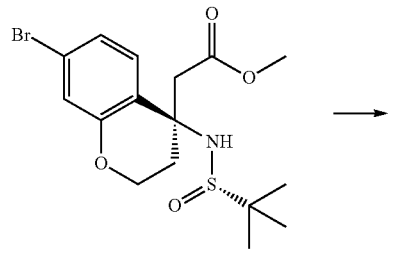
60

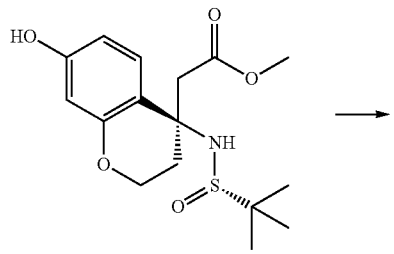
61

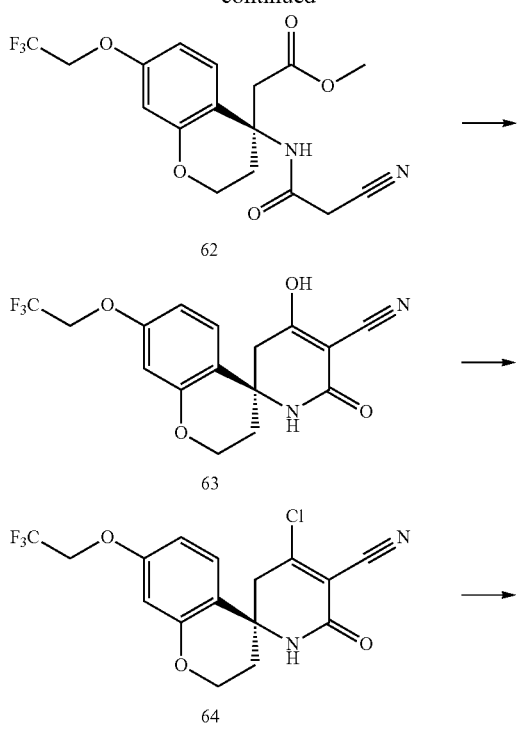

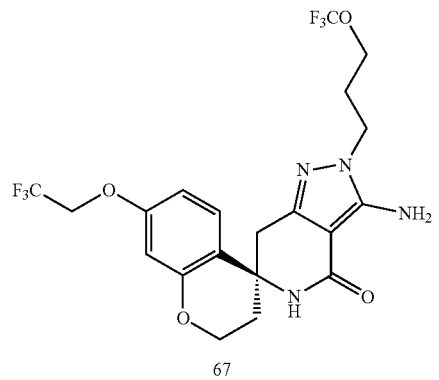
67

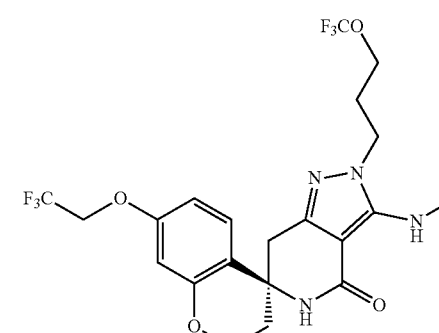
II-121

Step 1

(S)-2-methylpropane-2-sulfinamide (1.03 g, 8.45 mmol) and tetraethoxytitanium (3.22 mL, 6 mmol) were added to Compound 51 (1.75 g, 7.69 mmol), and the mixture was stirred at 100° C. for 2.5 hours. The reaction solution was diluted with ethyl acetate and water, followed by the extraction with ethyl acetate. After the organic layer was washed with saturated aqueous sodium chloride solution, the solvent was evaporated under reduced pressure, and the obtained residue was purified by silica gel column chromatography (hexane-ethyl acetate) to give Compound 59 (1.86 g, yield 73%).

$^1$H-NMR (CDCl3) δ: 1.32 (s, 9H), 3.24-3.31 (m, 2H), 3.46-3.53 (m, 2H), 4.28-4.41 (m, 2H), 7.09-7.13 (m, 2H), 7.84 (d, J=8.4 Hz, 1H).

Step 2

To a 1 mol/L lithium hexamethyldisilazide/tetrahydrofuran solution (9.01 mL, 9.01 mmol), tetrahydrofuran (15 mL) and methyl acetate (0.72 mL, 9.01 mmol) were added at −78° C. and stirred for 30 minutes. To the reaction solution, a hexane solution of 1 mol/L of titanium chloride triisopropoxide (11.3 mL, 11.3 mmol) was added dropwise at −78° C., and the mixture was stirred for 20 minutes. Thereafter, a solution of tetrahydrofuran (16 mL) of Compound 59 (1.86 g, 5.63 mmol) was added dropwise at −78° C., and the mixture was stirred for 1 hour. A saturated aqueous sodium chloride solution was added, followed by the extraction with ethyl acetate, and after the organic layer was washed with water, the solvent was evaporated under reduced pressure. The obtained residue was purified by silica gel column chromatography (hexane-ethyl acetate) to give Compound 60 (2.07 g, yield 77%).

$^1$H-NMR (CDCl3) δ: 1.22 (s, 9H), 2.22-2.29 (m, 1H), 2.56-2.61 (m, 2H), 2.78 (d, J=15.8 Hz, 1H), 2.93 (d, J=15.8 Hz, 1H), 3.71 (s, 3H), 4.20-4.25 (m, 1H), 4.43-4.49 (m, 1H), 5.17 (s, 1H), 7.02-7.05 (m, 2H), 7.11 (d, J=8.3 Hz, 1H).

Step 3

Bis(pinacolato)diboron (341 mg, 1.34 mmol), potassium acetate (359 mg, 3.66 mmol), and [1,1'-bis(diphenylphosphino)ferrocene]palladium (II) dichloride dichloromethane adduct (19.9 mg, 0.024 mmol) was added to a solution of 1,4-dioxane (5 mL) of Compound 60 (512 mg, 1.22 mmol), and after three repetitions of pressure reduction and nitrogen substitution, heating under reflux was continued for 3 hours. After cooling to room temperature, a residue obtained by filtration of insoluble matter through celite and evaporation of the solvent under reduced pressure was diluted with tetrahydrofuran (5 mL), and 30% aqueous hydrogen peroxide solution (277 mg, 2.44 mmol) and a 1 mol/L aqueous sodium hydroxide solution (0.244 mL, 0.244 mmol) were added. The mixture was stirred at room temperature for 19.5 hours. The reaction solution was treated with sodium thiosulfate pentahydrate (606 mg, 2.44 mmol), followed by the extraction with ethyl acetate. After the organic layer was washed with water, the solvent was evaporated under reduced pressure, and the obtained residue was powdered with hexane-ethyl acetate to give Compound 61 (391 mg, yield 94%).

$^1$H-NMR (CDCl3) δ: 1.23 (s, 9H), 2.21-2.28 (m, 1H), 2.45-2.50 (m, 1H), 2.78 (d, J=15.9 Hz, 1H), 2.99 (d, J=15.9 Hz, 1H), 3.71 (s, 3H), 4.17-4.22 (m, 1H), 4.43-4.50 (m, 1H), 5.10 (s, 1H), 6.23 (s, 1H), 6.34 (s, 1H), 6.40 (d, J=8.3 Hz, 1H), 7.05 (d, J=8.6 Hz, 1H).

Step 4

2,2,2-trifluoroethyl trifluoromethanesulfonate (310 mg, 1.34 mmol) and potassium carbonate (185 mg, 1.34 mmol) were added to a solution of N,N-dimethylformamide (1.5 mL) of Compound 61 (380 mg, 1.11 mmol), and after the mixture was stirred at room temperature for 14 hours, the mixture was heated to 60° C. and further stirred for 2 hours. The reaction solution was diluted with ethyl acetate and water, and after the organic layer was washed with water, the solvent was evaporated under reduced pressure. A 4 mol/L dioxane hydrochloride solution (0.557 mL, 2.23 mmol) was added to a solution of methanol (2 mL) of the obtained residue, and the mixture was stirred at room temperature for 1 hour. The solvent of the reaction solution was evaporated under reduced pressure, and toluene was further added to evaporate the solvent under reduced pressure. To a solution of dichloromethane (4 mL) of the obtained residue, 2-cyanoacetic acid (161 mg, 1.89 mmol), 1-(3-dimethylaminopropyl)-3-ethylcarbodiimide hydrochloride (363 mg, 1.89 mmol) and triethylamine (0.463 mL, 3.34 mmol) were added and stirred at room temperature for 19 hours. The solvent of the reaction solution was evaporated under reduced pressure and diluted with ethyl acetate and water. The organic layer was washed with water, and the solvent was evaporated under reduced pressure to give a crude product of Compound 62.

Step 5

60% sodium hydride (270 mg, 6.75 mmol) was added to a solution of methanol (4 mL) of the crude product of Compound 62, and the mixture was stirred at room temperature for 5 hours. After a 2 mol/L aqueous solution of hydrochloric acid (3.34 mL, 6.68 mmol) was added, the solvent was evaporated under reduced pressure and diluted with ethyl acetate and water. After the organic layer was washed with water, the solvent was evaporated under reduced pressure, and the obtained residue was powdered with hexane-ethyl acetate to give Compound 63 (324 mg, yield 82%).

$^1$H-NMR (DMSO-D$_6$) δ: 1.99-2.13 (m, 2H), 2.65 (d, J=17.1 Hz, 1H), 3.19 (d, J=17.1 Hz, 1H), 4.09-4.17 (m, 1H), 4.20-4.25 (m, 1H), 4.72 (q, J=8.9 Hz, 2H), 6.48 (d, J=2.3 Hz, 1H), 6.64 (dd, J=8.8, 2.3 Hz, 1H), 7.41 (d, J=8.8 Hz, 1H), 7.84 (s, 1H).

Step 6

N,N-dimethylformamide (63.5 mg, 0.869 mmol) and phosphorus oxychloride (133 mg, 0.869 mmol) were added to a suspension of 1,2-dichloroethane (6.2 mL) of Compound 63 (308 mg, 0.869 mmol), and the mixture was stirred at room temperature for 18.5 hours. Water was added to the reaction solution, and the precipitated solid was collected by filtration to give Compound 64 (312 mg, yield 96%).

$^1$H-NMR (CDCl3) δ: 2.26 (2H, t, J=5.5 Hz), 3.00 (1H, d, J=18.8 Hz), 3.44 (1H, d, J=18.8 Hz), 4.15-4.29 (2H, m), 4.30 (1H, d, J=7.9 Hz), 4.34 (1H, d, J=7.9 Hz), 5.83 (1H, s), 6.42 (1H, d, J=2.5 Hz), 6.63 (1H, dd, J=8.8, 2.4 Hz), 7.33 (1H, d, J=8.8 Hz).

Step 7

Hydrazine monohydrate (225 mg, 3.35 mmol) was added to a solution of tetrahydrofuran (4 mL) of Compound 64 (500 mg, 1.34 mmol), and the mixture was stirred at room temperature for 1 hour. Water was added to the reaction solution, followed by the extraction with ethyl acetate. The solvent was evaporated under reduced pressure. The obtained residue was purified by silica gel column chromatography (chloroform-methanol) to give the compound 65 (432 mg, yield 87%).

[M+H]=369.00, measurement condition C

Step 8

Compound 66 (324 mg, 1.09 mmol) and cesium carbonate (397 mg, 1.22 mmol) were added to a solution of acetonitrile (2 mL) of Compound 65 (333 mg, 0.91 mmol), and the mixture was stirred at 80° C. for 1 hour. Water was added to the reaction solution, followed by the extraction with ethyl acetate. The solvent was evaporated under reduced pressure. The obtained residue was purified by silica gel column chromatography (chloroform-methanol) to give the compound 67 (137 mg, yield 31%).

$^1$H-NMR (CDCl3) δ: 2.14-2.26 (m, 4H), 2.93 (d, J=16.1 Hz, 1H), 3.21 (d, J=16.1 Hz, 1H), 3.97-4.03 (m, 4H), 4.19-4.21 (m, 2H), 4.32 (q, J=8.1 Hz, 2H), 4.83 (s, 2H), 5.19 (s, 1H), 6.41 (d, J=2.5 Hz, 1H), 6.60 (dd, J=8.8, 2.5 Hz, 1H), 7.46 (d, J=8.8 Hz, 1H).

Step 9

To a solution of toluene (2 mL) of Compound 67 (137 mg, 0.28 mmol), 2-(methanesulfonyl)acetic acid (191 mg, 1.38 mmol) and N,N'-diisopropylcarbodiimide (0.22 ml, 1.38 mmol) were added at room temperature, and the mixture was stirred for 3 hours. Water was added at room temperature, followed by extraction with ethyl acetate. After the organic layer was washed with saturated sodium bicarbonate water, the solvent was evaporated under reduced pressure. The obtained residue was purified by silica gel column chromatography (chloroform-methanol) and powdered with methanol-water to give Compound 11-121 (82.4 mg, yield 49%).

$^1$H-NMR (CDCl3) δ: 2.09-2.18 (m, 2H), 2.29-2.36 (m, 2H), 3.03 (d, J=16.3 Hz, 1H), 3.21 (s, 3H), 3.31 (d, J=16.3 Hz, 1H), 3.99-4.35 (m, 10H), 5.92 (s, 1H), 6.40 (d, J=2.4 Hz, 1H), 6.60 (dd, J=8.8, 2.4 Hz, 1H), 7.41 (d, J=8.8 Hz, 1H), 9.56 (s, 1H).

Example 13

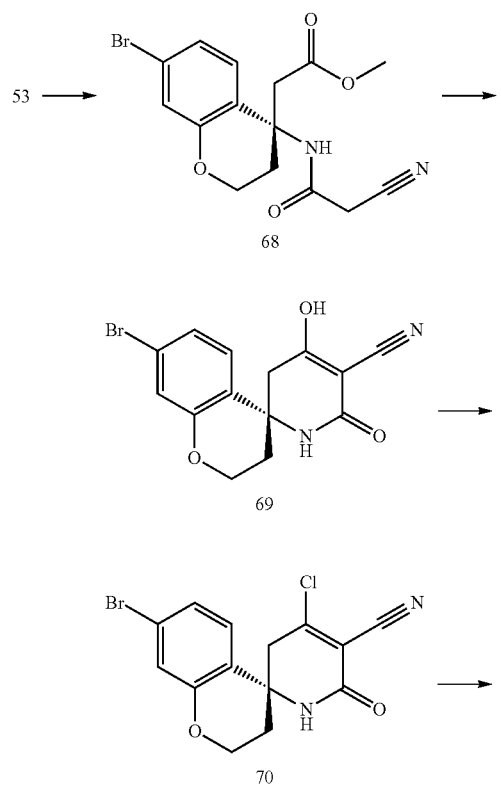

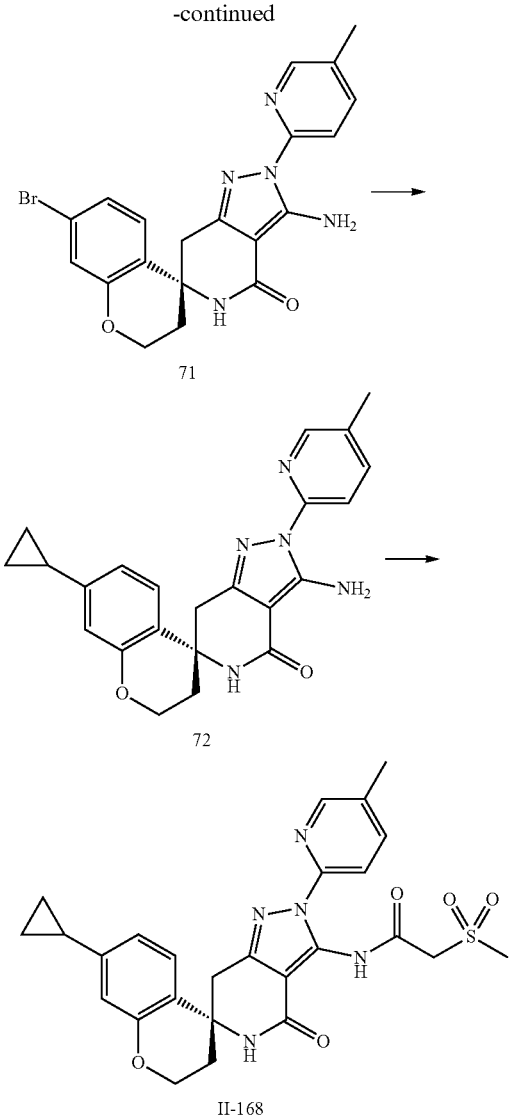

Step 1

A 4 mol/L dioxane hydrochloride solution (3.40 mL, 13.6 mmol) was added to a solution of methanol (60 mL) of Compound 53 (5.50 g, 13.6 mmol), and the mixture was stirred at room temperature for 1 hour. Thereafter, after the solvent was evaporated under reduced pressure, the obtained residue was dissolved in tetrahydrofuran (60 ml), and 2-cyanoacetic acid (2.31 g, 27.2 mmol), 1-ethyl-3-(3-dimethylaminopropyl)carbodiimide hydrochloride (5.22 g, 27.2 mmol), and triethylamine (7.54 mL, 54.4 mmol) were added. The mixture was stirred at room temperature for 1 hour. A saturated ammonium chloride solution was added to the reaction solution, followed by the extraction with ethyl acetate. After washing with water, drying was performed over anhydrous sodium sulfate, and the solvent was evaporated under reduced pressure. The obtained residue was purified by the silica gel column chromatography (hexane-ethyl acetate) to give Compound 68 (4.80 g, yield 96%).

Step 2

A 1 mol/L sodium methoxide methanol solution (26.1 mL, 26.1 mmol) was added to Compound 68 (4.80 g, 13.1 mmol), and the mixture was stirred at room temperature for 3 hours. A 1 mol/L aqueous solution of hydrochloric acid (150 mL) was added to the reaction solution, followed by the extraction with ethyl acetate. The organic layer was washed with water, and then dried over anhydrous sodium sulfate. After concentration, the obtained residue was powdered with hexane-ethyl acetate to give Compound 69 (3.75 g, 86%).

¹H-NMR (DMSO-d6) δ: 2.06-2.12 (2H, m), 2.71 (1H, d, J=17.5 Hz), 3.19 (1H, d, J=17.0 Hz), 4.12-4.17 (1H, m), 4.22-4.27 (1H, m), 7.01 (1H, d, J=2.0 Hz), 7.11 (1H, dd, J=8.5, 2.0 Hz), 7.42 (1H, d, J=8.5 Hz), 7.91 (1H, s).

Step 3

DMF (4.64 mL, 59.7 mmol) and phosphoryl chloride (0.61 mL, 6.56 mmol) were added to a solution of dichloroethane (20 mL) of Compound 69 (2.00 g, 5.97 mmol), and the mixture was stirred at room temperature for 19 hours. Water was added to the reaction solution, followed by the extraction with chloroform. After washing with saturated sodium bicarbonate water and saturated aqueous sodium chloride solution, drying was performed over anhydrous magnesium sulfate, and the solvent was evaporated under reduced pressure. The obtained residue was purified by silica gel column chromatography (hexane-ethyl acetate) and powdered with hexane-ethyl acetate to give Compound 70 (1.03 g, yield 49%).

¹H-NMR (CDCl3) δ: 2.27 (br-s, 2H), 3.03 (d, J=18.6 Hz, 1H), 3.41 (d, J=18.8 Hz, 1H), 4.17-4.31 (m, 2H), 5.96 (s, 1H), 7.07-7.27 (m, 3H).

Step 4

2-hydrazinyl-5-methylpyridine hydrochloride (135 mg, 0.85 mmol) and sodium bicarbonate (148 mg, 1.77 mmol) were added to a solution of ethanol (5 mL) of Compound 70 (250 mg, 0.71 mmol), and the mixture was stirred at 70° C. for 1 hour. Water was added to the reaction solution, extracted with chloroform, and dried over anhydrous magnesium sulfate, and the solvent was evaporated under reduced pressure. Diisopropyl ether was added to the obtained residue to be powdered, and thus to give Compound 71 (237 mg, yield 76%).

¹H-NMR (CDCl3) δ: 2.15-2.29 (m, 2H), 2.36 (s, 3H), 3.03 (d, J=16.1 Hz, 1H), 3.24 (d, J=16.1 Hz, 1H), 4.22-4.24 (m, 2H), 5.23 (s, 1H), 7.04 (d, J=2.0 Hz, 1H), 7.10 (dd, J=8.4, 2.0 Hz, 1H), 7.19 (br-s, 2H), 7.42 (d, J=8.4 Hz, 1H), 7.61-7.64 (m, 1H), 7.76 (d, J=8.5 Hz, 1H), 8.19 (br-s, 1H).

Step 5

Potassium cyclopropyl trifluoroborate (101 mg, 0.68 mmol), [1,1'-bis(di-tert-butylphosphino)ferrocene]palladium (II) dichloride (0.148 g, 0.227 mmol) and cesium carbonate (0.222 g, 0.681 mmol) were added to a solution of toluene (2 mL) of Compound 71 (100 mg, 0.23 mmol) and water (0.4 mL), and the mixture was stirred at 100° C. for 3 hours. Water was added to the reaction solution, followed by the extraction with ethyl acetate, and the organic layer was washed with saturated aqueous sodium chloride solution and dried over anhydrous magnesium sulfate. The solvent was evaporated under reduced pressure. The obtained residue was purified by silica gel column chromatography (hexane-ethyl acetate) and powdered with hexane-ethyl acetate to give Compound 72 (20.4 mg, yield 22%).

Step 6

To a solution of dichloromethane (1 mL) of Compound 72 (20.4 mg, 0.051 mmol), a solution of dichloromethane (0.3 ml) of 2-(methanesulfonyl)acetyl chloride (0.20 mmol) and pyridine (0.016 ml, 0.20 mmol) were added at 0° C., and the mixture was stirred for 3 hours. At room temperature, water was added to the reaction solution, followed by the extraction with ethyl acetate, and the resultant was dried over magnesium sulfate. The solvent was evaporated under reduced pressure, and the obtained residue was purified by silica gel column chromatography (chloroform-methanol, amino silica gel) to give Compound 11-168 (14.2 mg, 54%).

¹H-NMR (CDCl3) δ: 0.68-0.72 (m, 2H), 0.95-1.00 (m, 2H), 1.81-1.88 (m, 1H), 2.19-2.28 (m, 2H), 2.40 (s, 3H), 3.11 (d, J=16.3 Hz, 1H), 3.23 (s, 3H), 3.42 (d, J=16.3 Hz, 1H), 4.14 (s, 2H), 4.20-4.22 (m, 2H), 5.61 (s, 1H), 6.57 (d, J=1.8 Hz, 1H), 6.73 (dd, J=8.2, 1.8 Hz, 1H), 7.42 (d, J=8.2 Hz, 1H), 7.70 (dd, J=8.4, 1.8 Hz, 1H), 7.81 (d, J=8.4 Hz, 1H), 8.30 (s, 1H), 11.17 (s, 1H).

Example 14

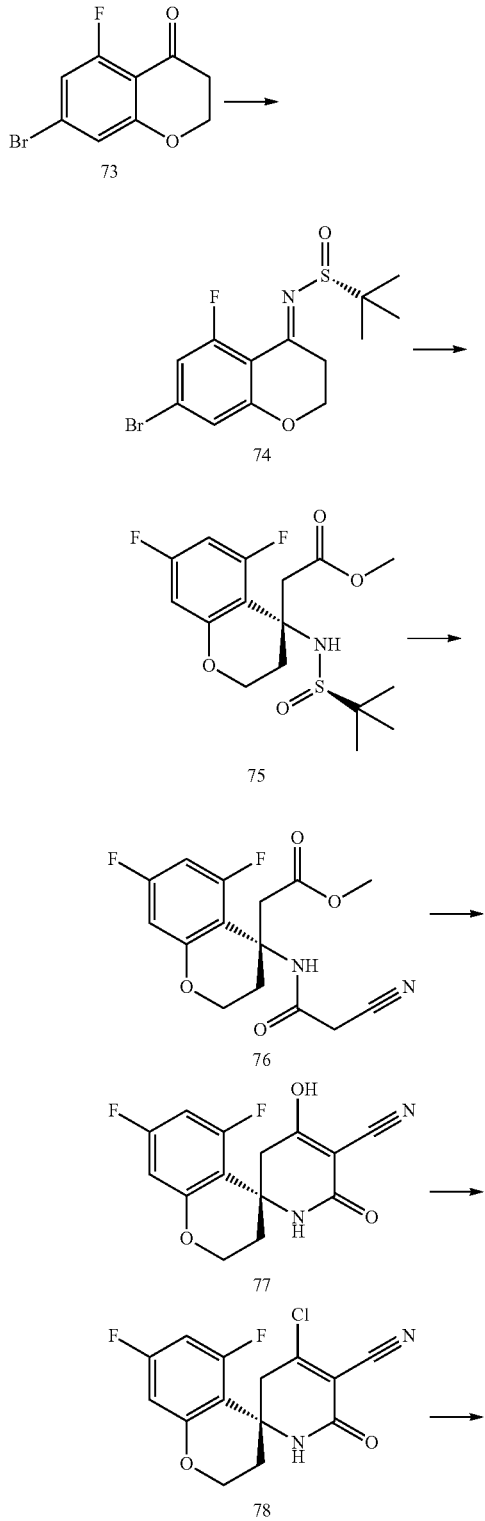

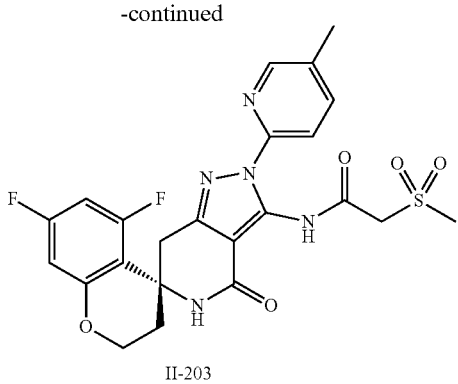

II-203

Step 1

Tetraethoxytitanium (0.654 mL, 3.12 mmol) was added to a solution of toluene (2.5 mL) of (R)-2-methylpropane-2-sulfinamide (631 mg, 5.21 mmol), and a solution of toluene (2.5 mL) of Compound 73 (384 mg, 2.08 mmol) was added. The mixture was stirred at 100° C. for 3 hours. Aqueous citric acid solution and ethyl acetate were added to the reaction solution at room temperature, and insoluble matter was filtered, followed by the extraction with ethyl acetate. The organic layer was washed with saturated sodium chloride solution, and then dried over anhydrous magnesium sulfate. The solvent was evaporated under reduced pressure, and the obtained residue was purified by the silica gel column chromatography (hexane-ethyl acetate) to give Compound 74 (428 mg, yield 72%).

$^1$H-NMR (CDCl3) δ: 1.32 (s, 9H), 3.31-3.38 (m, 1H), 3.45-3.52 (m, 1H), 4.27-4.33 (m, 1H), 4.36-4.41 (m, 1H), 6.43-6.49 (m, 2H).

Step 2

To a 1 mol/L lithium hexamethyldisilazide/tetrahydrofuran solution (2.23 mL, 2.23 mmol), tetrahydrofuran (1 mL) and methyl acetate (0.178 mL, 2.23 mmol) were added at −78° C. and stirred for 1 hour. Thereafter, a 1 mol/L titanium chloride triisopropoxide/hexane solution (2.98 mL, 2.98 mmol) was added dropwise at −78° C., and the mixture was stirred for 30 minutes. Thereafter, a solution of tetrahydrofuran (1 mL) of Compound 74 (428 mg, 1.49 mmol) was added dropwise at −78° C., and the mixture was stirred for 4 hours. A 10% aqueous citric acid solution and Rochelle salt were added to the reaction solution, and the mixture was warmed to room temperature and stirred for 12 hours, followed by the extraction with ethyl acetate. The organic layer was washed with saturated sodium bicarbonate water and saturated aqueous sodium chloride solution, and then dried over anhydrous magnesium sulfate. The solvent was evaporated under reduced pressure, and the obtained residue was purified by the silica gel column chromatography (hexane-ethyl acetate) to give Compound 75 (305 mg, yield 57%).

$^1$H-NMR (CDCl3) δ: 1.22 (s, 9H), 2.19-2.27 (m, 1H), 2.45-2.49 (m, 1H), 2.74 (d, J=15.9 Hz, 1H), 3.40 (d, J=15.9 Hz, 1H), 3.70 (s, 3H), 4.19-4.24 (m, 1H), 4.51-4.57 (m, 1H), 5.02 (s, 1H), 6.36-6.47 (m, 2H).

Step 3

A 4 mol/L dioxane hydrochloride solution (0.44 mL, 1.77 mmol) was added to a solution of methanol (2.6 mL) of Compound 75 (305 mg, 0.85 mmol), and the mixture was stirred at 0° C. for 1 hour. After the solvent of the reaction solution was evaporated under reduced pressure, the obtained residue was dissolved in tetrahydrofuran (2.5 ml), and 2-cyanoacetic acid (108 mg, 1.27 mmol), HATU (482 mg, 1.27 mmol), and triethylamine (0.29 mL, 2.11 mmol) were added. The mixture was stirred at room temperature for 4 hours. Water was added to the reaction solution, followed by the extraction with ethyl acetate. After washing with saturated sodium bicarbonate water and saturated aqueous sodium chloride solution, drying was performed over anhydrous sodium sulfate, and the solvent was evaporated under reduced pressure. The obtained residue was purified by silica gel column chromatography (hexane-ethyl acetate) and powdered with hexane-ethyl acetate to give Compound 76 (170 mg, yield 62%).

$^1$H-NMR (CDCl3) δ: 2.08-2.14 (m, 1H), 2.83-2.90 (m, 1H), 2.96 (d, J=14.7 Hz, 1H), 3.26-3.33 (m, 3H), 3.75 (s, 3H), 4.13-4.18 (m, 1H), 4.27-4.33 (m, 1H), 6.35-6.44 (m, 2H), 7.51 (s, 1H).

Step 4

A 1 mol/L sodium methoxide methanol solution (2.6 mL, 2.6 mmol) was added to methanol (4 mL) of Compound 76 (393 mg, 1.21 mmol) and a tetrahydrofuran (1 mL) solution, and the mixture was stirred at room temperature for 7 hours. A 2 mol/L aqueous solution of hydrochloric acid (1.3 mL) was added to the reaction solution, and methanol was added to the residue obtained after concentration. Insoluble matter was removed by filtration, and the solvent was evaporated under reduced pressure. Ethyl acetate was added to the obtained residue to be powdered, and thus to give Compound 77 (213 mg, 60%).

$^1$H-NMR (DMSO-D$_6$) δ: 2.07-2.17 (m, 2H), 2.72 (d, J=17.7 Hz, 1H), 3.19 (d, J=17.7 Hz, 1H), 4.10-4.22 (m, 2H), 6.61 (br-d, J=10.2 Hz, 1H), 6.78-6.84 (m, 1H), 7.89 (s, 1H).

Step 5

DMF (2.66 mL, 34.2 mmol) and phosphoryl chloride (0.35 mL, 3.76 mmol) were added to a solution of dichloroethane (10 mL) of Compound 77 (1.0 g, 3.42 mmol), and the mixture was stirred at room temperature for 20 hours. Water was added to the reaction solution, followed by the extraction with chloroform. After washing with saturated sodium bicarbonate water and saturated aqueous sodium chloride solution, drying was performed over anhydrous magnesium sulfate, and the solvent was evaporated under reduced pressure. The obtained residue was purified by the silica gel column chromatography (hexane-ethyl acetate) to give Compound 78 (413 mg, yield 39%).

[M+H]=310.95, measurement condition C

Step 6

2-hydrazinyl-5-methylpyridine hydrochloride (30.8 mg, 0.19 mmol) and sodium bicarbonate (34 mg, 0.40 mmol) were added to a solution of ethanol (1 mL) of Compound 78 (50 mg, 0.16 mmol), and the mixture was stirred at 80° C. for 2 hours. Water was added to the reaction solution, followed by the extraction with ethyl acetate, and after washing with saturated aqueous sodium chloride solution, drying was performed over anhydrous magnesium sulfate. The solvent was evaporated under reduced pressure. The obtained residue was dissolved in dichloromethane (1.0 mL), and a solution of dichloromethane (1.0 ml) of 2-(methanesulfonyl)acetyl chloride (0.64 mmol) and pyridine (0.052 ml, 0.64 mmol) were added at 0° C. The mixture was stirred for 3 hours. At room temperature, water was added, followed by the extraction with ethyl acetate, and the resultant was dried over magnesium sulfate. The solvent was evaporated under reduced pressure. The obtained residue was purified by silica gel column chromatography (chloroform-methanol, amino silica gel), and powdered with hexane-ethyl acetate to give Compound 11-203 (52.7 mg, 41%).

$^1$H-NMR (CDCl3) δ: 2.19-2.26 (m, 1H), 2.32-2.40 (m, 4H), 2.99 (d, J=16.2 Hz, 1H), 3.22 (s, 3H), 3.81 (d, J=16.2 Hz, 1H), 4.15-4.20 (m, 4H), 5.77 (s, 1H), 6.47-6.52 (m, 2H), 7.69-7.71 (m, 1H), 7.81 (d, J=8.3 Hz, 1H), 8.30 (br-s, 1H).

The following compounds were synthesized in the same manner.

TABLE 1
| No. | Structure |
|---|---|
| I-1 | 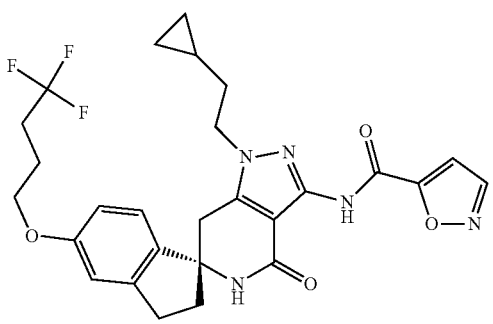 [SMILES: O=C(Nc1nn(CCC2CC2)c2c1C(=O)N[C@@]1(CCc3cc(OCCCC(F)(F)F)ccc31)C2)c1ccno1] |
| I-2 | 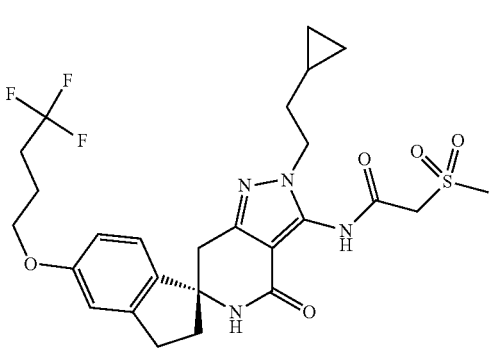 [SMILES: CS(=O)(=O)CC(=O)Nc1c2c(nn1CCC1CC1)C[C@]1(CCc3cc(OCCCC(F)(F)F)ccc31)NC2=O] |
| I-3 | 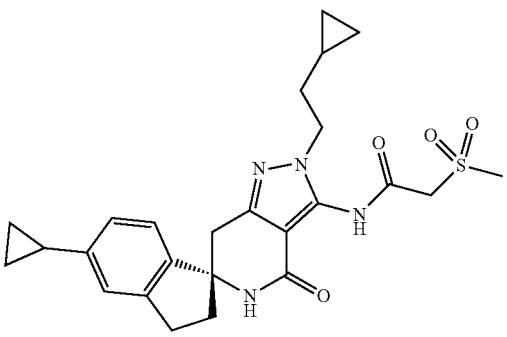 [SMILES: CS(=O)(=O)CC(=O)Nc1c2c(nn1CCC1CC1)C[C@]1(CCc3cc(C4CC4)ccc31)NC2=O] |
| I-4 | 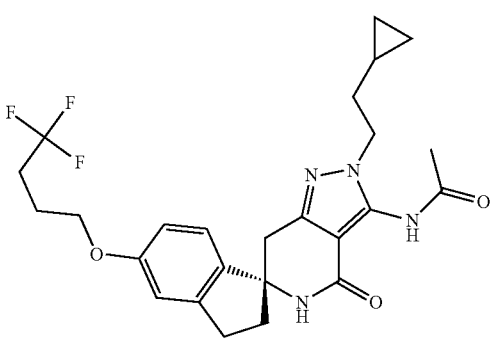 [SMILES: CC(=O)Nc1c2c(nn1CCC1CC1)C[C@]1(CCc3cc(OCCCC(F)(F)F)ccc31)NC2=O] |

TABLE 1-continued

| No. | Structure |
|---|---|
| I-5 | 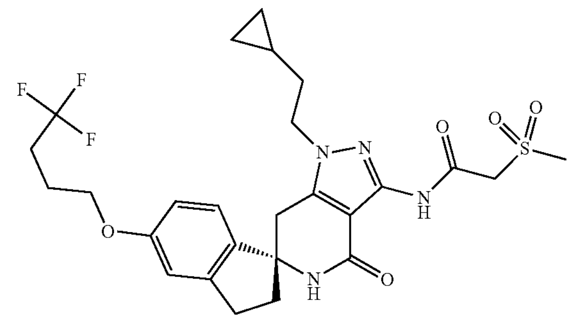 [SMILES: CS(=O)(=O)CC(=O)Nc1nn(CCC2CC2)c2c1C(=O)N[C@@]1(CCc3cc(OCCCC(F)(F)F)ccc31)C2] |
| I-6 | 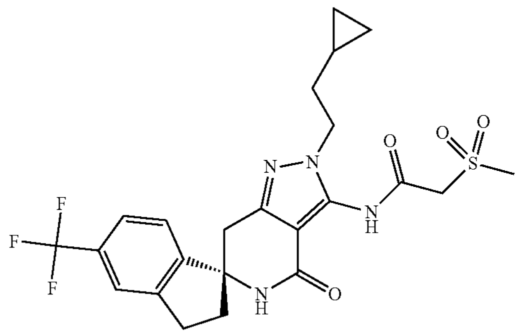 [SMILES: CS(=O)(=O)CC(=O)Nc1c2c(nn1CCC1CC1)C[C@]1(CCc3cc(C(F)(F)F)ccc31)NC2=O] |
| I-7 | 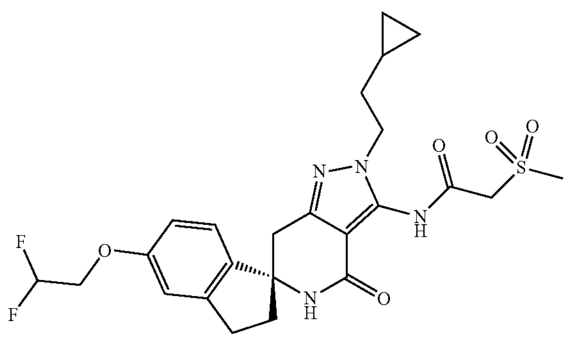 [SMILES: CS(=O)(=O)CC(=O)Nc1c2c(nn1CCC1CC1)C[C@]1(CCc3cc(OCC(F)F)ccc31)NC2=O] |
| I-8 | 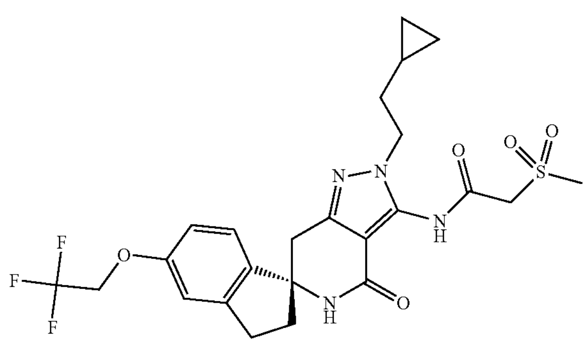 [SMILES: CS(=O)(=O)CC(=O)Nc1c2c(nn1CCC1CC1)C[C@]1(CCc3cc(OCC(F)(F)F)ccc31)NC2=O] |

TABLE 1-continued
| No. | Structure |
|---|---|
| I-9 | 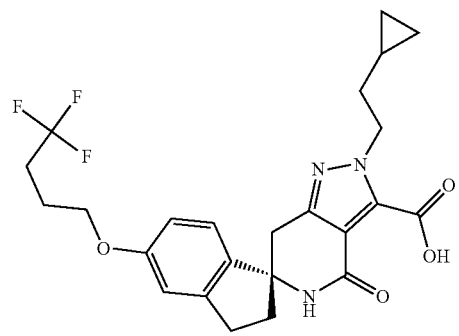 [SMILES: O=C1N[C@@]2(CCc3cc(OCCCC(F)(F)F)ccc32)Cc2nn(CCC3CC3)c(C(=O)O)c21] |
| I-11 | 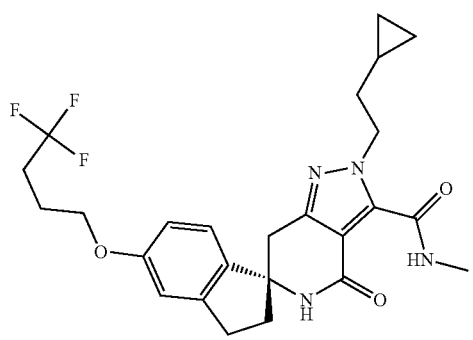 [SMILES: CNC(=O)c1c2c(nn1CCC1CC1)C[C@]1(CCc3cc(OCCCC(F)(F)F)ccc31)NC2=O] |
| I-13 | 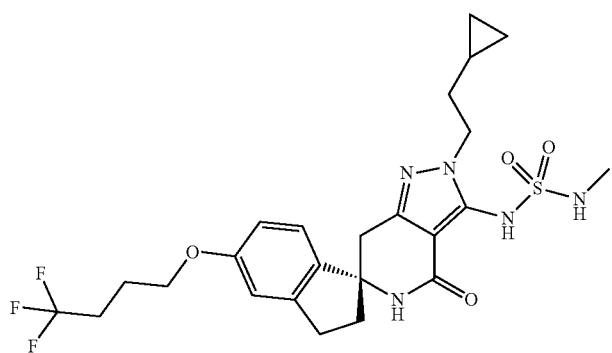 [SMILES: CNS(=O)(=O)Nc1c2c(nn1CCC1CC1)C[C@]1(CCc3cc(OCCCC(F)(F)F)ccc31)NC2=O] |
| I-14 | 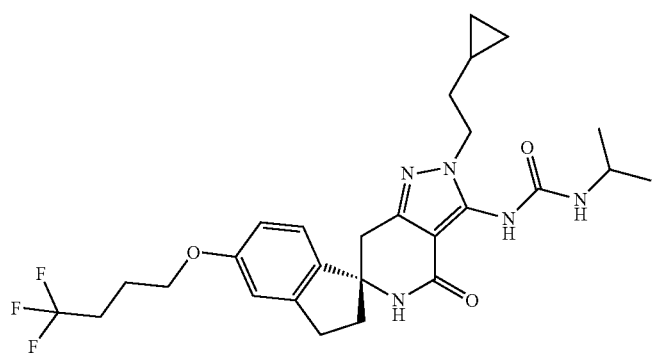 [SMILES: CC(C)NC(=O)Nc1c2c(nn1CCC1CC1)C[C@]1(CCc3cc(OCCCC(F)(F)F)ccc31)NC2=O] |

TABLE 1-continued
| No. | Structure |
|---|---|
| I-15 | 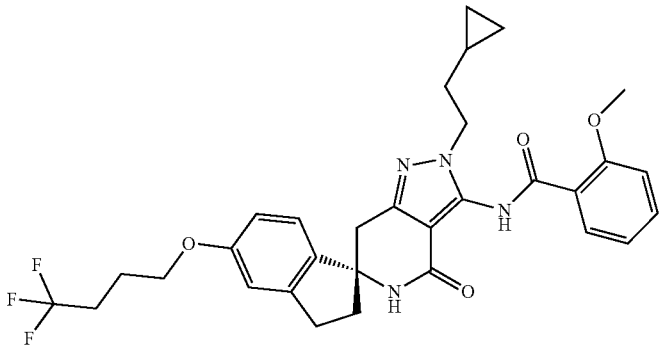 [SMILES: COc1ccccc1C(=O)Nc1c2c(nn1CCC1CC1)C[C@]1(CCc3cc(OCCCC(F)(F)F)ccc31)NC2=O] |
| I-16 | 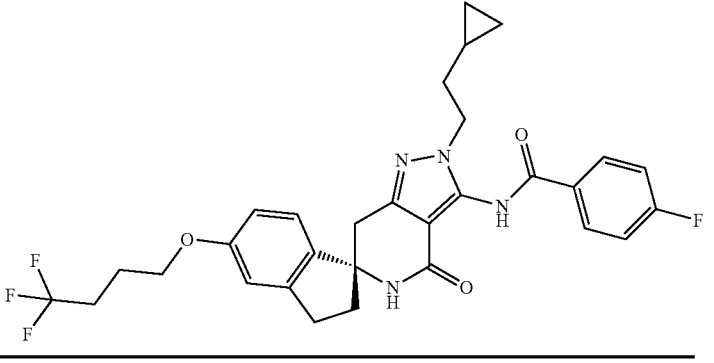 |
TABLE 2
| I-17 | 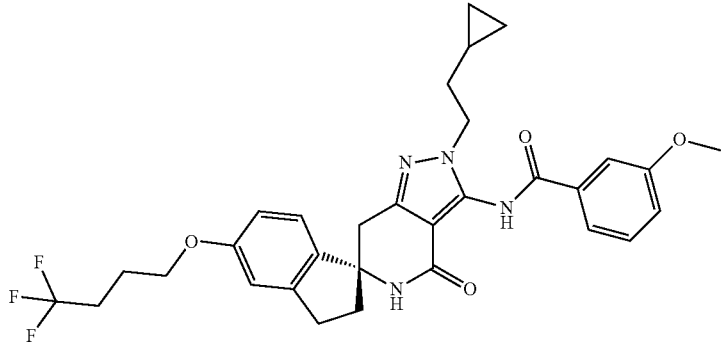 [SMILES: COc1cccc(C(=O)Nc2c3c(nn2CCC2CC2)C[C@]2(CCc4cc(OCCCC(F)(F)F)ccc42)NC3=O)c1] |
|---|---|
| I-18 | 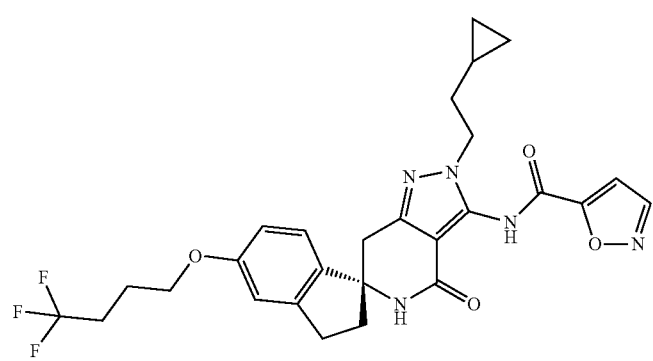 [SMILES: O=C(Nc1c2c(nn1CCC1CC1)C[C@]1(CCc3cc(OCCCC(F)(F)F)ccc31)NC2=O)c1ccno1] |

TABLE 2-continued
I-19
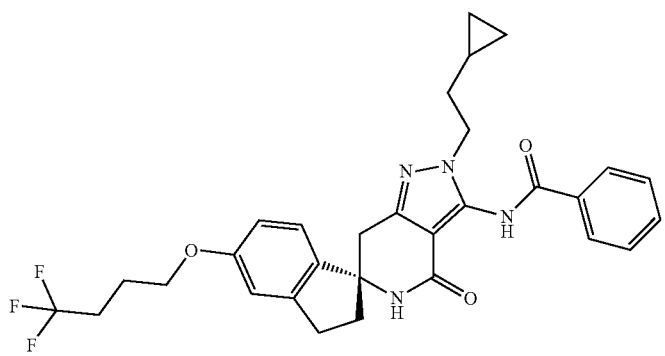 [SMILES: O=C(Nc1c2c(nn1CCC1CC1)C[C@]1(CCc3cc(OCCCC(F)(F)F)ccc31)NC2=O)c1ccccc1]
I-20
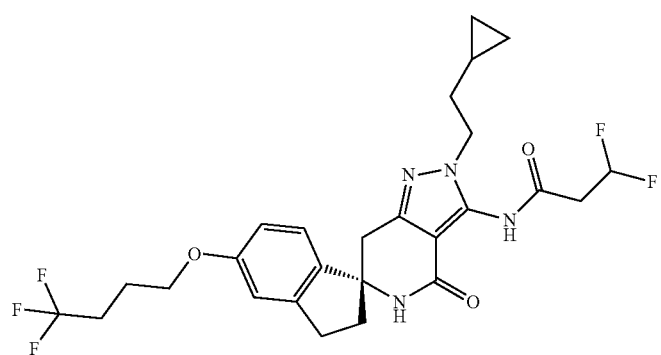 [SMILES: O=C(CC(F)F)Nc1c2c(nn1CCC1CC1)C[C@]1(CCc3cc(OCCCC(F)(F)F)ccc31)NC2=O]
I-21
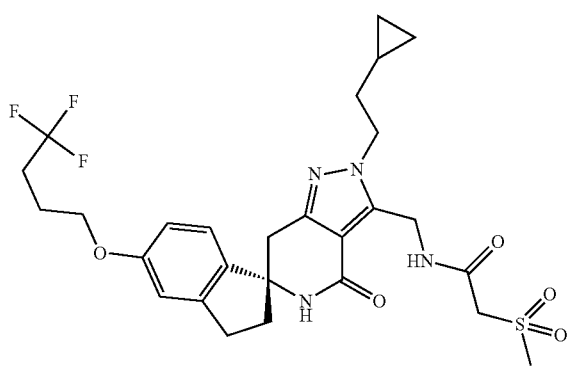 [SMILES: CS(=O)(=O)CC(=O)NCc1c2c(nn1CCC1CC1)C[C@]1(CCc3cc(OCCCC(F)(F)F)ccc31)NC2=O]
I-22
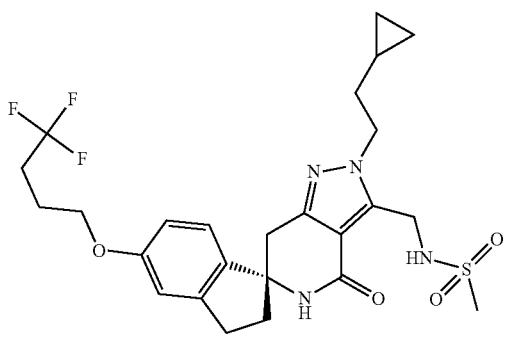 [SMILES: CS(=O)(=O)NCc1c2c(nn1CCC1CC1)C[C@]1(CCc3cc(OCCCC(F)(F)F)ccc31)NC2=O]

TABLE 2-continued
I-23
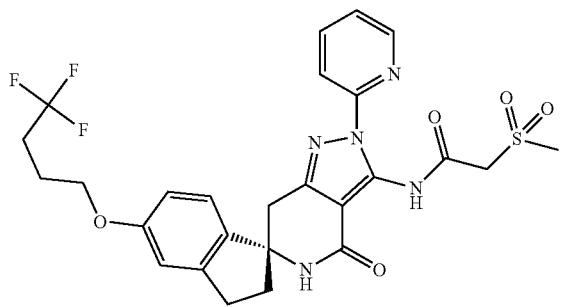 [SMILES: CS(=O)(=O)CC(=O)Nc1c2c(nn1-c1ccccn1)C[C@]1(CCc3cc(OCCCC(F)(F)F)ccc31)NC2=O]
I-25
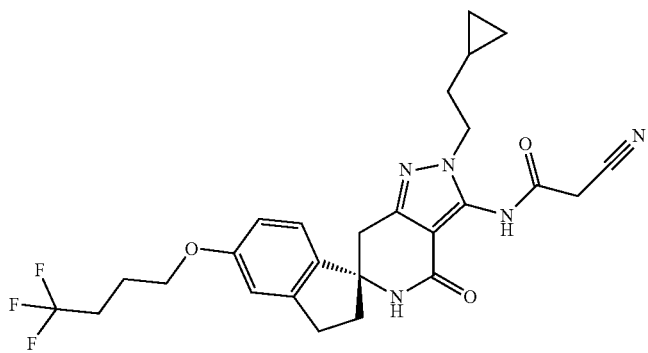 [SMILES: N#CCC(=O)Nc1c2c(nn1CCC1CC1)C[C@]1(CCc3cc(OCCCC(F)(F)F)ccc31)NC2=O]
I-26
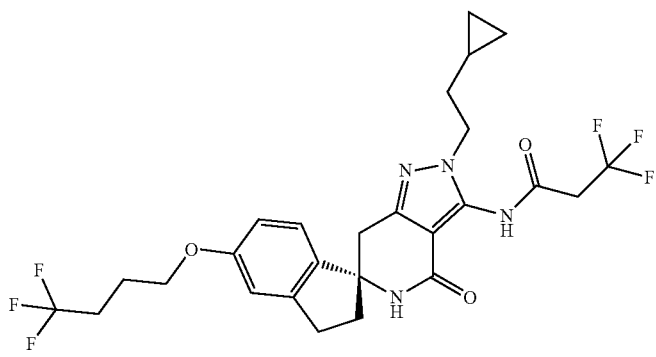 [SMILES: O=C(CC(F)(F)F)Nc1c2c(nn1CCC1CC1)C[C@]1(CCc3cc(OCCCC(F)(F)F)ccc31)NC2=O]
I-27
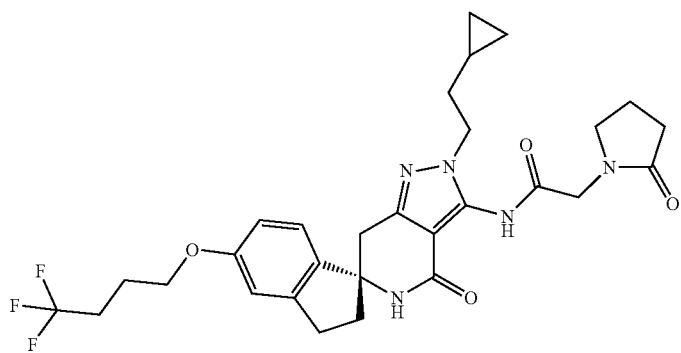 [SMILES: O=C(CN1CCCC1=O)Nc1c2c(nn1CCC1CC1)C[C@]1(CCc3cc(OCCCC(F)(F)F)ccc31)NC2=O]

| | |
|---|---|
| I-28 | 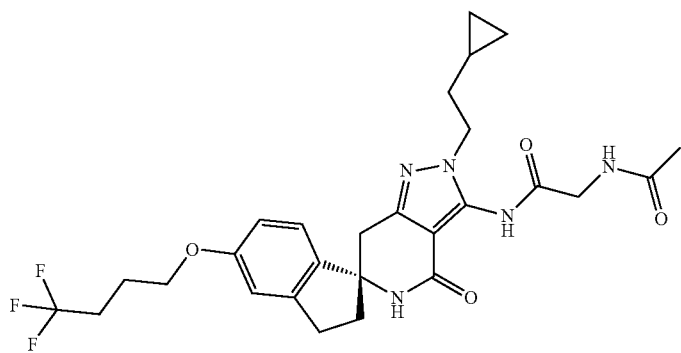 [SMILES: CC(=O)NCC(=O)Nc1c2c(nn1CCC1CC1)C[C@]1(CCc3cc(OCCCC(F)(F)F)ccc31)NC2=O] |
| I-29 | 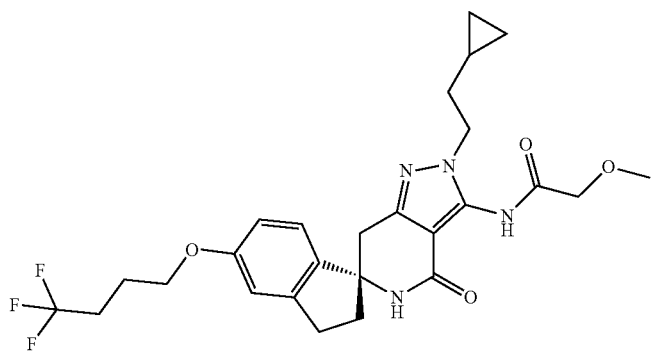 [SMILES: COCC(=O)Nc1c2c(nn1CCC1CC1)C[C@]1(CCc3cc(OCCCC(F)(F)F)ccc31)NC2=O] |
| I-30 | 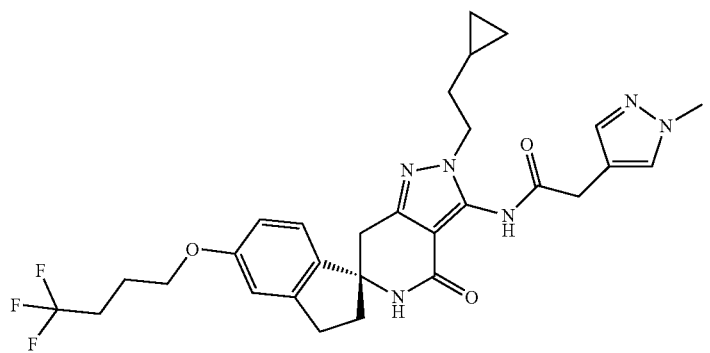 [SMILES: Cn1cc(CC(=O)Nc2c3c(nn2CCC2CC2)C[C@]2(CCc4cc(OCCCC(F)(F)F)ccc42)NC3=O)cn1] |
| I-31 | 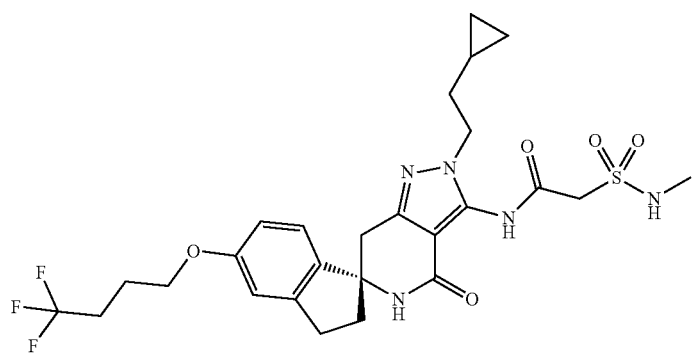 [SMILES: CNS(=O)(=O)CC(=O)Nc1c2c(nn1CCC1CC1)C[C@]1(CCc3cc(OCCCC(F)(F)F)ccc31)NC2=O] |

TABLE 3
I-32
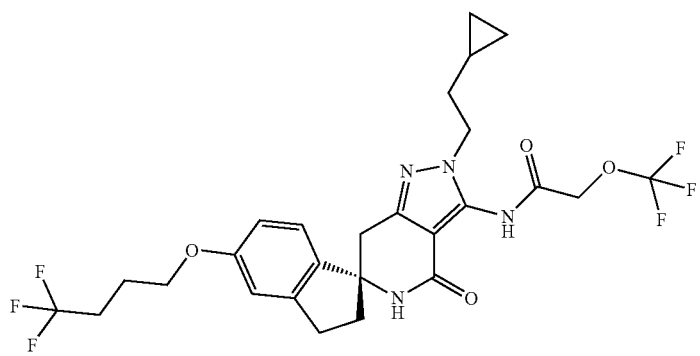 [SMILES: O=C(COC(F)(F)F)Nc1c2c(nn1CCC1CC1)C[C@]1(CCc3cc(OCCCC(F)(F)F)ccc31)NC2=O]
I-33
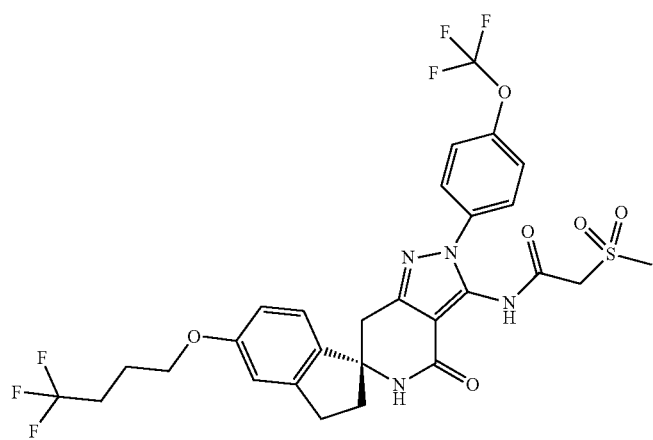 [SMILES: CS(=O)(=O)CC(=O)Nc1c2c(nn1-c1ccc(OC(F)(F)F)cc1)C[C@]1(CCc3cc(OCCCC(F)(F)F)ccc31)NC2=O]
I-35
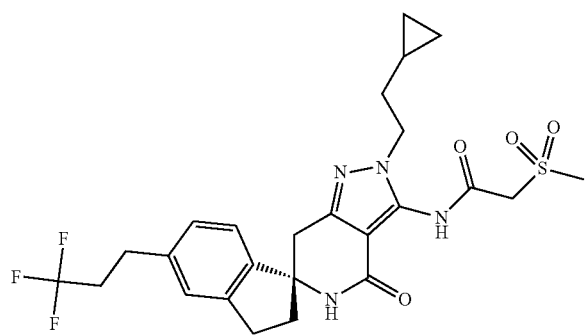 [SMILES: CS(=O)(=O)CC(=O)Nc1c2c(nn1CCC1CC1)C[C@]1(CCc3cc(CCC(F)(F)F)ccc31)NC2=O]
I-36
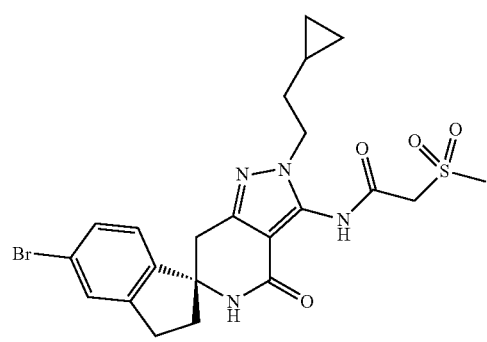 [SMILES: CS(=O)(=O)CC(=O)Nc1c2c(nn1CCC1CC1)C[C@]1(CCc3cc(Br)ccc31)NC2=O]

TABLE 3-continued
I-37
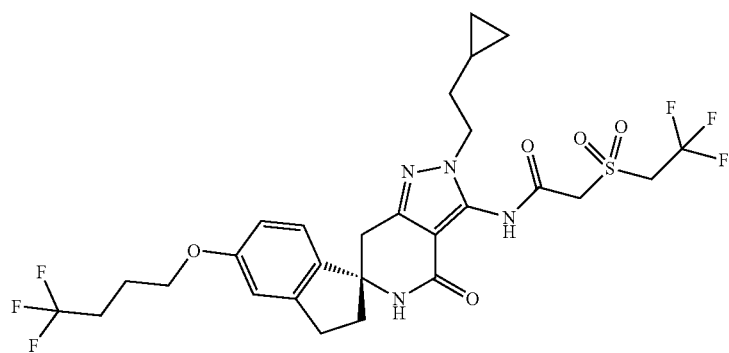 [SMILES: O=C(CS(=O)(=O)CC(F)(F)F)Nc1c2c(nn1CCC1CC1)C[C@]1(CCc3cc(OCCCC(F)(F)F)ccc31)NC2=O]
I-38
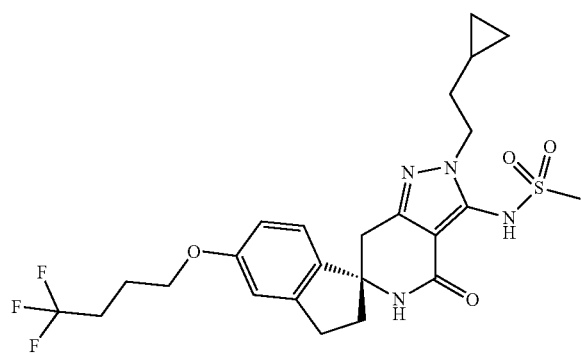 [SMILES: CS(=O)(=O)Nc1c2c(nn1CCC1CC1)C[C@]1(CCc3cc(OCCCC(F)(F)F)ccc31)NC2=O]
I-39
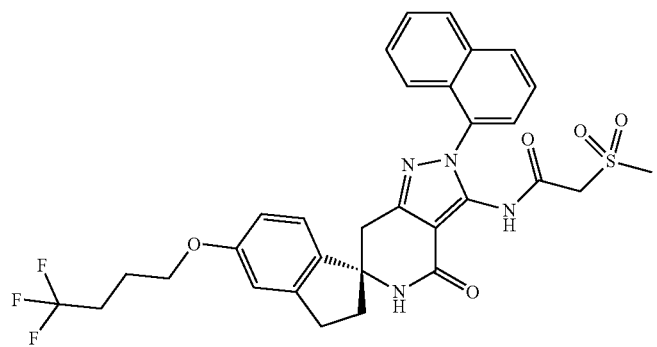 [SMILES: CS(=O)(=O)CC(=O)Nc1c2c(nn1-c1cccc3ccccc13)C[C@]1(CCc3cc(OCCCC(F)(F)F)ccc31)NC2=O]
I-40
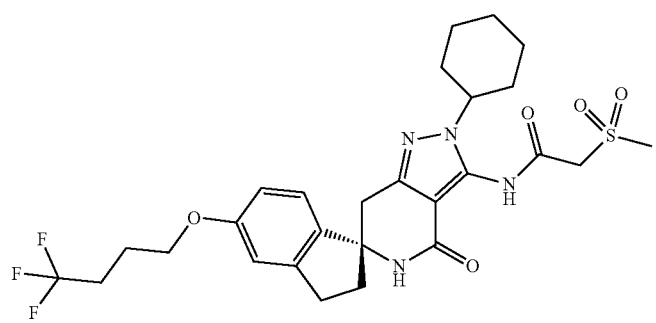 [SMILES: CS(=O)(=O)CC(=O)Nc1c2c(nn1C1CCCCC1)C[C@]1(CCc3cc(OCCCC(F)(F)F)ccc31)NC2=O]

TABLE 3-continued
I-41
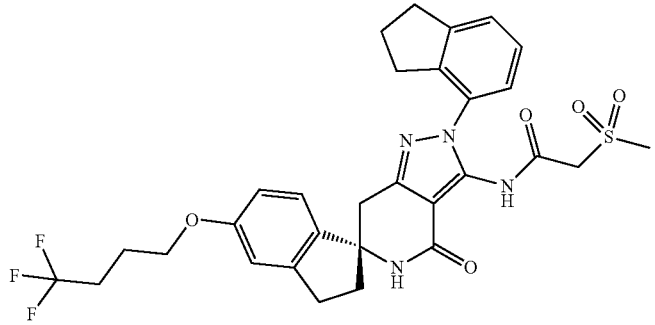 [SMILES: CS(=O)(=O)CC(=O)Nc1c2c(nn1-c1cccc3c1CCC3)C[C@]1(CCc3cc(OCCCC(F)(F)F)ccc31)NC2=O]
I-42
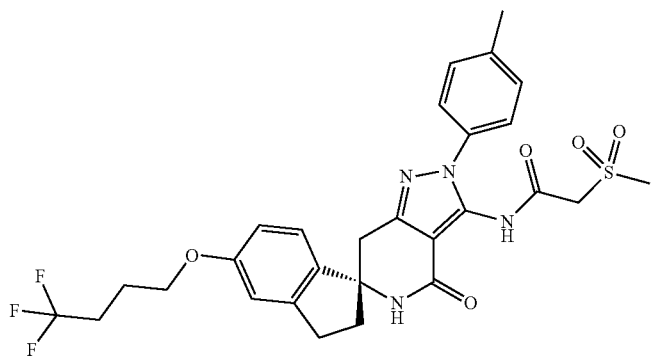 [SMILES: Cc1ccc(-n2nc3c(c2NC(=O)CS(C)(=O)=O)C(=O)N[C@@]2(CCc4cc(OCCCC(F)(F)F)ccc42)C3)cc1]
I-43
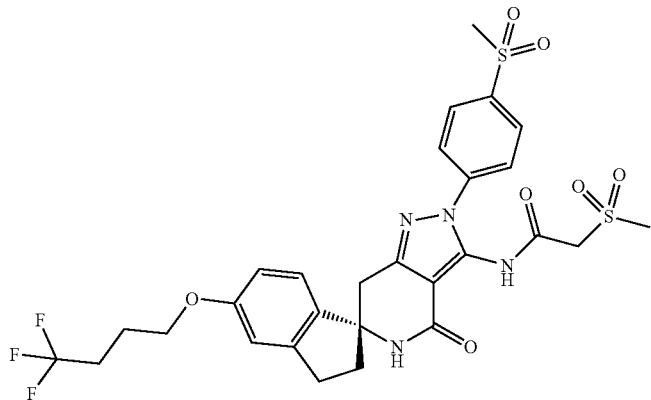 [SMILES: CS(=O)(=O)CC(=O)Nc1c2c(nn1-c1ccc(S(C)(=O)=O)cc1)C[C@]1(CCc3cc(OCCCC(F)(F)F)ccc31)NC2=O]
I-44
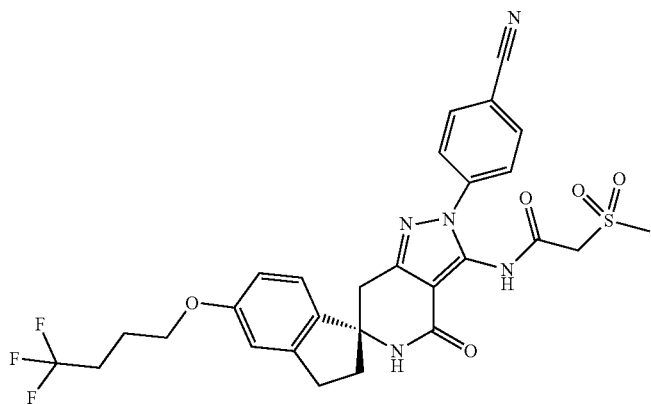 [SMILES: CS(=O)(=O)CC(=O)Nc1c2c(nn1-c1ccc(C#N)cc1)C[C@]1(CCc3cc(OCCCC(F)(F)F)ccc31)NC2=O]

TABLE 3-continued
I-45
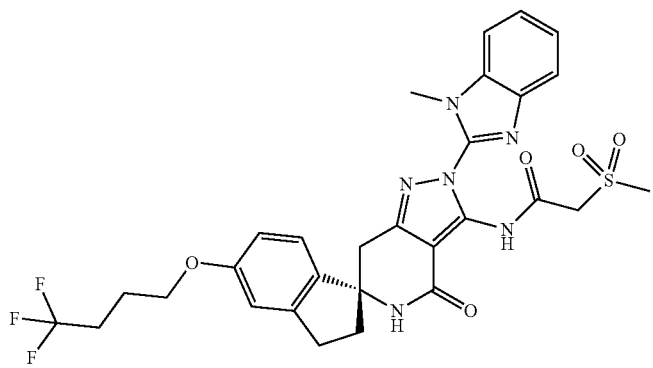 [SMILES: Cn1c(-n2nc3c(c2NC(=O)CS(C)(=O)=O)C(=O)N[C@@]2(CCc4cc(OCCCC(F)(F)F)ccc42)C3)nc2ccccc21]
I-46
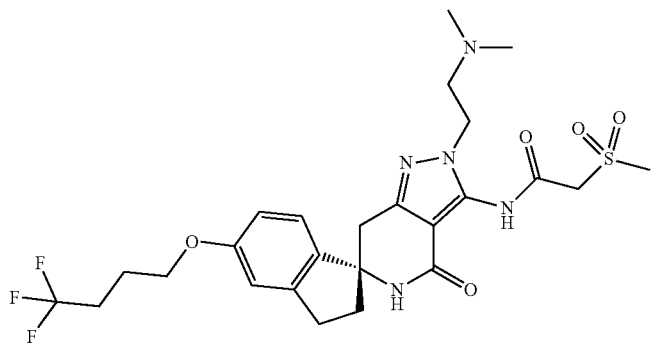 [SMILES: CN(C)CCn1nc2c(c1NC(=O)CS(C)(=O)=O)C(=O)N[C@@]1(CCc3cc(OCCCC(F)(F)F)ccc31)C2]
TABLE 4
I-47
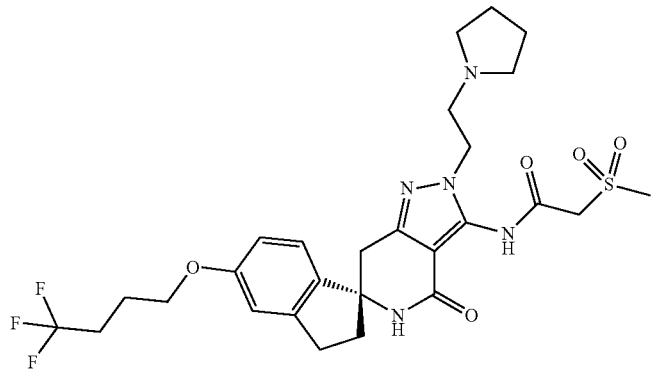 [SMILES: CS(=O)(=O)CC(=O)Nc1c2c(nn1CCN1CCCC1)C[C@]1(CCc3cc(OCCCC(F)(F)F)ccc31)NC2=O]
I-48
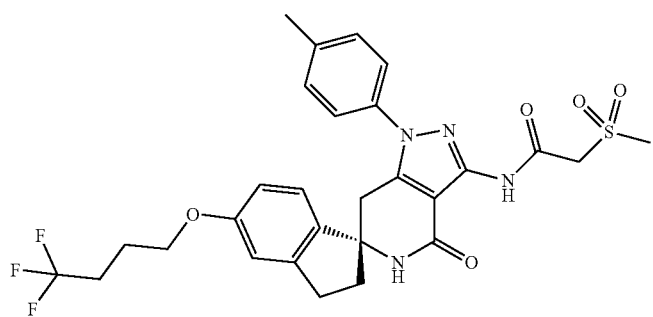 [SMILES: Cc1ccc(-n2nc(NC(=O)CS(C)(=O)=O)c3c2C[C@]2(CCc4cc(OCCCC(F)(F)F)ccc42)NC3=O)cc1]

TABLE 4-continued
I-49
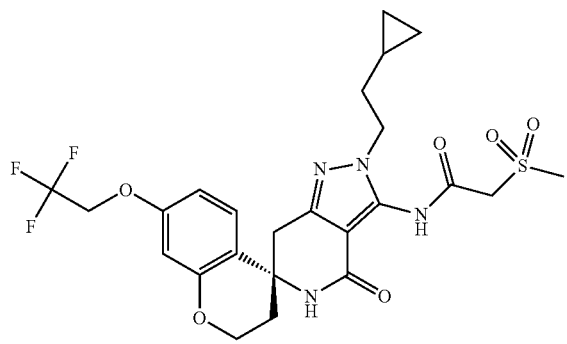 [SMILES: CS(=O)(=O)CC(=O)Nc1c2c(nn1CCC1CC1)C[C@]1(CCOc3cc(OCC(F)(F)F)ccc31)NC2=O]
I-50
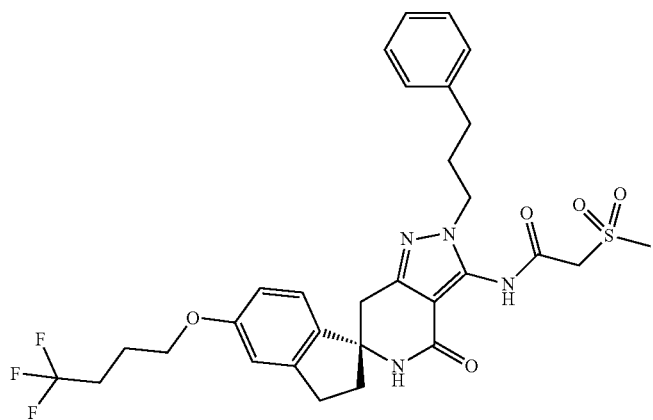 [SMILES: CS(=O)(=O)CC(=O)Nc1c2c(nn1CCCc1ccccc1)C[C@]1(CCc3cc(OCCCC(F)(F)F)ccc31)NC2=O]
I-51
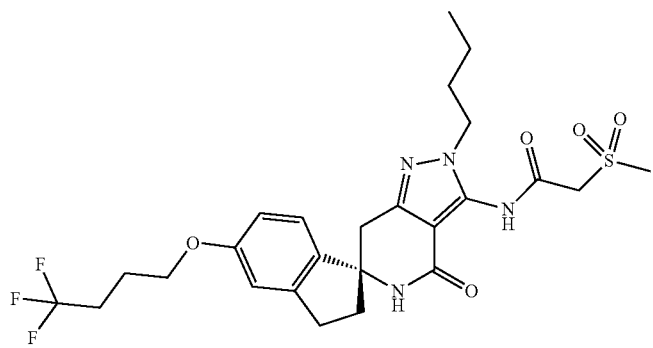 [SMILES: CCCCn1nc2c(c1NC(=O)CS(C)(=O)=O)C(=O)N[C@@]1(CCc3cc(OCCCC(F)(F)F)ccc31)C2]
I-52
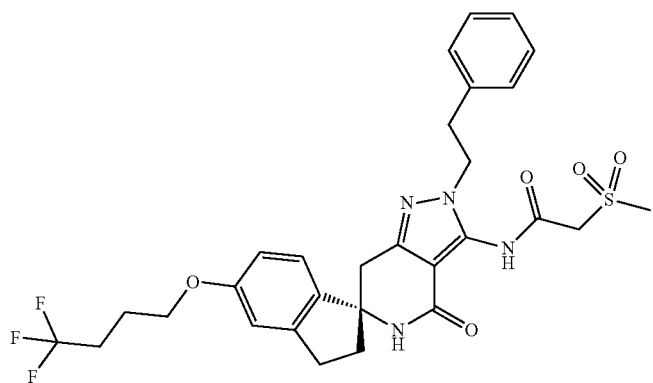 [SMILES: CS(=O)(=O)CC(=O)Nc1c2c(nn1CCc1ccccc1)C[C@]1(CCc3cc(OCCCC(F)(F)F)ccc31)NC2=O]

TABLE 4-continued
I-53
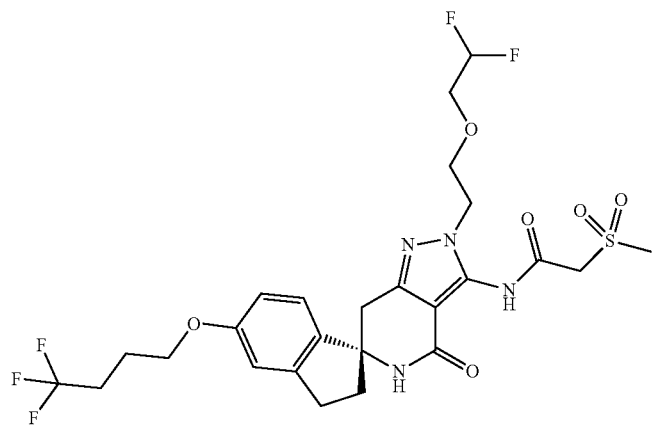 [SMILES: CS(=O)(=O)CC(=O)Nc1c2c(nn1CCOCC(F)F)C[C@]1(CCc3cc(OCCCC(F)(F)F)ccc31)NC2=O]
I-54
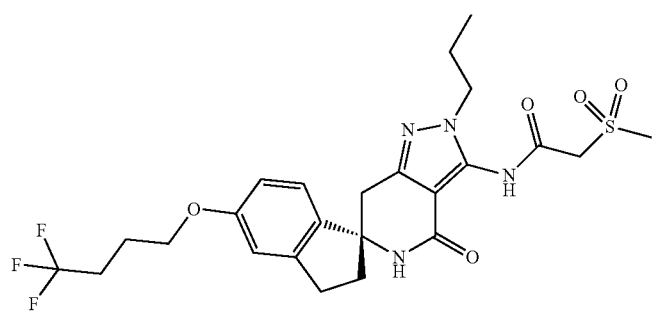 [SMILES: CCCn1nc2c(c1NC(=O)CS(C)(=O)=O)C(=O)N[C@@]1(CCc3cc(OCCCC(F)(F)F)ccc31)C2]
I-56
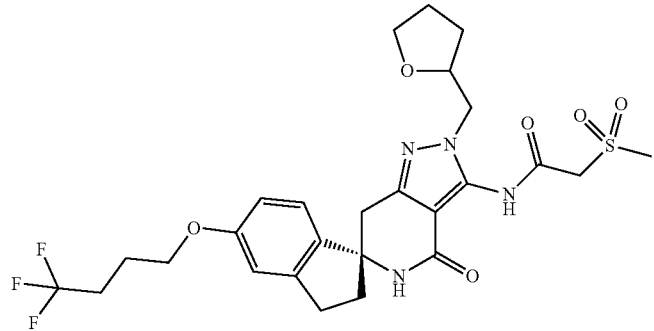 [SMILES: CS(=O)(=O)CC(=O)Nc1c2c(nn1CC1CCCO1)C[C@]1(CCc3cc(OCCCC(F)(F)F)ccc31)NC2=O]
I-57
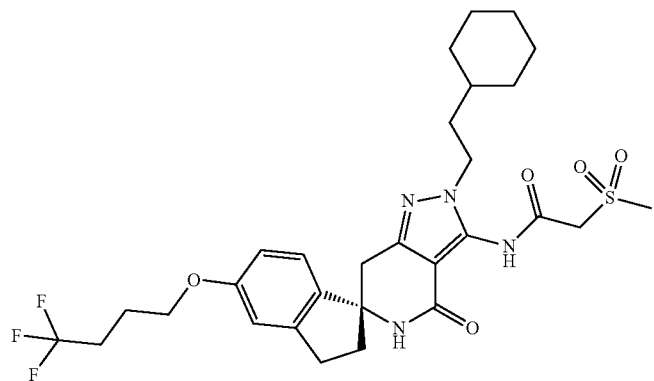 [SMILES: CS(=O)(=O)CC(=O)Nc1c2c(nn1CCC1CCCCC1)C[C@]1(CCc3cc(OCCCC(F)(F)F)ccc31)NC2=O]

TABLE 4-continued
I-58
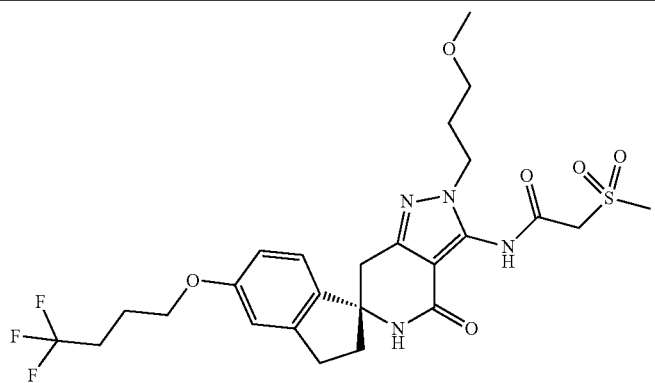
I-59
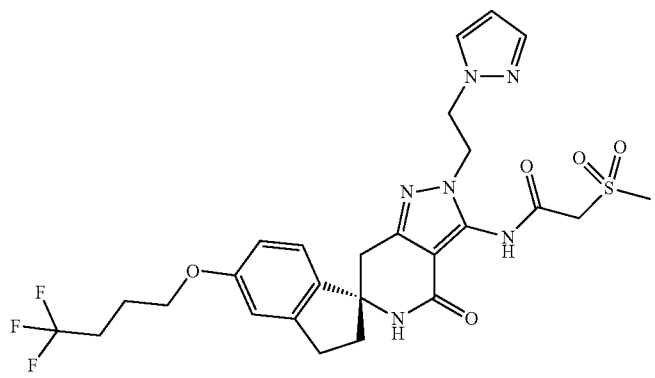 [SMILES: CS(=O)(=O)CC(=O)Nc1c2c(nn1CCn1cccn1)C[C@]1(CCc3cc(OCCCC(F)(F)F)ccc31)NC2=O]
TABLE 5
I-60
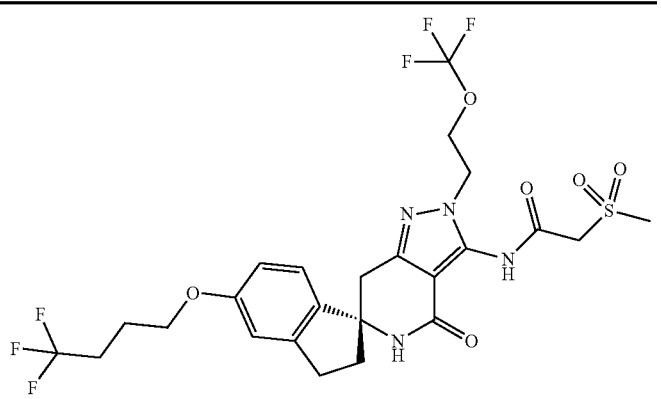

TABLE 5-continued
I-61
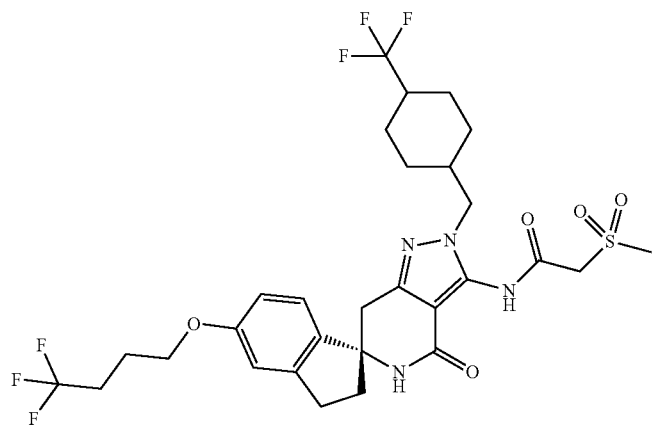 [SMILES: CS(=O)(=O)CC(=O)Nc1c2c(nn1CC1CCC(C(F)(F)F)CC1)C[C@]1(CCc3cc(OCCCC(F)(F)F)ccc31)NC2=O]
I-62
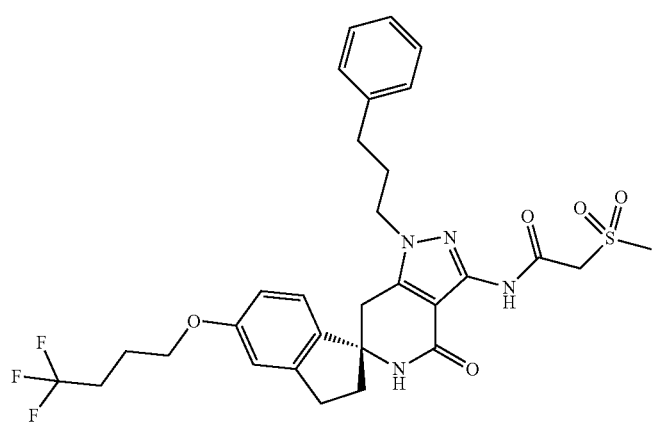 [SMILES: CS(=O)(=O)CC(=O)Nc1nn(CCCc2ccccc2)c2c1C(=O)N[C@@]1(CCc3cc(OCCCC(F)(F)F)ccc31)C2]
I-63
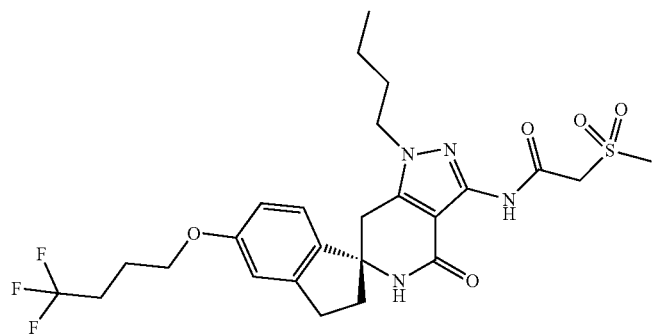 [SMILES: CCCCn1nc(NC(=O)CS(C)(=O)=O)c2c1C[C@]1(CCc3cc(OCCCC(F)(F)F)ccc31)NC2=O]
I-64
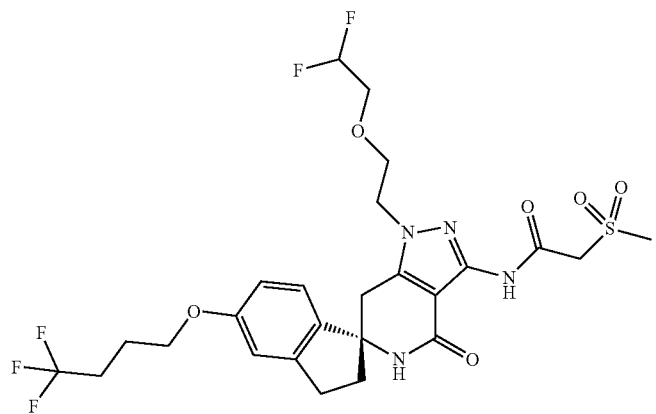 [SMILES: CS(=O)(=O)CC(=O)Nc1nn(CCOCC(F)F)c2c1C(=O)N[C@@]1(CCc3cc(OCCCC(F)(F)F)ccc31)C2]

TABLE 5-continued
I-65
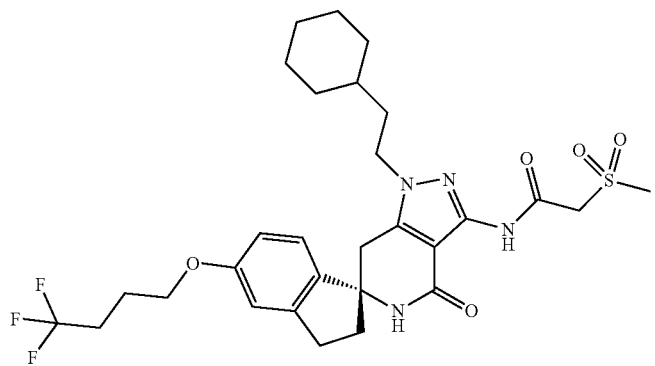 [SMILES: CS(=O)(=O)CC(=O)Nc1nn(CCC2CCCCC2)c2c1C(=O)N[C@@]1(CCc3cc(OCCCC(F)(F)F)ccc31)C2]
I-66
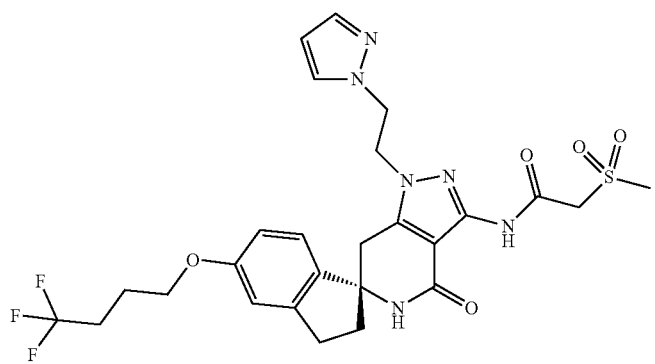 [SMILES: CS(=O)(=O)CC(=O)Nc1nn(CCn2cccn2)c2c1C(=O)N[C@@]1(CCc3cc(OCCCC(F)(F)F)ccc31)C2]
I-67
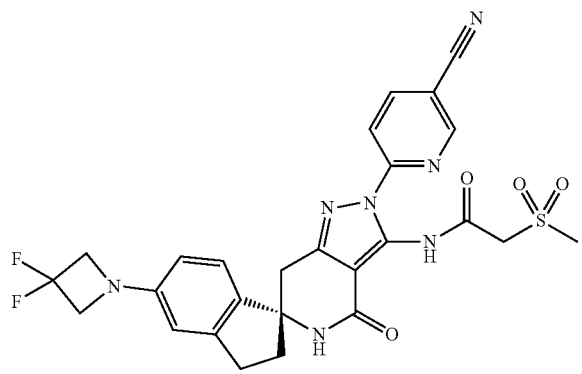 [SMILES: CS(=O)(=O)CC(=O)Nc1c2c(nn1-c1ccc(C#N)cn1)C[C@]1(CCc3cc(N4CC(F)(F)C4)ccc31)NC2=O]
I-68
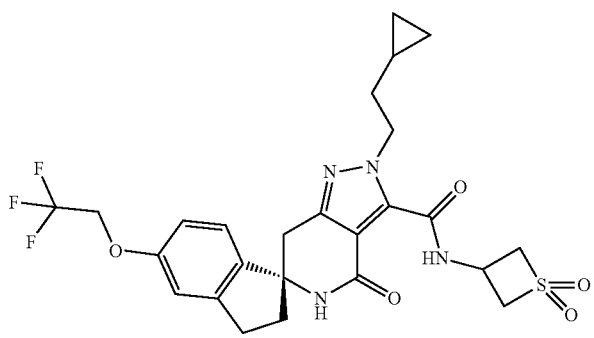 [SMILES: O=C1N[C@@]2(CCc3cc(OCC(F)(F)F)ccc32)Cc2nn(CCC3CC3)c(C(=O)NC3CS(=O)(=O)C3)c21]

TABLE 5-continued
I-69
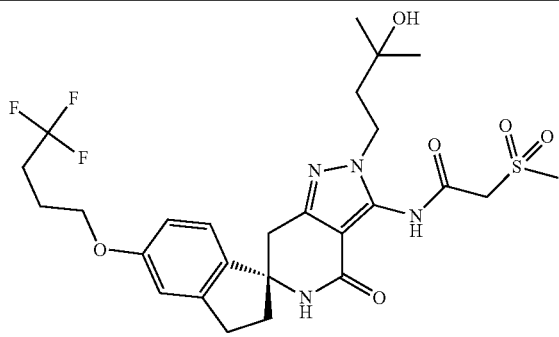
I-70
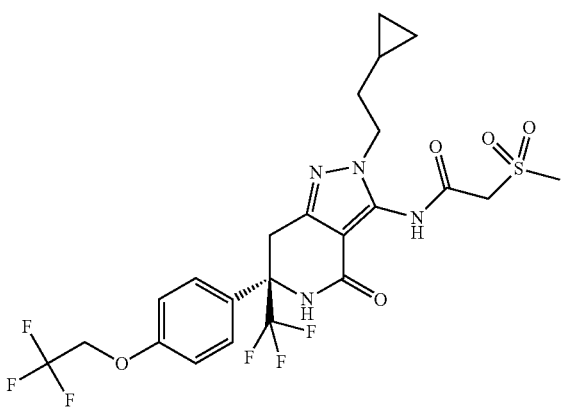 [SMILES: CS(=O)(=O)CC(=O)Nc1c2c(nn1CCC1CC1)C[C@](c1ccc(OCC(F)(F)F)cc1)(C(F)(F)F)NC2=O]
I-71
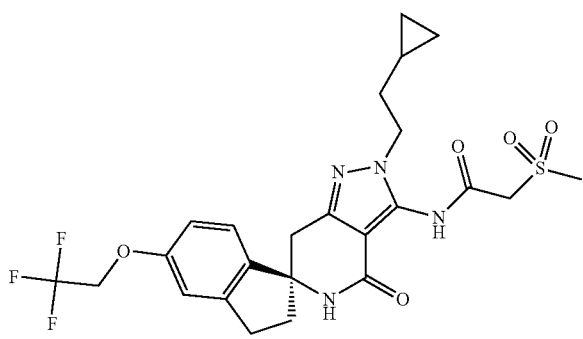 [SMILES: CS(=O)(=O)CC(=O)Nc1c2c(nn1CCC1CC1)C[C@@]1(CCc3cc(OCC(F)(F)F)ccc31)NC2=O]
TABLE 6
I-72
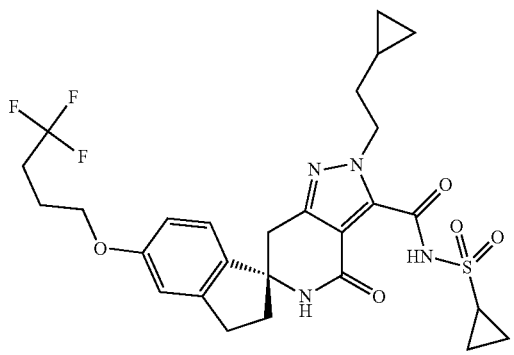 [SMILES: O=C1N[C@@]2(CCc3cc(OCCCC(F)(F)F)ccc32)Cc2nn(CCC3CC3)c(C(=O)NS(=O)(=O)C3CC3)c21]

TABLE 6-continued
I-73
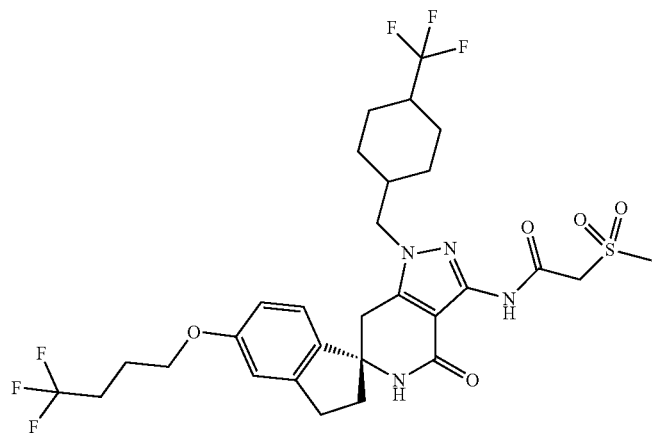 [SMILES: CS(=O)(=O)CC(=O)Nc1nn(CC2CCC(C(F)(F)F)CC2)c2c1C(=O)N[C@@]1(CCc3cc(OCCCC(F)(F)F)ccc31)C2]
I-74
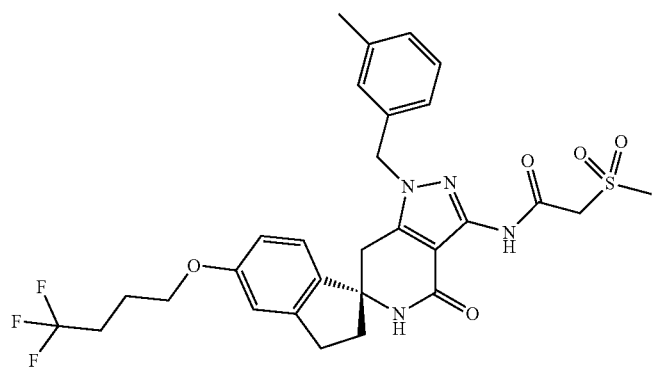 [SMILES: Cc1cccc(Cn2nc(NC(=O)CS(C)(=O)=O)c3c2C[C@]2(CCc4cc(OCCCC(F)(F)F)ccc42)NC3=O)c1]
I-75
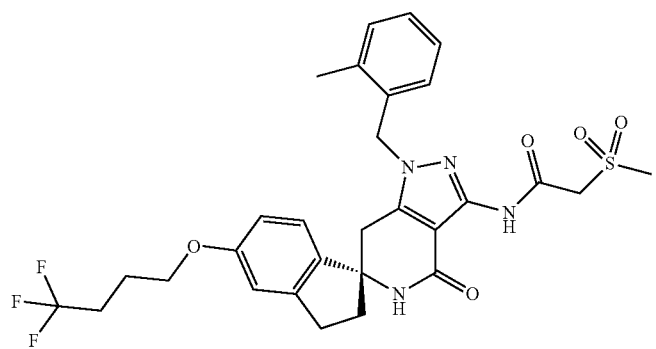 [SMILES: Cc1ccccc1Cn1nc(NC(=O)CS(C)(=O)=O)c2c1C[C@]1(CCc3cc(OCCCC(F)(F)F)ccc31)NC2=O]
I-76
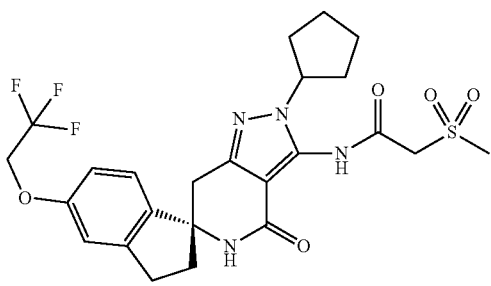 [SMILES: CS(=O)(=O)CC(=O)Nc1c2c(nn1C1CCCC1)C[C@]1(CCc3cc(OCC(F)(F)F)ccc31)NC2=O]

TABLE 6-continued
I-77
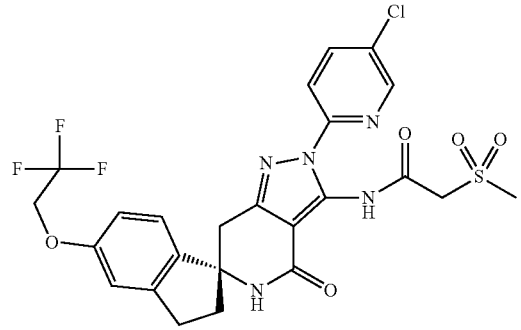
I-78
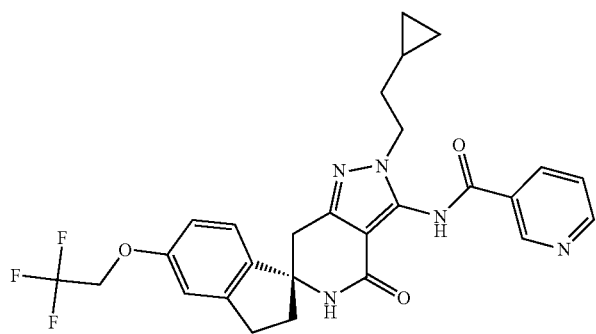 [SMILES: O=C(Nc1c2c(nn1CCC1CC1)C[C@]1(CCc3cc(OCC(F)(F)F)ccc31)NC2=O)c1cccnc1]
I-79
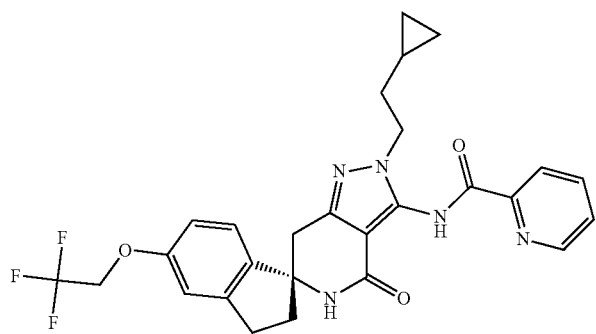 [SMILES: O=C(Nc1c2c(nn1CCC1CC1)C[C@]1(CCc3cc(OCC(F)(F)F)ccc31)NC2=O)c1ccccn1]
I-80
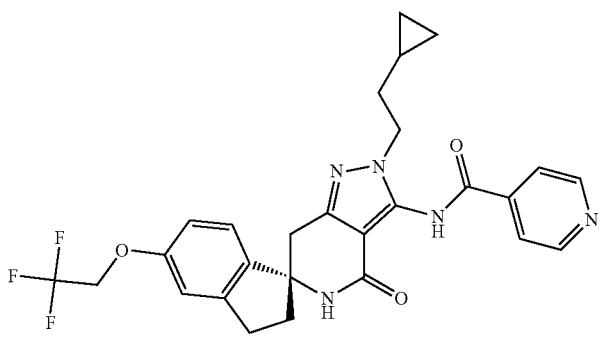 [SMILES: O=C(Nc1c2c(nn1CCC1CC1)C[C@]1(CCc3cc(OCC(F)(F)F)ccc31)NC2=O)c1ccncc1]

TABLE 6-continued
I-81
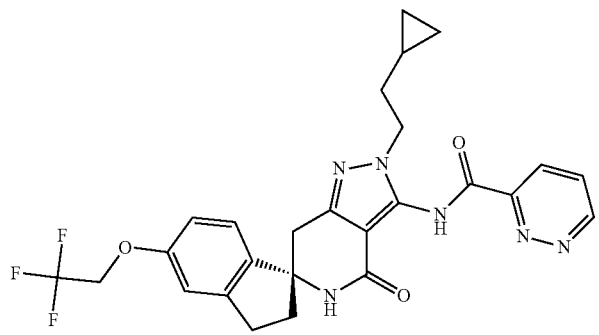 [SMILES: O=C(Nc1c2c(nn1CCC1CC1)C[C@]1(CCc3cc(OCC(F)(F)F)ccc31)NC2=O)c1cccnn1]
I-82
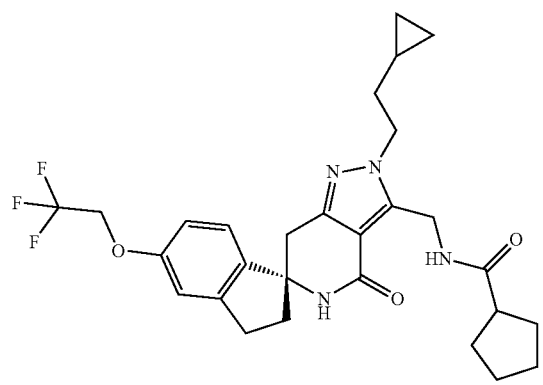 [SMILES: O=C1N[C@@]2(CCc3cc(OCC(F)(F)F)ccc32)Cc2nn(CCC3CC3)c(CNC(=O)C3CCCC3)c21]
I-83
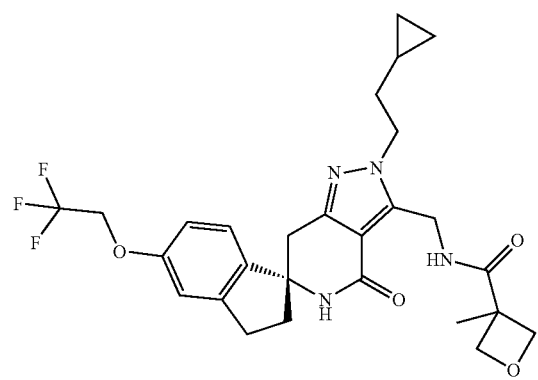 [SMILES: CC1(C(=O)NCc2c3c(nn2CCC2CC2)C[C@]2(CCc4cc(OCC(F)(F)F)ccc42)NC3=O)COC1]
TABLE 7
I-84
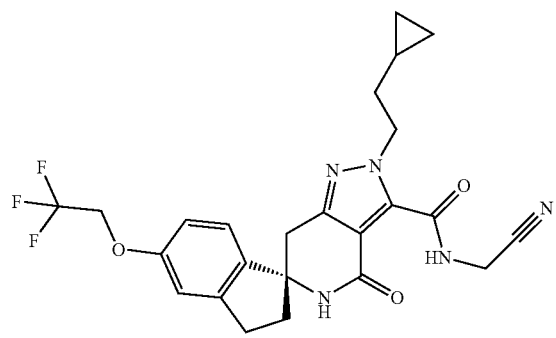 [SMILES: N#CCNC(=O)c1c2c(nn1CCC1CC1)C[C@]1(CCc3cc(OCC(F)(F)F)ccc31)NC2=O]

TABLE 7-continued
I-85
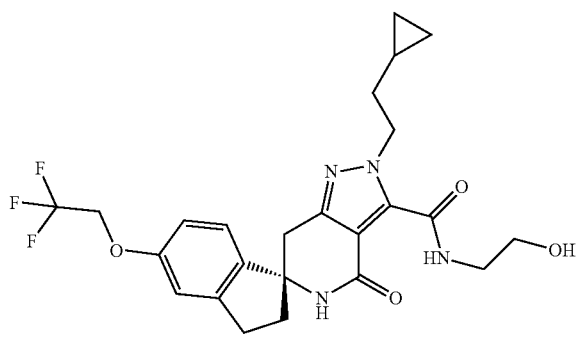 [SMILES: O=C1N[C@@]2(CCc3cc(OCC(F)(F)F)ccc32)Cc2nn(CCC3CC3)c(C(=O)NCCO)c21]
I-86
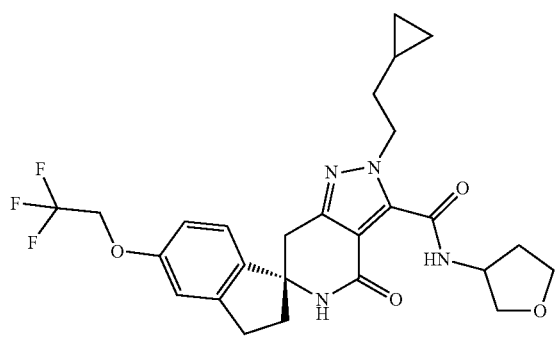 [SMILES: O=C1N[C@@]2(CCc3cc(OCC(F)(F)F)ccc32)Cc2nn(CCC3CC3)c(C(=O)NC3CCOC3)c21]
I-87
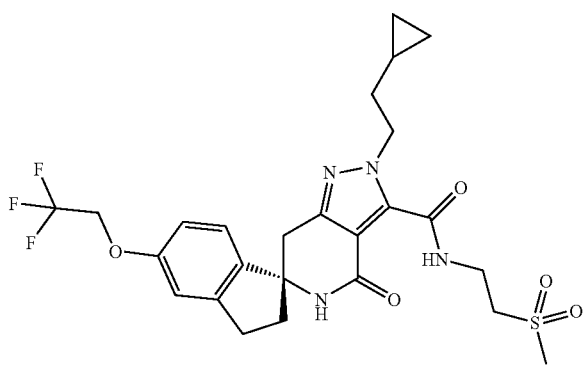 [SMILES: CS(=O)(=O)CCNC(=O)c1c2c(nn1CCC1CC1)C[C@]1(CCc3cc(OCC(F)(F)F)ccc31)NC2=O]
I-88
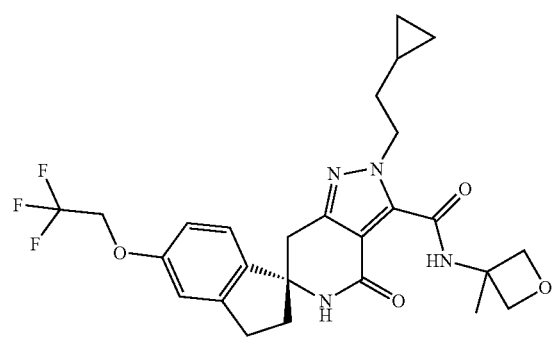 [SMILES: CC1(NC(=O)c2c3c(nn2CCC2CC2)C[C@]2(CCc4cc(OCC(F)(F)F)ccc42)NC3=O)COC1]

TABLE 7-continued
I-89
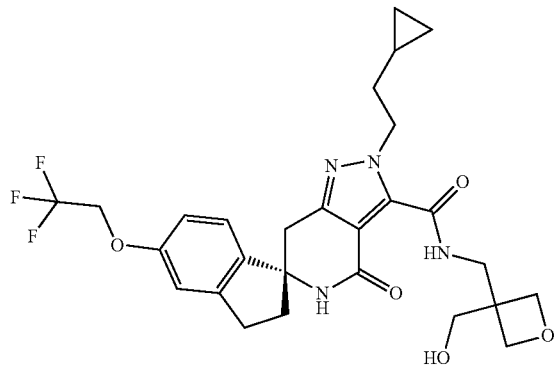 [SMILES: O=C1N[C@@]2(CCc3cc(OCC(F)(F)F)ccc32)Cc2nn(CCC3CC3)c(C(=O)NCC3(CO)COC3)c21]
I-90
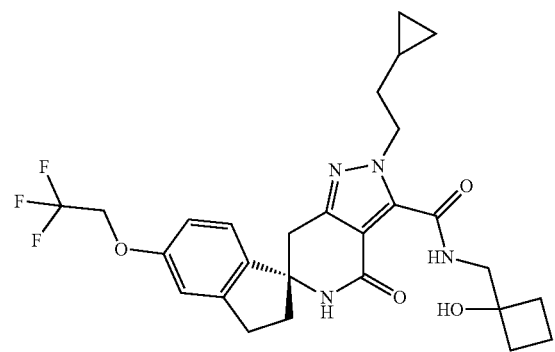 [SMILES: O=C1N[C@@]2(CCc3cc(OCC(F)(F)F)ccc32)Cc2nn(CCC3CC3)c(C(=O)NCC3(O)CCC3)c21]
I-91
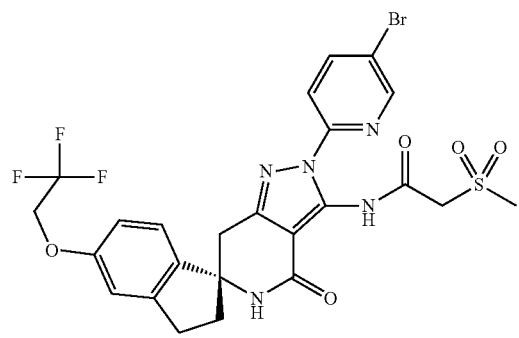 [SMILES: CS(=O)(=O)CC(=O)Nc1c2c(nn1-c1ccc(Br)cn1)C[C@]1(CCc3cc(OCC(F)(F)F)ccc31)NC2=O]
I-92
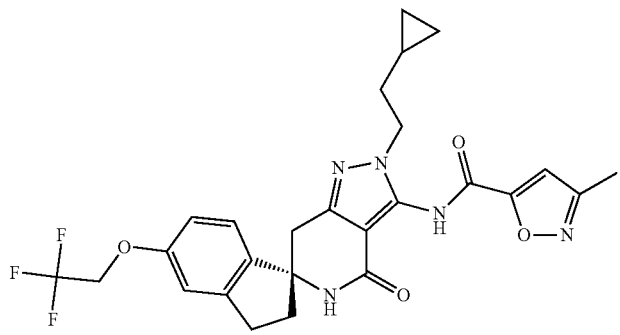 [SMILES: Cc1cc(C(=O)Nc2c3c(nn2CCC2CC2)C[C@]2(CCc4cc(OCC(F)(F)F)ccc42)NC3=O)on1]

TABLE 7-continued
I-93
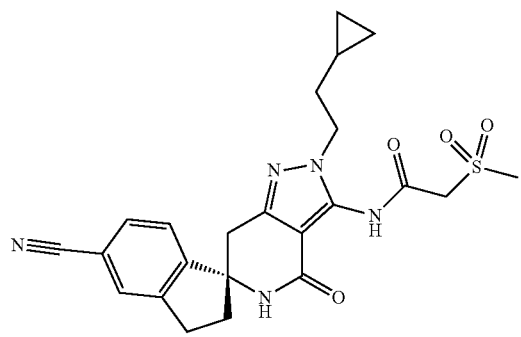 [SMILES: CS(=O)(=O)CC(=O)Nc1c2c(nn1CCC1CC1)C[C@]1(CCc3cc(C#N)ccc31)NC2=O]
I-94
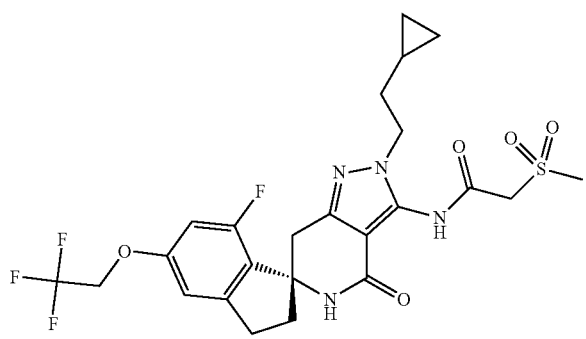 [SMILES: CS(=O)(=O)CC(=O)Nc1c2c(nn1CCC1CC1)C[C@]1(CCc3cc(OCC(F)(F)F)cc(F)c31)NC2=O]
I-95
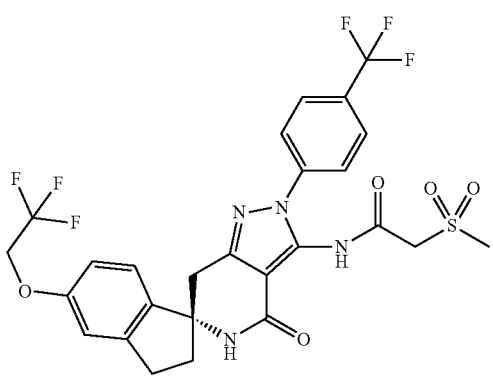 [SMILES: CS(=O)(=O)CC(=O)Nc1c2c(nn1-c1ccc(C(F)(F)F)cc1)C[C@]1(CCc3cc(OCC(F)(F)F)ccc31)NC2=O]
TABLE 8
I-96
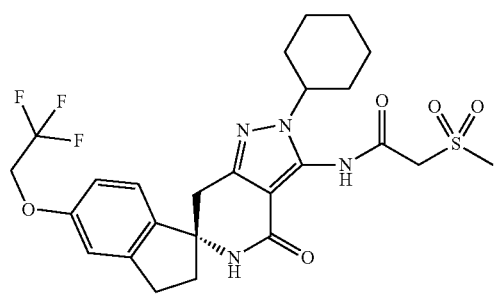 [SMILES: CS(=O)(=O)CC(=O)Nc1c2c(nn1C1CCCCC1)C[C@]1(CCc3cc(OCC(F)(F)F)ccc31)NC2=O]

TABLE 8-continued
I-97
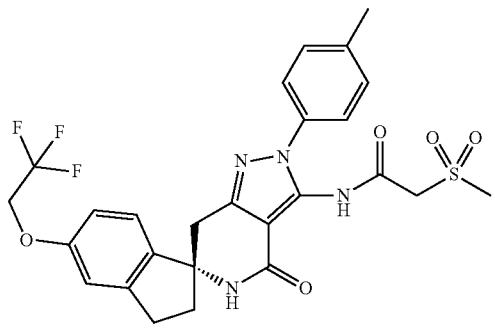 [SMILES: Cc1ccc(-n2nc3c(c2NC(=O)CS(C)(=O)=O)C(=O)N[C@@]2(CCc4cc(OCC(F)(F)F)ccc42)C3)cc1]
I-98
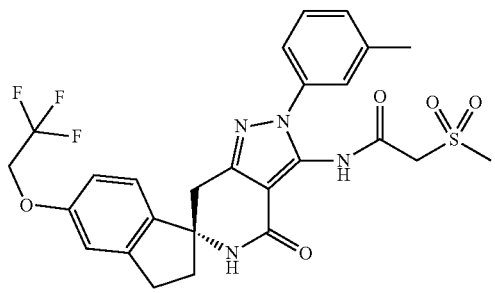 [SMILES: Cc1cccc(-n2nc3c(c2NC(=O)CS(C)(=O)=O)C(=O)N[C@@]2(CCc4cc(OCC(F)(F)F)ccc42)C3)c1]
I-99
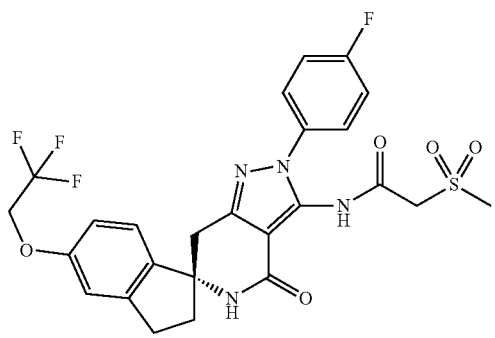 [SMILES: CS(=O)(=O)CC(=O)Nc1c2c(nn1-c1ccc(F)cc1)C[C@]1(CCc3cc(OCC(F)(F)F)ccc31)NC2=O]
I-100
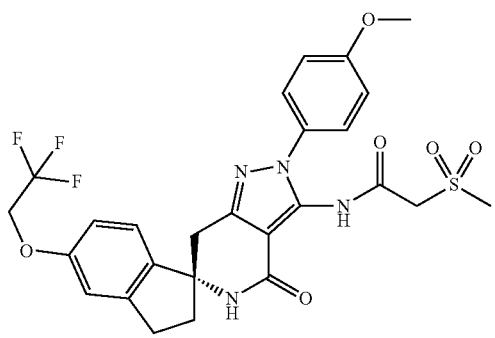 [SMILES: COc1ccc(-n2nc3c(c2NC(=O)CS(C)(=O)=O)C(=O)N[C@@]2(CCc4cc(OCC(F)(F)F)ccc42)C3)cc1]
I-101
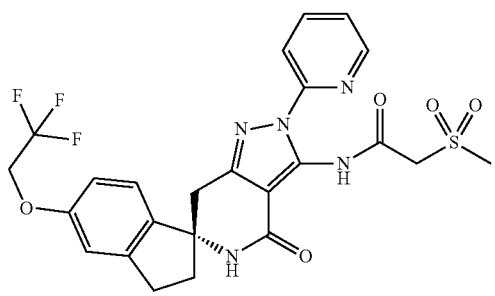 [SMILES: CS(=O)(=O)CC(=O)Nc1c2c(nn1-c1ccccn1)C[C@]1(CCc3cc(OCC(F)(F)F)ccc31)NC2=O]

TABLE 8-continued
I-102
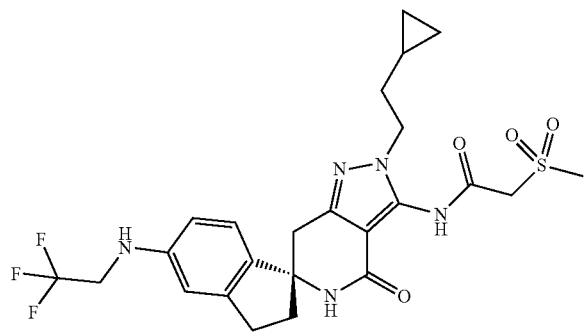 [SMILES: CS(=O)(=O)CC(=O)Nc1c2c(nn1CCC1CC1)C[C@]1(CCc3cc(NCC(F)(F)F)ccc31)NC2=O]
I-103
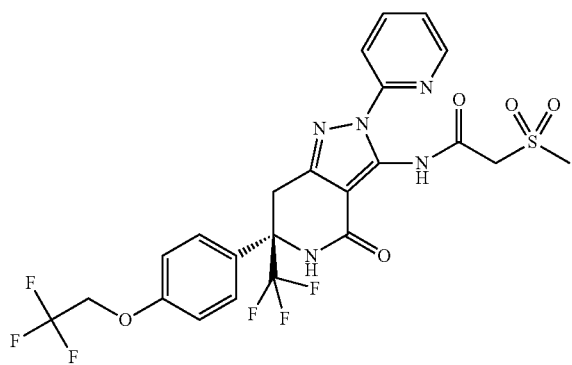 [SMILES: CS(=O)(=O)CC(=O)Nc1c2c(nn1-c1ccccn1)C[C@](c1ccc(OCC(F)(F)F)cc1)(C(F)(F)F)NC2=O]
I-104
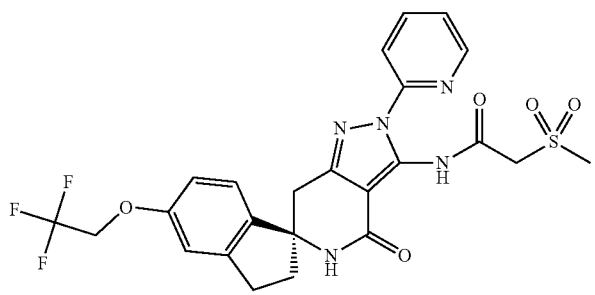 [SMILES: CS(=O)(=O)CC(=O)Nc1c2c(nn1-c1ccccn1)C[C@@]1(CCc3cc(OCC(F)(F)F)ccc31)NC2=O]
I-105
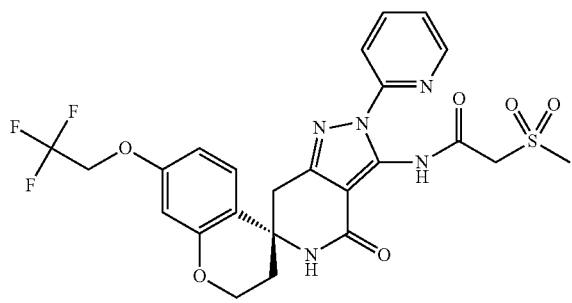 [SMILES: CS(=O)(=O)CC(=O)Nc1c2c(nn1-c1ccccn1)C[C@]1(CCOc3cc(OCC(F)(F)F)ccc31)NC2=O]

TABLE 8-continued
I-106
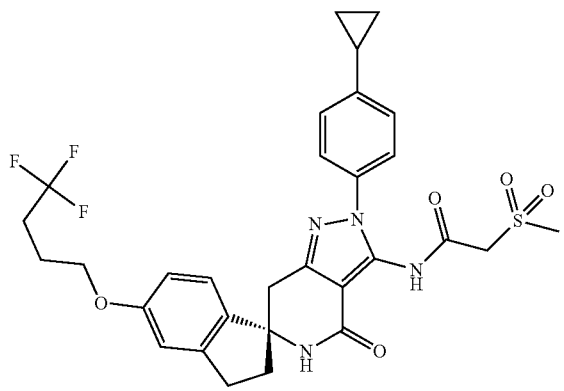 [SMILES: CS(=O)(=O)CC(=O)Nc1c2c(nn1-c1ccc(C3CC3)cc1)C[C@]1(CCc3cc(OCCCC(F)(F)F)ccc31)NC2=O]
I-107
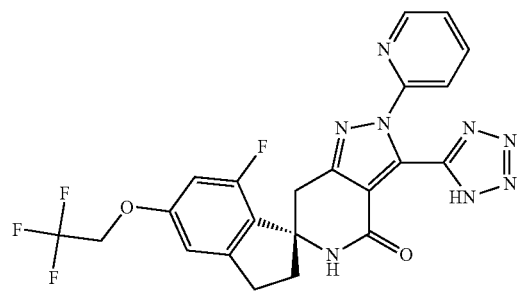 [SMILES: O=C1N[C@@]2(CCc3cc(OCC(F)(F)F)cc(F)c32)Cc2nn(-c3ccccn3)c(-c3nnn[nH]3)c21]
I-108
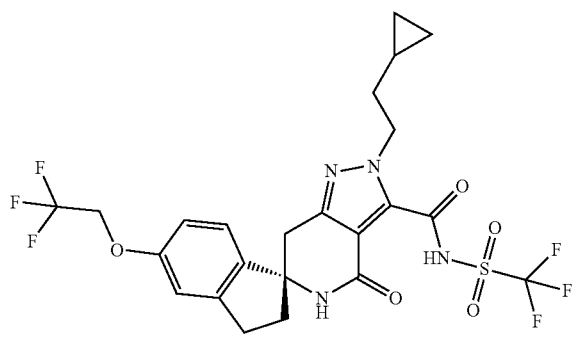 [SMILES: O=C1N[C@@]2(CCc3cc(OCC(F)(F)F)ccc32)Cc2nn(CCC3CC3)c(C(=O)NS(=O)(=O)C(F)(F)F)c21]
I-109
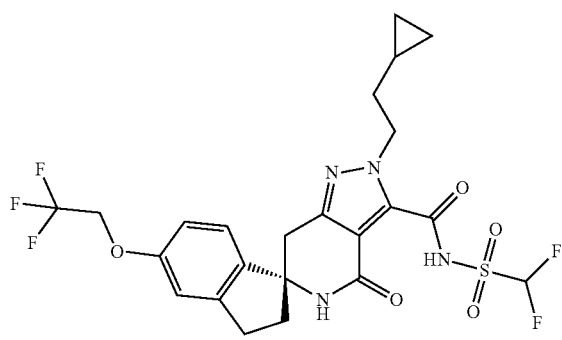 [SMILES: O=C1N[C@@]2(CCc3cc(OCC(F)(F)F)ccc32)Cc2nn(CCC3CC3)c(C(=O)NS(=O)(=O)C(F)F)c21]

TABLE 9
I-110
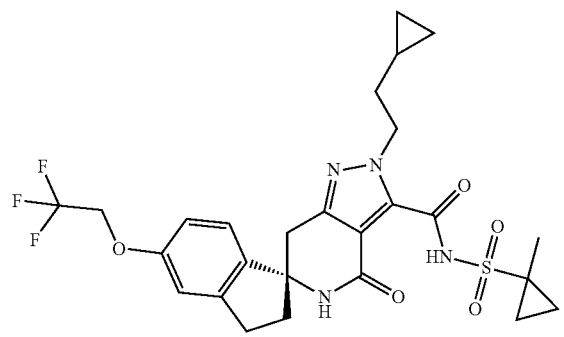 [SMILES: CC1(S(=O)(=O)NC(=O)c2c3c(nn2CCC2CC2)C[C@]2(CCc4cc(OCC(F)(F)F)ccc42)NC3=O)CC1]
I-111
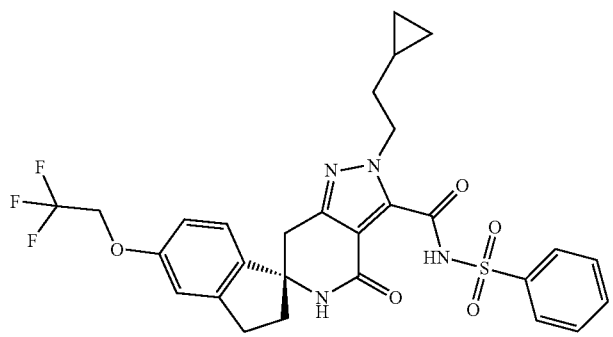 [SMILES: O=C1N[C@@]2(CCc3cc(OCC(F)(F)F)ccc32)Cc2nn(CCC3CC3)c(C(=O)NS(=O)(=O)c3ccccc3)c21]
I-112
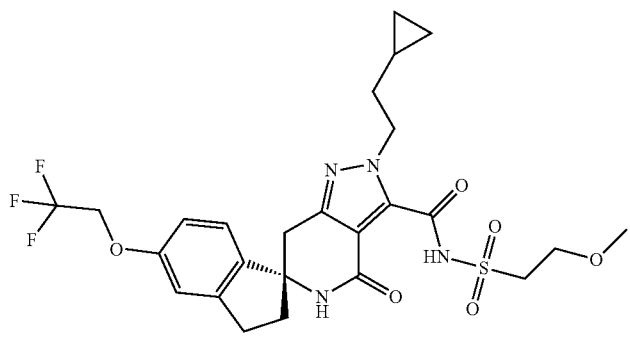 [SMILES: COCCS(=O)(=O)NC(=O)c1c2c(nn1CCC1CC1)C[C@]1(CCc3cc(OCC(F)(F)F)ccc31)NC2=O]
I-113
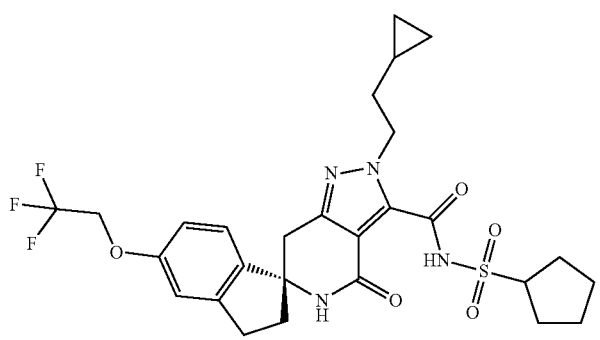 [SMILES: O=C1N[C@@]2(CCc3cc(OCC(F)(F)F)ccc32)Cc2nn(CCC3CC3)c(C(=O)NS(=O)(=O)C3CCCC3)c21]

TABLE 9-continued
I-114
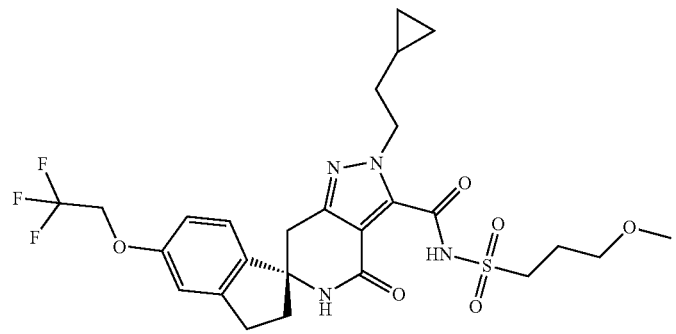 [SMILES: COCCCS(=O)(=O)NC(=O)c1c2c(nn1CCC1CC1)C[C@]1(CCc3cc(OCC(F)(F)F)ccc31)NC2=O]
I-115
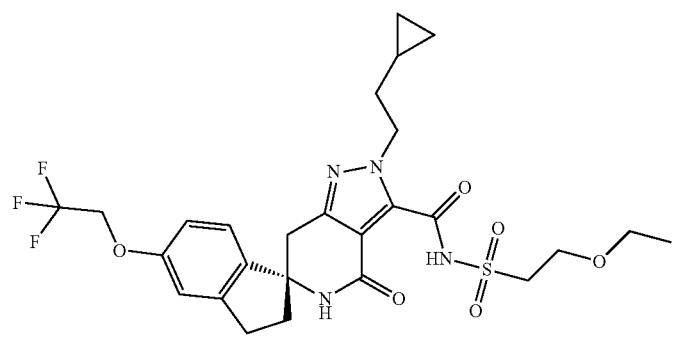 [SMILES: CCOCCS(=O)(=O)NC(=O)c1c2c(nn1CCC1CC1)C[C@]1(CCc3cc(OCC(F)(F)F)ccc31)NC2=O]
I-116
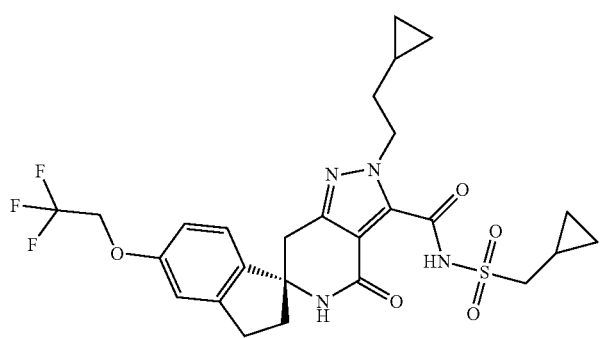 [SMILES: O=C1N[C@@]2(CCc3cc(OCC(F)(F)F)ccc32)Cc2nn(CCC3CC3)c(C(=O)NS(=O)(=O)CC3CC3)c21]
I-117
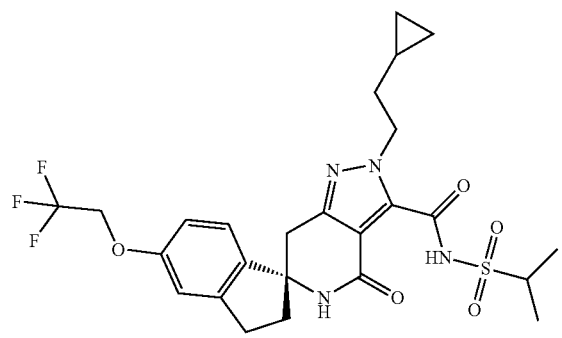 [SMILES: CC(C)S(=O)(=O)NC(=O)c1c2c(nn1CCC1CC1)C[C@]1(CCc3cc(OCC(F)(F)F)ccc31)NC2=O]

TABLE 9-continued
I-118
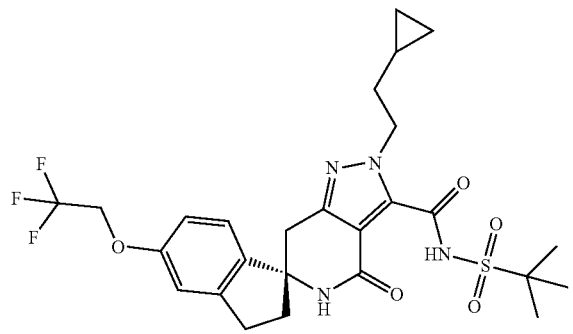 [SMILES: CC(C)(C)S(=O)(=O)NC(=O)c1c2c(nn1CCC1CC1)C[C@]1(CCc3cc(OCC(F)(F)F)ccc31)NC2=O]
I-119
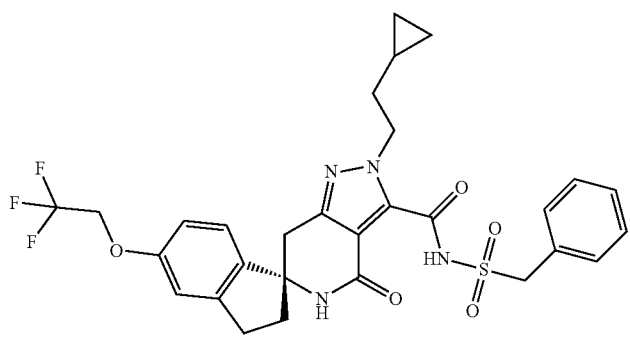 [SMILES: O=C1N[C@@]2(CCc3cc(OCC(F)(F)F)ccc32)Cc2nn(CCC3CC3)c(C(=O)NS(=O)(=O)Cc3ccccc3)c21]
I-120
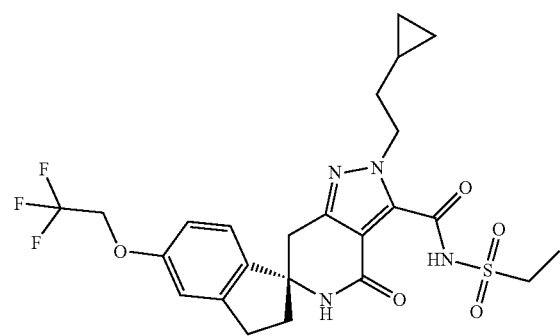 [SMILES: CCS(=O)(=O)NC(=O)c1c2c(nn1CCC1CC1)C[C@]1(CCc3cc(OCC(F)(F)F)ccc31)NC2=O]
I-121
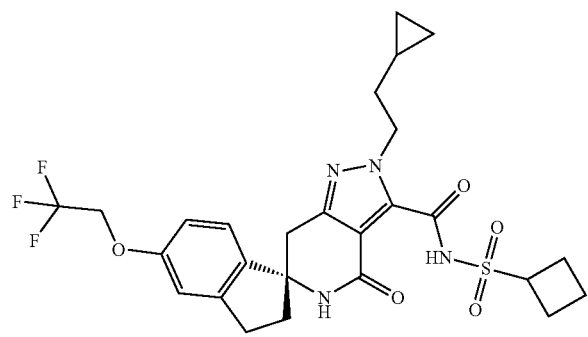 [SMILES: O=C1N[C@@]2(CCc3cc(OCC(F)(F)F)ccc32)Cc2nn(CCC3CC3)c(C(=O)NS(=O)(=O)C3CCC3)c21]

TABLE 9-continued
I-122
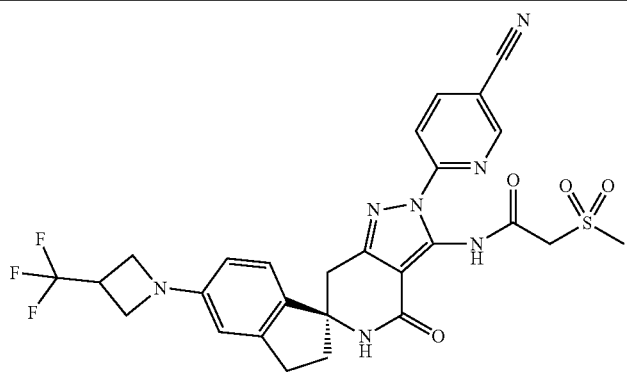
I-123
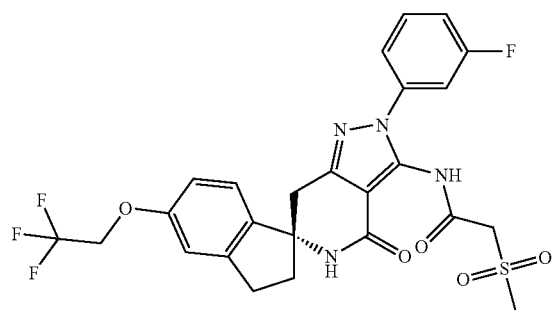 [SMILES: CS(=O)(=O)CC(=O)Nc1c2c(nn1-c1cccc(F)c1)C[C@]1(CCc3cc(OCC(F)(F)F)ccc31)NC2=O]
TABLE 10
I-124
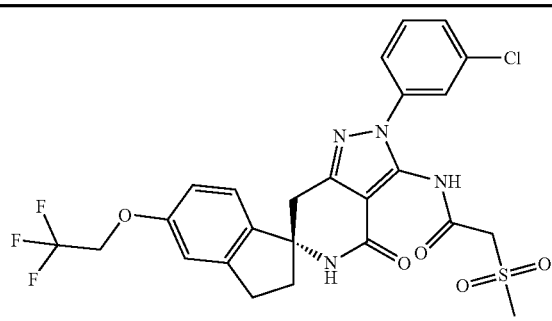
I-125
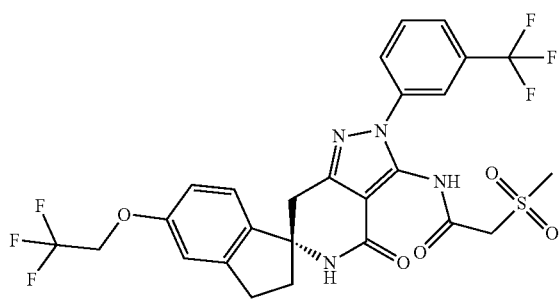 [SMILES: CS(=O)(=O)CC(=O)Nc1c2c(nn1-c1cccc(C(F)(F)F)c1)C[C@]1(CCc3cc(OCC(F)(F)F)ccc31)NC2=O]

TABLE 10-continued
I-126
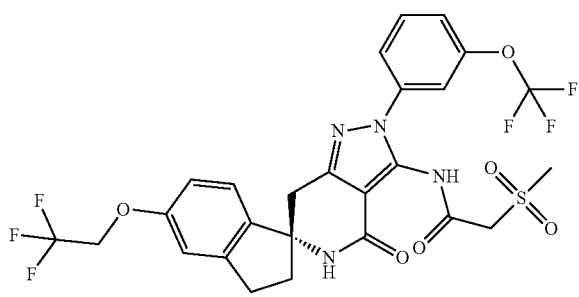 [SMILES: CS(=O)(=O)CC(=O)Nc1c2c(nn1-c1cccc(OC(F)(F)F)c1)C[C@]1(CCc3cc(OCC(F)(F)F)ccc31)NC2=O]
I-127
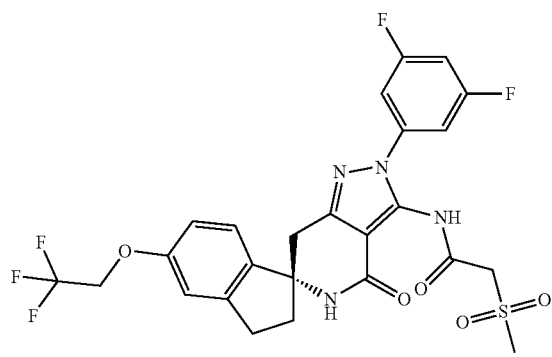 [SMILES: CS(=O)(=O)CC(=O)Nc1c2c(nn1-c1cc(F)cc(F)c1)C[C@]1(CCc3cc(OCC(F)(F)F)ccc31)NC2=O]
I-128
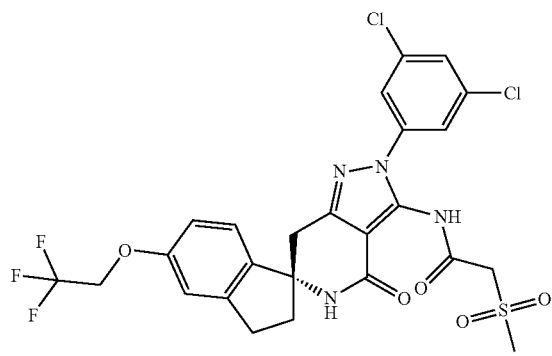 [SMILES: CS(=O)(=O)CC(=O)Nc1c2c(nn1-c1cc(Cl)cc(Cl)c1)C[C@]1(CCc3cc(OCC(F)(F)F)ccc31)NC2=O]
I-129
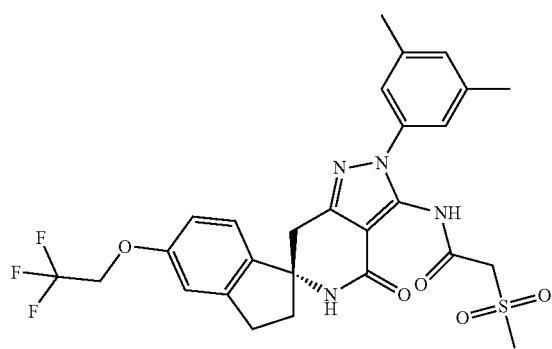 [SMILES: Cc1cc(C)cc(-n2nc3c(c2NC(=O)CS(C)(=O)=O)C(=O)N[C@@]2(CCc4cc(OCC(F)(F)F)ccc42)C3)c1]

TABLE 10-continued
I-130
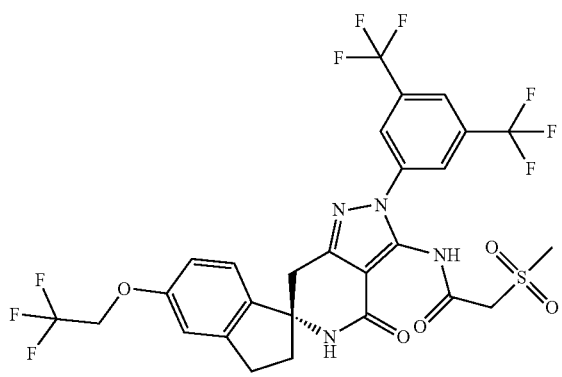 [SMILES: CS(=O)(=O)CC(=O)Nc1c2c(nn1-c1cc(C(F)(F)F)cc(C(F)(F)F)c1)C[C@]1(CCc3cc(OCC(F)(F)F)ccc31)NC2=O]
I-131
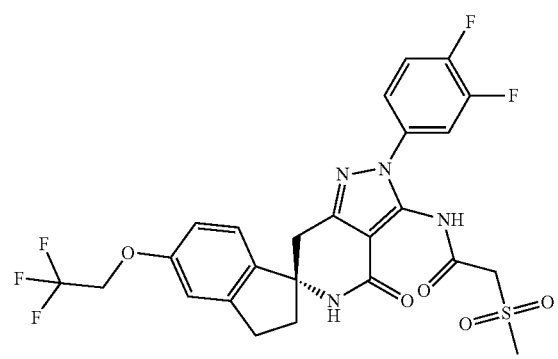 [SMILES: CS(=O)(=O)CC(=O)Nc1c2c(nn1-c1ccc(F)c(F)c1)C[C@]1(CCc3cc(OCC(F)(F)F)ccc31)NC2=O]
I-132
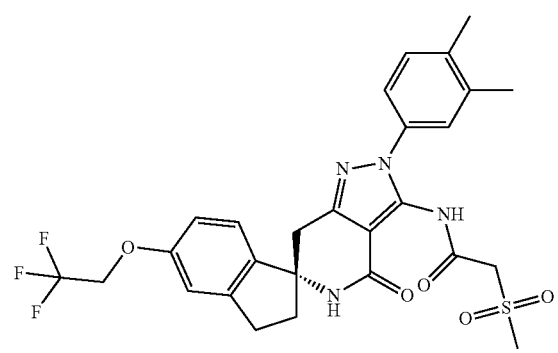 [SMILES: Cc1ccc(-n2nc3c(c2NC(=O)CS(C)(=O)=O)C(=O)N[C@@]2(CCc4cc(OCC(F)(F)F)ccc42)C3)cc1C]
I-133
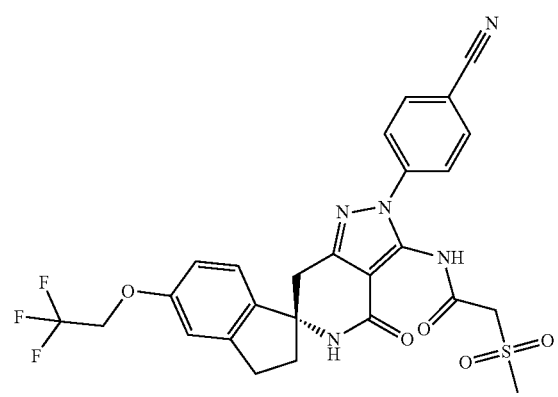 [SMILES: CS(=O)(=O)CC(=O)Nc1c2c(nn1-c1ccc(C#N)cc1)C[C@]1(CCc3cc(OCC(F)(F)F)ccc31)NC2=O]

TABLE 10-continued
I-134
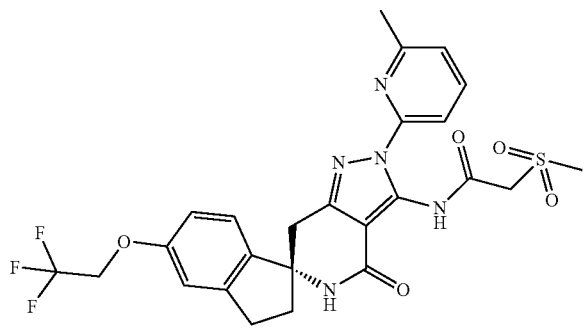 [SMILES: Cc1cccc(-n2nc3c(c2NC(=O)CS(C)(=O)=O)C(=O)N[C@@]2(CCc4cc(OCC(F)(F)F)ccc42)C3)n1]
I-135
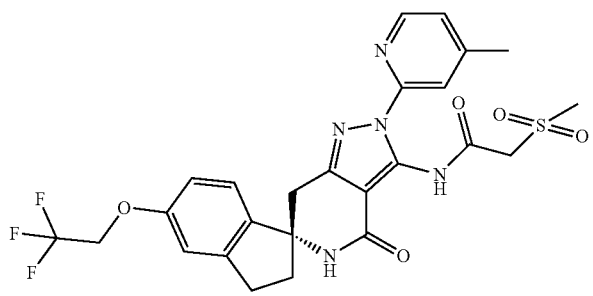 [SMILES: Cc1ccnc(-n2nc3c(c2NC(=O)CS(C)(=O)=O)C(=O)N[C@@]2(CCc4cc(OCC(F)(F)F)ccc42)C3)c1]
I-136
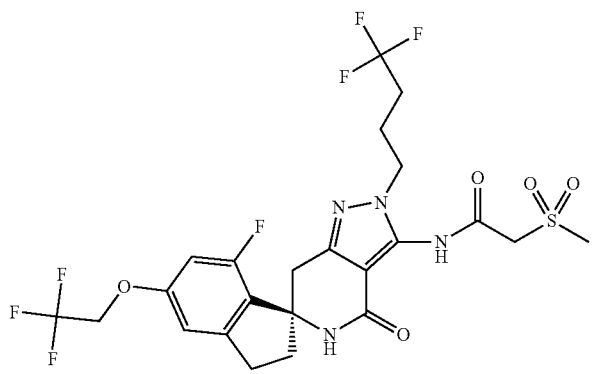 [SMILES: CS(=O)(=O)CC(=O)Nc1c2c(nn1CCCC(F)(F)F)C[C@@]1(CCc3cc(OCC(F)(F)F)cc(F)c31)NC2=O]
I-137
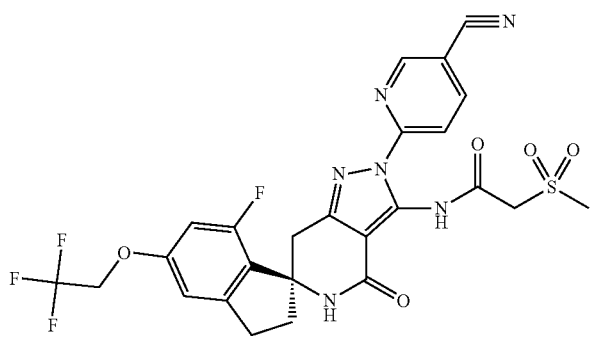 [SMILES: CS(=O)(=O)CC(=O)Nc1c2c(nn1-c1ccc(C#N)cn1)C[C@@]1(CCc3cc(OCC(F)(F)F)cc(F)c31)NC2=O]

TABLE 11
I-138
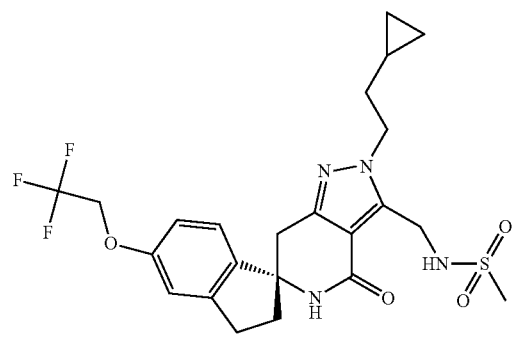 [SMILES: CS(=O)(=O)NCc1c2c(nn1CCC1CC1)C[C@]1(CCc3cc(OCC(F)(F)F)ccc31)NC2=O]
I-139
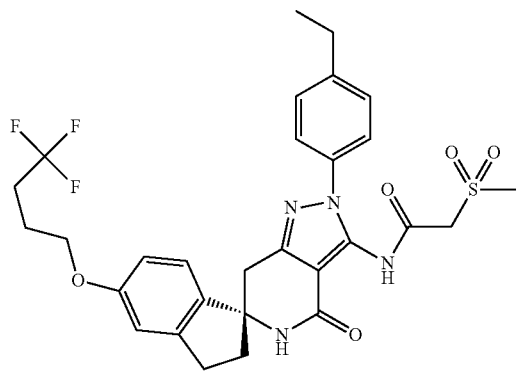 [SMILES: CCc1ccc(-n2nc3c(c2NC(=O)CS(C)(=O)=O)C(=O)N[C@@]2(CCc4cc(OCCCC(F)(F)F)ccc42)C3)cc1]
I-140
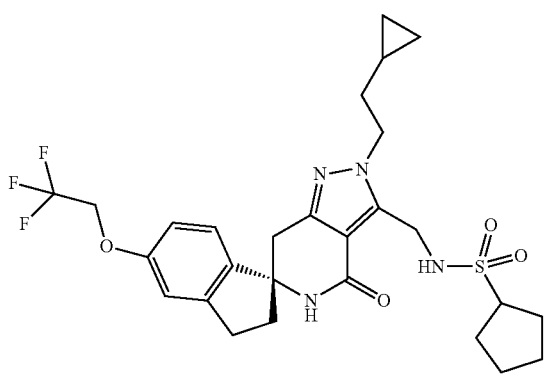 [SMILES: O=C1N[C@@]2(CCc3cc(OCC(F)(F)F)ccc32)Cc2nn(CCC3CC3)c(CNS(=O)(=O)C3CCCC3)c21]
I-141
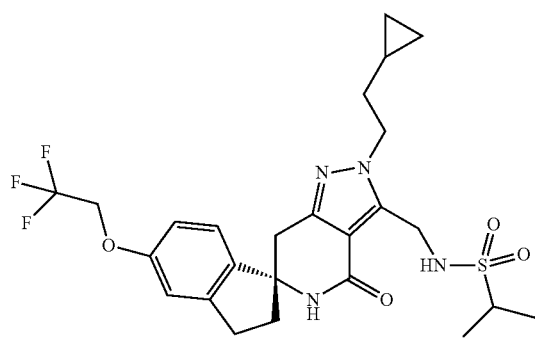 [SMILES: CC(C)S(=O)(=O)NCc1c2c(nn1CCC1CC1)C[C@]1(CCc3cc(OCC(F)(F)F)ccc31)NC2=O]

TABLE 11-continued
I-142
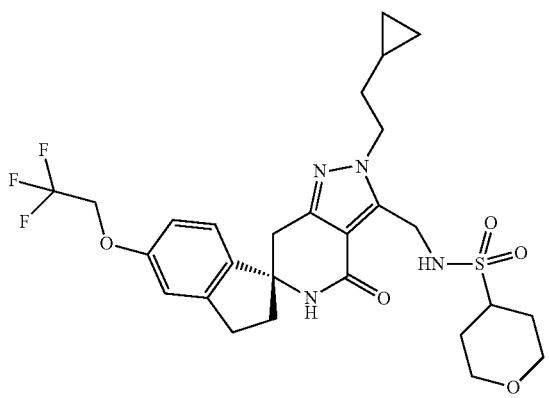 [SMILES: O=C1N[C@@]2(CCc3cc(OCC(F)(F)F)ccc32)Cc2nn(CCC3CC3)c(CNS(=O)(=O)C3CCOCC3)c21]
I-143
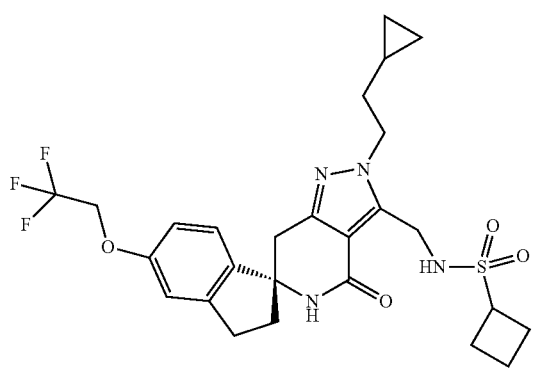 [SMILES: O=C1N[C@@]2(CCc3cc(OCC(F)(F)F)ccc32)Cc2nn(CCC3CC3)c(CNS(=O)(=O)C3CCC3)c21]
I-144
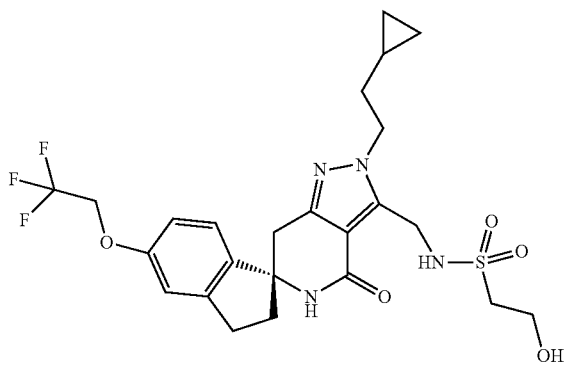 [SMILES: O=C1N[C@@]2(CCc3cc(OCC(F)(F)F)ccc32)Cc2nn(CCC3CC3)c(CNS(=O)(=O)CCO)c21]
I-145
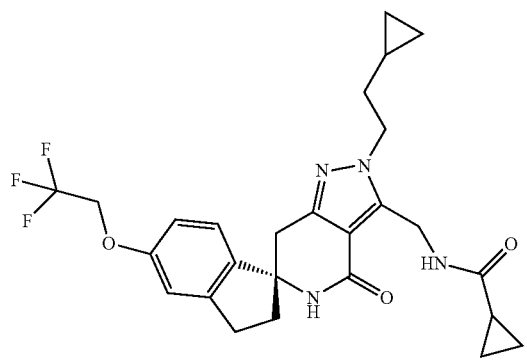 [SMILES: O=C1N[C@@]2(CCc3cc(OCC(F)(F)F)ccc32)Cc2nn(CCC3CC3)c(CNC(=O)C3CC3)c21]

TABLE 11-continued
I-146
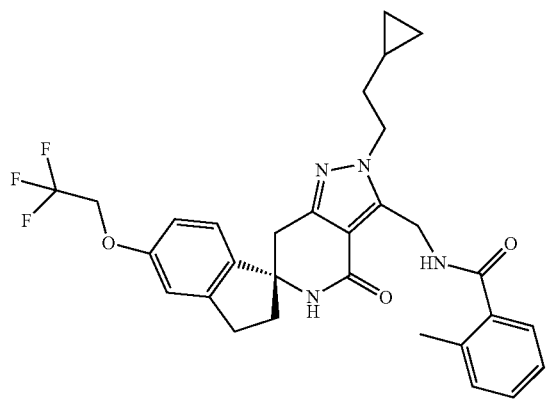 [SMILES: Cc1ccccc1C(=O)NCc1c2c(nn1CCC1CC1)C[C@]1(CCc3cc(OCC(F)(F)F)ccc31)NC2=O]
I-147
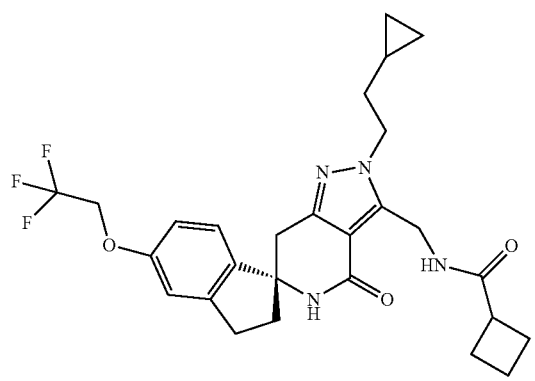 [SMILES: O=C1N[C@@]2(CCc3cc(OCC(F)(F)F)ccc32)Cc2nn(CCC3CC3)c(CNC(=O)C3CCC3)c21]
I-148
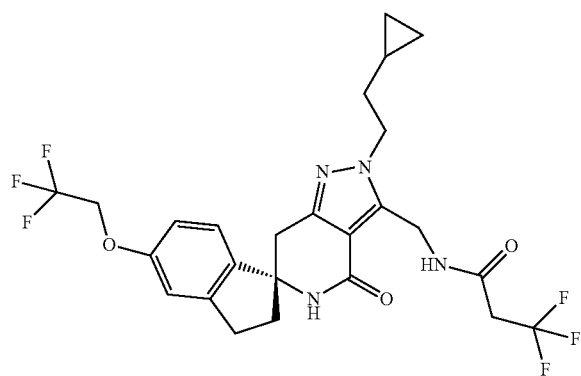 [SMILES: O=C(CC(F)(F)F)NCc1c2c(nn1CCC1CC1)C[C@]1(CCc3cc(OCC(F)(F)F)ccc31)NC2=O]
I-149
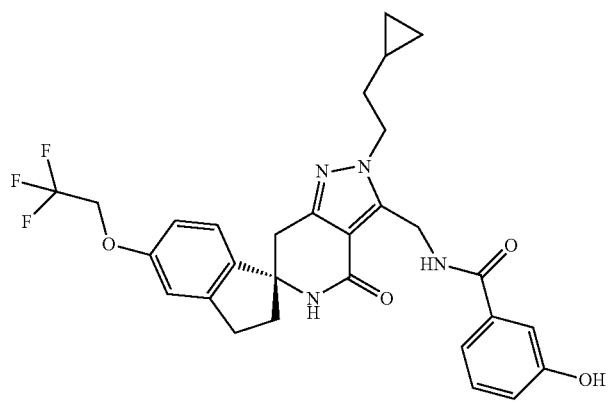 [SMILES: O=C(NCc1c2c(nn1CCC1CC1)C[C@]1(CCc3cc(OCC(F)(F)F)ccc31)NC2=O)c1cccc(O)c1]

TABLE 12
I-150
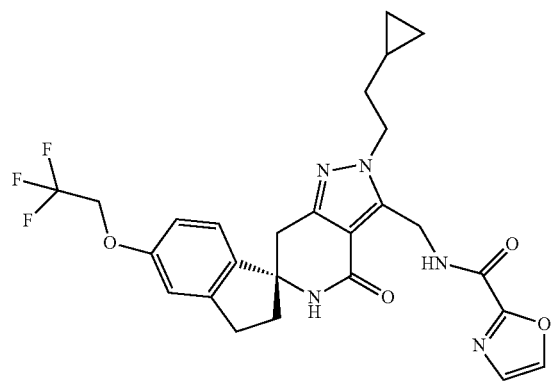
I-151
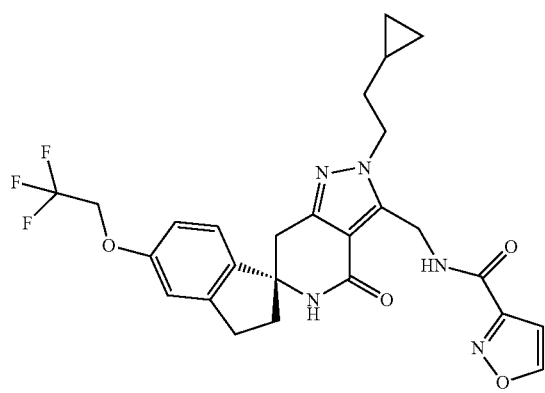 [SMILES: O=C(NCc1c2c(nn1CCC1CC1)C[C@]1(CCc3cc(OCC(F)(F)F)ccc31)NC2=O)c1ccon1]
I-152
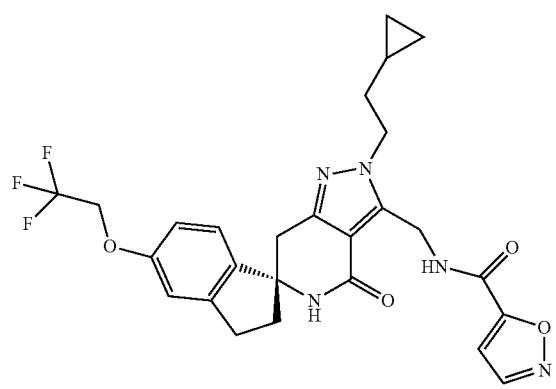 [SMILES: O=C(NCc1c2c(nn1CCC1CC1)C[C@]1(CCc3cc(OCC(F)(F)F)ccc31)NC2=O)c1ccno1]
I-153
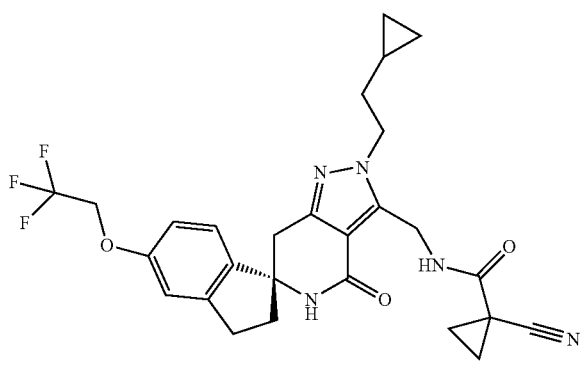 [SMILES: N#CC1(C(=O)NCc2c3c(nn2CCC2CC2)C[C@]2(CCc4cc(OCC(F)(F)F)ccc42)NC3=O)CC1]

TABLE 12-continued
I-154
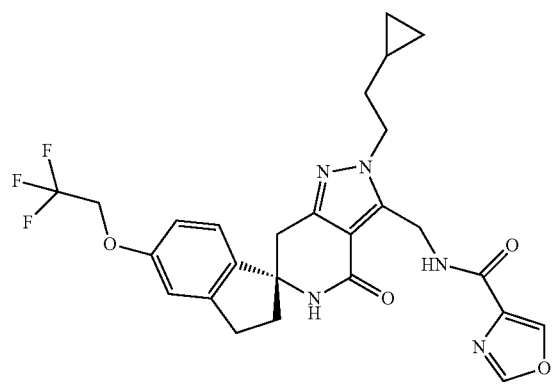 [SMILES: O=C(NCc1c2c(nn1CCC1CC1)C[C@]1(CCc3cc(OCC(F)(F)F)ccc31)NC2=O)c1cocn1]
I-155
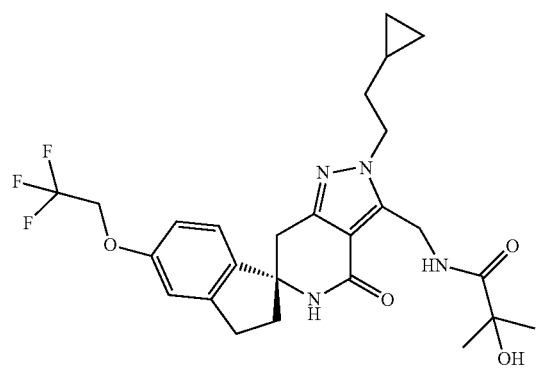 [SMILES: CC(C)(O)C(=O)NCc1c2c(nn1CCC1CC1)C[C@]1(CCc3cc(OCC(F)(F)F)ccc31)NC2=O]
I-156
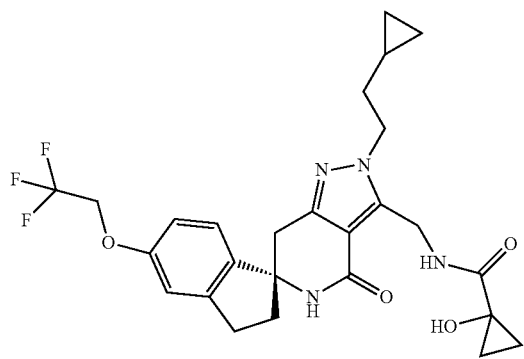 [SMILES: O=C1N[C@@]2(CCc3cc(OCC(F)(F)F)ccc32)Cc2nn(CCC3CC3)c(CNC(=O)C3(O)CC3)c21]
I-157
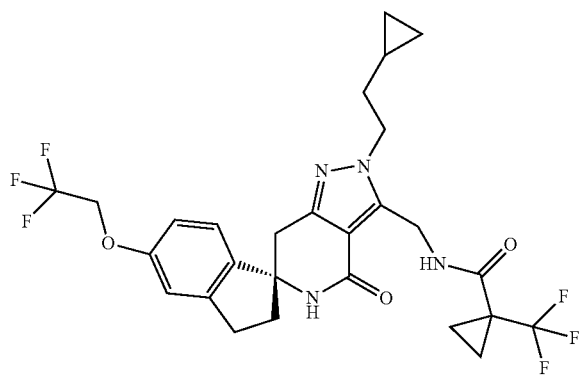 [SMILES: O=C1N[C@@]2(CCc3cc(OCC(F)(F)F)ccc32)Cc2nn(CCC3CC3)c(CNC(=O)C3(C(F)(F)F)CC3)c21]

TABLE 12-continued
I-158
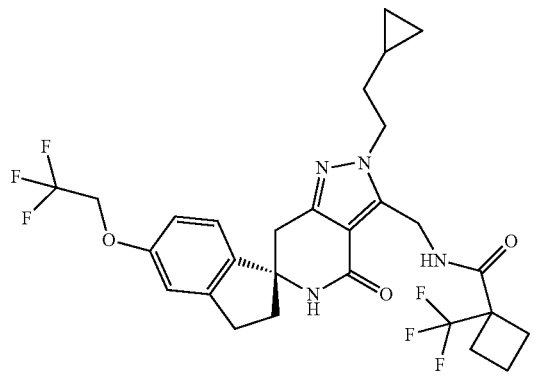 [SMILES: O=C1N[C@@]2(CCc3cc(OCC(F)(F)F)ccc32)Cc2nn(CCC3CC3)c(CNC(=O)C3(C(F)(F)F)CCC3)c21]
I-159
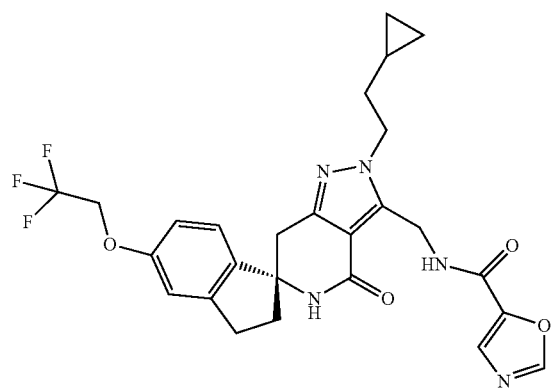 [SMILES: O=C(NCc1c2c(nn1CCC1CC1)C[C@]1(CCc3cc(OCC(F)(F)F)ccc31)NC2=O)c1cnco1]
I-160
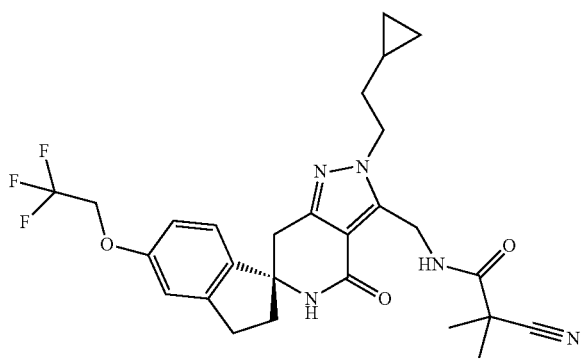 [SMILES: CC(C)(C#N)C(=O)NCc1c2c(nn1CCC1CC1)C[C@]1(CCc3cc(OCC(F)(F)F)ccc31)NC2=O]
I-161
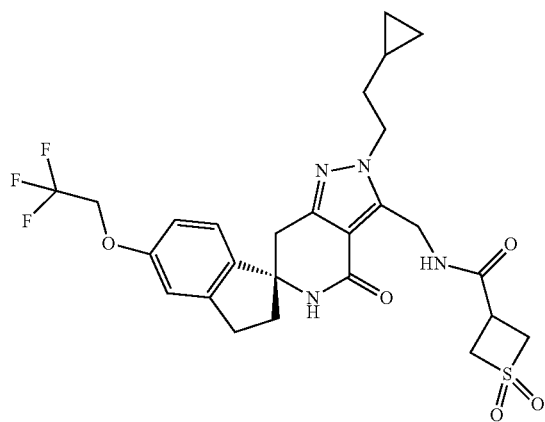 [SMILES: O=C1N[C@@]2(CCc3cc(OCC(F)(F)F)ccc32)Cc2nn(CCC3CC3)c(CNC(=O)C3CS(=O)(=O)C3)c21]

TABLE 13
I-162
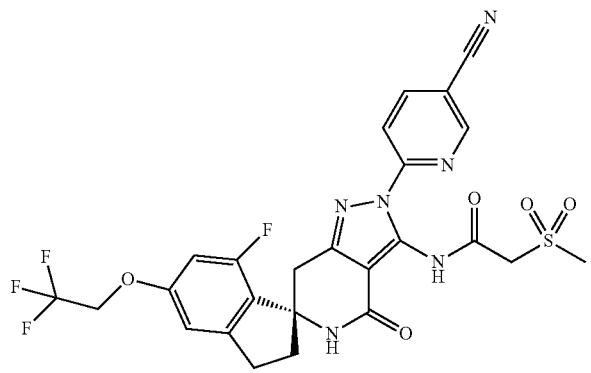 [SMILES: CS(=O)(=O)CC(=O)Nc1c2c(nn1-c1ccc(C#N)cn1)C[C@]1(CCc3cc(OCC(F)(F)F)cc(F)c31)NC2=O]
I-163
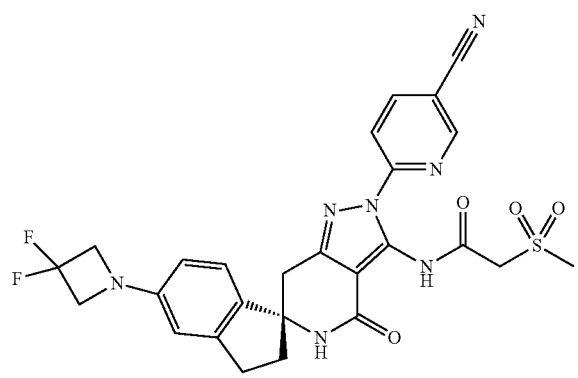 [SMILES: CS(=O)(=O)CC(=O)Nc1c2c(nn1-c1ccc(C#N)cn1)C[C@]1(CCc3cc(N4CC(F)(F)C4)ccc31)NC2=O]
I-164
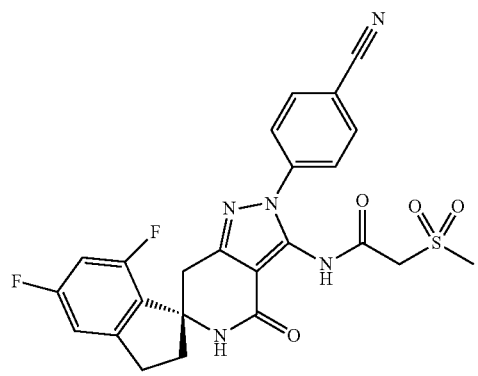 [SMILES: CS(=O)(=O)CC(=O)Nc1c2c(nn1-c1ccc(C#N)cc1)C[C@]1(CCc3cc(F)cc(F)c31)NC2=O]
I-165
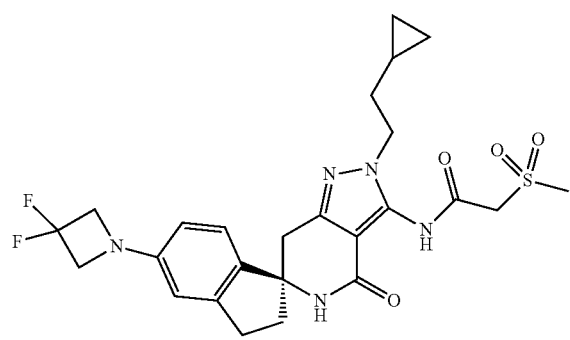 [SMILES: CS(=O)(=O)CC(=O)Nc1c2c(nn1CCC1CC1)C[C@@]1(CCc3cc(N4CC(F)(F)C4)ccc31)NC2=O]

TABLE 13-continued
I-166
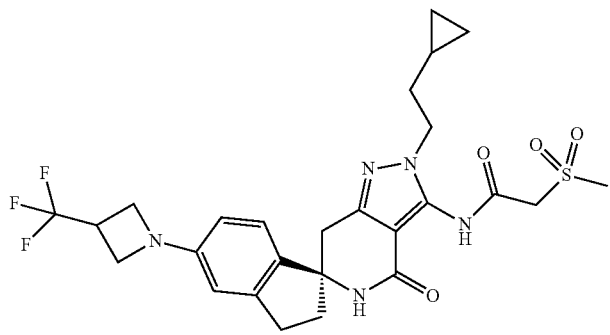 [SMILES: CS(=O)(=O)CC(=O)Nc1c2c(nn1CCC1CC1)C[C@@]1(CCc3cc(N4CC(C(F)(F)F)C4)ccc31)NC2=O]
I-167
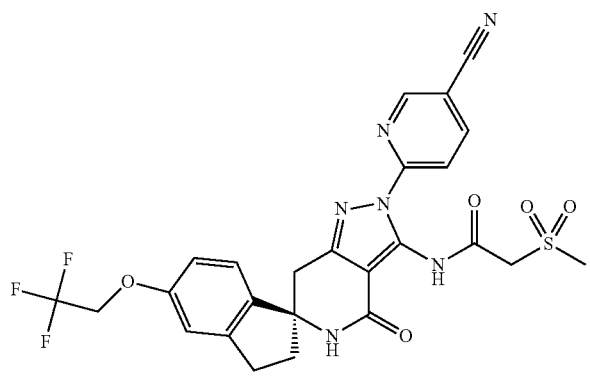 [SMILES: CS(=O)(=O)CC(=O)Nc1c2c(nn1-c1ccc(C#N)cn1)C[C@@]1(CCc3cc(OCC(F)(F)F)ccc31)NC2=O]
I-168
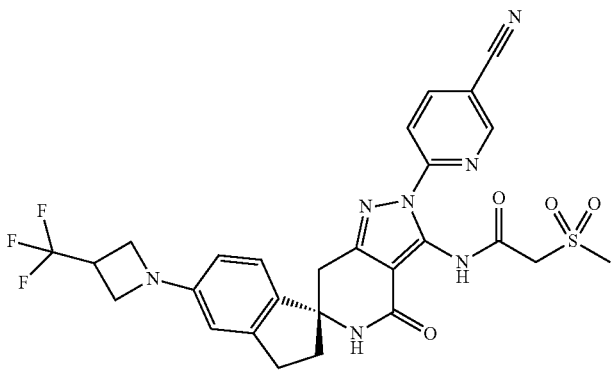 [SMILES: CS(=O)(=O)CC(=O)Nc1c2c(nn1-c1ccc(C#N)cn1)C[C@]1(CCc3cc(N4CC(C(F)(F)F)C4)ccc31)NC2=O]
I-169
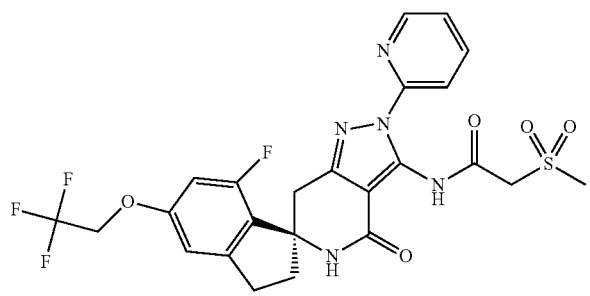 [SMILES: CS(=O)(=O)CC(=O)Nc1c2c(nn1-c1ccccn1)C[C@@]1(CCc3cc(OCC(F)(F)F)cc(F)c31)NC2=O]

TABLE 13-continued
I-170
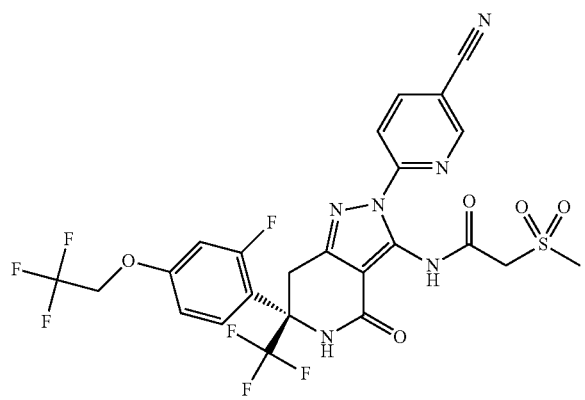 [SMILES: CS(=O)(=O)CC(=O)Nc1c2c(nn1-c1ccc(C#N)cn1)C[C@](c1ccc(OCC(F)(F)F)cc1F)(C(F)(F)F)NC2=O]
I-171
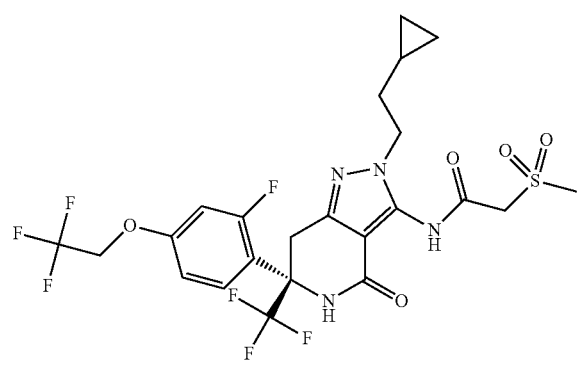 [SMILES: CS(=O)(=O)CC(=O)Nc1c2c(nn1CCC1CC1)C[C@](c1ccc(OCC(F)(F)F)cc1F)(C(F)(F)F)NC2=O]
I-172
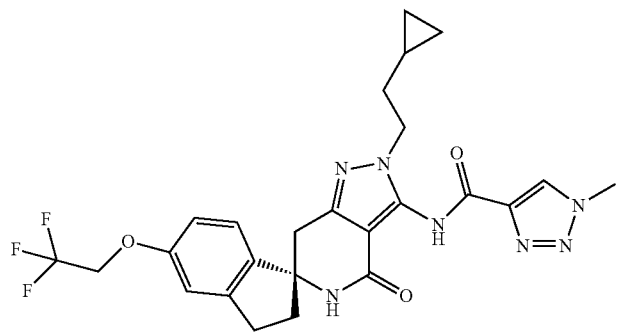 [SMILES: Cn1cc(C(=O)Nc2c3c(nn2CCC2CC2)C[C@]2(CCc4cc(OCC(F)(F)F)ccc42)NC3=O)nn1]
I-173
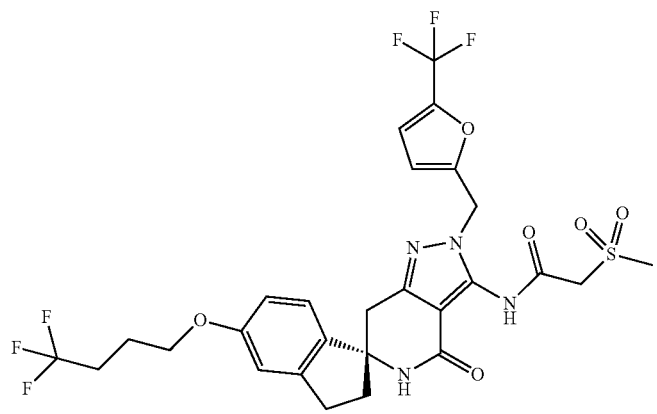 [SMILES: CS(=O)(=O)CC(=O)Nc1c2c(nn1Cc1ccc(C(F)(F)F)o1)C[C@]1(CCc3cc(OCCCC(F)(F)F)ccc31)NC2=O]

TABLE 14
I-174
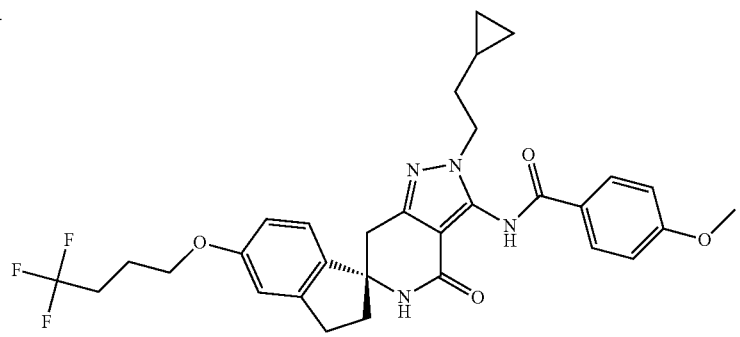
I-175
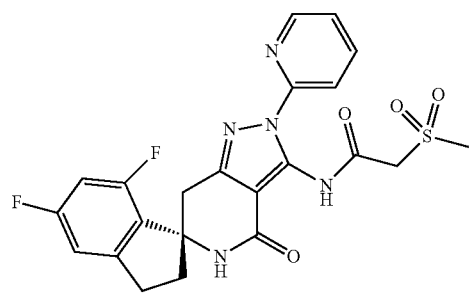 [SMILES: CS(=O)(=O)CC(=O)Nc1c2c(nn1-c1ccccn1)C[C@]1(CCc3cc(F)cc(F)c31)NC2=O]
I-176
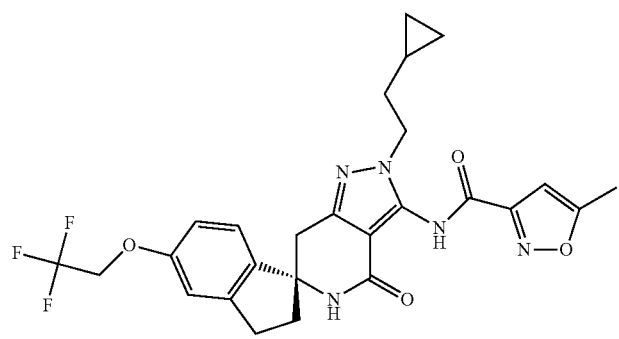 [SMILES: Cc1cc(C(=O)Nc2c3c(nn2CCC2CC2)C[C@]2(CCc4cc(OCC(F)(F)F)ccc42)NC3=O)no1]
I-177
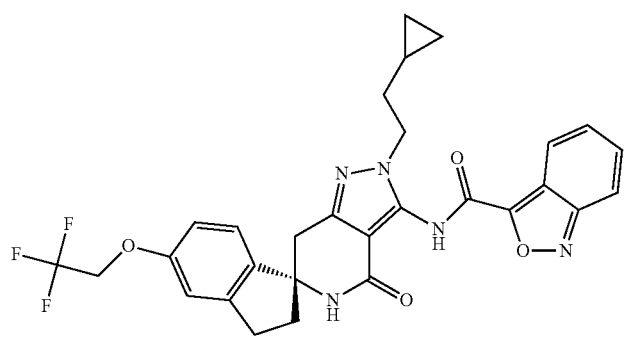 [SMILES: O=C1N[C@@]2(CCc3cc(OCC(F)(F)F)ccc32)Cc2nn(CCC3CC3)c(NC(=O)c3onc4ccccc34)c21]
I-178
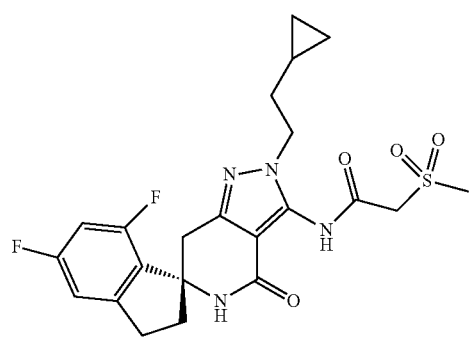 [SMILES: CS(=O)(=O)CC(=O)Nc1c2c(nn1CCC1CC1)C[C@]1(CCc3cc(F)cc(F)c31)NC2=O]

TABLE 14-continued
I-179 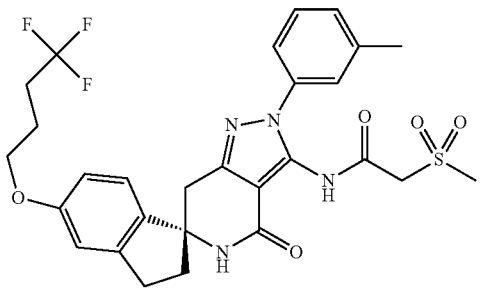 [SMILES: Cc1cccc(-n2nc3c(c2NC(=O)CS(C)(=O)=O)C(=O)N[C@@]2(CCc4cc(OCCCC(F)(F)F)ccc42)C3)c1]
I-180 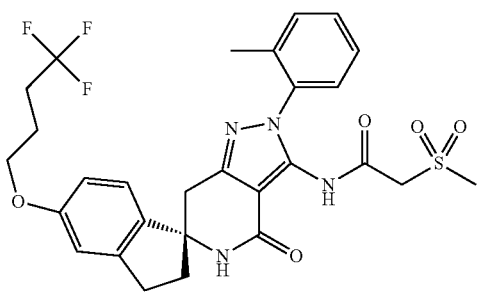 [SMILES: Cc1ccccc1-n1nc2c(c1NC(=O)CS(C)(=O)=O)C(=O)N[C@@]1(CCc3cc(OCCCC(F)(F)F)ccc31)C2]
I-181 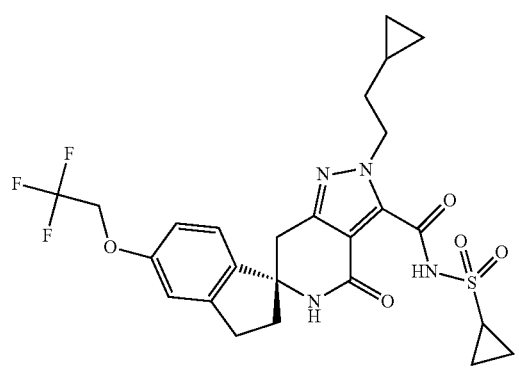 [SMILES: O=C1N[C@@]2(CCc3cc(OCC(F)(F)F)ccc32)Cc2nn(CCC3CC3)c(C(=O)NS(=O)(=O)C3CC3)c21]
I-182 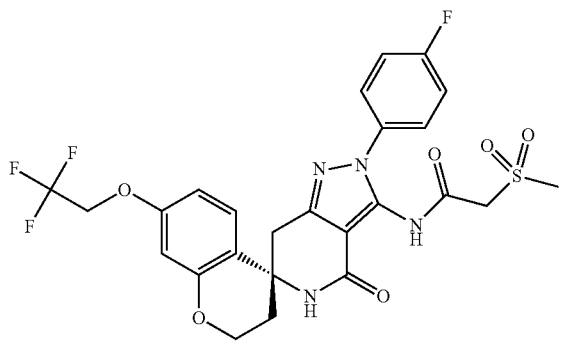 [SMILES: CS(=O)(=O)CC(=O)Nc1c2c(nn1-c1ccc(F)cc1)C[C@]1(CCOc3cc(OCC(F)(F)F)ccc31)NC2=O]
I-183 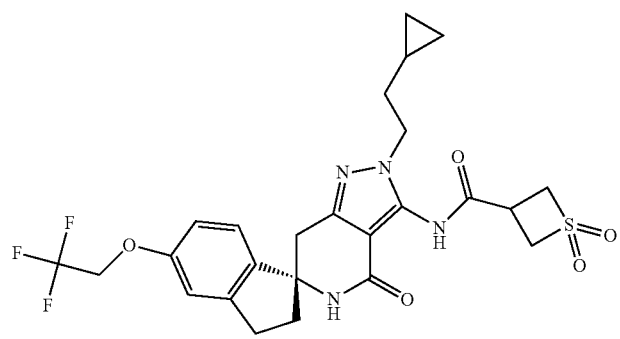 [SMILES: O=C1N[C@@]2(CCc3cc(OCC(F)(F)F)ccc32)Cc2nn(CCC3CC3)c(NC(=O)C3CS(=O)(=O)C3)c21]

TABLE 14-continued
I-184
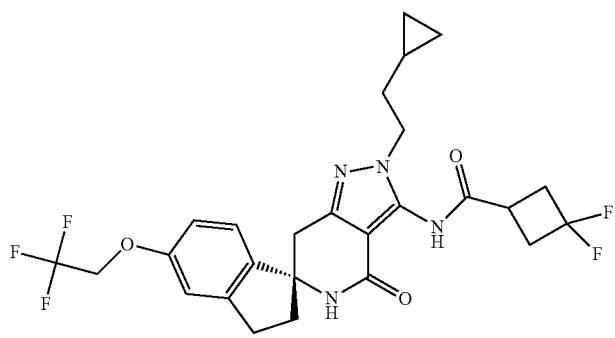 [SMILES: O=C1N[C@@]2(CCc3cc(OCC(F)(F)F)ccc32)Cc2nn(CCC3CC3)c(NC(=O)C3CC(F)(F)C3)c21]
I-185
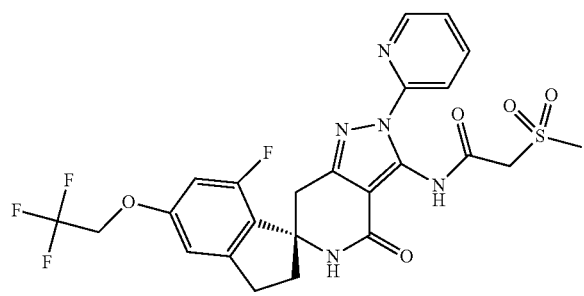 [SMILES: CS(=O)(=O)CC(=O)Nc1c2c(nn1-c1ccccn1)C[C@]1(CCc3cc(OCC(F)(F)F)cc(F)c31)NC2=O]
I-186
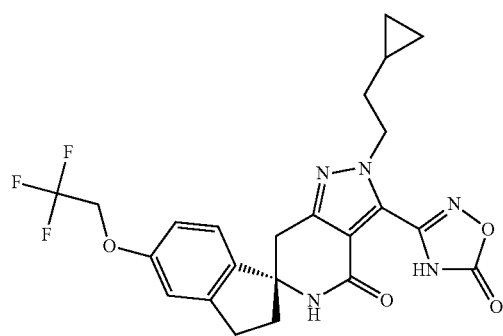 [SMILES: O=C1N[C@@]2(CCc3cc(OCC(F)(F)F)ccc32)Cc2nn(CCC3CC3)c(-c3noc(=O)[nH]3)c21]
I-187
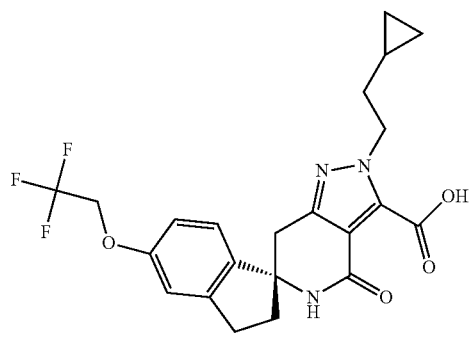 [SMILES: O=C1N[C@@]2(CCc3cc(OCC(F)(F)F)ccc32)Cc2nn(CCC3CC3)c(C(=O)O)c21]

TABLE 15
I-188
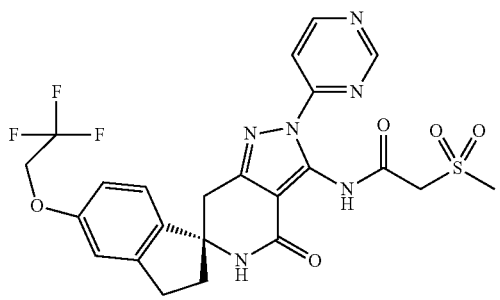 [SMILES: CS(=O)(=O)CC(=O)Nc1c2c(nn1-c1ccncn1)C[C@]1(CCc3cc(OCC(F)(F)F)ccc31)NC2=O]
I-189
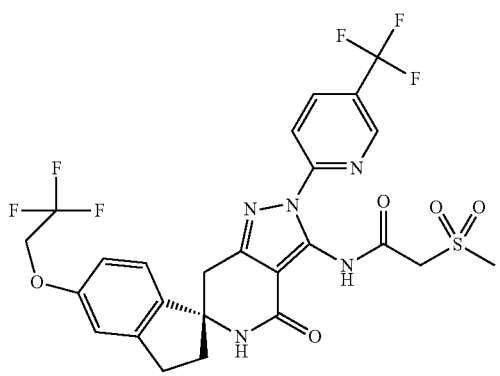 [SMILES: CS(=O)(=O)CC(=O)Nc1c2c(nn1-c1ccc(C(F)(F)F)cn1)C[C@]1(CCc3cc(OCC(F)(F)F)ccc31)NC2=O]
I-190
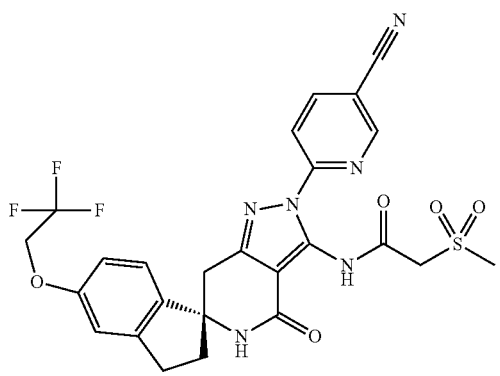 [SMILES: CS(=O)(=O)CC(=O)Nc1c2c(nn1-c1ccc(C#N)cn1)C[C@]1(CCc3cc(OCC(F)(F)F)ccc31)NC2=O]
I-191
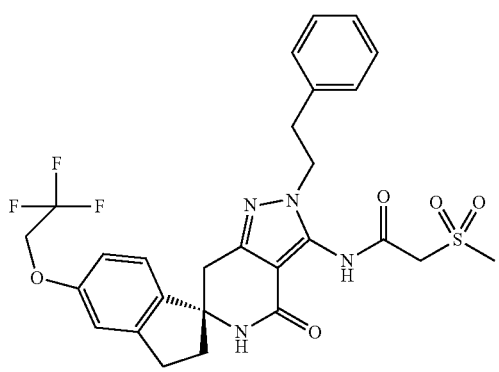 [SMILES: CS(=O)(=O)CC(=O)Nc1c2c(nn1CCc1ccccc1)C[C@]1(CCc3cc(OCC(F)(F)F)ccc31)NC2=O]

TABLE 15-continued
I-192
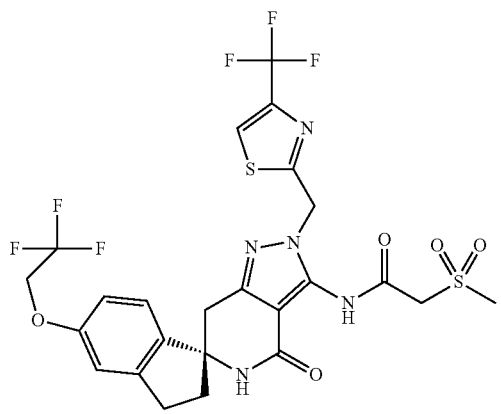 [SMILES: CS(=O)(=O)CC(=O)Nc1c2c(nn1Cc1nc(C(F)(F)F)cs1)C[C@]1(CCc3cc(OCC(F)(F)F)ccc31)NC2=O]
I-193
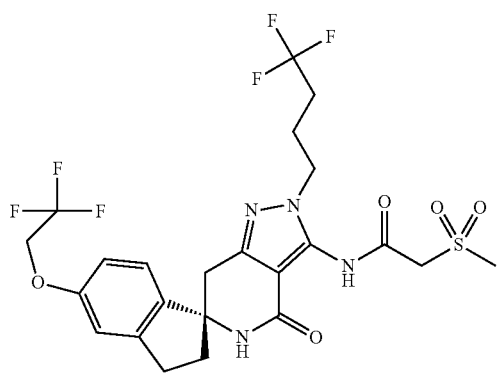 [SMILES: CS(=O)(=O)CC(=O)Nc1c2c(nn1CCCC(F)(F)F)C[C@]1(CCc3cc(OCC(F)(F)F)ccc31)NC2=O]
I-194
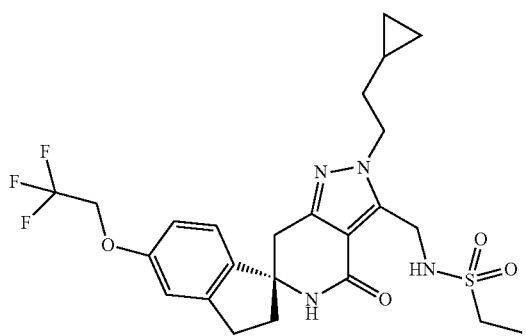 [SMILES: CCS(=O)(=O)NCc1c2c(nn1CCC1CC1)C[C@]1(CCc3cc(OCC(F)(F)F)ccc31)NC2=O]
I-195
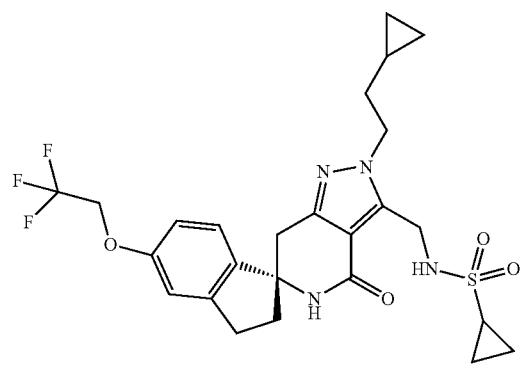 [SMILES: O=C1N[C@@]2(CCc3cc(OCC(F)(F)F)ccc32)Cc2nn(CCC3CC3)c(CNS(=O)(=O)C3CC3)c21]

TABLE 15-continued
I-196
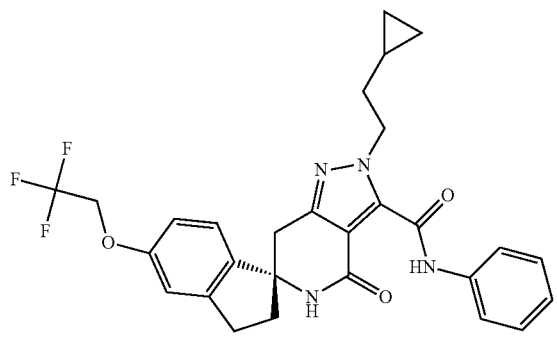 [SMILES: O=C1N[C@@]2(CCc3cc(OCC(F)(F)F)ccc32)Cc2nn(CCC3CC3)c(C(=O)Nc3ccccc3)c21]
I-197
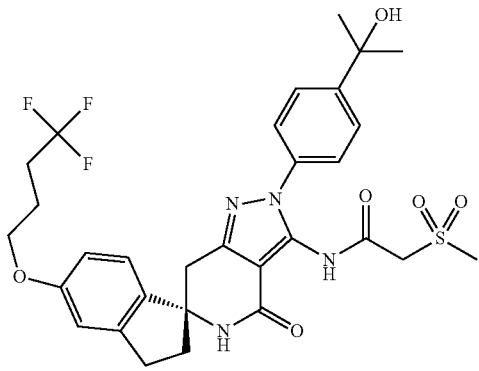 [SMILES: CC(C)(O)c1ccc(-n2nc3c(c2NC(=O)CS(C)(=O)=O)C(=O)N[C@@]2(CCc4cc(OCCCC(F)(F)F)ccc42)C3)cc1]
I-198
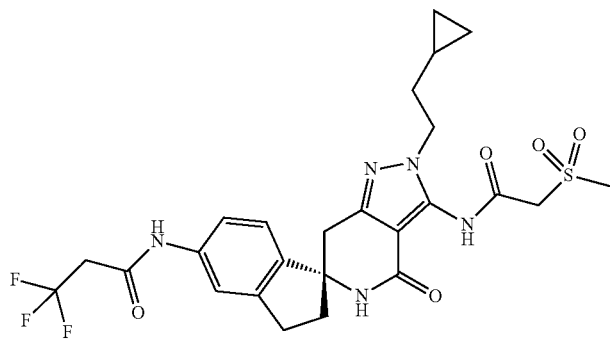 [SMILES: CS(=O)(=O)CC(=O)Nc1c2c(nn1CCC1CC1)C[C@]1(CCc3cc(NC(=O)CC(F)(F)F)ccc31)NC2=O]
I-199
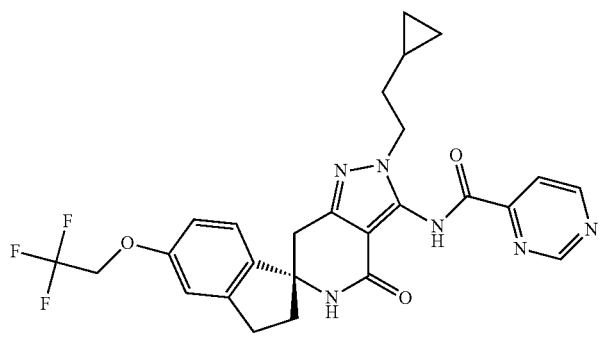 [SMILES: O=C(Nc1c2c(nn1CCC1CC1)C[C@]1(CCc3cc(OCC(F)(F)F)ccc31)NC2=O)c1ccncn1]

TABLE 16
I-200
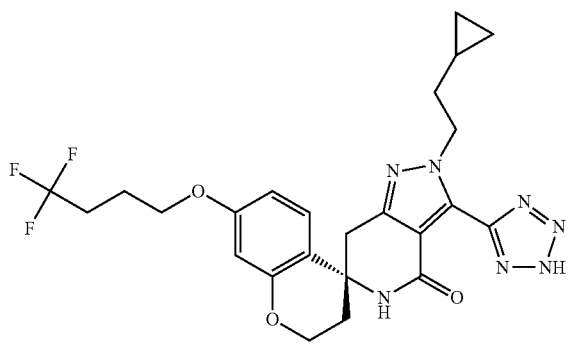 [SMILES: O=C1N[C@@]2(CCOc3cc(OCCCC(F)(F)F)ccc32)Cc2nn(CCC3CC3)c(-c3nn[nH]n3)c21]
I-202
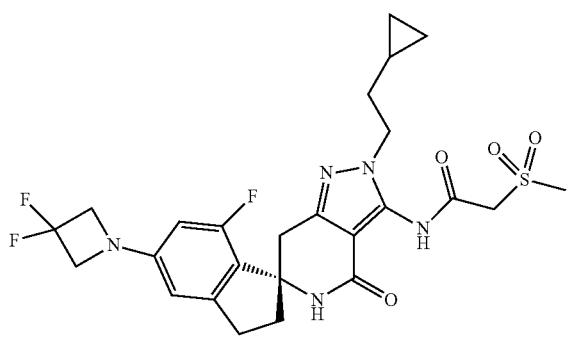 [SMILES: CS(=O)(=O)CC(=O)Nc1c2c(nn1CCC1CC1)C[C@]1(CCc3cc(N4CC(F)(F)C4)cc(F)c31)NC2=O]
I-203
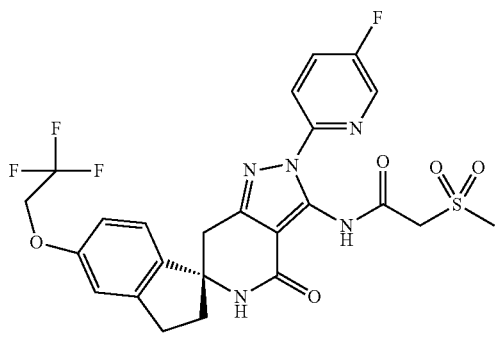 [SMILES: CS(=O)(=O)CC(=O)Nc1c2c(nn1-c1ccc(F)cn1)C[C@]1(CCc3cc(OCC(F)(F)F)ccc31)NC2=O]
I-204
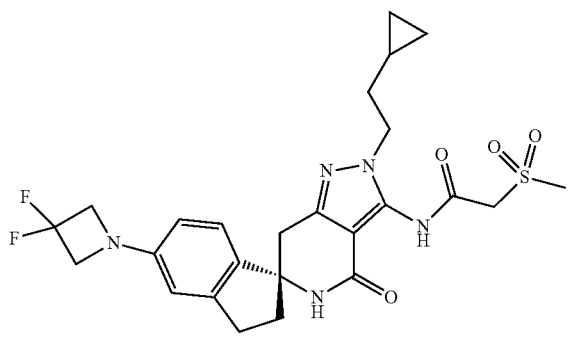 [SMILES: CS(=O)(=O)CC(=O)Nc1c2c(nn1CCC1CC1)C[C@]1(CCc3cc(N4CC(F)(F)C4)ccc31)NC2=O]

TABLE 16-continued
I-205
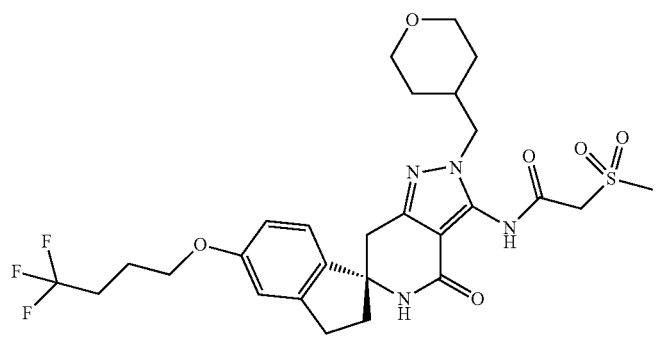 [SMILES: CS(=O)(=O)CC(=O)Nc1c2c(nn1CC1CCOCC1)C[C@]1(CCc3cc(OCCCC(F)(F)F)ccc31)NC2=O]
I-206
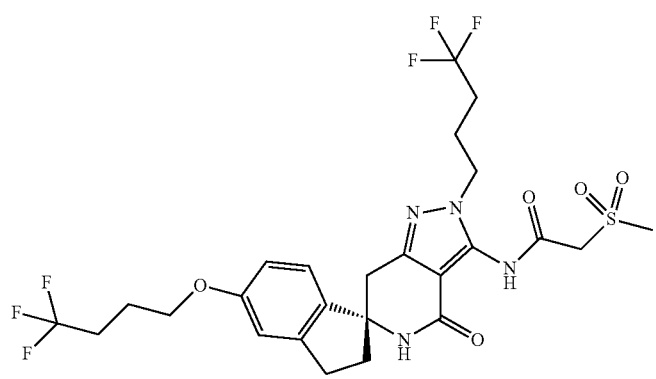 [SMILES: CS(=O)(=O)CC(=O)Nc1c2c(nn1CCCC(F)(F)F)C[C@]1(CCc3cc(OCCCC(F)(F)F)ccc31)NC2=O]
I-207
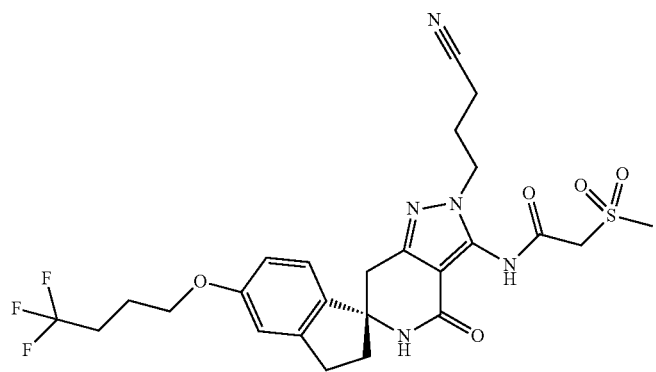 [SMILES: CS(=O)(=O)CC(=O)Nc1c2c(nn1CCCC#N)C[C@]1(CCc3cc(OCCCC(F)(F)F)ccc31)NC2=O]
I-208
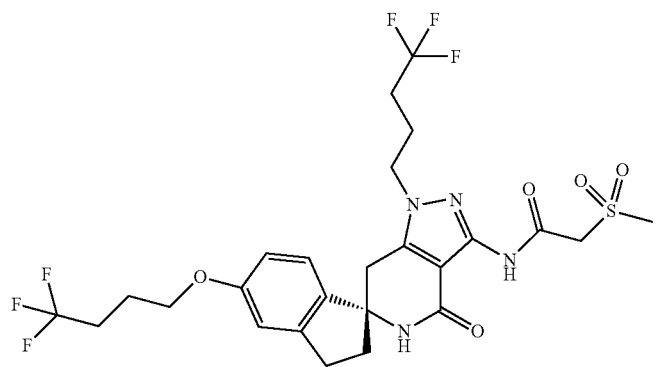 [SMILES: CS(=O)(=O)CC(=O)Nc1nn(CCCC(F)(F)F)c2c1C(=O)N[C@@]1(CCc3cc(OCCCC(F)(F)F)ccc31)C2]

TABLE 16-continued
I-209
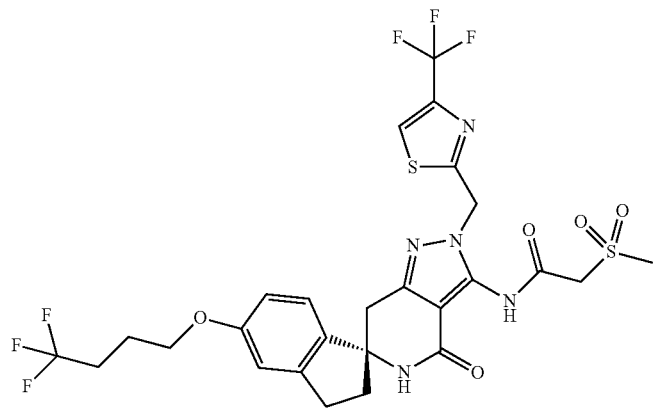 [SMILES: CS(=O)(=O)CC(=O)Nc1c2c(nn1Cc1nc(C(F)(F)F)cs1)C[C@]1(CCc3cc(OCCCC(F)(F)F)ccc31)NC2=O]
I-210
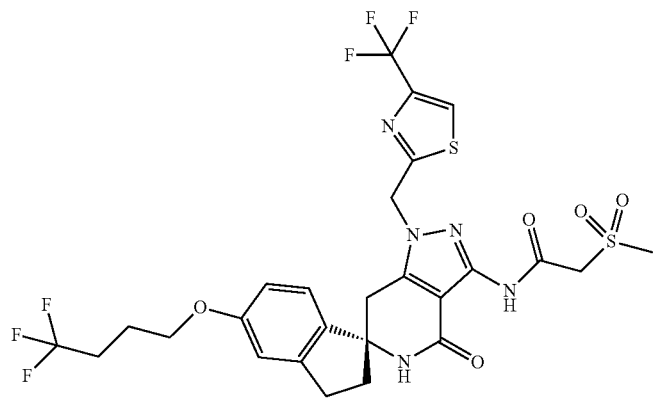 [SMILES: CS(=O)(=O)CC(=O)Nc1nn(Cc2nc(C(F)(F)F)cs2)c2c1C(=O)N[C@@]1(CCc3cc(OCCCC(F)(F)F)ccc31)C2]
I-211
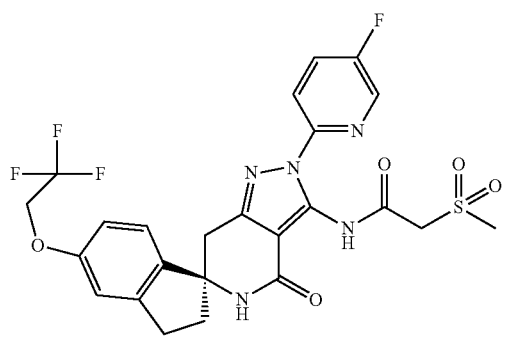 [SMILES: CS(=O)(=O)CC(=O)Nc1c2c(nn1-c1ccc(F)cn1)C[C@@]1(CCc3cc(OCC(F)(F)F)ccc31)NC2=O]
I-212
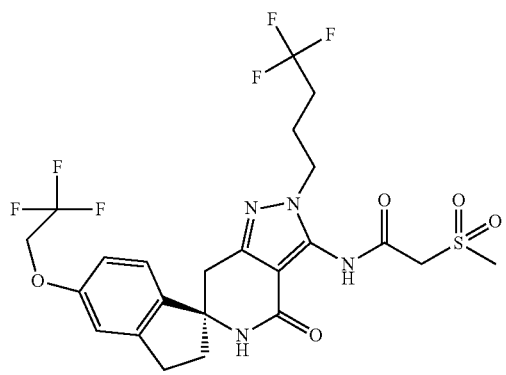 [SMILES: CS(=O)(=O)CC(=O)Nc1c2c(nn1CCCC(F)(F)F)C[C@@]1(CCc3cc(OCC(F)(F)F)ccc31)NC2=O]

TABLE 17
I-213
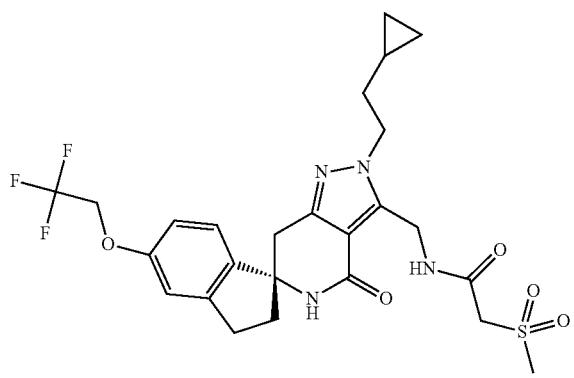 [SMILES: CS(=O)(=O)CC(=O)NCc1c2c(nn1CCC1CC1)C[C@]1(CCc3cc(OCC(F)(F)F)ccc31)NC2=O]
I-214
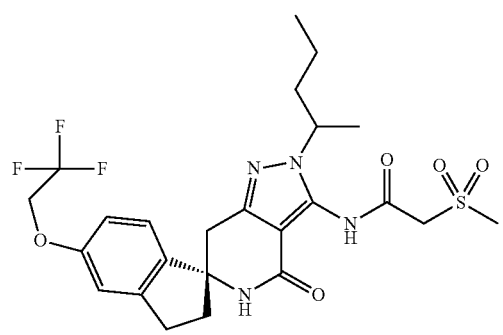 [SMILES: CCCC(C)n1nc2c(c1NC(=O)CS(C)(=O)=O)C(=O)N[C@@]1(CCc3cc(OCC(F)(F)F)ccc31)C2]
I-215
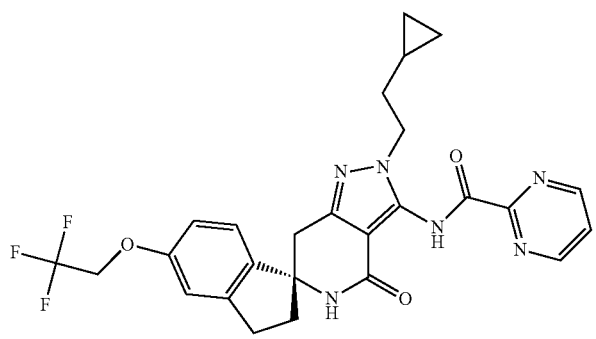 [SMILES: O=C(Nc1c2c(nn1CCC1CC1)C[C@]1(CCc3cc(OCC(F)(F)F)ccc31)NC2=O)c1ncccn1]
I-216
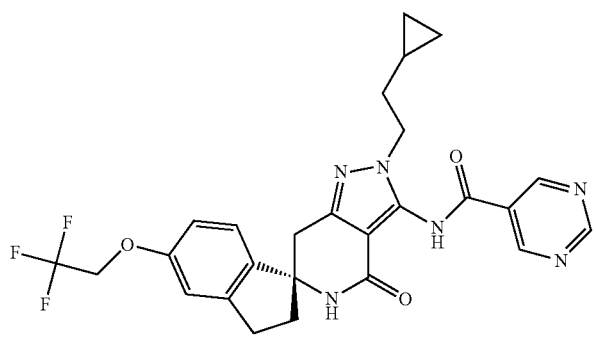 [SMILES: O=C(Nc1c2c(nn1CCC1CC1)C[C@]1(CCc3cc(OCC(F)(F)F)ccc31)NC2=O)c1cncnc1]

TABLE 17-continued
I-217
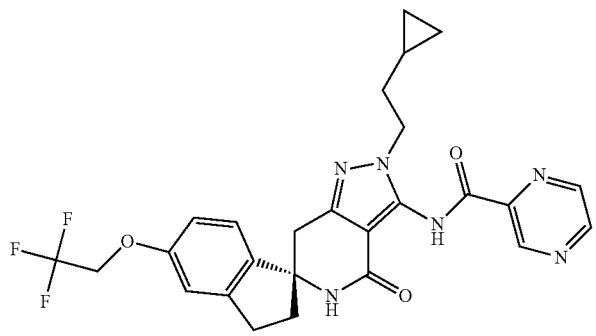 [SMILES: O=C(Nc1c2c(nn1CCC1CC1)C[C@]1(CCc3cc(OCC(F)(F)F)ccc31)NC2=O)c1cnccn1]
I-218
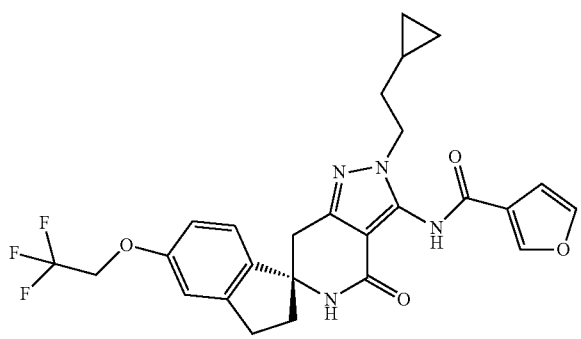 [SMILES: O=C(Nc1c2c(nn1CCC1CC1)C[C@]1(CCc3cc(OCC(F)(F)F)ccc31)NC2=O)c1ccoc1]
I-219
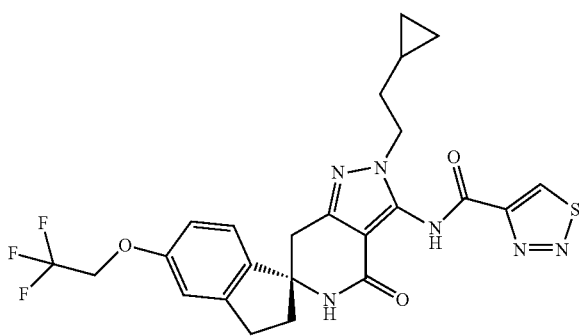 [SMILES: O=C(Nc1c2c(nn1CCC1CC1)C[C@]1(CCc3cc(OCC(F)(F)F)ccc31)NC2=O)c1csnn1]
I-220
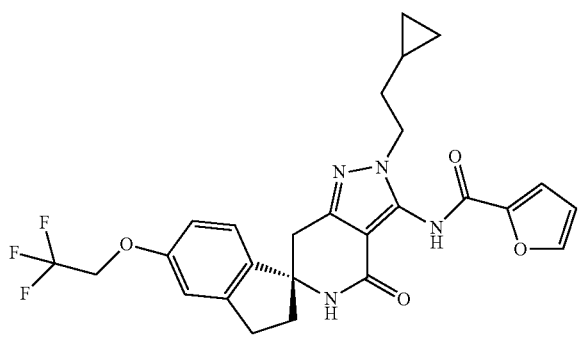 [SMILES: O=C(Nc1c2c(nn1CCC1CC1)C[C@]1(CCc3cc(OCC(F)(F)F)ccc31)NC2=O)c1ccco1]

TABLE 17-continued
I-221
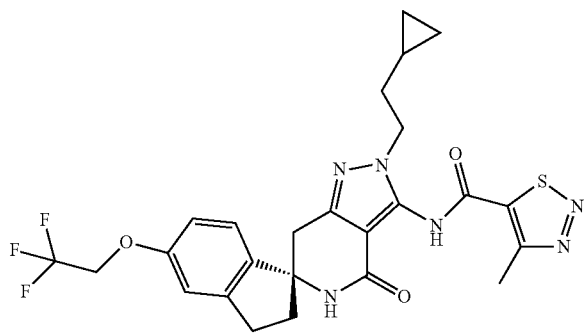 [SMILES: Cc1nnsc1C(=O)Nc1c2c(nn1CCC1CC1)C[C@]1(CCc3cc(OCC(F)(F)F)ccc31)NC2=O]
I-222
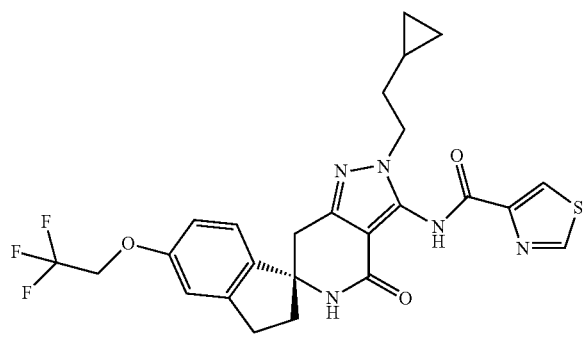 [SMILES: O=C(Nc1c2c(nn1CCC1CC1)C[C@]1(CCc3cc(OCC(F)(F)F)ccc31)NC2=O)c1cscn1]
I-223
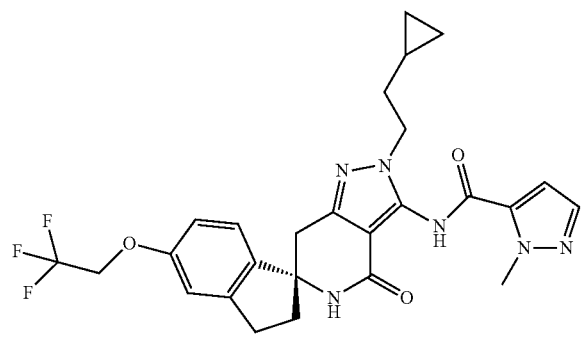 [SMILES: Cn1nccc1C(=O)Nc1c2c(nn1CCC1CC1)C[C@]1(CCc3cc(OCC(F)(F)F)ccc31)NC2=O]
I-224
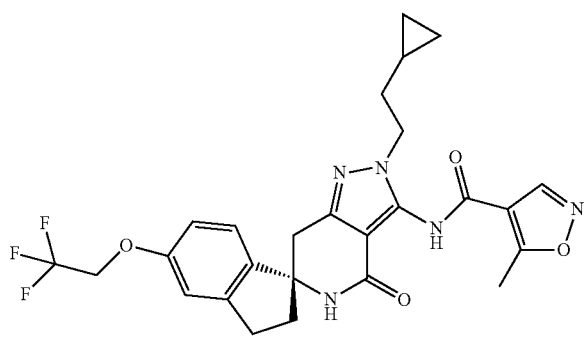 [SMILES: Cc1oncc1C(=O)Nc1c2c(nn1CCC1CC1)C[C@]1(CCc3cc(OCC(F)(F)F)ccc31)NC2=O]

TABLE 17-continued
I-225
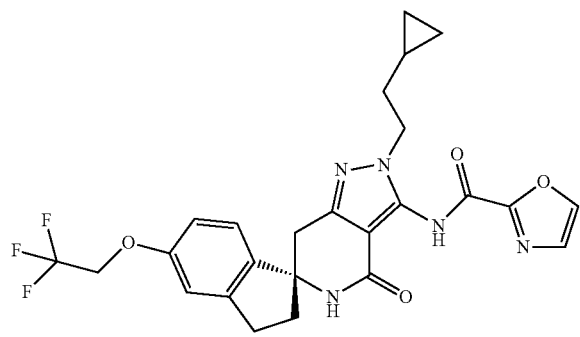 [SMILES: O=C(Nc1c2c(nn1CCC1CC1)C[C@]1(CCc3cc(OCC(F)(F)F)ccc31)NC2=O)c1ncco1]
I-226
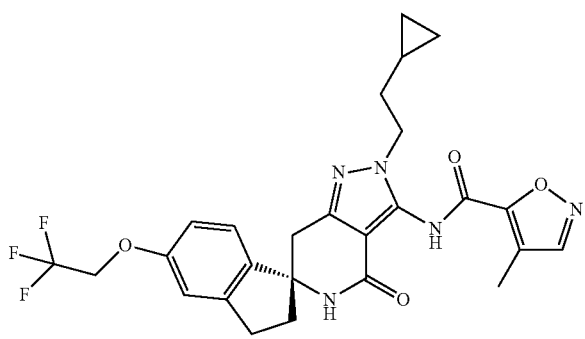 [SMILES: Cc1cnoc1C(=O)Nc1c2c(nn1CCC1CC1)C[C@]1(CCc3cc(OCC(F)(F)F)ccc31)NC2=O]
TABLE 18
I-227
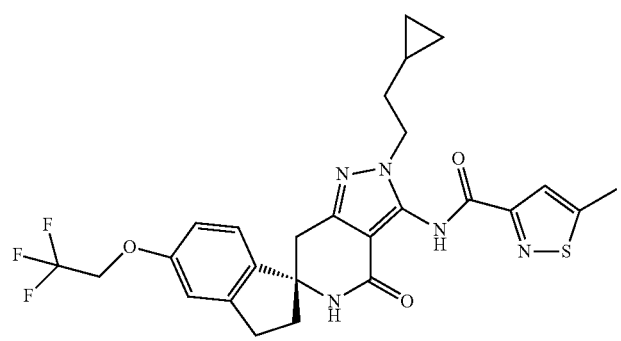 [SMILES: Cc1cc(C(=O)Nc2c3c(nn2CCC2CC2)C[C@]2(CCc4cc(OCC(F)(F)F)ccc42)NC3=O)ns1]
I-228
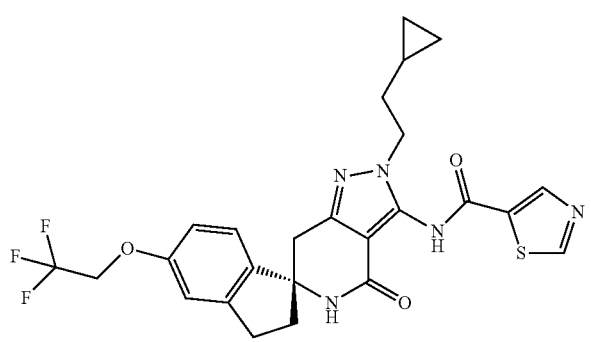 [SMILES: O=C(Nc1c2c(nn1CCC1CC1)C[C@]1(CCc3cc(OCC(F)(F)F)ccc31)NC2=O)c1cncs1]

TABLE 18-continued
I-229
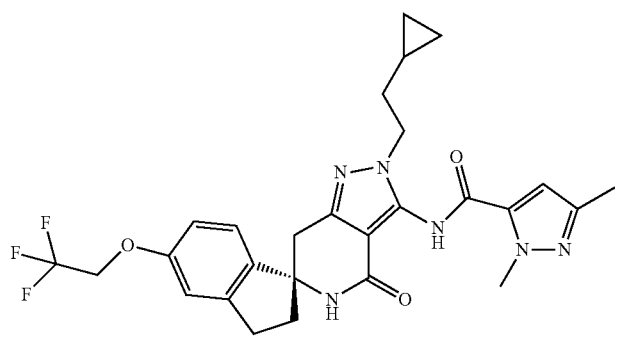 [SMILES: Cc1cc(C(=O)Nc2c3c(nn2CCC2CC2)C[C@]2(CCc4cc(OCC(F)(F)F)ccc42)NC3=O)n(C)n1]
I-230
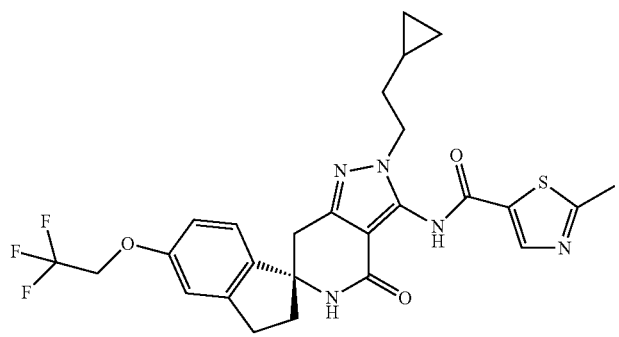 [SMILES: Cc1ncc(C(=O)Nc2c3c(nn2CCC2CC2)C[C@]2(CCc4cc(OCC(F)(F)F)ccc42)NC3=O)s1]
I-231
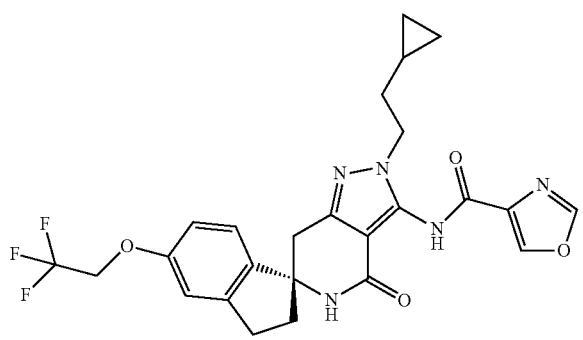 [SMILES: O=C(Nc1c2c(nn1CCC1CC1)C[C@]1(CCc3cc(OCC(F)(F)F)ccc31)NC2=O)c1cocn1]
I-232
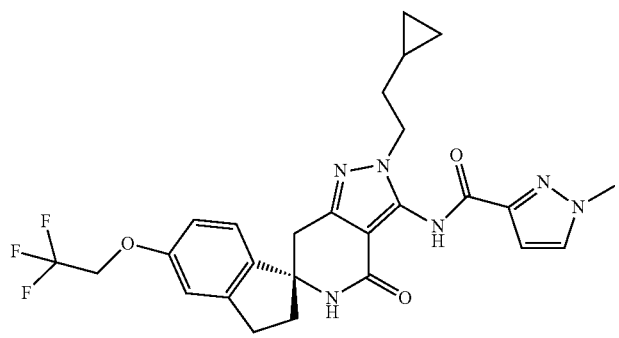 [SMILES: Cn1ccc(C(=O)Nc2c3c(nn2CCC2CC2)C[C@]2(CCc4cc(OCC(F)(F)F)ccc42)NC3=O)n1]

TABLE 18-continued
I-233
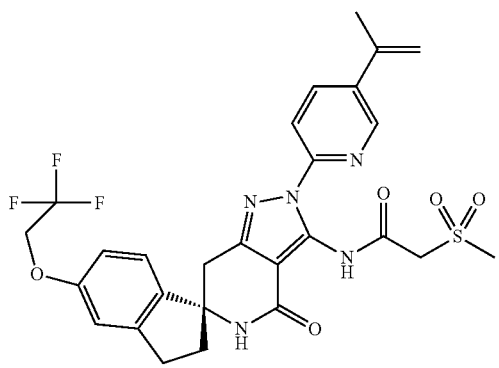 [SMILES: C=C(C)c1ccc(-n2nc3c(c2NC(=O)CS(C)(=O)=O)C(=O)N[C@@]2(CCc4cc(OCC(F)(F)F)ccc42)C3)nc1]
I-234
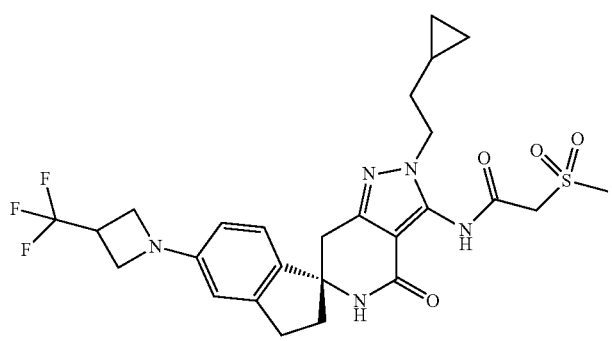 [SMILES: CS(=O)(=O)CC(=O)Nc1c2c(nn1CCC1CC1)C[C@]1(CCc3cc(N4CC(C(F)(F)F)C4)ccc31)NC2=O]
I-235
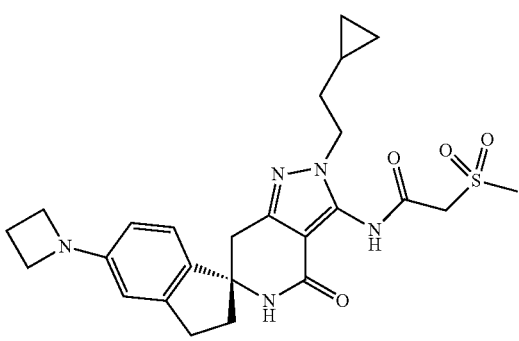 [SMILES: CS(=O)(=O)CC(=O)Nc1c2c(nn1CCC1CC1)C[C@]1(CCc3cc(N4CCC4)ccc31)NC2=O]
I-236
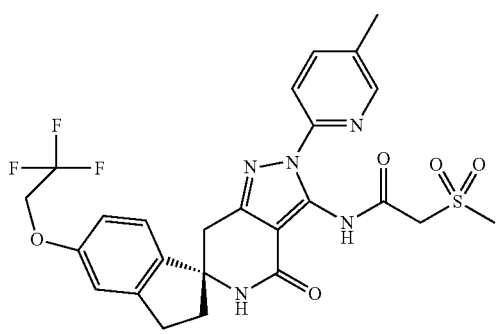 [SMILES: Cc1ccc(-n2nc3c(c2NC(=O)CS(C)(=O)=O)C(=O)N[C@@]2(CCc4cc(OCC(F)(F)F)ccc42)C3)nc1]

TABLE 18-continued
I-237
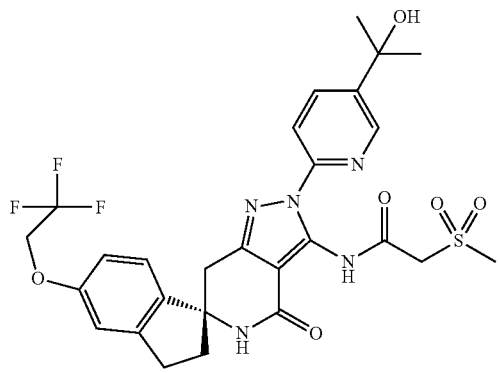 [SMILES: CC(C)(O)c1ccc(-n2nc3c(c2NC(=O)CS(C)(=O)=O)C(=O)N[C@@]2(CCc4cc(OCC(F)(F)F)ccc42)C3)nc1]
I-238
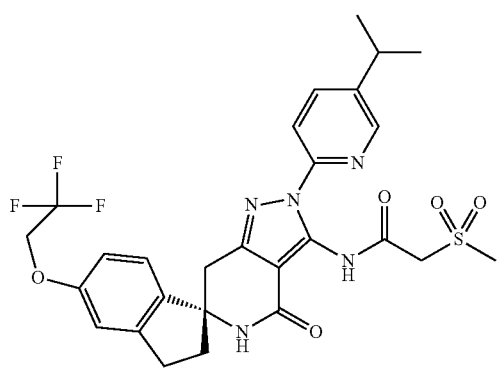 [SMILES: CC(C)c1ccc(-n2nc3c(c2NC(=O)CS(C)(=O)=O)C(=O)N[C@@]2(CCc4cc(OCC(F)(F)F)ccc42)C3)nc1]
I-239
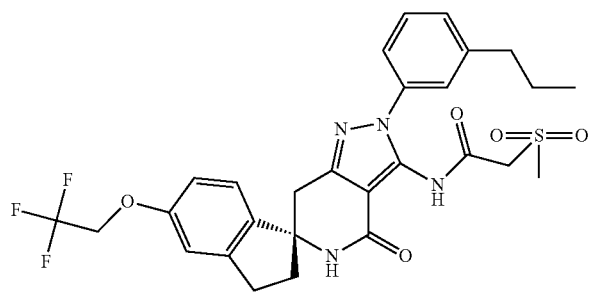 [SMILES: CCCc1cccc(-n2nc3c(c2NC(=O)CS(C)(=O)=O)C(=O)N[C@@]2(CCc4cc(OCC(F)(F)F)ccc42)C3)c1]
I-240
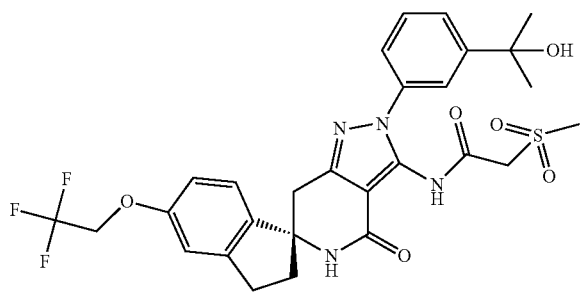 [SMILES: CC(C)(O)c1cccc(-n2nc3c(c2NC(=O)CS(C)(=O)=O)C(=O)N[C@@]2(CCc4cc(OCC(F)(F)F)ccc42)C3)c1]

TABLE 19
I-241
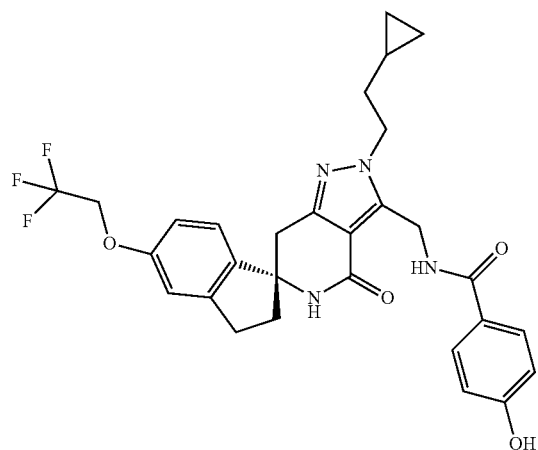 [SMILES: O=C(NCc1c2c(nn1CCC1CC1)C[C@]1(CCc3cc(OCC(F)(F)F)ccc31)NC2=O)c1ccc(O)cc1]
I-242
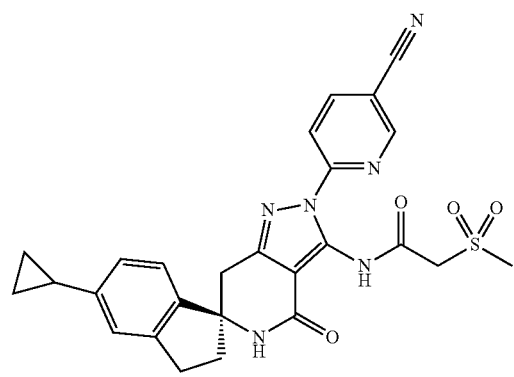 [SMILES: CS(=O)(=O)CC(=O)Nc1c2c(nn1-c1ccc(C#N)cn1)C[C@@]1(CCc3cc(C4CC4)ccc31)NC2=O]
I-243
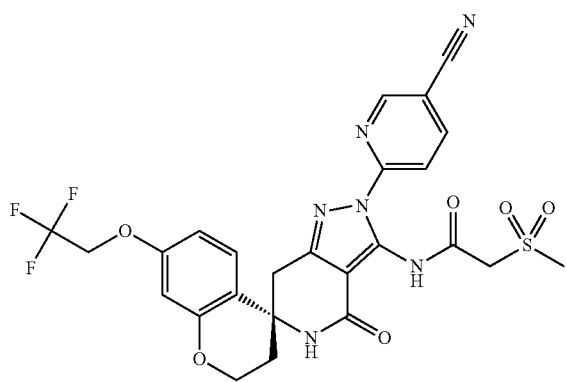 [SMILES: CS(=O)(=O)CC(=O)Nc1c2c(nn1-c1ccc(C#N)cn1)C[C@]1(CCOc3cc(OCC(F)(F)F)ccc31)NC2=O]
I-244
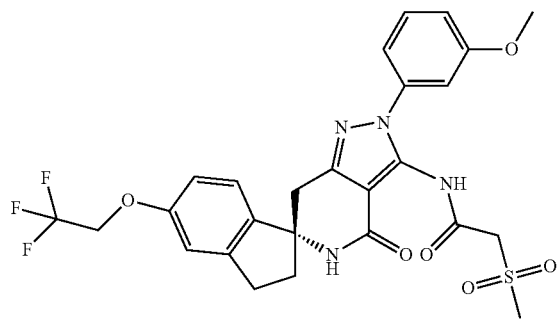 [SMILES: COc1cccc(-n2nc3c(c2NC(=O)CS(C)(=O)=O)C(=O)N[C@@]2(CCc4cc(OCC(F)(F)F)ccc42)C3)c1]

TABLE 19-continued
I-245
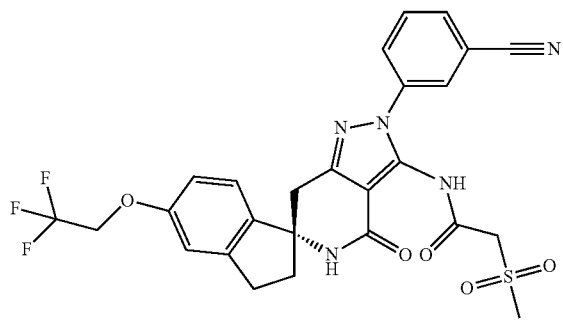 [SMILES: CS(=O)(=O)CC(=O)Nc1c2c(nn1-c1cccc(C#N)c1)C[C@]1(CCc3cc(OCC(F)(F)F)ccc31)NC2=O]
I-246
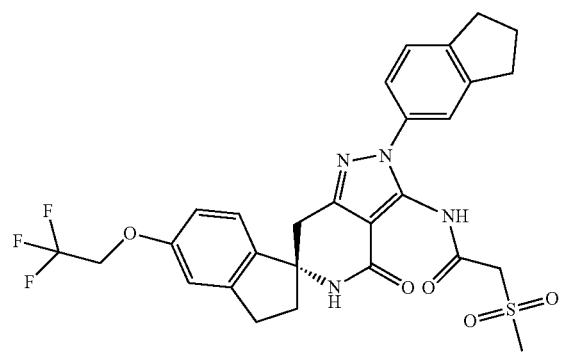 [SMILES: CS(=O)(=O)CC(=O)Nc1c2c(nn1-c1ccc3c(c1)CCC3)C[C@]1(CCc3cc(OCC(F)(F)F)ccc31)NC2=O]
I-247
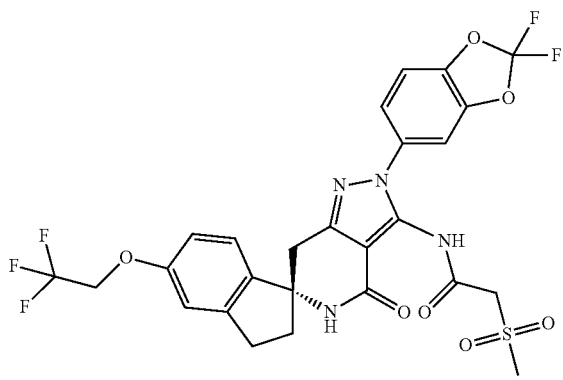 [SMILES: CS(=O)(=O)CC(=O)Nc1c2c(nn1-c1ccc3c(c1)OC(F)(F)O3)C[C@]1(CCc3cc(OCC(F)(F)F)ccc31)NC2=O]
I-248
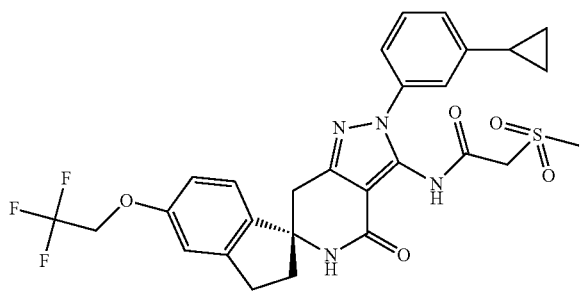 [SMILES: CS(=O)(=O)CC(=O)Nc1c2c(nn1-c1cccc(C3CC3)c1)C[C@]1(CCc3cc(OCC(F)(F)F)ccc31)NC2=O]

TABLE 19-continued
I-249
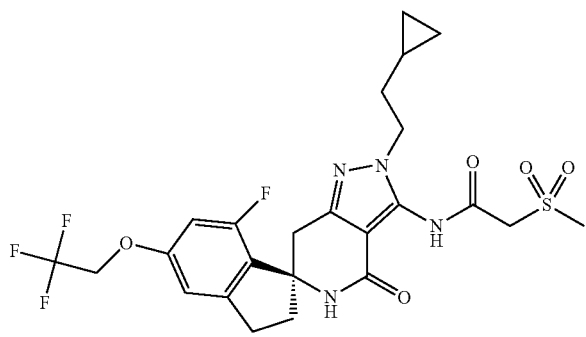 [SMILES: CS(=O)(=O)CC(=O)Nc1c2c(nn1CCC1CC1)C[C@@]1(CCc3cc(OCC(F)(F)F)cc(F)c31)NC2=O]
I-250
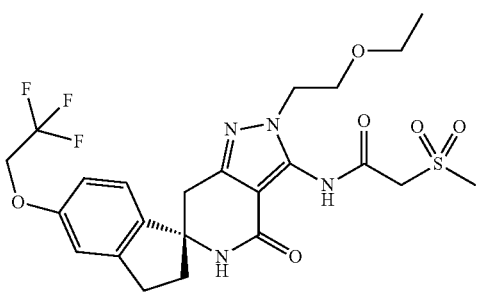 [SMILES: CCOCCn1nc2c(c1NC(=O)CS(C)(=O)=O)C(=O)N[C@@]1(CCc3cc(OCC(F)(F)F)ccc31)C2]
I-251
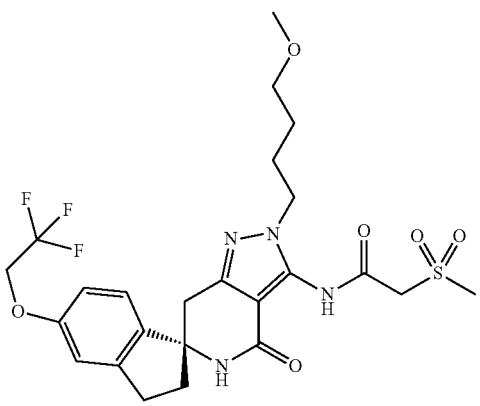 [SMILES: COCCCCn1nc2c(c1NC(=O)CS(C)(=O)=O)C(=O)N[C@@]1(CCc3cc(OCC(F)(F)F)ccc31)C2]
I-252
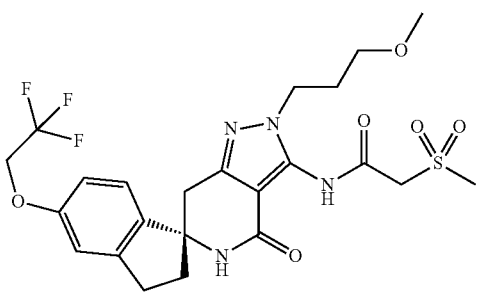 [SMILES: COCCCn1nc2c(c1NC(=O)CS(C)(=O)=O)C(=O)N[C@@]1(CCc3cc(OCC(F)(F)F)ccc31)C2]

TABLE 20
I-253
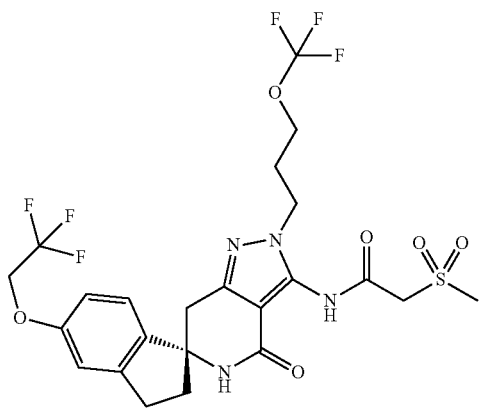 [SMILES: CS(=O)(=O)CC(=O)Nc1c2c(nn1CCCOC(F)(F)F)C[C@]1(CCc3cc(OCC(F)(F)F)ccc31)NC2=O]
I-254
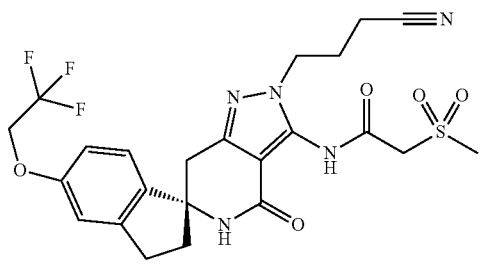 [SMILES: CS(=O)(=O)CC(=O)Nc1c2c(nn1CCCC#N)C[C@]1(CCc3cc(OCC(F)(F)F)ccc31)NC2=O]
I-255
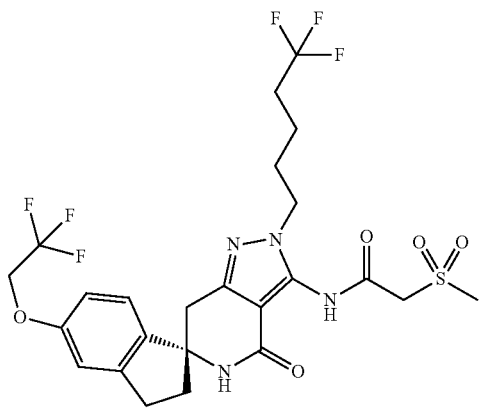
I-256
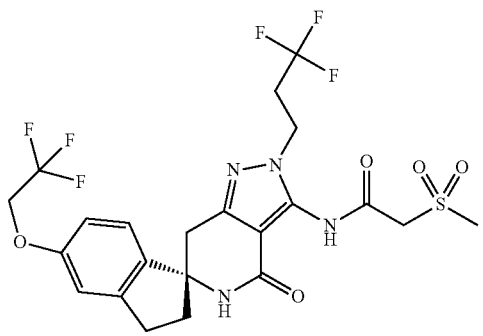 [SMILES: CS(=O)(=O)CC(=O)Nc1c2c(nn1CCC(F)(F)F)C[C@]1(CCc3cc(OCC(F)(F)F)ccc31)NC2=O]

TABLE 20-continued
I-257 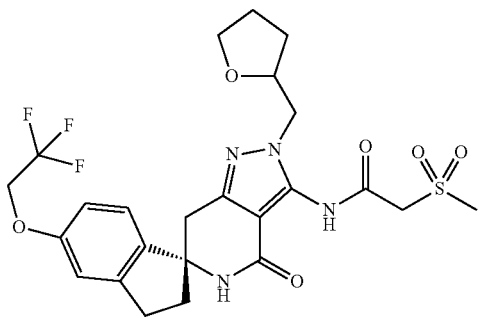 [SMILES: CS(=O)(=O)CC(=O)Nc1c2c(nn1CC1CCCO1)C[C@]1(CCc3cc(OCC(F)(F)F)ccc31)NC2=O]
I-258 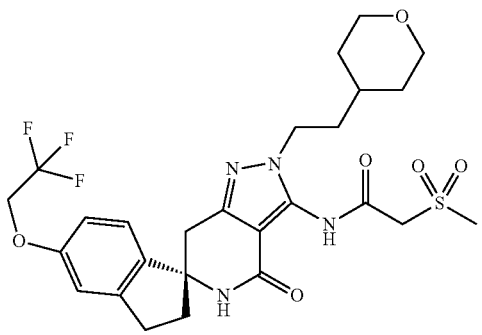 [SMILES: CS(=O)(=O)CC(=O)Nc1c2c(nn1CCC1CCOCC1)C[C@]1(CCc3cc(OCC(F)(F)F)ccc31)NC2=O]
I-259 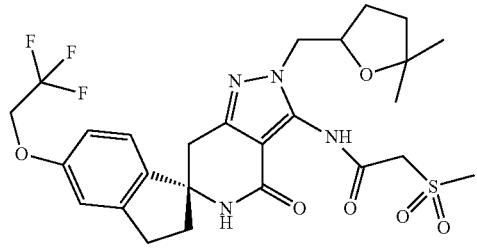 [SMILES: CC1(C)CCC(Cn2nc3c(c2NC(=O)CS(C)(=O)=O)C(=O)N[C@@]2(CCc4cc(OCC(F)(F)F)ccc42)C3)O1]
I-260 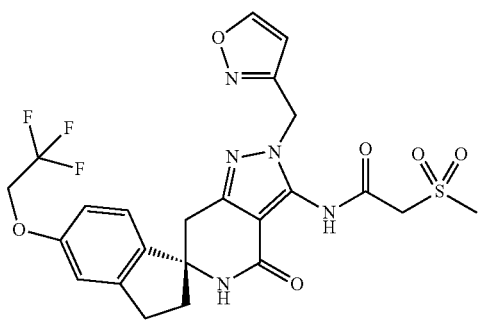 [SMILES: CS(=O)(=O)CC(=O)Nc1c2c(nn1Cc1ccon1)C[C@]1(CCc3cc(OCC(F)(F)F)ccc31)NC2=O]
I-261 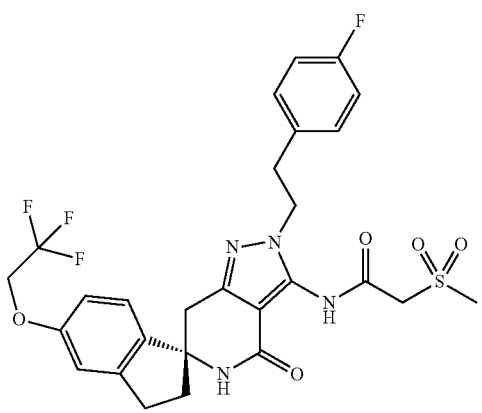 [SMILES: CS(=O)(=O)CC(=O)Nc1c2c(nn1CCc1ccc(F)cc1)C[C@]1(CCc3cc(OCC(F)(F)F)ccc31)NC2=O]

TABLE 20-continued
I-262
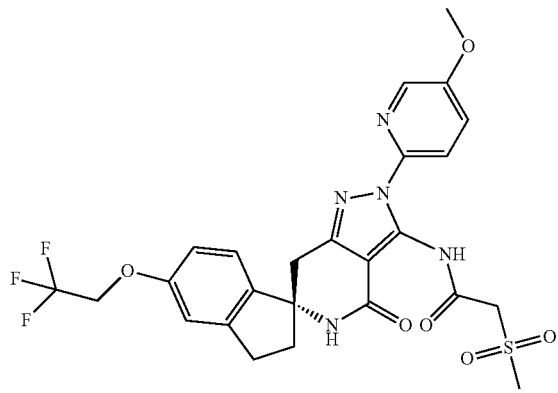 [SMILES: COc1ccc(-n2nc3c(c2NC(=O)CS(C)(=O)=O)C(=O)N[C@@]2(CCc4cc(OCC(F)(F)F)ccc42)C3)nc1]
I-263
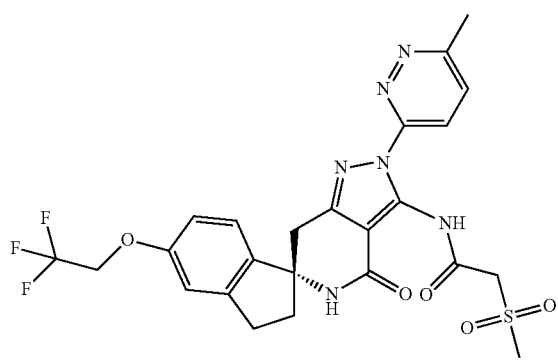 [SMILES: Cc1ccc(-n2nc3c(c2NC(=O)CS(C)(=O)=O)C(=O)N[C@@]2(CCc4cc(OCC(F)(F)F)ccc42)C3)nn1]
I-264
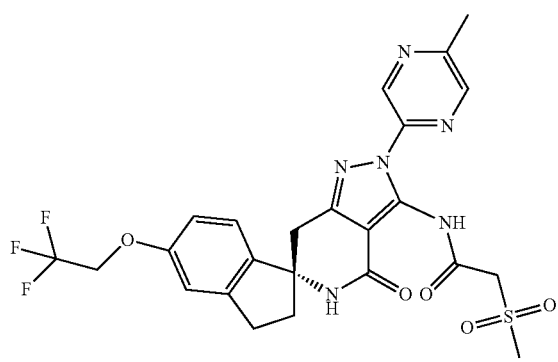 [SMILES: Cc1cnc(-n2nc3c(c2NC(=O)CS(C)(=O)=O)C(=O)N[C@@]2(CCc4cc(OCC(F)(F)F)ccc42)C3)cn1]
TABLE 21
I-265
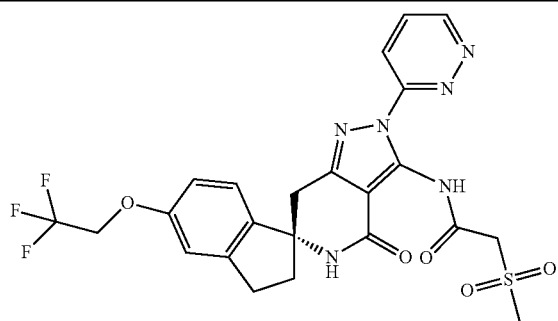

TABLE 21-continued
I-266
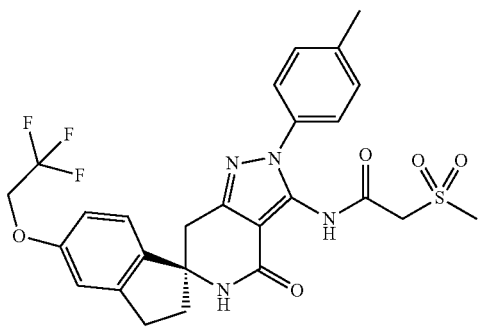
I-267
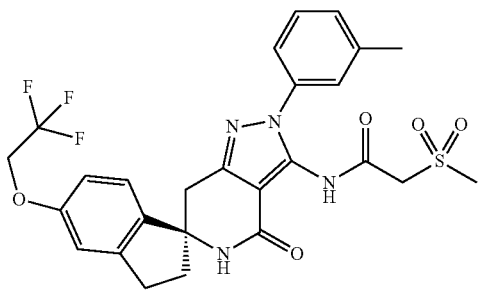 [SMILES: Cc1cccc(-n2nc3c(c2NC(=O)CS(C)(=O)=O)C(=O)N[C@]2(CCc4cc(OCC(F)(F)F)ccc42)C3)c1]
I-268
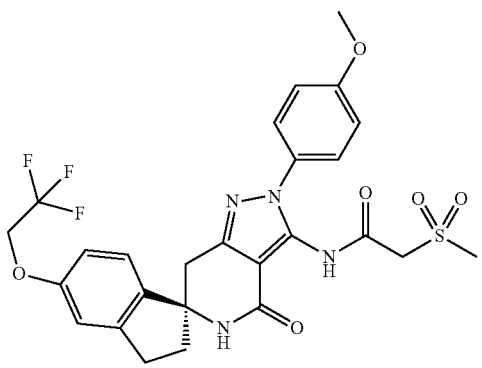 [SMILES: COc1ccc(-n2nc3c(c2NC(=O)CS(C)(=O)=O)C(=O)N[C@]2(CCc4cc(OCC(F)(F)F)ccc42)C3)cc1]
I-269
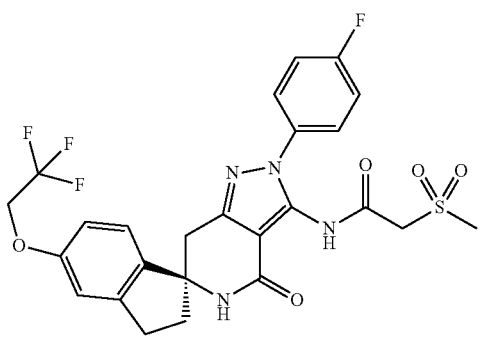 [SMILES: CS(=O)(=O)CC(=O)Nc1c2c(nn1-c1ccc(F)cc1)C[C@@]1(CCc3cc(OCC(F)(F)F)ccc31)NC2=O]
I-270
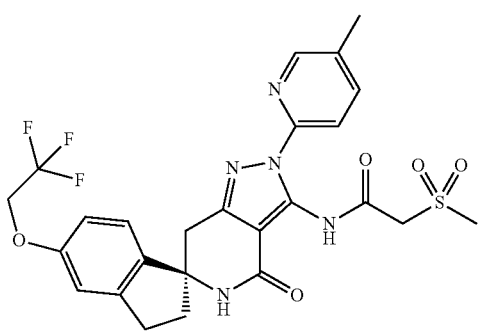 [SMILES: Cc1ccc(-n2nc3c(c2NC(=O)CS(C)(=O)=O)C(=O)N[C@]2(CCc4cc(OCC(F)(F)F)ccc42)C3)nc1]

TABLE 21-continued
I-271
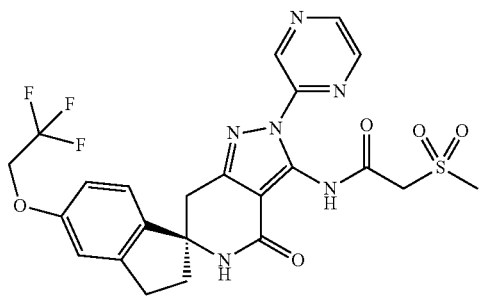 [SMILES: CS(=O)(=O)CC(=O)Nc1c2c(nn1-c1cnccn1)C[C@@]1(CCc3cc(OCC(F)(F)F)ccc31)NC2=O]
I-272
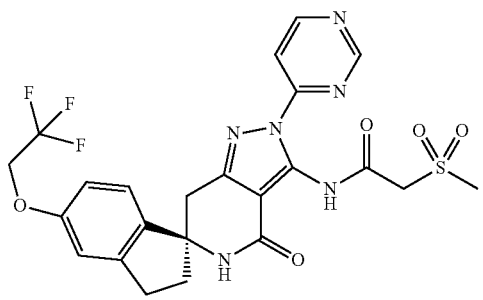 [SMILES: CS(=O)(=O)CC(=O)Nc1c2c(nn1-c1ccncn1)C[C@@]1(CCc3cc(OCC(F)(F)F)ccc31)NC2=O]
I-273
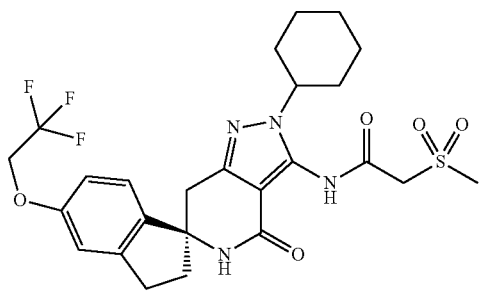 [SMILES: CS(=O)(=O)CC(=O)Nc1c2c(nn1C1CCCCC1)C[C@@]1(CCc3cc(OCC(F)(F)F)ccc31)NC2=O]
I-274
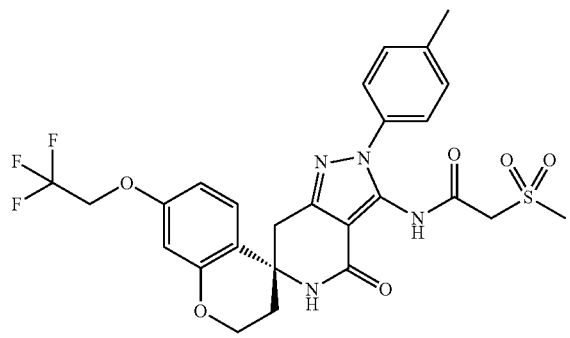 [SMILES: Cc1ccc(-n2nc3c(c2NC(=O)CS(C)(=O)=O)C(=O)N[C@@]2(CCOc4cc(OCC(F)(F)F)ccc42)C3)cc1]
I-275
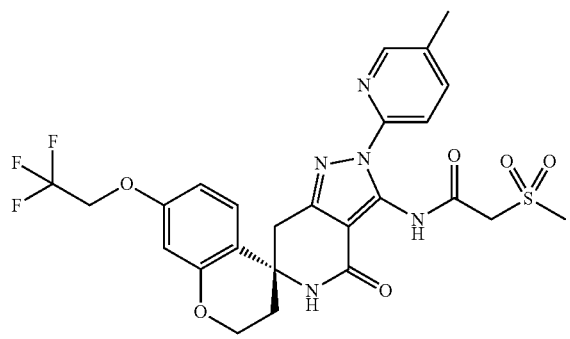 [SMILES: Cc1ccc(-n2nc3c(c2NC(=O)CS(C)(=O)=O)C(=O)N[C@@]2(CCOc4cc(OCC(F)(F)F)ccc42)C3)nc1]

TABLE 21-continued
I-276
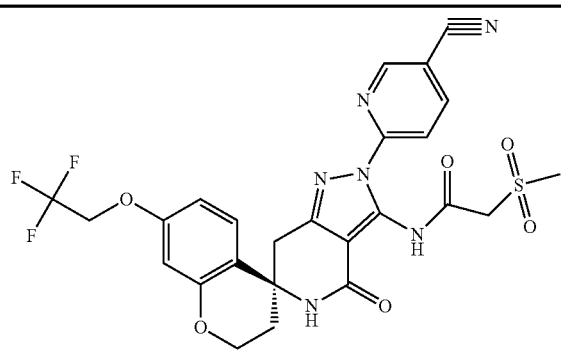
I-278
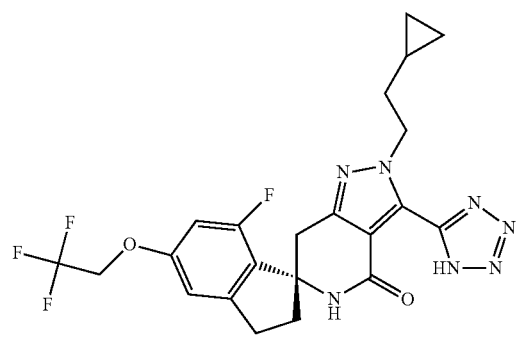 [SMILES: O=C1N[C@@]2(CCc3cc(OCC(F)(F)F)cc(F)c32)Cc2nn(CCC3CC3)c(-c3nnn[nH]3)c21]
I-279
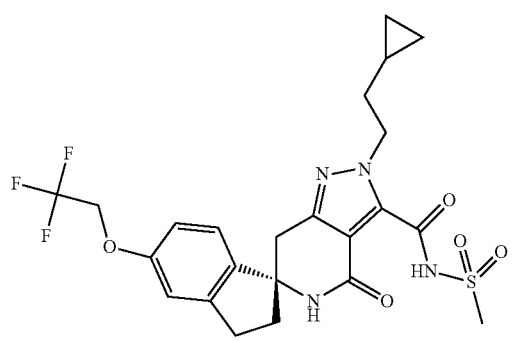 [SMILES: CS(=O)(=O)NC(=O)c1c2c(nn1CCC1CC1)C[C@]1(CCc3cc(OCC(F)(F)F)ccc31)NC2=O]
TABLE 22
I-280
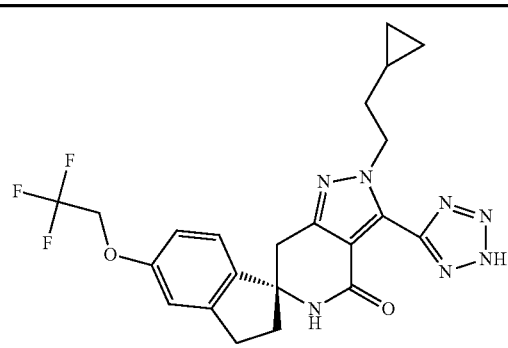

TABLE 22-continued
I-281
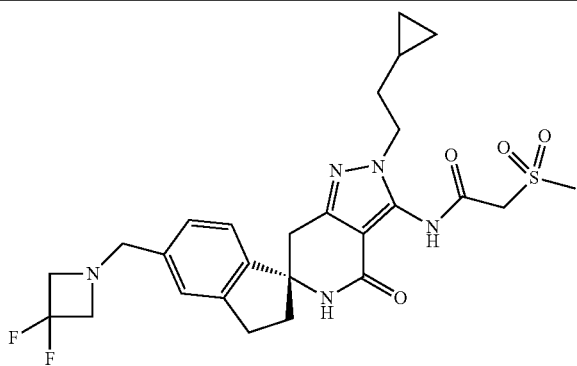
I-284
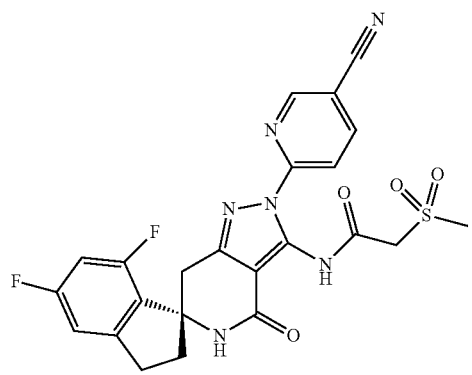 [SMILES: CS(=O)(=O)CC(=O)Nc1c2c(nn1-c1ccc(C#N)cn1)C[C@]1(CCc3cc(F)cc(F)c31)NC2=O]
I-285
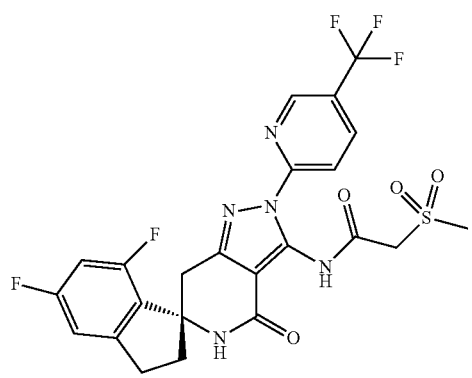 [SMILES: CS(=O)(=O)CC(=O)Nc1c2c(nn1-c1ccc(C(F)(F)F)cn1)C[C@]1(CCc3cc(F)cc(F)c31)NC2=O]
TABLE 23
| No. | Structure |
|---|---|
| II-1 | 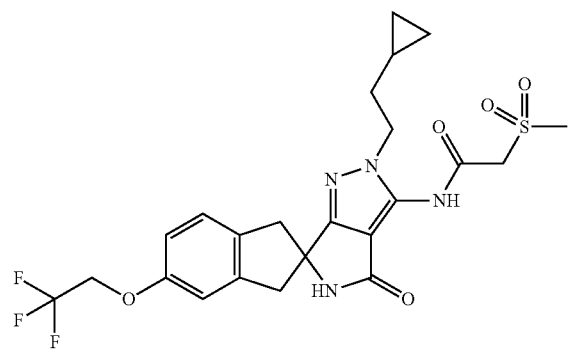 [SMILES: CS(=O)(=O)CC(=O)Nc1c2c(nn1CCC1CC1)C1(Cc3ccc(OCC(F)(F)F)cc3C1)NC2=O] |

TABLE 23-continued
| No. | Structure |
|---|---|
| II-4 | 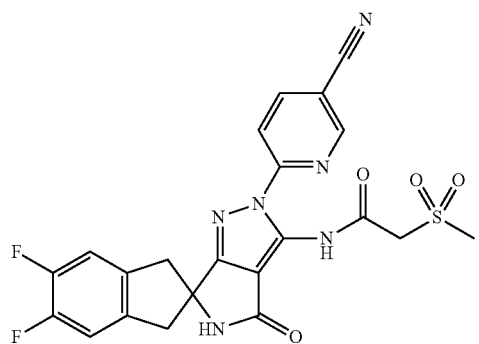 [SMILES: CS(=O)(=O)CC(=O)Nc1c2c(nn1-c1ccc(C#N)cn1)C1(Cc3cc(F)c(F)cc3C1)NC2=O] |
| II-5 | 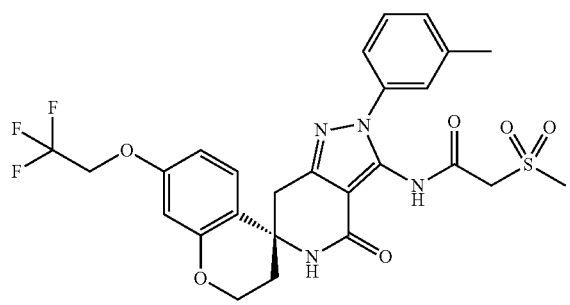 [SMILES: Cc1cccc(-n2nc3c(c2NC(=O)CS(C)(=O)=O)C(=O)N[C@@]2(CCOc4cc(OCC(F)(F)F)ccc42)C3)c1] |
| II-6 | 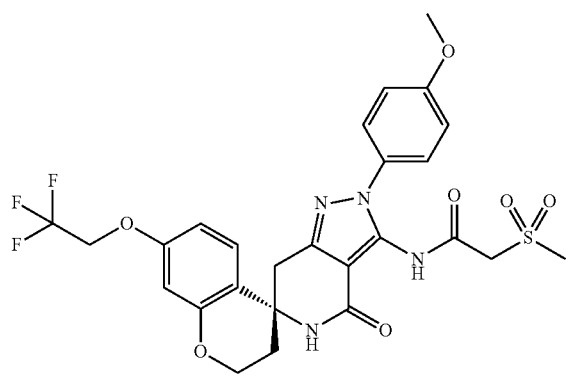 [SMILES: COc1ccc(-n2nc3c(c2NC(=O)CS(C)(=O)=O)C(=O)N[C@@]2(CCOc4cc(OCC(F)(F)F)ccc42)C3)cc1] |
| II-7 | 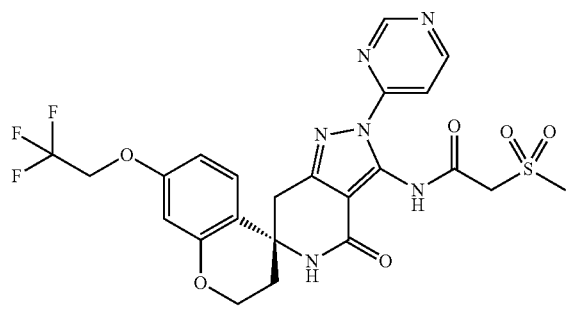 [SMILES: CS(=O)(=O)CC(=O)Nc1c2c(nn1-c1ccncn1)C[C@]1(CCOc3cc(OCC(F)(F)F)ccc31)NC2=O] |

TABLE 23-continued

| No. | Structure |
|---|---|
| II-8 | 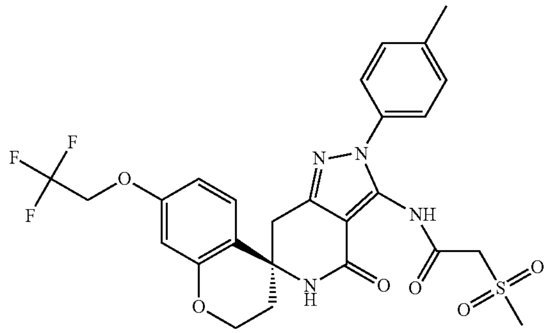 [SMILES: Cc1ccc(-n2nc3c(c2NC(=O)CS(C)(=O)=O)C(=O)N[C@]2(CCOc4cc(OCC(F)(F)F)ccc42)C3)cc1] |
| II-9 | 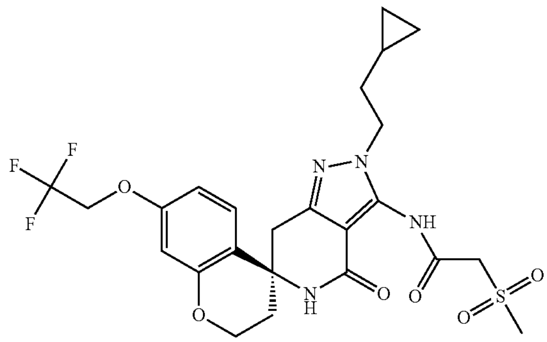 [SMILES: CS(=O)(=O)CC(=O)Nc1c2c(nn1CCC1CC1)C[C@@]1(CCOc3cc(OCC(F)(F)F)ccc31)NC2=O] |
| II-10 | 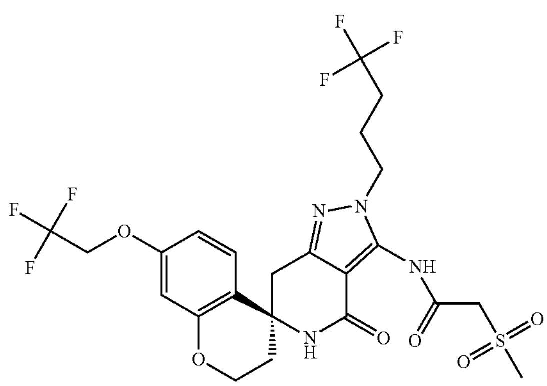 [SMILES: CS(=O)(=O)CC(=O)Nc1c2c(nn1CCCC(F)(F)F)C[C@@]1(CCOc3cc(OCC(F)(F)F)ccc31)NC2=O] |
| II-11 | 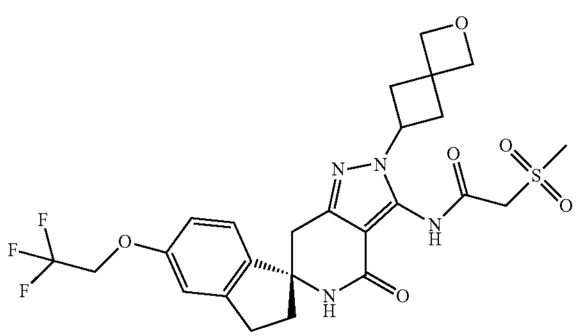 [SMILES: CS(=O)(=O)CC(=O)Nc1c2c(nn1C1CC3(COC3)C1)C[C@]1(CCc3cc(OCC(F)(F)F)ccc31)NC2=O] |

TABLE 23-continued

| No. | Structure |
|---|---|
| II-12 | 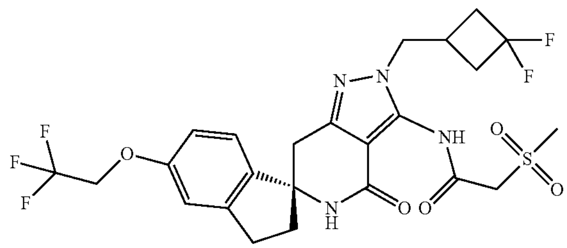 [SMILES: CS(=O)(=O)CC(=O)Nc1c2c(nn1CC1CC(F)(F)C1)C[C@]1(CCc3cc(OCC(F)(F)F)ccc31)NC2=O] |
| II-13 | 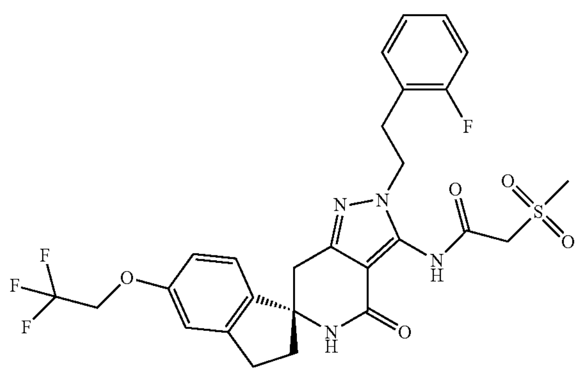 [SMILES: CS(=O)(=O)CC(=O)Nc1c2c(nn1CCc1ccccc1F)C[C@]1(CCc3cc(OCC(F)(F)F)ccc31)NC2=O] |
| II-15 | 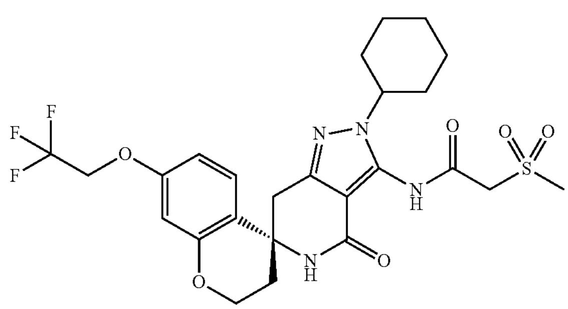 [SMILES: CS(=O)(=O)CC(=O)Nc1c2c(nn1C1CCCCC1)C[C@]1(CCOc3cc(OCC(F)(F)F)ccc31)NC2=O] |

TABLE 24
II-16
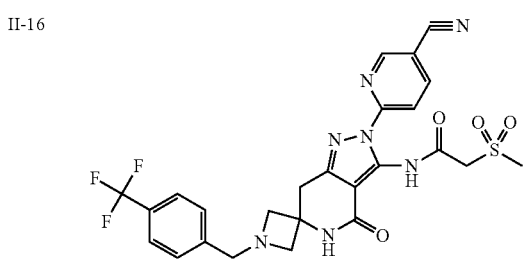
II-17
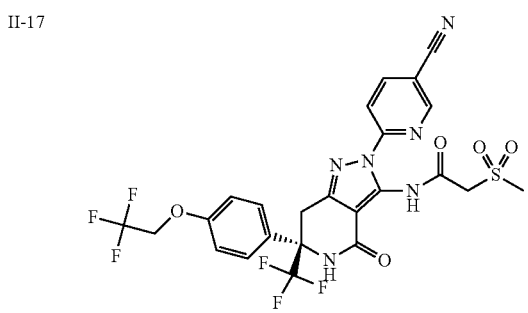
II-18
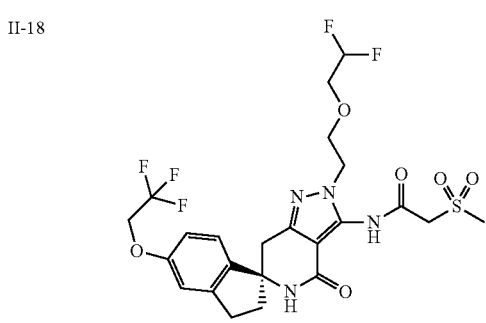
II-19
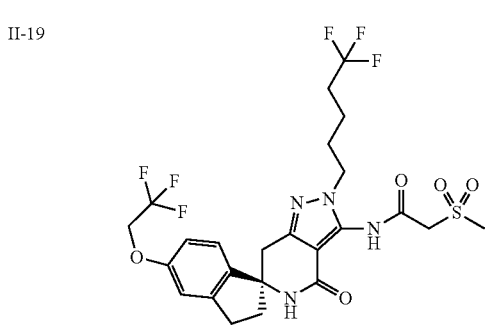
II-20
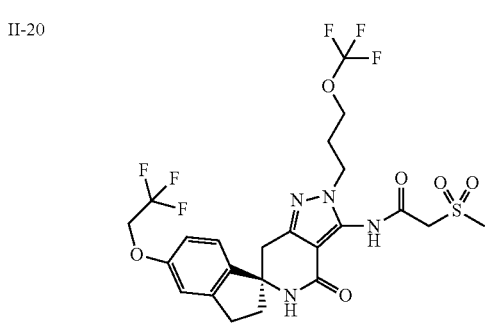
TABLE 24-continued
II-21
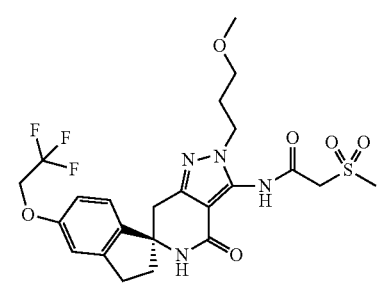 [SMILES: COCCCn1nc2c(c1NC(=O)CS(C)(=O)=O)C(=O)N[C@]1(CCc3cc(OCC(F)(F)F)ccc31)C2]
II-22
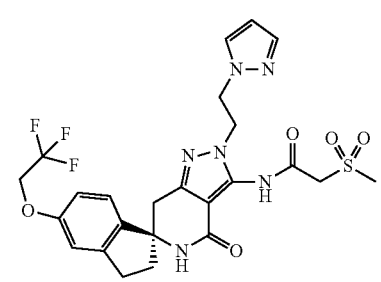 [SMILES: CS(=O)(=O)CC(=O)Nc1c2c(nn1CCn1cccn1)C[C@@]1(CCc3cc(OCC(F)(F)F)ccc31)NC2=O]
II-23
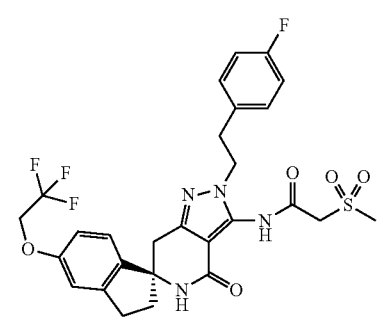 [SMILES: CS(=O)(=O)CC(=O)Nc1c2c(nn1CCc1ccc(F)cc1)C[C@@]1(CCc3cc(OCC(F)(F)F)ccc31)NC2=O]
II-24
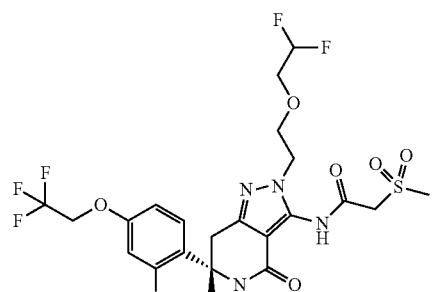
II-25
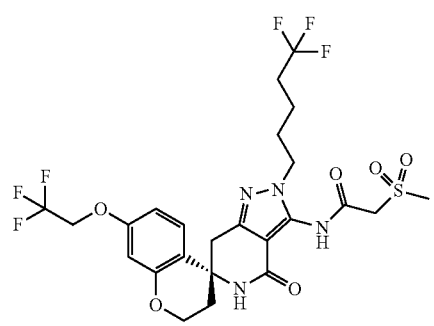 [SMILES: CS(=O)(=O)CC(=O)Nc1c2c(nn1CCCCC(F)(F)F)C[C@]1(CCOc3cc(OCC(F)(F)F)ccc31)NC2=O]

TABLE 24-continued
II-26 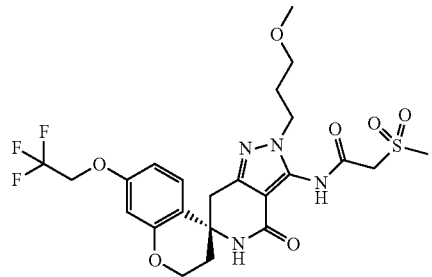 [SMILES: COCCCn1nc2c(c1NC(=O)CS(C)(=O)=O)C(=O)N[C@@]1(CCOc3cc(OCC(F)(F)F)ccc31)C2]
II-27 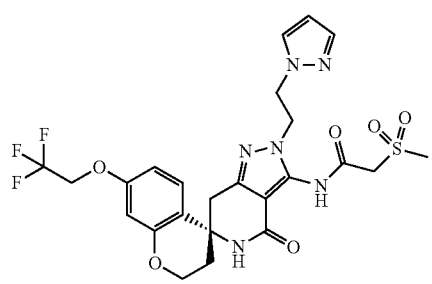 [SMILES: CS(=O)(=O)CC(=O)Nc1c2c(nn1CCn1cccn1)C[C@]1(CCOc3cc(OCC(F)(F)F)ccc31)NC2=O]
TABLE 25
II-28 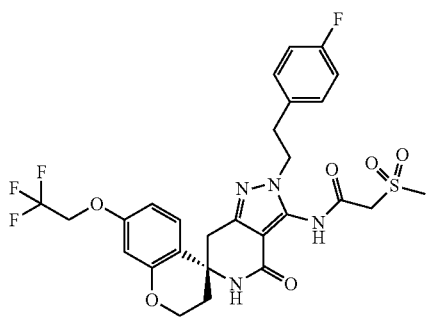 [SMILES: CS(=O)(=O)CC(=O)Nc1c2c(nn1CCc1ccc(F)cc1)C[C@]1(CCOc3cc(OCC(F)(F)F)ccc31)NC2=O]
II-29 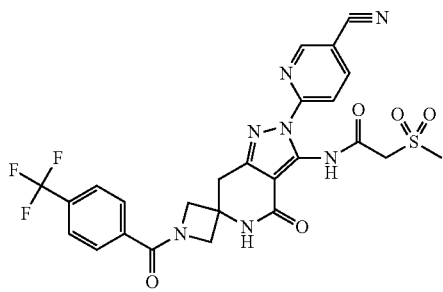 [SMILES: CS(=O)(=O)CC(=O)Nc1c2c(nn1-c1ccc(C#N)cn1)CC1(CN(C(=O)c3ccc(C(F)(F)F)cc3)C1)NC2=O]
II-30 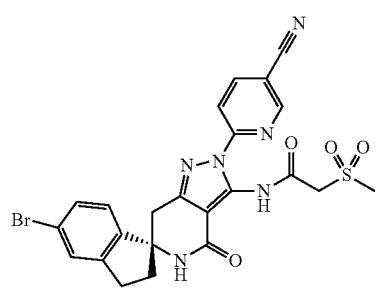 [SMILES: CS(=O)(=O)CC(=O)Nc1c2c(nn1-c1ccc(C#N)cn1)C[C@]1(CCc3cc(Br)ccc31)NC2=O]
TABLE 25-continued
II-31 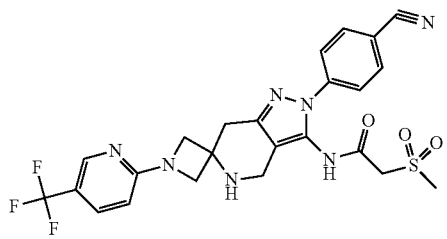 [SMILES: CS(=O)(=O)CC(=O)Nc1c2c(nn1-c1ccc(C#N)cc1)CC1(CN(c3ccc(C(F)(F)F)cn3)C1)NC2]
II-32 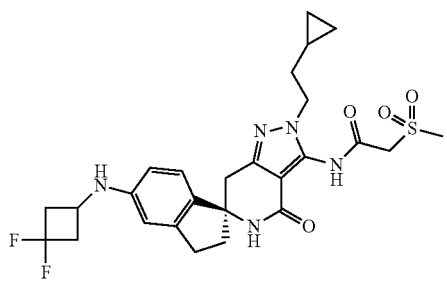 [SMILES: CS(=O)(=O)CC(=O)Nc1c2c(nn1CCC1CC1)C[C@@]1(CCc3cc(NC4CC(F)(F)C4)ccc31)NC2=O]
II-33 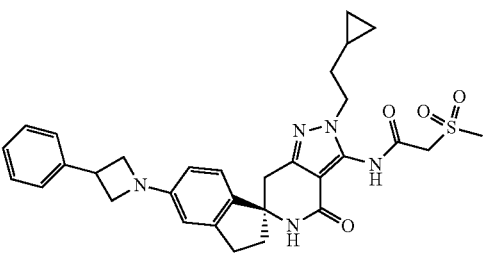 [SMILES: CS(=O)(=O)CC(=O)Nc1c2c(nn1CCC1CC1)C[C@@]1(CCc3cc(N4CC(c5ccccc5)C4)ccc31)NC2=O]
II-34 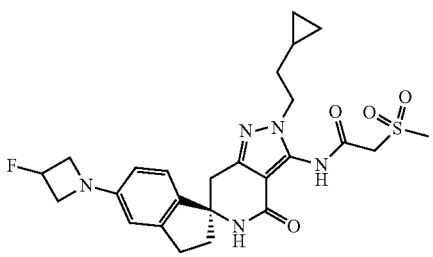 [SMILES: CS(=O)(=O)CC(=O)Nc1c2c(nn1CCC1CC1)C[C@@]1(CCc3cc(N4CC(F)C4)ccc31)NC2=O]
II-35 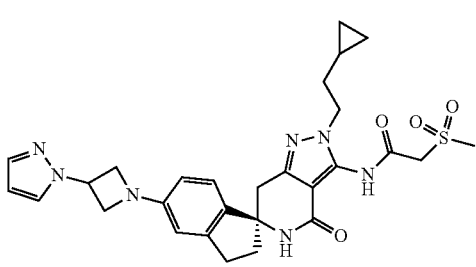 [SMILES: CS(=O)(=O)CC(=O)Nc1c2c(nn1CCC1CC1)C[C@@]1(CCc3cc(N4CC(n5cccn5)C4)ccc31)NC2=O]

TABLE 25-continued
II-36
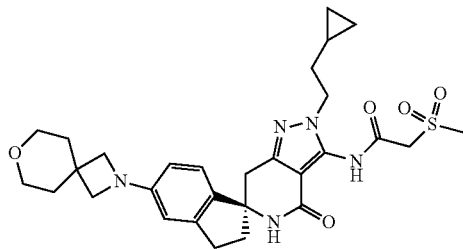 [SMILES: CS(=O)(=O)CC(=O)Nc1c2c(nn1CCC1CC1)C[C@@]1(CCc3cc(N4CC5(CCOCC5)C4)ccc31)NC2=O]
II-37
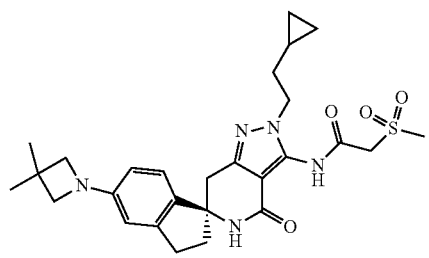
TABLE 25-continued
II-38
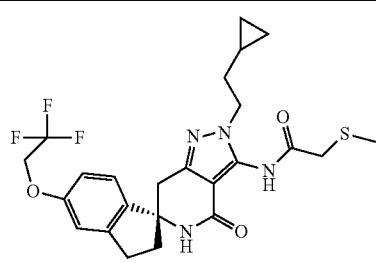
II-39
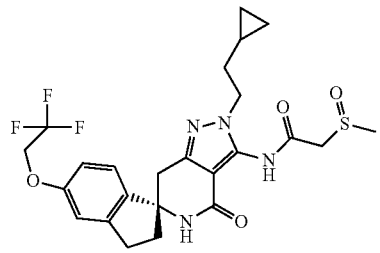 [SMILES: CS(=O)CC(=O)Nc1c2c(nn1CCC1CC1)C[C@]1(CCc3cc(OCC(F)(F)F)ccc31)NC2=O]
TABLE 26
II-40
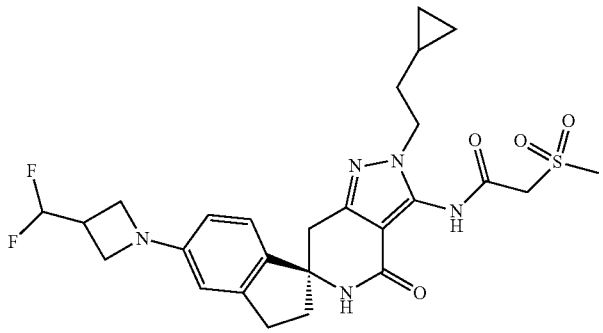 [SMILES: CS(=O)(=O)CC(=O)Nc1c2c(nn1CCC1CC1)C[C@@]1(CCc3cc(N4CC(C(F)F)C4)ccc31)NC2=O]
II-41
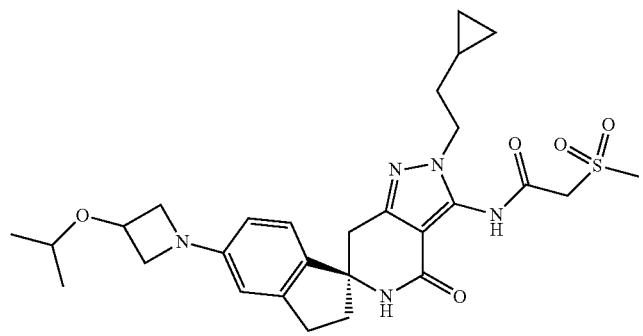 [SMILES: CC(C)OC1CN(c2ccc3c(c2)CC[C@@]32Cc3nn(CCC4CC4)c(NC(=O)CS(C)(=O)=O)c3C(=O)N2)C1]
II-42
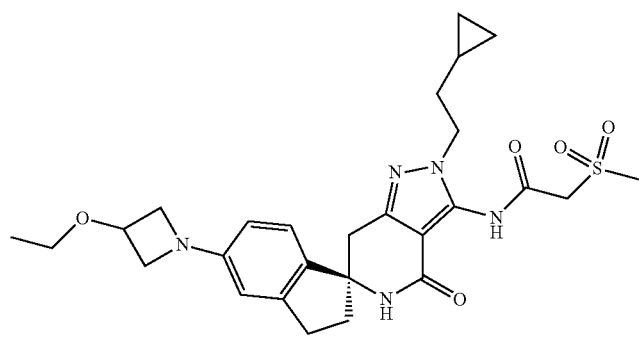 [SMILES: CCOC1CN(c2ccc3c(c2)CC[C@@]32Cc3nn(CCC4CC4)c(NC(=O)CS(C)(=O)=O)c3C(=O)N2)C1]

TABLE 26-continued
II-43
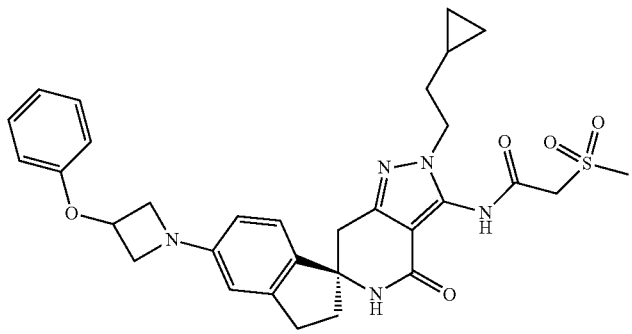 [SMILES: CS(=O)(=O)CC(=O)Nc1c2c(nn1CCC1CC1)C[C@@]1(CCc3cc(N4CC(Oc5ccccc5)C4)ccc31)NC2=O]
II-44
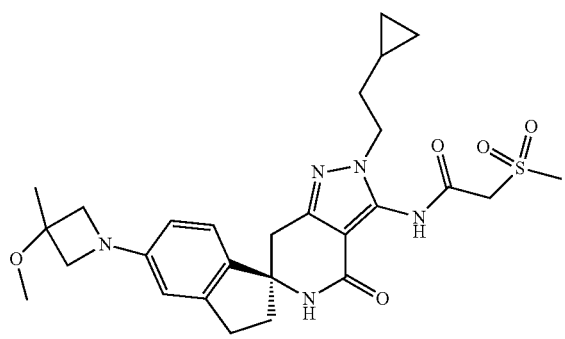 [SMILES: COC1(C)CN(c2ccc3c(c2)CC[C@@]32Cc3nn(CCC4CC4)c(NC(=O)CS(C)(=O)=O)c3C(=O)N2)C1]
II-45
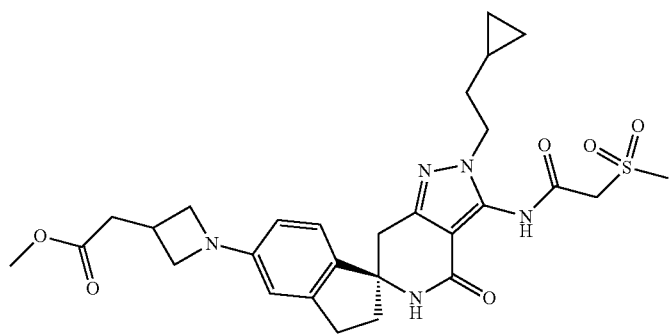
II-46
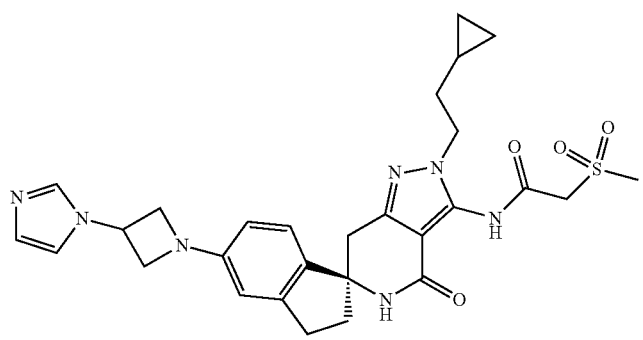 [SMILES: CS(=O)(=O)CC(=O)Nc1c2c(nn1CCC1CC1)C[C@@]1(CCc3cc(N4CC(n5ccnc5)C4)ccc31)NC2=O]

TABLE 26-continued
II-47
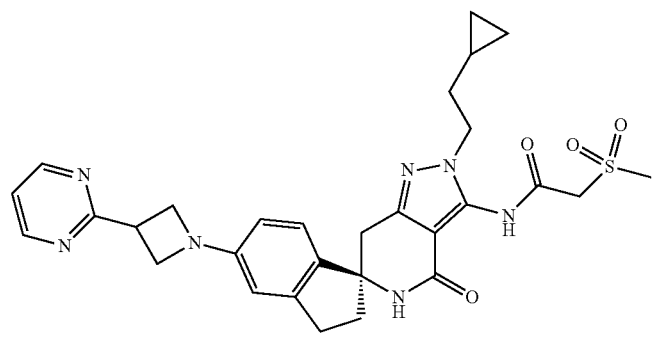 [SMILES: CS(=O)(=O)CC(=O)Nc1c2c(nn1CCC1CC1)C[C@@]1(CCc3cc(N4CC(c5ncccn5)C4)ccc31)NC2=O]
II-48
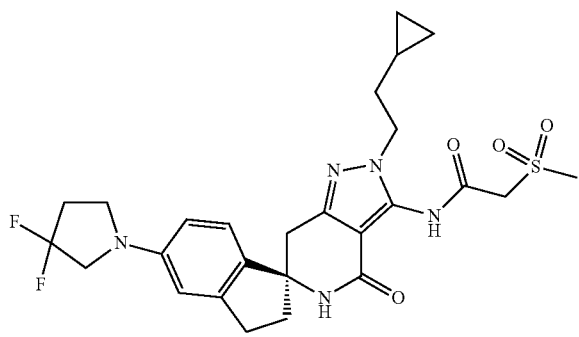 [SMILES: CS(=O)(=O)CC(=O)Nc1c2c(nn1CCC1CC1)C[C@@]1(CCc3cc(N4CCC(F)(F)C4)ccc31)NC2=O]
II-49
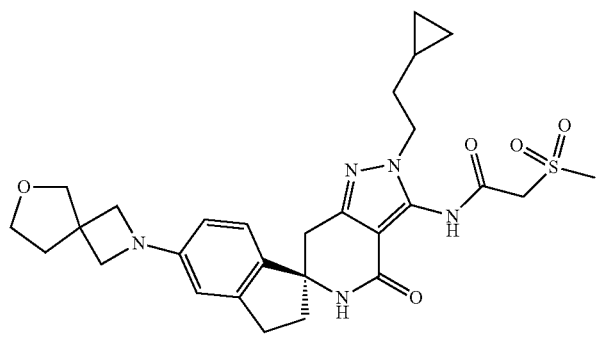 [SMILES: CS(=O)(=O)CC(=O)Nc1c2c(nn1CCC1CC1)C[C@@]1(CCc3cc(N4CC5(CCOC5)C4)ccc31)NC2=O]
II-50
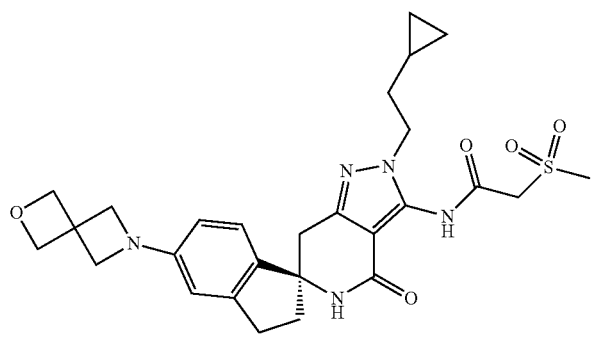 [SMILES: CS(=O)(=O)CC(=O)Nc1c2c(nn1CCC1CC1)C[C@@]1(CCc3cc(N4CC5(COC5)C4)ccc31)NC2=O]

TABLE 26-continued
II-51
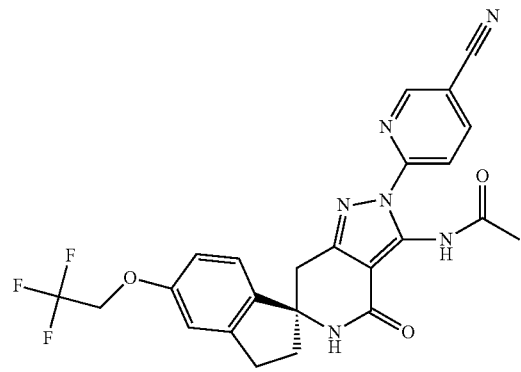 [SMILES: CC(=O)Nc1c2c(nn1-c1ccc(C#N)cn1)C[C@@]1(CCc3cc(OCC(F)(F)F)ccc31)NC2=O]
II-52
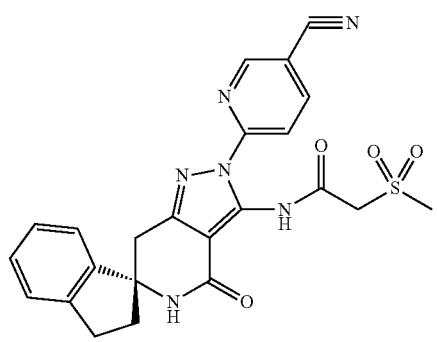 [SMILES: CS(=O)(=O)CC(=O)Nc1c2c(nn1-c1ccc(C#N)cn1)C[C@]1(CCc3ccccc31)NC2=O]
II-53
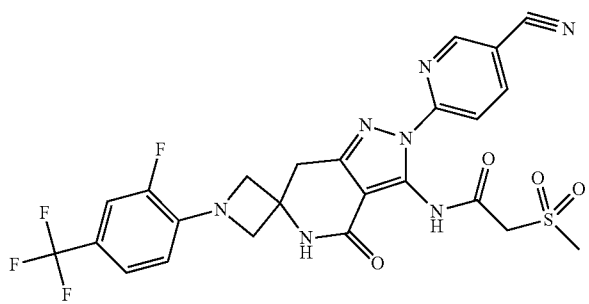 [SMILES: CS(=O)(=O)CC(=O)Nc1c2c(nn1-c1ccc(C#N)cn1)CC1(CN(c3ccc(C(F)(F)F)cc3F)C1)NC2=O]

TABLE 27
II-54
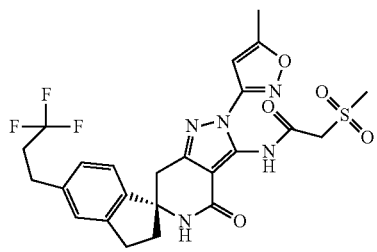 [SMILES: Cc1cc(-n2nc3c(c2NC(=O)CS(C)(=O)=O)C(=O)N[C@@]2(CCc4cc(CCC(F)(F)F)ccc42)C3)no1]
II-55
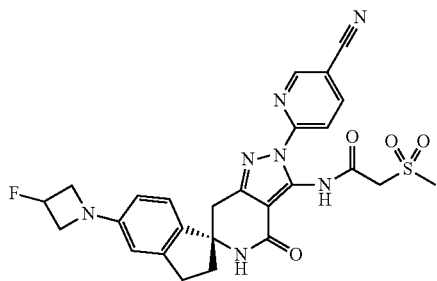 [SMILES: CS(=O)(=O)CC(=O)Nc1c2c(nn1-c1ccc(C#N)cn1)C[C@]1(CCc3cc(N4CC(F)C4)ccc31)NC2=O]
II-56
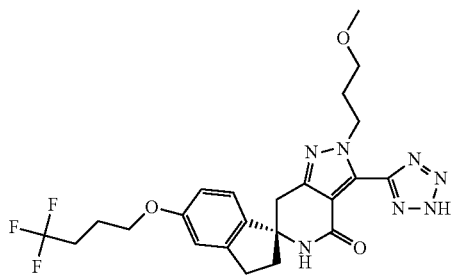 [SMILES: COCCCn1nc2c(c1-c1nn[nH]n1)C(=O)N[C@@]1(CCc3cc(OCCCC(F)(F)F)ccc31)C2]
II-57
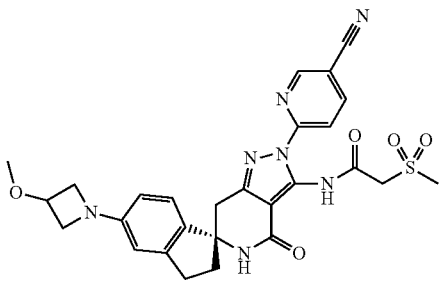
II-58
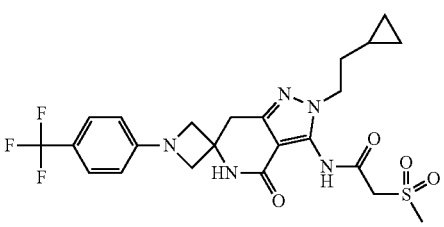 [SMILES: CS(=O)(=O)CC(=O)Nc1c2c(nn1CCC1CC1)CC1(CN(c3ccc(C(F)(F)F)cc3)C1)NC2=O]
II-59
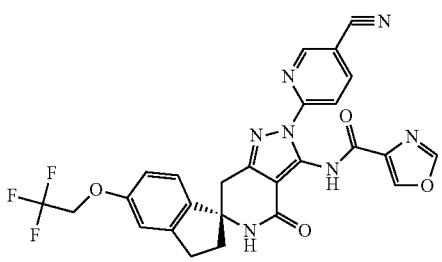 [SMILES: N#Cc1ccc(-n2nc3c(c2NC(=O)c2cocn2)C(=O)N[C@@]2(CCc4cc(OCC(F)(F)F)ccc42)C3)nc1]
TABLE 27-continued
II-60
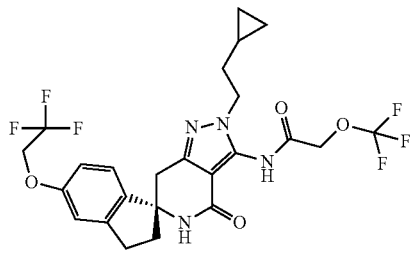 [SMILES: O=C(COC(F)(F)F)Nc1c2c(nn1CCC1CC1)C[C@]1(CCc3cc(OCC(F)(F)F)ccc31)NC2=O]
II-61
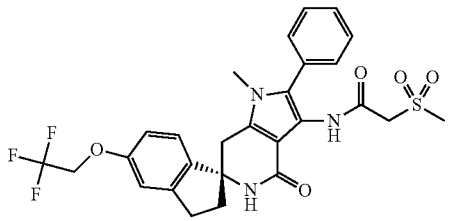 [SMILES: Cn1c2c(c(NC(=O)CS(C)(=O)=O)c1-c1ccccc1)C(=O)N[C@@]1(CCc3cc(OCC(F)(F)F)ccc31)C2]
II-62
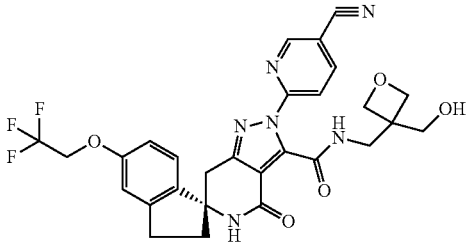 [SMILES: N#Cc1ccc(-n2nc3c(c2C(=O)NCC2(CO)COC2)C(=O)N[C@@]2(CCc4cc(OCC(F)(F)F)ccc42)C3)nc1]
II-63
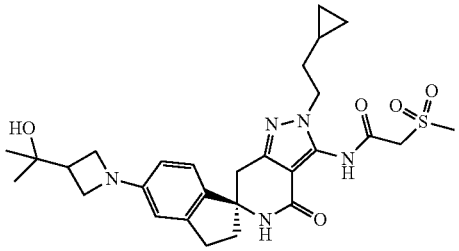 [SMILES: CC(C)(O)C1CN(c2ccc3c(c2)CC[C@@]32Cc3nn(CCC4CC4)c(NC(=O)CS(C)(=O)=O)c3C(=O)N2)C1]
II-64
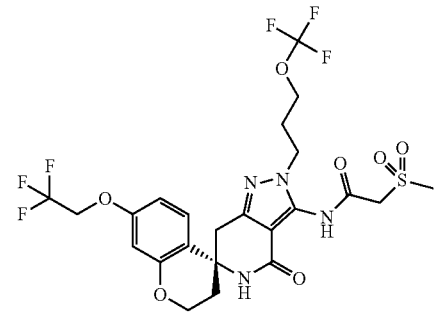 [SMILES: CS(=O)(=O)CC(=O)Nc1c2c(nn1CCCOC(F)(F)F)C[C@]1(CCOc3cc(OCC(F)(F)F)ccc31)NC2=O]
II-65
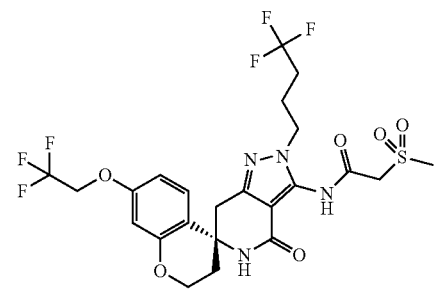 [SMILES: CS(=O)(=O)CC(=O)Nc1c2c(nn1CCCC(F)(F)F)C[C@]1(CCOc3cc(OCC(F)(F)F)ccc31)NC2=O]

TABLE 28
II-66
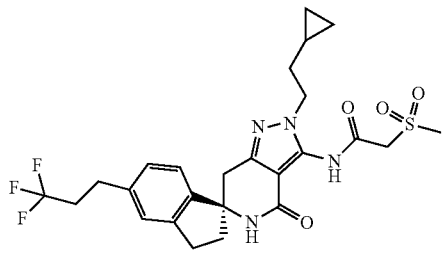 [SMILES: CS(=O)(=O)CC(=O)Nc1c2c(nn1CCC1CC1)C[C@@]1(CCc3cc(CCC(F)(F)F)ccc31)NC2=O]
II-67
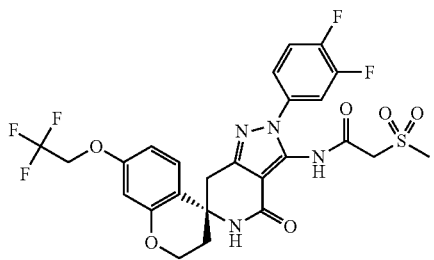 [SMILES: CS(=O)(=O)CC(=O)Nc1c2c(nn1-c1ccc(F)c(F)c1)C[C@]1(CCOc3cc(OCC(F)(F)F)ccc31)NC2=O]
II-68
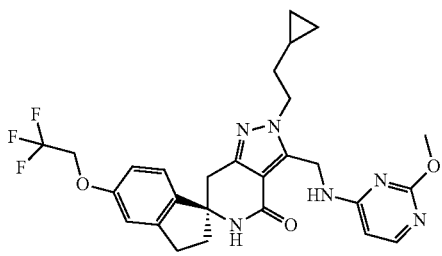 [SMILES: COc1nccc(NCc2c3c(nn2CCC2CC2)C[C@@]2(CCc4cc(OCC(F)(F)F)ccc42)NC3=O)n1]
II-69
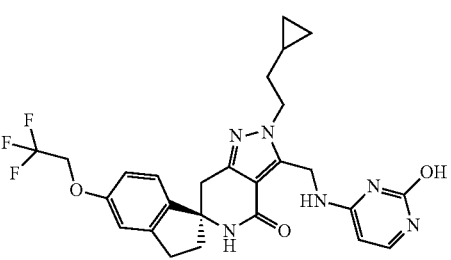 [SMILES: O=C1N[C@]2(CCc3cc(OCC(F)(F)F)ccc32)Cc2nn(CCC3CC3)c(CNc3ccnc(O)n3)c21]
II-70
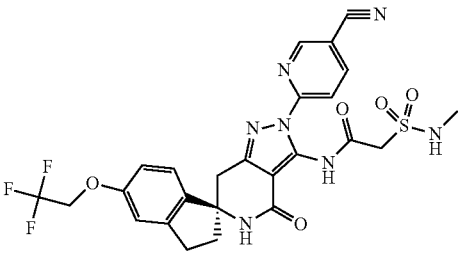 [SMILES: CNS(=O)(=O)CC(=O)Nc1c2c(nn1-c1ccc(C#N)cn1)C[C@@]1(CCc3cc(OCC(F)(F)F)ccc31)NC2=O]
II-71
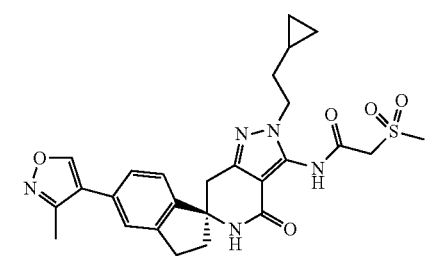 [SMILES: Cc1nocc1-c1ccc2c(c1)CC[C@@]21Cc2nn(CCC3CC3)c(NC(=O)CS(C)(=O)=O)c2C(=O)N1]
TABLE 28-continued
II-72
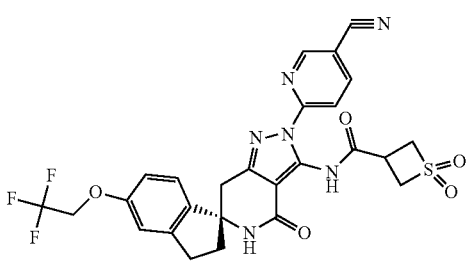 [SMILES: N#Cc1ccc(-n2nc3c(c2NC(=O)C2CS(=O)(=O)C2)C(=O)N[C@@]2(CCc4cc(OCC(F)(F)F)ccc42)C3)nc1]
II-73
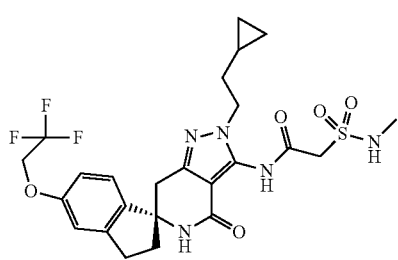 [SMILES: CNS(=O)(=O)CC(=O)Nc1c2c(nn1CCC1CC1)C[C@]1(CCc3cc(OCC(F)(F)F)ccc31)NC2=O]
II-74
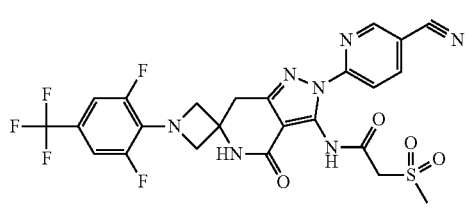 [SMILES: CS(=O)(=O)CC(=O)Nc1c2c(nn1-c1ccc(C#N)cn1)CC1(CN(c3c(F)cc(C(F)(F)F)cc3F)C1)NC2=O]
II-75
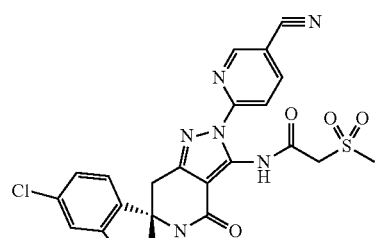
II-76
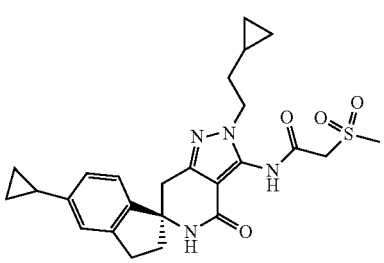 [SMILES: CS(=O)(=O)CC(=O)Nc1c2c(nn1CCC1CC1)C[C@@]1(CCc3cc(C4CC4)ccc31)NC2=O]
II-77
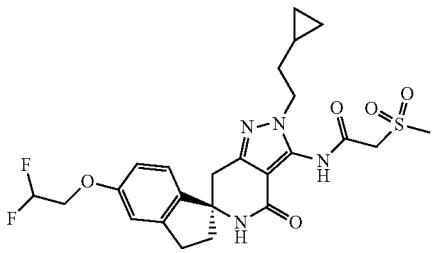 [SMILES: CS(=O)(=O)CC(=O)Nc1c2c(nn1CCC1CC1)C[C@@]1(CCc3cc(OCC(F)F)ccc31)NC2=O]

TABLE 29
II-78
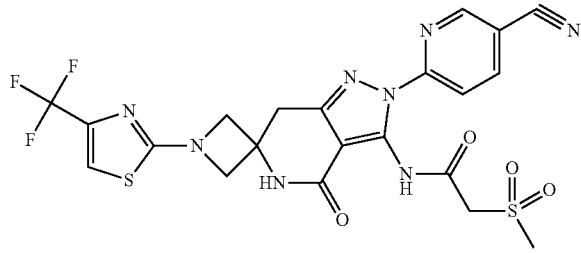 [SMILES: CS(=O)(=O)CC(=O)Nc1c2c(nn1-c1ccc(C#N)cn1)CC1(CN(c3nc(C(F)(F)F)cs3)C1)NC2=O]
II-79
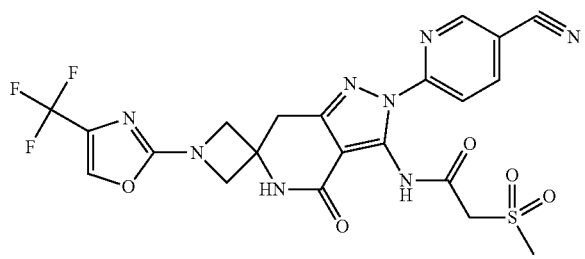
II-80
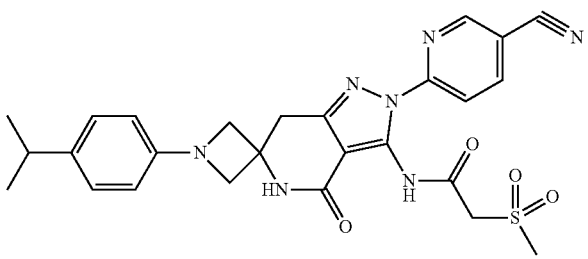 [SMILES: CC(C)c1ccc(N2CC3(Cc4nn(-c5ccc(C#N)cn5)c(NC(=O)CS(C)(=O)=O)c4C(=O)N3)C2)cc1]
II-81
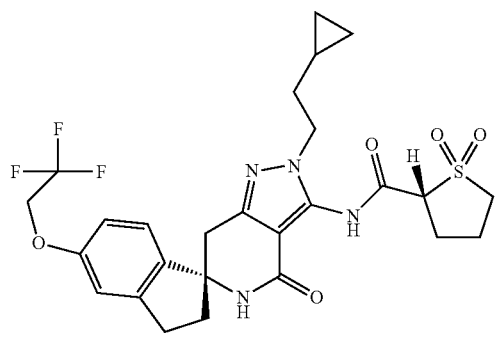 [SMILES: O=C1N[C@@]2(CCc3cc(OCC(F)(F)F)ccc32)Cc2nn(CCC3CC3)c(NC(=O)[C@H]3CCCS3(=O)=O)c21]
II-82
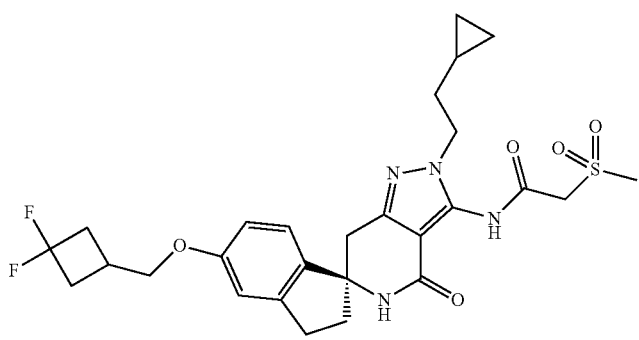 [SMILES: CS(=O)(=O)CC(=O)Nc1c2c(nn1CCC1CC1)C[C@@]1(CCc3cc(OCC4CC(F)(F)C4)ccc31)NC2=O]

TABLE 29-continued
II-83
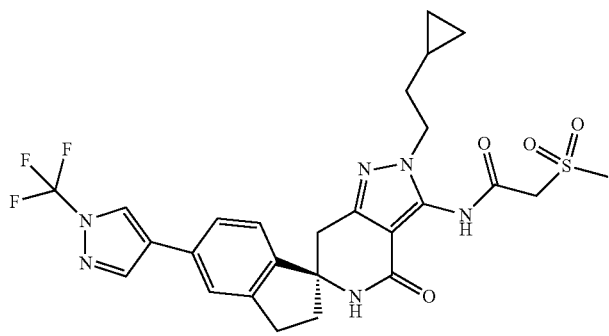 [SMILES: CS(=O)(=O)CC(=O)Nc1c2c(nn1CCC1CC1)C[C@@]1(CCc3cc(-c4cnn(C(F)(F)F)c4)ccc31)NC2=O]
II-84
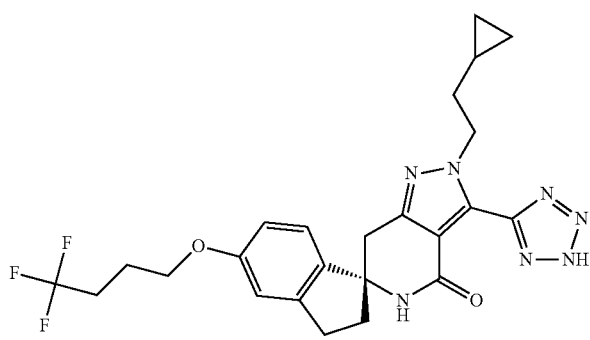 [SMILES: O=C1N[C@@]2(CCc3cc(OCCCC(F)(F)F)ccc32)Cc2nn(CCC3CC3)c(-c3nn[nH]n3)c21]
II-85
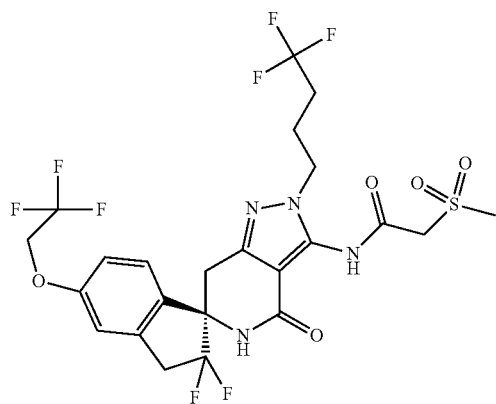 [SMILES: CS(=O)(=O)CC(=O)Nc1c2c(nn1CCCC(F)(F)F)C[C@@]1(NC2=O)c2ccc(OCC(F)(F)F)cc2CC1(F)F]
II-86
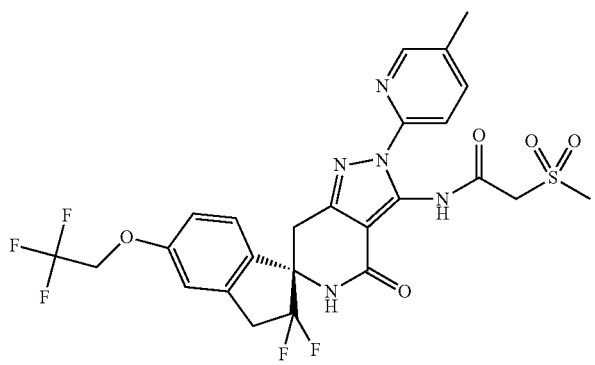 [SMILES: Cc1ccc(-n2nc3c(c2NC(=O)CS(C)(=O)=O)C(=O)N[C@@]2(C3)c3ccc(OCC(F)(F)F)cc3CC2(F)F)nc1]

TABLE 29-continued
II-87
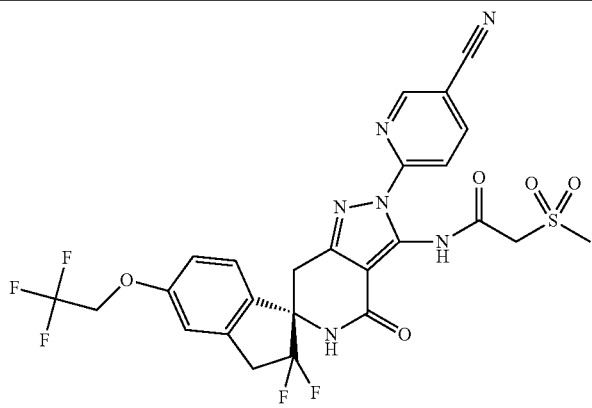
II-88
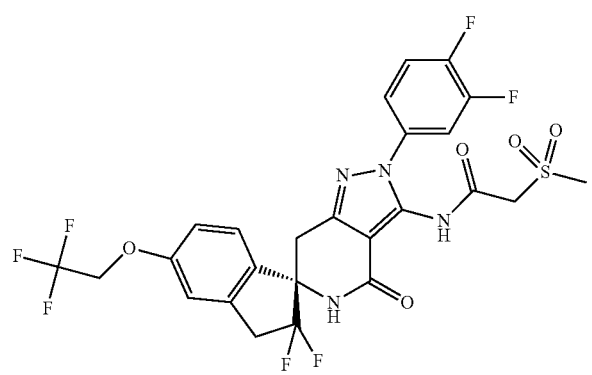 [SMILES: CS(=O)(=O)CC(=O)Nc1c2c(nn1-c1ccc(F)c(F)c1)C[C@]1(NC2=O)c2ccc(OCC(F)(F)F)cc2CC1(F)F]
II-89
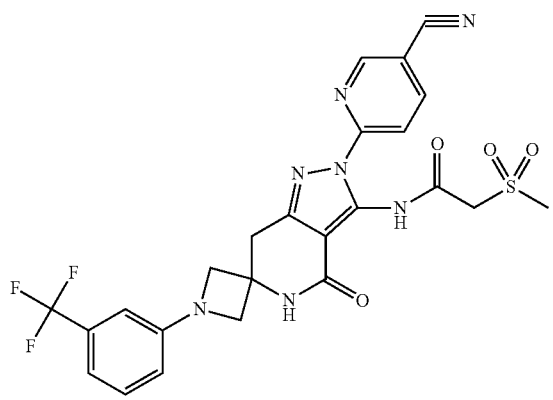 [SMILES: CS(=O)(=O)CC(=O)Nc1c2c(nn1-c1ccc(C#N)cn1)CC1(CN(c3cccc(C(F)(F)F)c3)C1)NC2=O]
TABLE 30
II-90
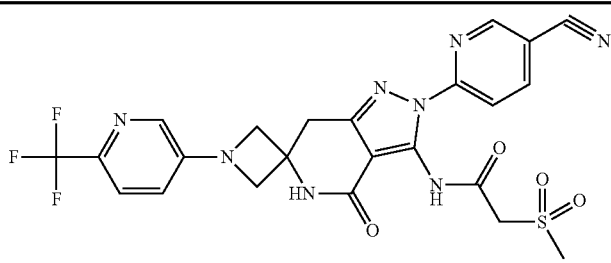

TABLE 30-continued
II-91
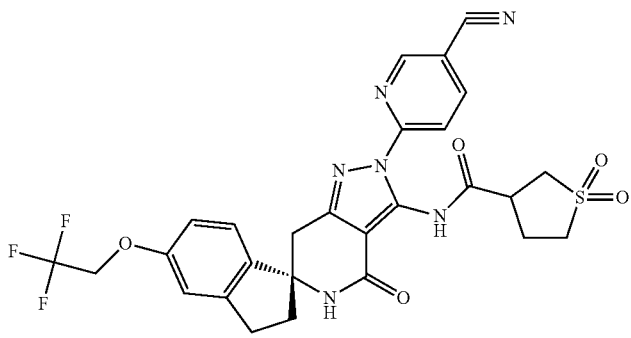 [SMILES: N#Cc1ccc(-n2nc3c(c2NC(=O)C2CCS(=O)(=O)C2)C(=O)N[C@@]2(CCc4cc(OCC(F)(F)F)ccc42)C3)nc1]
II-92
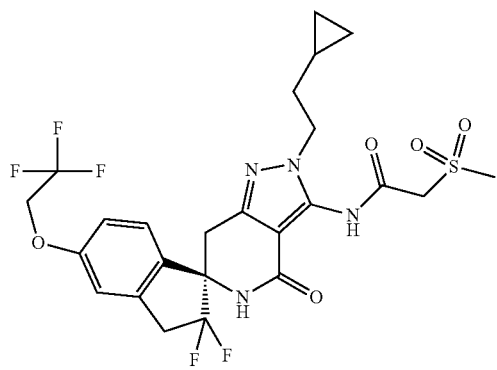 [SMILES: CS(=O)(=O)CC(=O)Nc1c2c(nn1CCC1CC1)C[C@@]1(NC2=O)c2ccc(OCC(F)(F)F)cc2CC1(F)F]
II-93
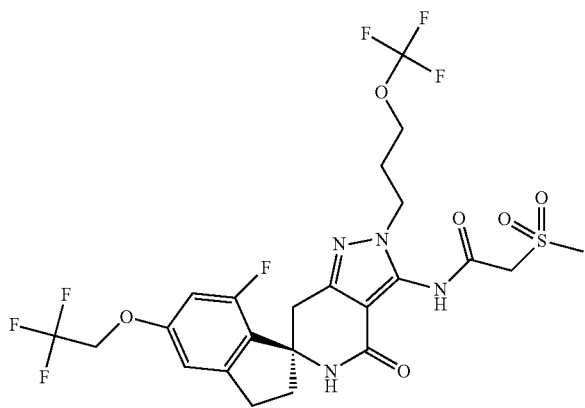 [SMILES: CS(=O)(=O)CC(=O)Nc1c2c(nn1CCCOC(F)(F)F)C[C@@]1(CCc3cc(OCC(F)(F)F)cc(F)c31)NC2=O]
II-94
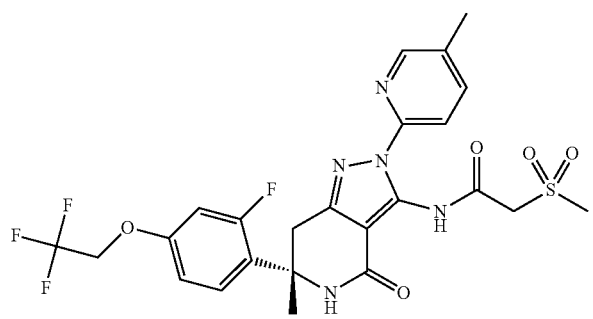 [SMILES: Cc1ccc(-n2nc3c(c2NC(=O)CS(C)(=O)=O)C(=O)N[C@](C)(c2ccc(OCC(F)(F)F)cc2F)C3)nc1]

TABLE 30-continued
II-95
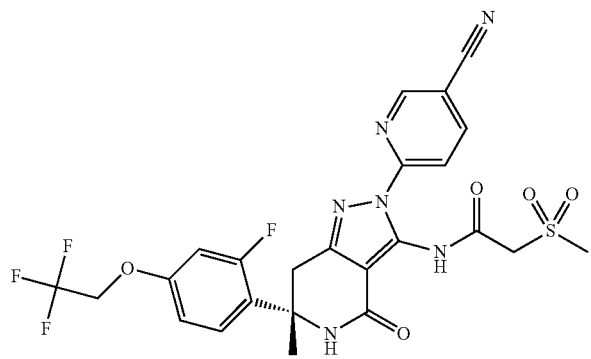 [SMILES: C[C@@]1(c2ccc(OCC(F)(F)F)cc2F)Cc2nn(-c3ccc(C#N)cn3)c(NC(=O)CS(C)(=O)=O)c2C(=O)N1]
II-96
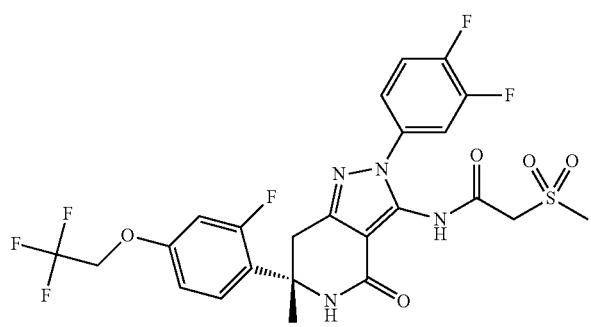 [SMILES: C[C@@]1(c2ccc(OCC(F)(F)F)cc2F)Cc2nn(-c3ccc(F)c(F)c3)c(NC(=O)CS(C)(=O)=O)c2C(=O)N1]
II-97
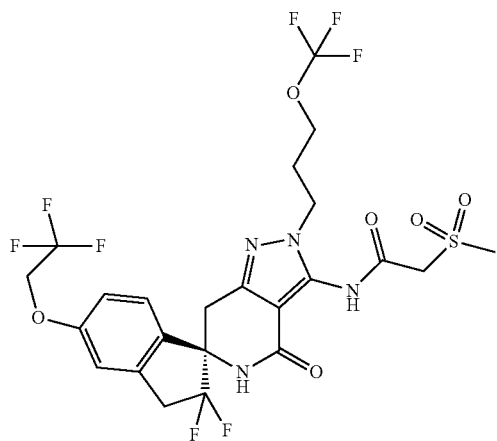 [SMILES: CS(=O)(=O)CC(=O)Nc1c2c(nn1CCCOC(F)(F)F)C[C@@]1(NC2=O)c2ccc(OCC(F)(F)F)cc2CC1(F)F]
II-98
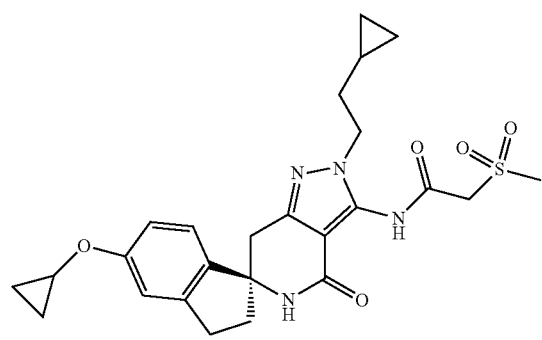 [SMILES: CS(=O)(=O)CC(=O)Nc1c2c(nn1CCC1CC1)C[C@@]1(CCc3cc(OC4CC4)ccc31)NC2=O]

TABLE 30-continued
II-99
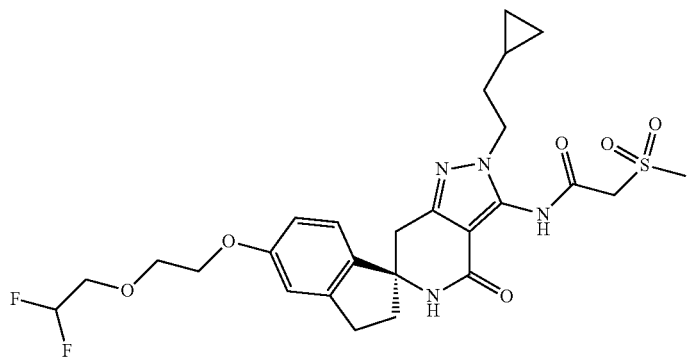 [SMILES: CS(=O)(=O)CC(=O)Nc1c2c(nn1CCC1CC1)C[C@@]1(CCc3cc(OCCOCC(F)F)ccc31)NC2=O]
II-100
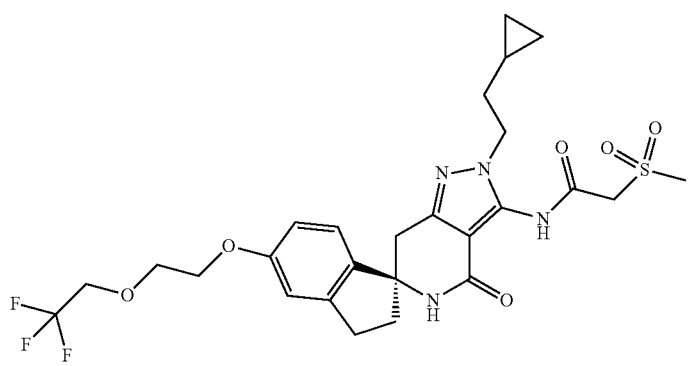 [SMILES: CS(=O)(=O)CC(=O)Nc1c2c(nn1CCC1CC1)C[C@@]1(CCc3cc(OCCOCC(F)(F)F)ccc31)NC2=O]
II-101
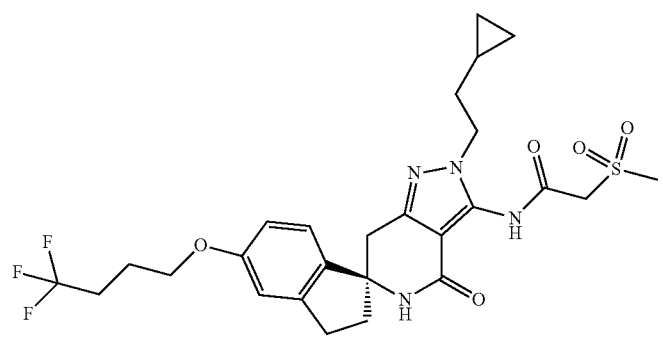 [SMILES: CS(=O)(=O)CC(=O)Nc1c2c(nn1CCC1CC1)C[C@@]1(CCc3cc(OCCCC(F)(F)F)ccc31)NC2=O]
TABLE 31
II-102
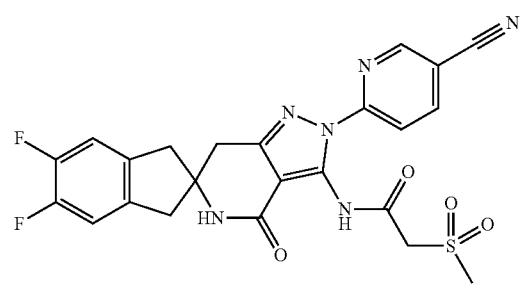 [SMILES: CS(=O)(=O)CC(=O)Nc1c2c(nn1-c1ccc(C#N)cn1)CC1(Cc3cc(F)c(F)cc3C1)NC2=O]

TABLE 31-continued
II-103
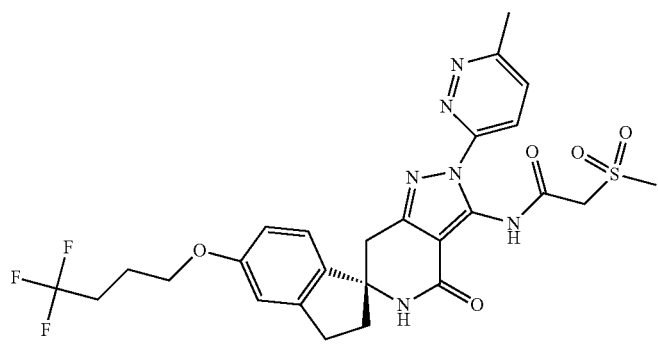 [SMILES: Cc1ccc(-n2nc3c(c2NC(=O)CS(C)(=O)=O)C(=O)N[C@@]2(CCc4cc(OCCCC(F)(F)F)ccc42)C3)nn1]
II-104
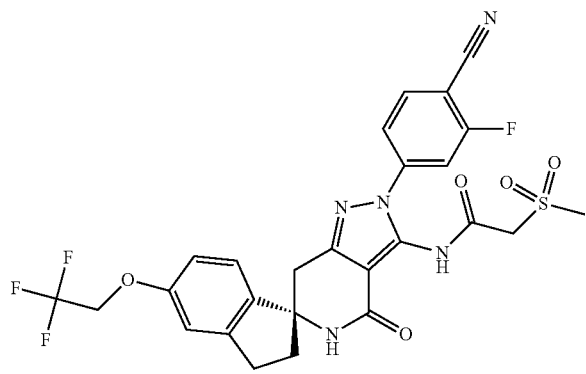 [SMILES: CS(=O)(=O)CC(=O)Nc1c2c(nn1-c1ccc(C#N)c(F)c1)C[C@]1(CCc3cc(OCC(F)(F)F)ccc31)NC2=O]
II-105
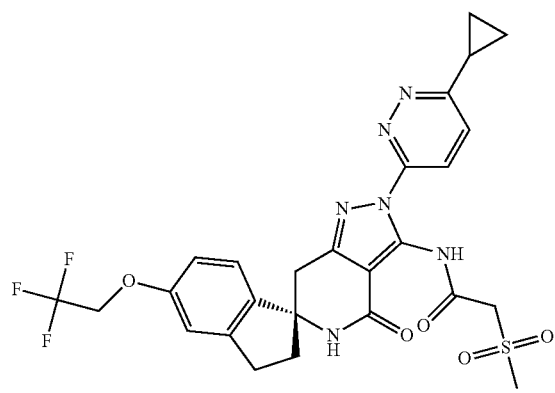 [SMILES: CS(=O)(=O)CC(=O)Nc1c2c(nn1-c1ccc(C3CC3)nn1)C[C@]1(CCc3cc(OCC(F)(F)F)ccc31)NC2=O]
II-106
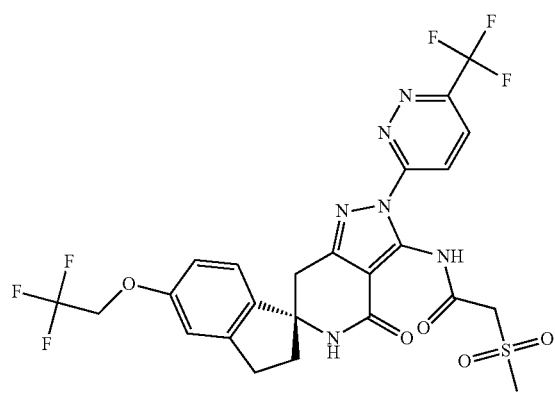 [SMILES: CS(=O)(=O)CC(=O)Nc1c2c(nn1-c1ccc(C(F)(F)F)nn1)C[C@]1(CCc3cc(OCC(F)(F)F)ccc31)NC2=O]

II-107
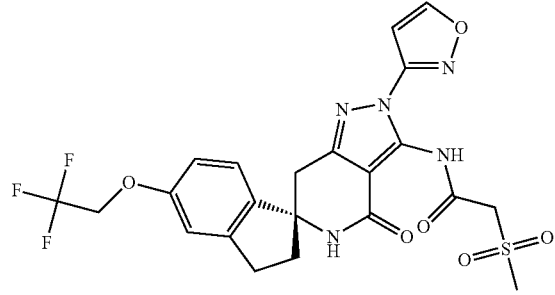 [SMILES: CS(=O)(=O)CC(=O)Nc1c2c(nn1-c1ccon1)C[C@]1(CCc3cc(OCC(F)(F)F)ccc31)NC2=O]
II-108
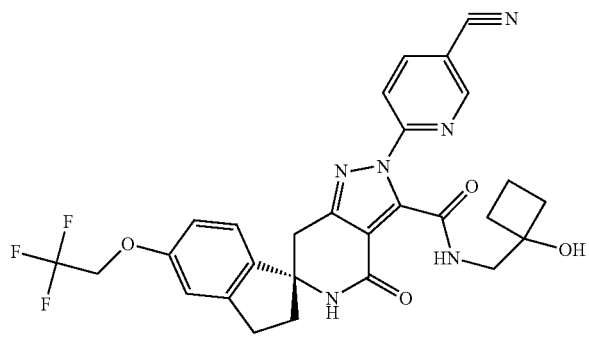 [SMILES: N#Cc1ccc(-n2nc3c(c2C(=O)NCC2(O)CCC2)C(=O)N[C@@]2(CCc4cc(OCC(F)(F)F)ccc42)C3)nc1]
II-109
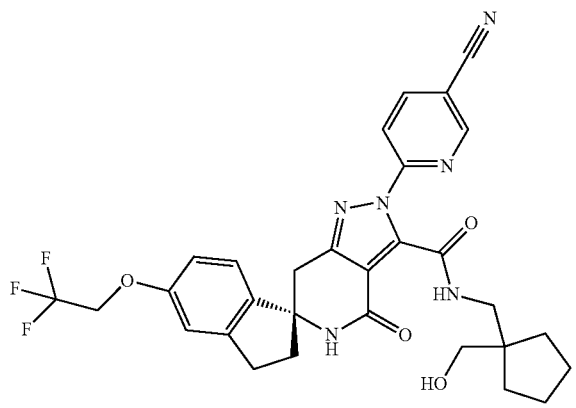 [SMILES: N#Cc1ccc(-n2nc3c(c2C(=O)NCC2(CO)CCCC2)C(=O)N[C@@]2(CCc4cc(OCC(F)(F)F)ccc42)C3)nc1]
II-110
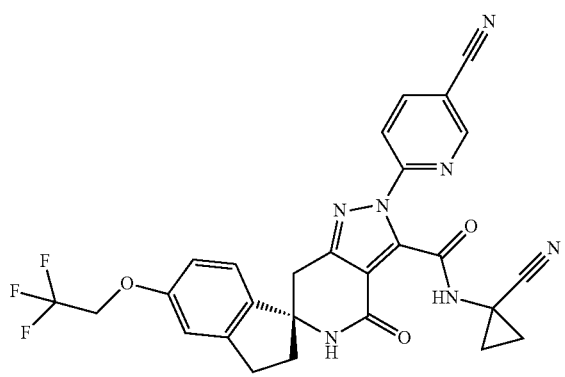 [SMILES: N#Cc1ccc(-n2nc3c(c2C(=O)NC2(C#N)CC2)C(=O)N[C@@]2(CCc4cc(OCC(F)(F)F)ccc42)C3)nc1]

TABLE 31-continued
II-111
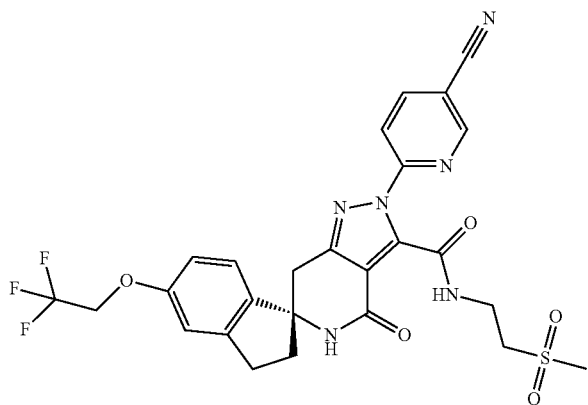 [SMILES: CS(=O)(=O)CCNC(=O)c1c2c(nn1-c1ccc(C#N)cn1)C[C@]1(CCc3cc(OCC(F)(F)F)ccc31)NC2=O]
II-112
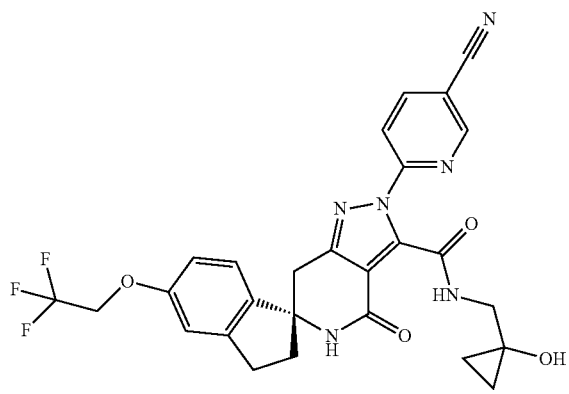 [SMILES: N#Cc1ccc(-n2nc3c(c2C(=O)NCC2(O)CC2)C(=O)N[C@@]2(CCc4cc(OCC(F)(F)F)ccc42)C3)nc1]
II-113
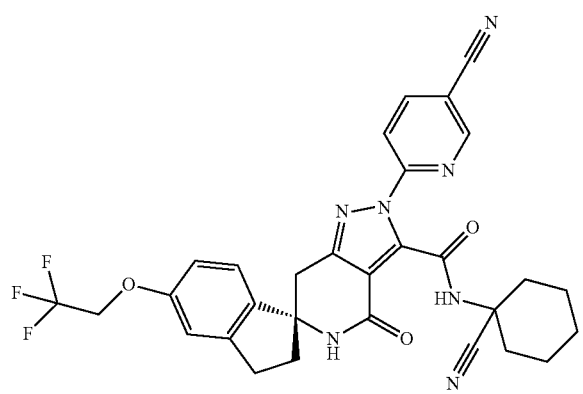 [SMILES: N#Cc1ccc(-n2nc3c(c2C(=O)NC2(C#N)CCCCC2)C(=O)N[C@@]2(CCc4cc(OCC(F)(F)F)ccc42)C3)nc1]

TABLE 32

II-114, II-115, II-116, II-117, II-118, II-119, II-120, II-122, II-123, II-124

TABLE 33
II-125
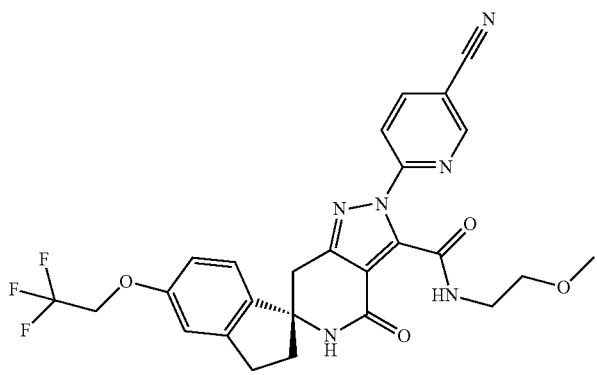 [SMILES: COCCNC(=O)c1c2c(nn1-c1ccc(C#N)cn1)C[C@]1(CCc3cc(OCC(F)(F)F)ccc31)NC2=O]
II-126
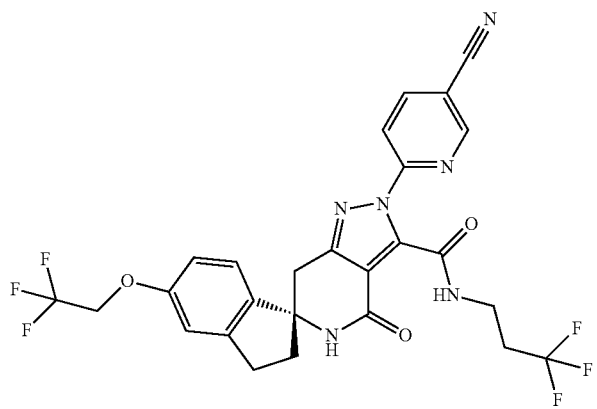 [SMILES: N#Cc1ccc(-n2nc3c(c2C(=O)NCCC(F)(F)F)C(=O)N[C@@]2(CCc4cc(OCC(F)(F)F)ccc42)C3)nc1]
II-127
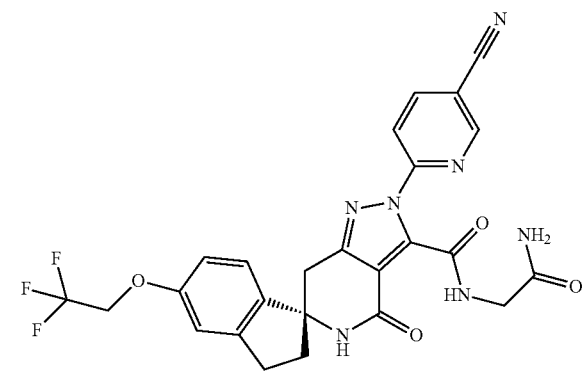 [SMILES: N#Cc1ccc(-n2nc3c(c2C(=O)NCC(N)=O)C(=O)N[C@@]2(CCc4cc(OCC(F)(F)F)ccc42)C3)nc1]
II-128
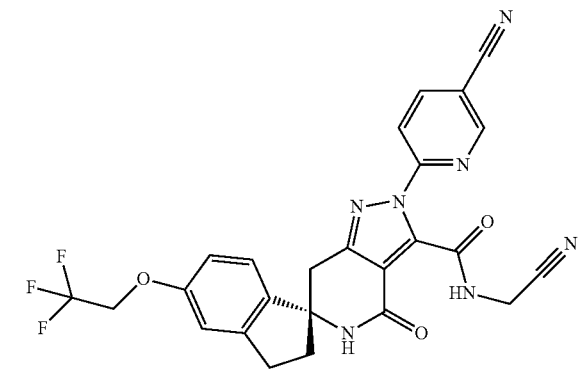 [SMILES: N#CCNC(=O)c1c2c(nn1-c1ccc(C#N)cn1)C[C@]1(CCc3cc(OCC(F)(F)F)ccc31)NC2=O]

TABLE 33-continued
II-129
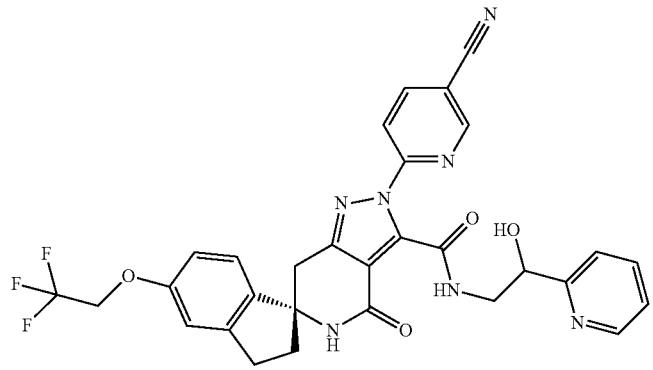 [SMILES: N#Cc1ccc(-n2nc3c(c2C(=O)NCC(O)c2ccccn2)C(=O)N[C@@]2(CCc4cc(OCC(F)(F)F)ccc42)C3)nc1]
II-130
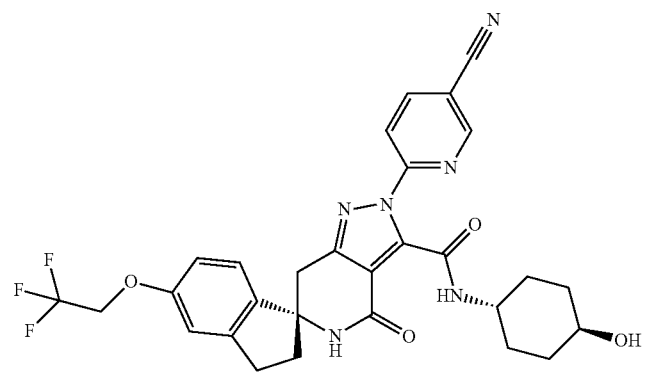 [SMILES: N#Cc1ccc(-n2nc3c(c2C(=O)N[C@H]2CC[C@H](O)CC2)C(=O)N[C@@]2(CCc4cc(OCC(F)(F)F)ccc42)C3)nc1]
II-131
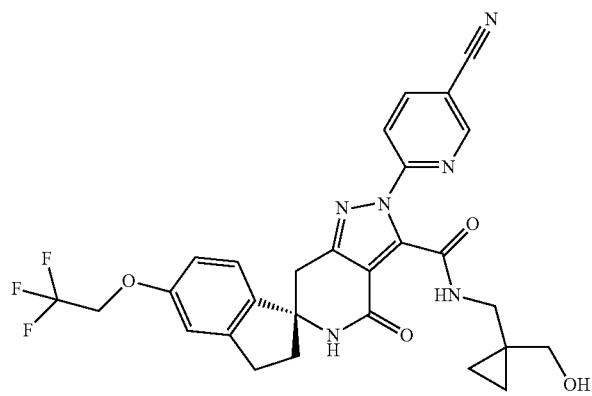 [SMILES: N#Cc1ccc(-n2nc3c(c2C(=O)NCC2(CO)CC2)C(=O)N[C@@]2(CCc4cc(OCC(F)(F)F)ccc42)C3)nc1]
II-132
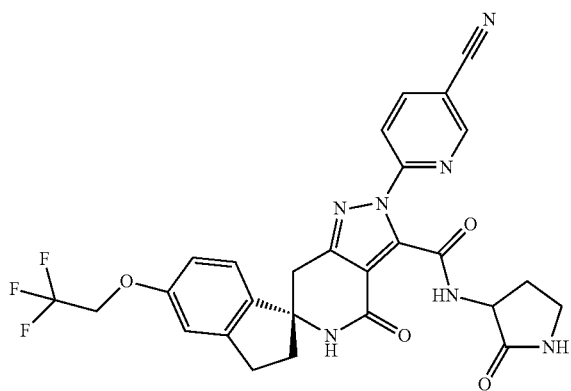 [SMILES: N#Cc1ccc(-n2nc3c(c2C(=O)NC2CCNC2=O)C(=O)N[C@@]2(CCc4cc(OCC(F)(F)F)ccc42)C3)nc1]

TABLE 33-continued
II-133
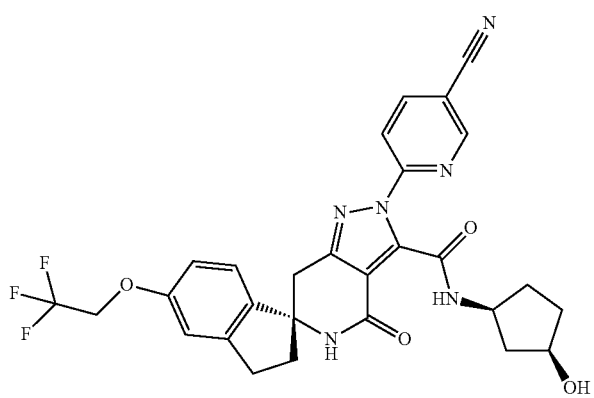 [SMILES: N#Cc1ccc(-n2nc3c(c2C(=O)N[C@H]2CC[C@@H](O)C2)C(=O)N[C@@]2(CCc4cc(OCC(F)(F)F)ccc42)C3)nc1]
II-134
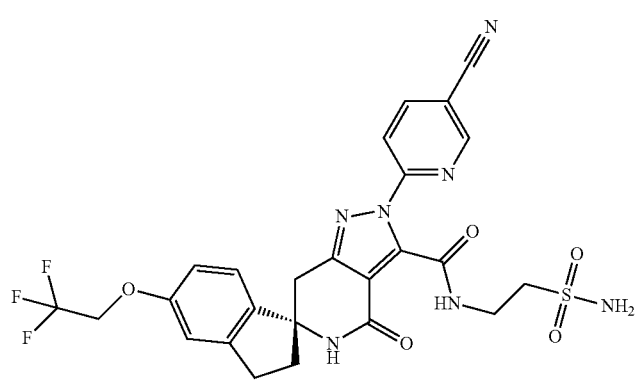 [SMILES: N#Cc1ccc(-n2nc3c(c2C(=O)NCCS(N)(=O)=O)C(=O)N[C@@]2(CCc4cc(OCC(F)(F)F)ccc42)C3)nc1]
II-135
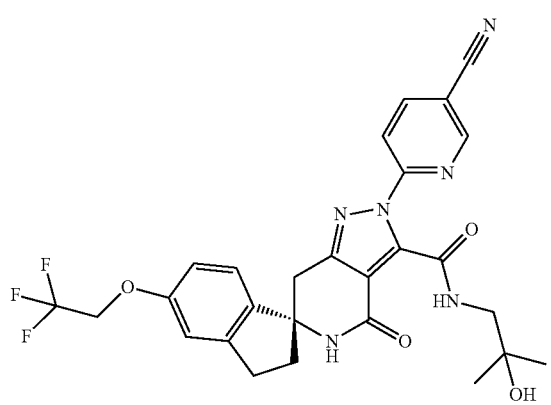 [SMILES: CC(C)(O)CNC(=O)c1c2c(nn1-c1ccc(C#N)cn1)C[C@]1(CCc3cc(OCC(F)(F)F)ccc31)NC2=O]
II-136
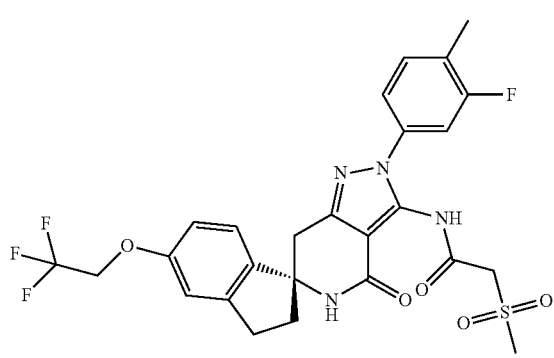 [SMILES: Cc1ccc(-n2nc3c(c2NC(=O)CS(C)(=O)=O)C(=O)N[C@@]2(CCc4cc(OCC(F)(F)F)ccc42)C3)cc1F]

TABLE 34
II-137 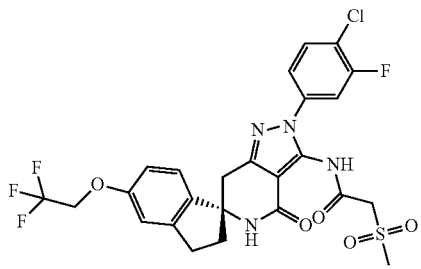 [SMILES: CS(=O)(=O)CC(=O)Nc1c2c(nn1-c1ccc(Cl)c(F)c1)C[C@]1(CCc3cc(OCC(F)(F)F)ccc31)NC2=O]
II-138 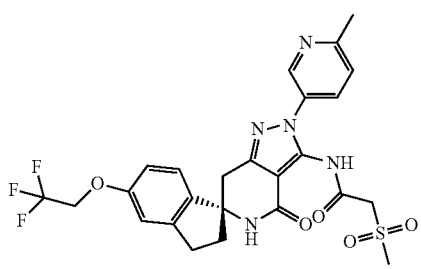 [SMILES: Cc1ccc(-n2nc3c(c2NC(=O)CS(C)(=O)=O)C(=O)N[C@@]2(CCc4cc(OCC(F)(F)F)ccc42)C3)cn1]
II-139 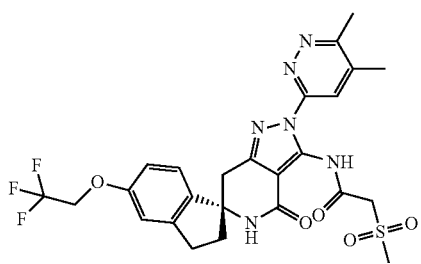 [SMILES: Cc1cc(-n2nc3c(c2NC(=O)CS(C)(=O)=O)C(=O)N[C@@]2(CCc4cc(OCC(F)(F)F)ccc42)C3)nnc1C]
II-140 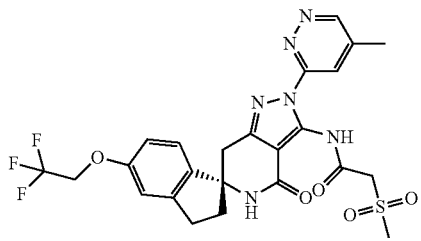 [SMILES: Cc1cnnc(-n2nc3c(c2NC(=O)CS(C)(=O)=O)C(=O)N[C@@]2(CCc4cc(OCC(F)(F)F)ccc42)C3)c1]
II-141 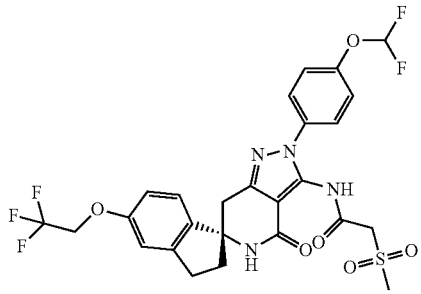 [SMILES: CS(=O)(=O)CC(=O)Nc1c2c(nn1-c1ccc(OC(F)F)cc1)C[C@]1(CCc3cc(OCC(F)(F)F)ccc31)NC2=O]
II-142 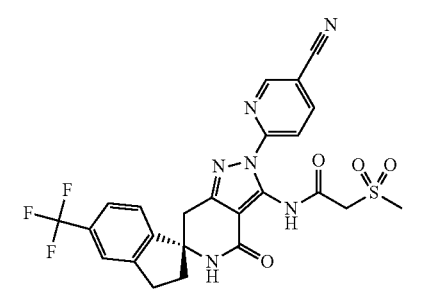 [SMILES: CS(=O)(=O)CC(=O)Nc1c2c(nn1-c1ccc(C#N)cn1)C[C@]1(CCc3cc(C(F)(F)F)ccc31)NC2=O]
TABLE 34-continued
II-143 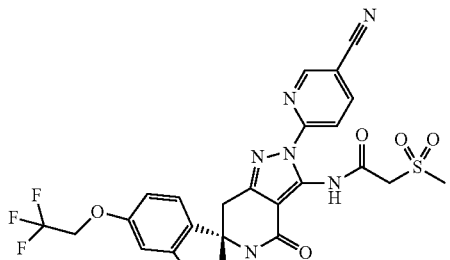
II-144 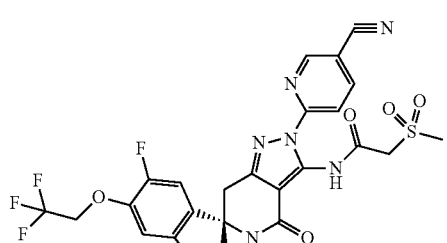
II-145 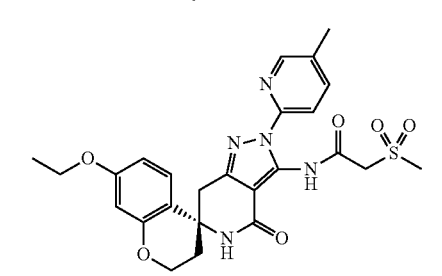
II-146 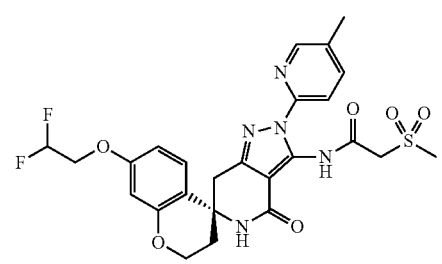 [SMILES: Cc1ccc(-n2nc3c(c2NC(=O)CS(C)(=O)=O)C(=O)N[C@@]2(CCOc4cc(OCC(F)F)ccc42)C3)nc1]
II-147 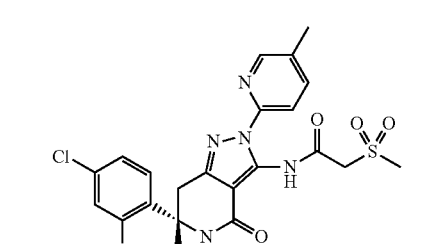
II-148 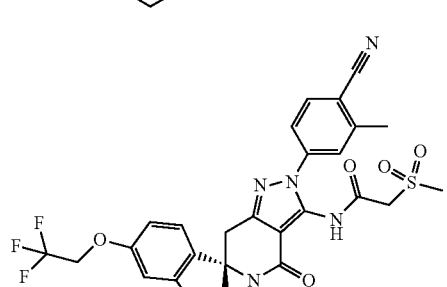

TABLE 35
II-149
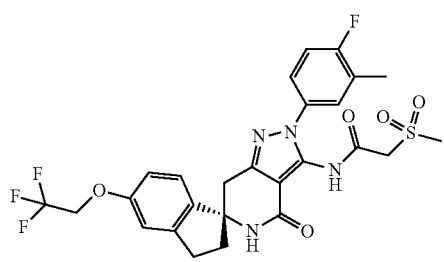 [SMILES: Cc1cc(-n2nc3c(c2NC(=O)CS(C)(=O)=O)C(=O)N[C@@]2(CCc4cc(OCC(F)(F)F)ccc42)C3)ccc1F]
II-150
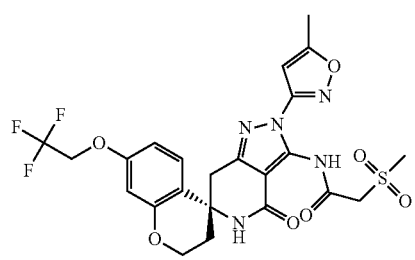 [SMILES: Cc1cc(-n2nc3c(c2NC(=O)CS(C)(=O)=O)C(=O)N[C@@]2(CCOc4cc(OCC(F)(F)F)ccc42)C3)no1]
II-151
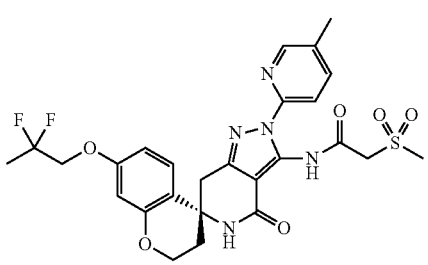 [SMILES: Cc1ccc(-n2nc3c(c2NC(=O)CS(C)(=O)=O)C(=O)N[C@@]2(CCOc4cc(OCC(C)(F)F)ccc42)C3)nc1]
II-152
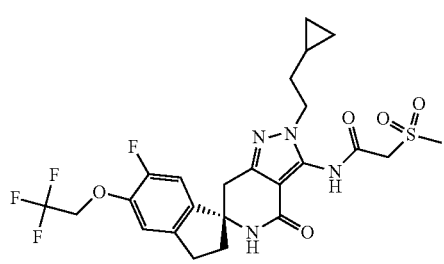 [SMILES: CS(=O)(=O)CC(=O)Nc1c2c(nn1CCC1CC1)C[C@]1(CCc3cc(OCC(F)(F)F)c(F)cc31)NC2=O]
II-153
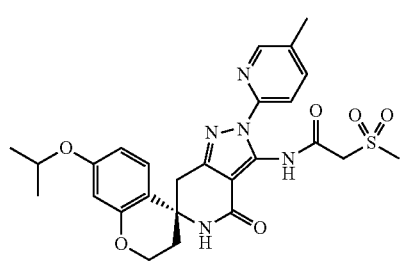 [SMILES: Cc1ccc(-n2nc3c(c2NC(=O)CS(C)(=O)=O)C(=O)N[C@@]2(CCOc4cc(OC(C)C)ccc42)C3)nc1]
II-154
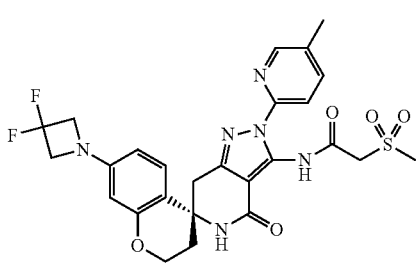 [SMILES: Cc1ccc(-n2nc3c(c2NC(=O)CS(C)(=O)=O)C(=O)N[C@@]2(CCOc4cc(N5CC(F)(F)C5)ccc42)C3)nc1]
TABLE 35-continued
II-156
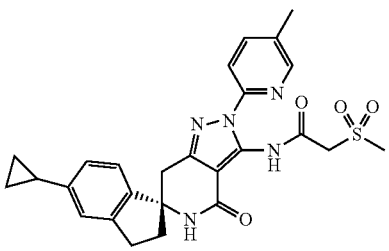 [SMILES: Cc1ccc(-n2nc3c(c2NC(=O)CS(C)(=O)=O)C(=O)N[C@@]2(CCc4cc(C5CC5)ccc42)C3)nc1]
II-157
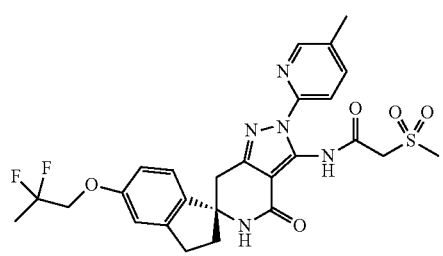 [SMILES: Cc1ccc(-n2nc3c(c2NC(=O)CS(C)(=O)=O)C(=O)N[C@@]2(CCc4cc(OCC(C)(F)F)ccc42)C3)nc1]
II-158
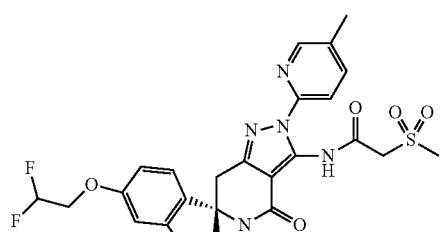
II-159
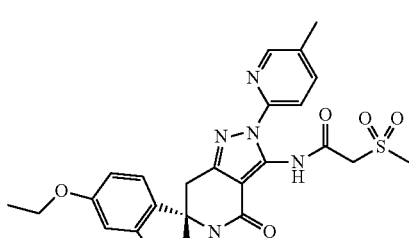
II-160
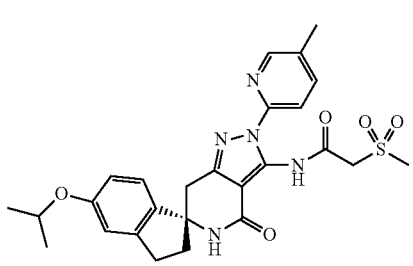 [SMILES: CCOc1ccc2c(c1)CC[C@]21Cc2nn(-c3ccc(C)cn3)c(NC(=O)CS(C)(=O)=O)c2C(=O)N1]

TABLE 35-continued
II-161
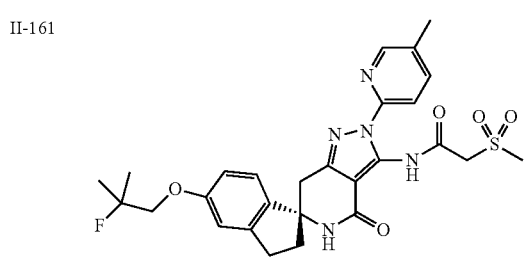
II-162
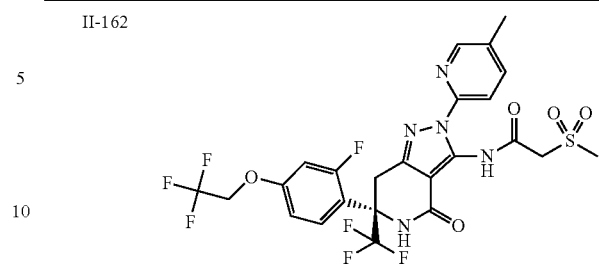
TABLE 36
II-163
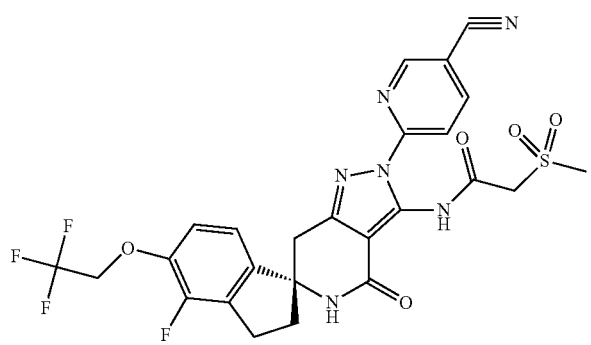 [SMILES: CS(=O)(=O)CC(=O)Nc1c2c(nn1-c1ccc(C#N)cn1)C[C@]1(CCc3c1ccc(OCC(F)(F)F)c3F)NC2=O]
II-164
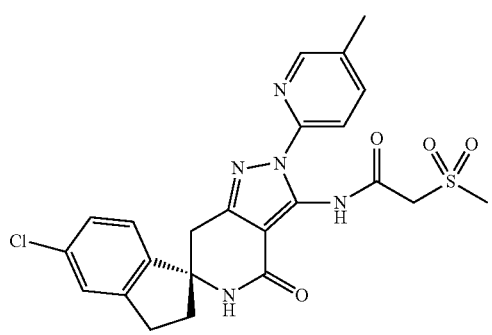 [SMILES: Cc1ccc(-n2nc3c(c2NC(=O)CS(C)(=O)=O)C(=O)N[C@@]2(CCc4cc(Cl)ccc42)C3)nc1]
II-165
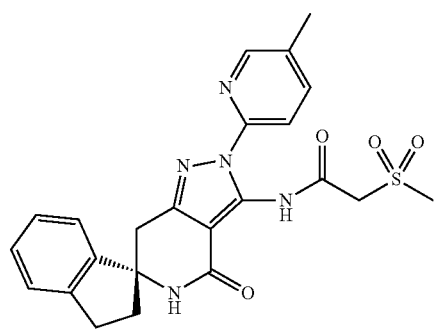 [SMILES: Cc1ccc(-n2nc3c(c2NC(=O)CS(C)(=O)=O)C(=O)N[C@@]2(CCc4ccccc42)C3)nc1]

TABLE 36-continued
II-166
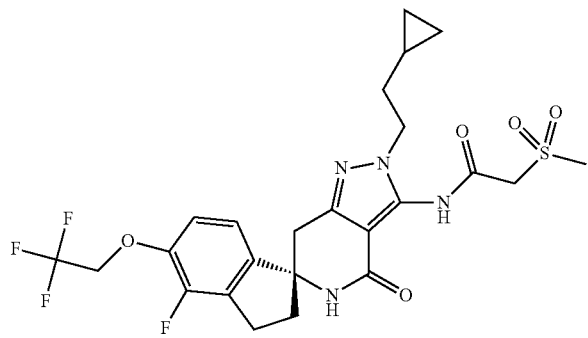 [SMILES: CS(=O)(=O)CC(=O)Nc1c2c(nn1CCC1CC1)C[C@]1(CCc3c1ccc(OCC(F)(F)F)c3F)NC2=O]
II-167
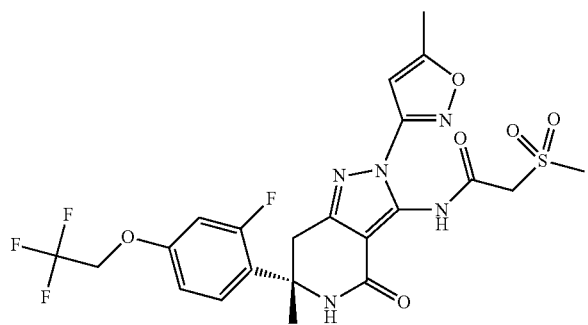 [SMILES: Cc1cc(-n2nc3c(c2NC(=O)CS(C)(=O)=O)C(=O)N[C@](C)(c2ccc(OCC(F)(F)F)cc2F)C3)no1]
II-169
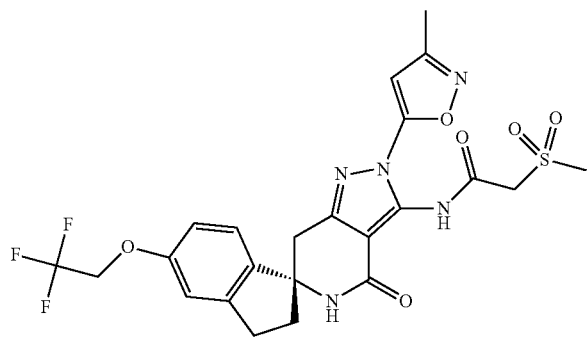 [SMILES: Cc1cc(-n2nc3c(c2NC(=O)CS(C)(=O)=O)C(=O)N[C@@]2(CCc4cc(OCC(F)(F)F)ccc42)C3)on1]
II-170
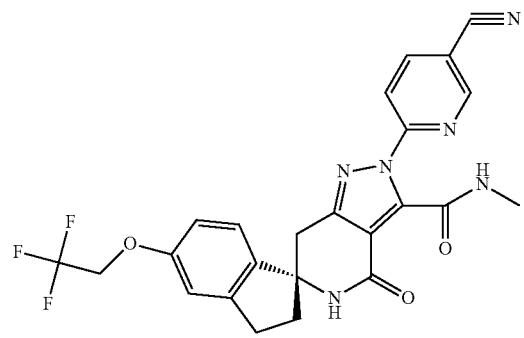 [SMILES: CNC(=O)c1c2c(nn1-c1ccc(C#N)cn1)C[C@]1(CCc3cc(OCC(F)(F)F)ccc31)NC2=O]

TABLE 36-continued
II-171
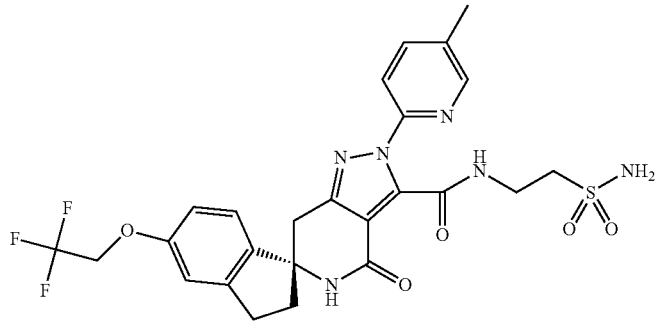 [SMILES: Cc1ccc(-n2nc3c(c2C(=O)NCCS(N)(=O)=O)C(=O)N[C@@]2(CCc4cc(OCC(F)(F)F)ccc42)C3)nc1]
II-172
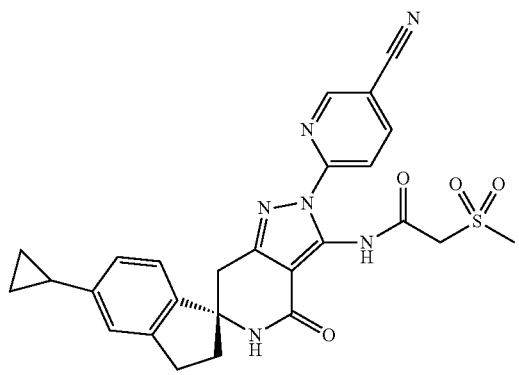 [SMILES: CS(=O)(=O)CC(=O)Nc1c2c(nn1-c1ccc(C#N)cn1)C[C@]1(CCc3cc(C4CC4)ccc31)NC2=O]
II-173
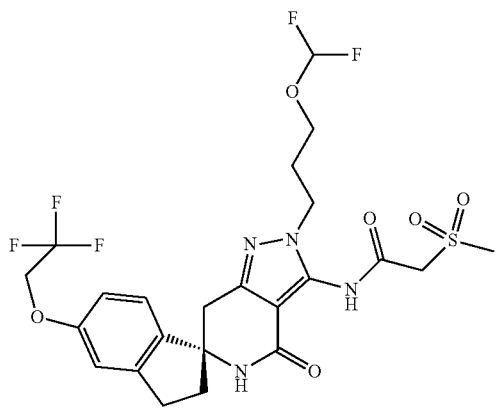 [SMILES: CS(=O)(=O)CC(=O)Nc1c2c(nn1CCCOC(F)F)C[C@]1(CCc3cc(OCC(F)(F)F)ccc31)NC2=O]
II-174
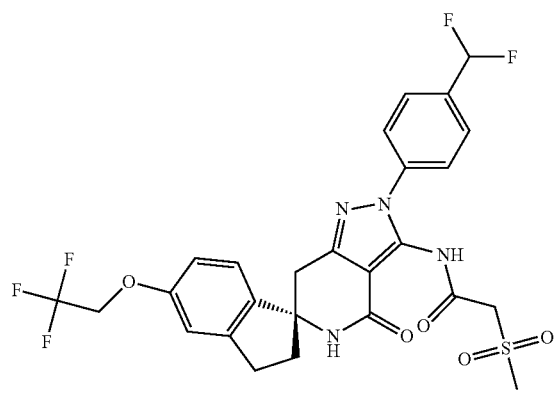 [SMILES: CS(=O)(=O)CC(=O)Nc1c2c(nn1-c1ccc(C(F)F)cc1)C[C@]1(CCc3cc(OCC(F)(F)F)ccc31)NC2=O]

TABLE 36-continued
II-175 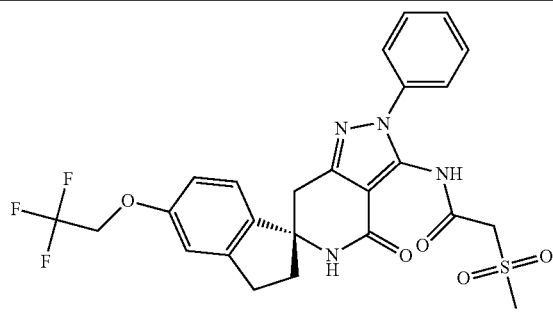
TABLE 37
II-176 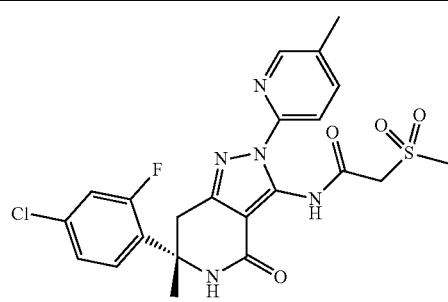
II-177 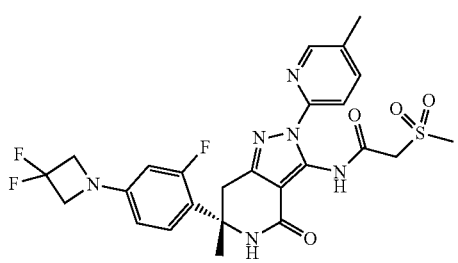 [SMILES: Cc1ccc(-n2nc3c(c2NC(=O)CS(C)(=O)=O)C(=O)N[C@](C)(c2ccc(N4CC(F)(F)C4)cc2F)C3)nc1]
II-178 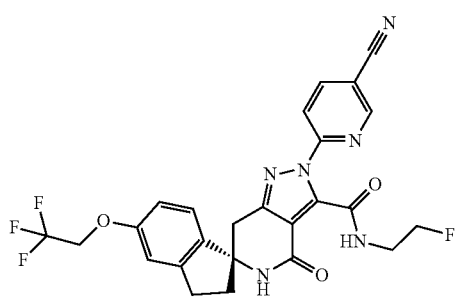 [SMILES: N#Cc1ccc(-n2nc3c(c2C(=O)NCCF)C(=O)N[C@@]2(CCc4cc(OCC(F)(F)F)ccc42)C3)nc1]
II-179 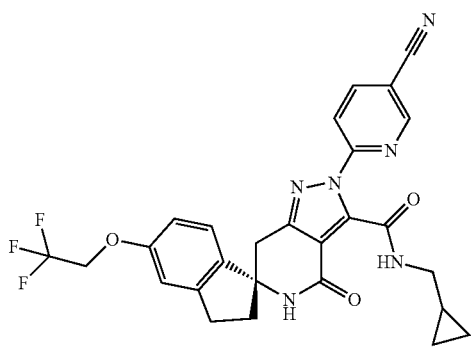 [SMILES: N#Cc1ccc(-n2nc3c(c2C(=O)NCC2CC2)C(=O)N[C@@]2(CCc4cc(OCC(F)(F)F)ccc42)C3)nc1]
TABLE 37-continued
II-180 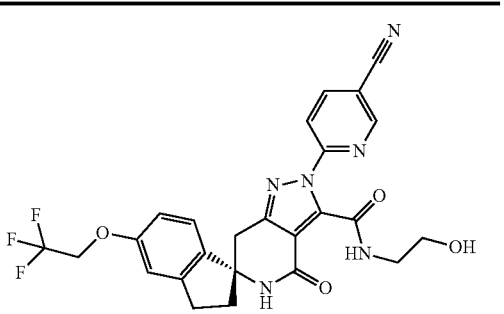
II-181 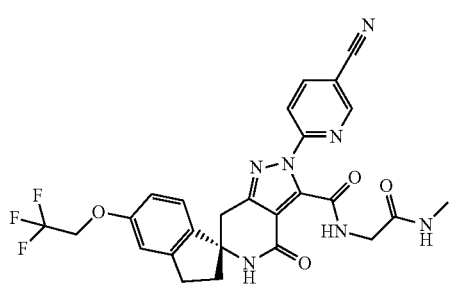 [SMILES: CNC(=O)CNC(=O)c1c2c(nn1-c1ccc(C#N)cn1)C[C@]1(CCc3cc(OCC(F)(F)F)ccc31)NC2=O]
II-182 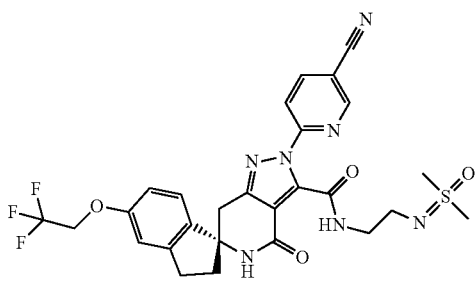 [SMILES: CS(C)(=O)=NCCNC(=O)c1c2c(nn1-c1ccc(C#N)cn1)C[C@]1(CCc3cc(OCC(F)(F)F)ccc31)NC2=O]
II-183 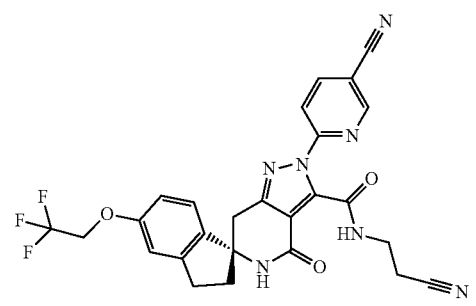 [SMILES: N#CCCNC(=O)c1c2c(nn1-c1ccc(C#N)cn1)C[C@]1(CCc3cc(OCC(F)(F)F)ccc31)NC2=O]

TABLE 37-continued
II-184
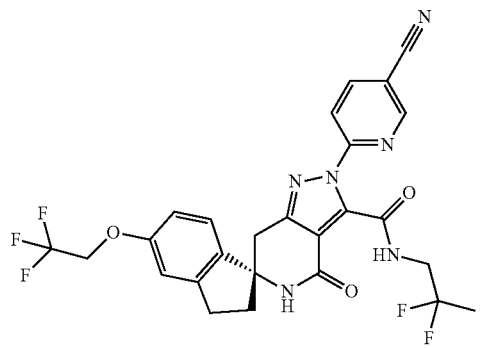 [SMILES: CC(F)(F)CNC(=O)c1c2c(nn1-c1ccc(C#N)cn1)C[C@]1(CCc3cc(OCC(F)(F)F)ccc31)NC2=O]
II-185
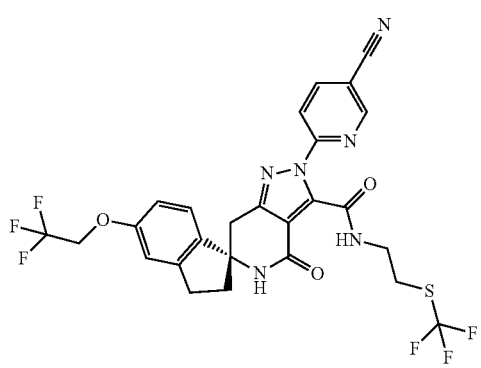 [SMILES: N#Cc1ccc(-n2nc3c(c2C(=O)NCCSC(F)(F)F)C(=O)N[C@@]2(CCc4cc(OCC(F)(F)F)ccc42)C3)nc1]
II-186
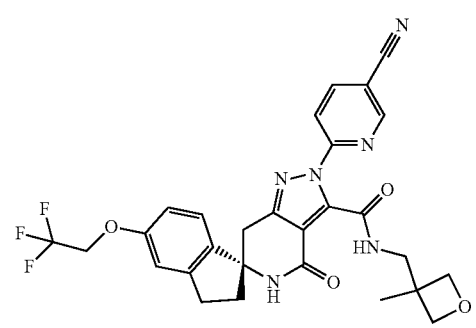 [SMILES: CC1(CNC(=O)c2c3c(nn2-c2ccc(C#N)cn2)C[C@]2(CCc4cc(OCC(F)(F)F)ccc42)NC3=O)COC1]
II-187
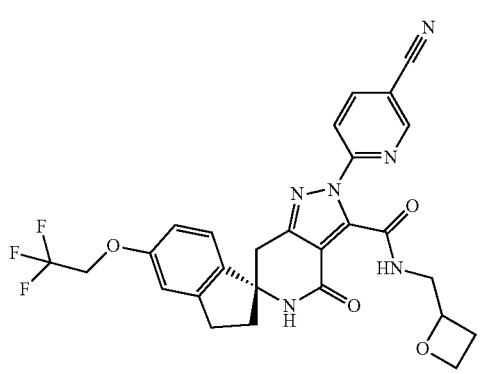 [SMILES: N#Cc1ccc(-n2nc3c(c2C(=O)NCC2CCO2)C(=O)N[C@@]2(CCc4cc(OCC(F)(F)F)ccc42)C3)nc1]
TABLE 38
II-188
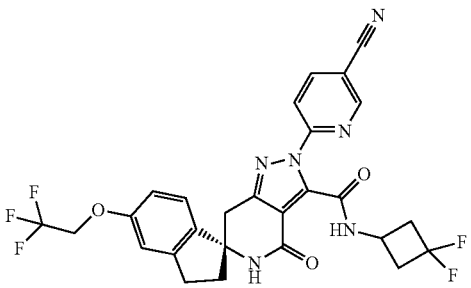 [SMILES: N#Cc1ccc(-n2nc3c(c2C(=O)NC2CC(F)(F)C2)C(=O)N[C@@]2(CCc4cc(OCC(F)(F)F)ccc42)C3)nc1]
II-189
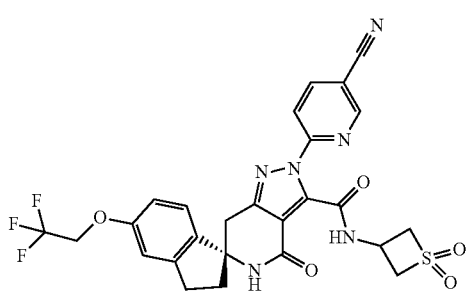 [SMILES: N#Cc1ccc(-n2nc3c(c2C(=O)NC2CS(=O)(=O)C2)C(=O)N[C@@]2(CCc4cc(OCC(F)(F)F)ccc42)C3)nc1]
II-190
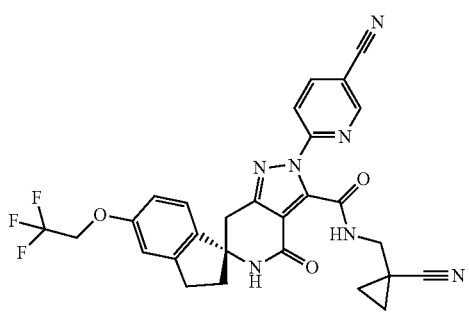 [SMILES: N#Cc1ccc(-n2nc3c(c2C(=O)NCC2(C#N)CC2)C(=O)N[C@@]2(CCc4cc(OCC(F)(F)F)ccc42)C3)nc1]
II-191
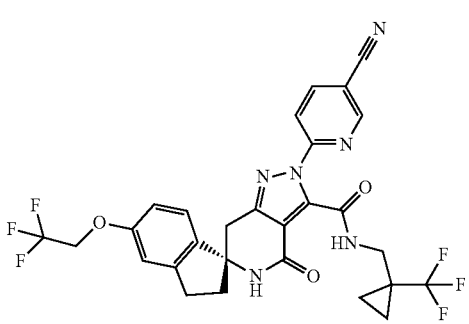 [SMILES: N#Cc1ccc(-n2nc3c(c2C(=O)NCC2(C(F)(F)F)CC2)C(=O)N[C@@]2(CCc4cc(OCC(F)(F)F)ccc42)C3)nc1]
II-192
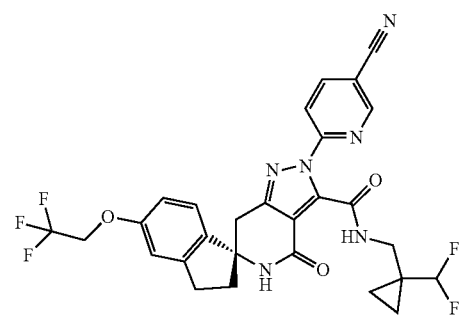 [SMILES: N#Cc1ccc(-n2nc3c(c2C(=O)NCC2(C(F)F)CC2)C(=O)N[C@@]2(CCc4cc(OCC(F)(F)F)ccc42)C3)nc1]

TABLE 38-continued
II-193
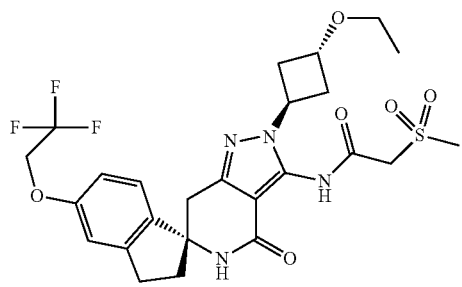 [SMILES: CCO[C@H]1C[C@H](n2nc3c(c2NC(=O)CS(C)(=O)=O)C(=O)N[C@@]2(CCc4cc(OCC(F)(F)F)ccc42)C3)C1]
II-194
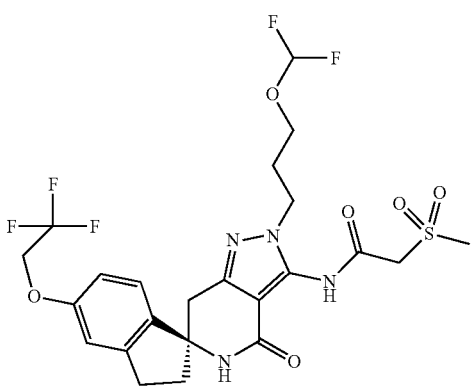 [SMILES: CS(=O)(=O)CC(=O)Nc1c2c(nn1CCCOC(F)F)C[C@@]1(CCc3cc(OCC(F)(F)F)ccc31)NC2=O]
II-195
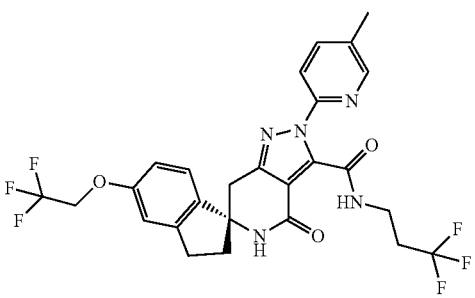 [SMILES: Cc1ccc(-n2nc3c(c2C(=O)NCCC(F)(F)F)C(=O)N[C@@]2(CCc4cc(OCC(F)(F)F)ccc42)C3)nc1]
II-196
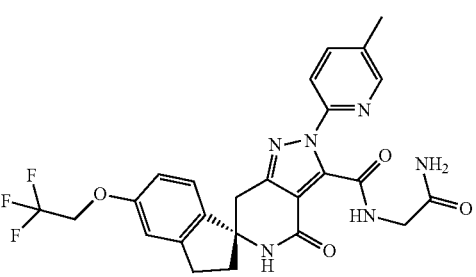 [SMILES: Cc1ccc(-n2nc3c(c2C(=O)NCC(N)=O)C(=O)N[C@@]2(CCc4cc(OCC(F)(F)F)ccc42)C3)nc1]
II-197
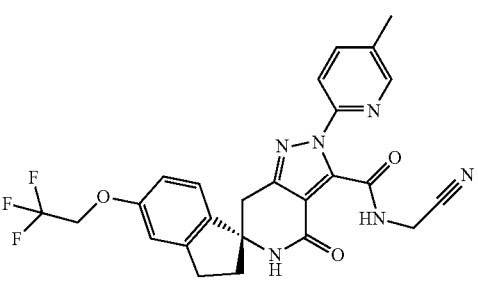 [SMILES: Cc1ccc(-n2nc3c(c2C(=O)NCC#N)C(=O)N[C@@]2(CCc4cc(OCC(F)(F)F)ccc42)C3)nc1]
TABLE 38-continued
II-198
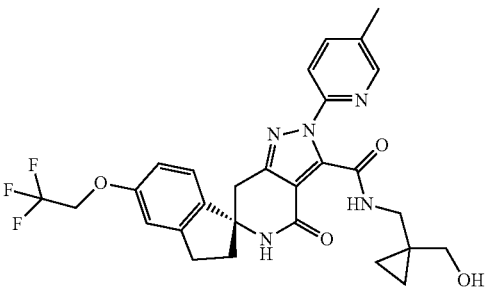 [SMILES: Cc1ccc(-n2nc3c(c2C(=O)NCC2(CO)CC2)C(=O)N[C@@]2(CCc4cc(OCC(F)(F)F)ccc42)C3)nc1]
II-199
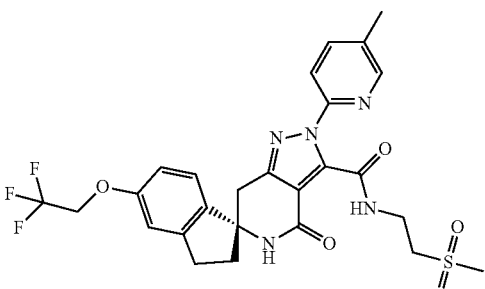
TABLE 39
II-200
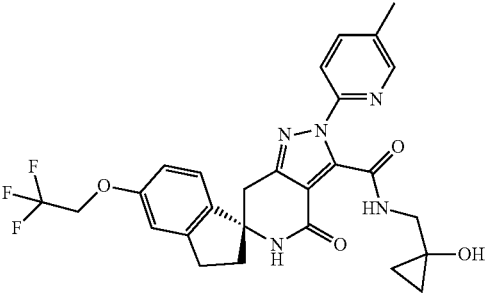 [SMILES: Cc1ccc(-n2nc3c(c2C(=O)NCC2(O)CC2)C(=O)N[C@@]2(CCc4cc(OCC(F)(F)F)ccc42)C3)nc1]
II-201
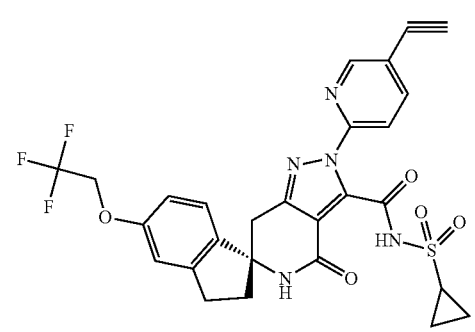 [SMILES: C#Cc1ccc(-n2nc3c(c2C(=O)NS(=O)(=O)C2CC2)C(=O)N[C@@]2(CCc4cc(OCC(F)(F)F)ccc42)C3)nc1]
II-202
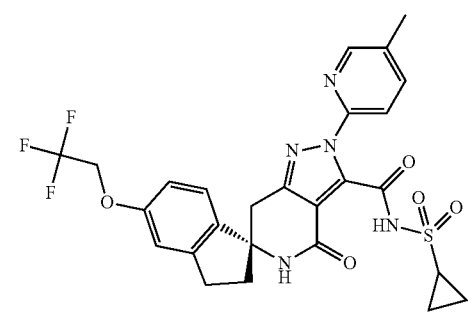 [SMILES: Cc1ccc(-n2nc3c(c2C(=O)NS(=O)(=O)C2CC2)C(=O)N[C@@]2(CCc4cc(OCC(F)(F)F)ccc42)C3)nc1]

TABLE 39-continued
II-204
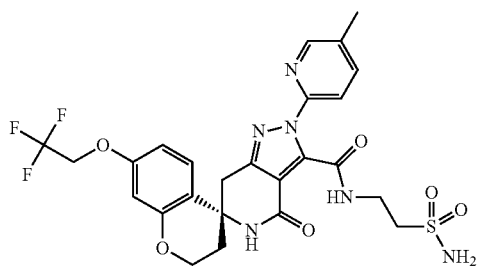 [SMILES: Cc1ccc(-n2nc3c(c2C(=O)NCCS(N)(=O)=O)C(=O)N[C@@]2(CCOc4cc(OCC(F)(F)F)ccc42)C3)nc1]
II-205
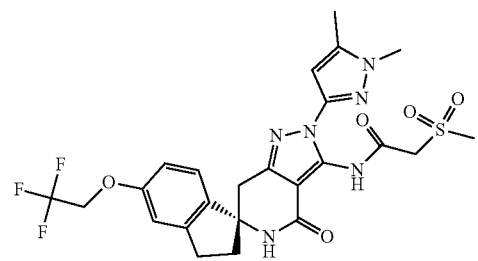 [SMILES: Cc1cc(-n2nc3c(c2NC(=O)CS(C)(=O)=O)C(=O)N[C@@]2(CCc4cc(OCC(F)(F)F)ccc42)C3)nn1C]
II-206
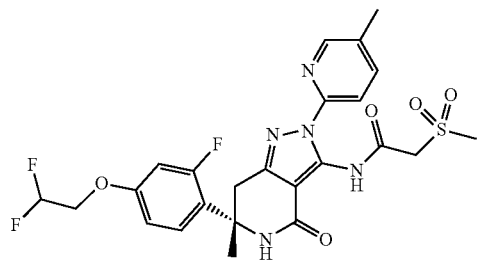 [SMILES: Cc1ccc(-n2nc3c(c2NC(=O)CS(C)(=O)=O)C(=O)N[C@](C)(c2ccc(OCC(F)F)cc2F)C3)nc1]
II-207
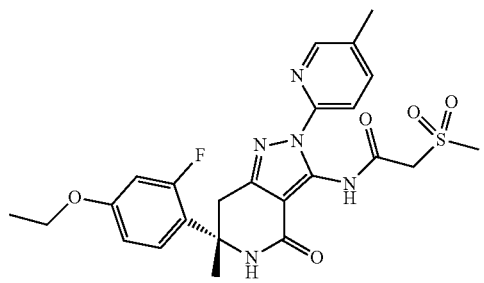 [SMILES: CCOc1ccc([C@]2(C)Cc3nn(-c4ccc(C)cn4)c(NC(=O)CS(C)(=O)=O)c3C(=O)N2)c(F)c1]
II-208
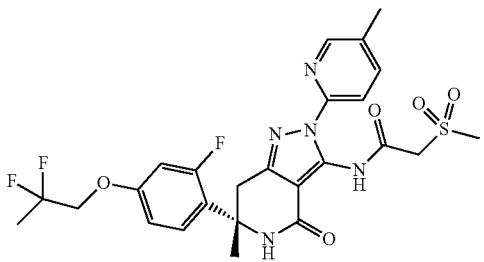 [SMILES: Cc1ccc(-n2nc3c(c2NC(=O)CS(C)(=O)=O)C(=O)N[C@](C)(c2ccc(OCC(C)(F)F)cc2F)C3)nc1]
II-209
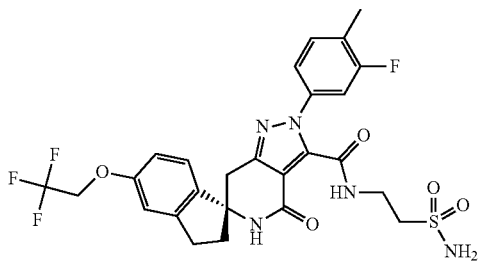 [SMILES: Cc1ccc(-n2nc3c(c2C(=O)NCCS(N)(=O)=O)C(=O)N[C@@]2(CCc4cc(OCC(F)(F)F)ccc42)C3)cc1F]
TABLE 39-continued
II-210
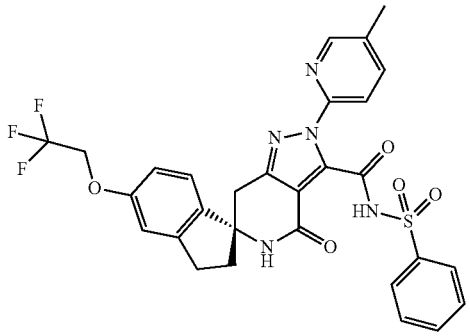 [SMILES: Cc1ccc(-n2nc3c(c2C(=O)NS(=O)(=O)c2ccccc2)C(=O)N[C@@]2(CCc4cc(OCC(F)(F)F)ccc42)C3)nc1]
II-211
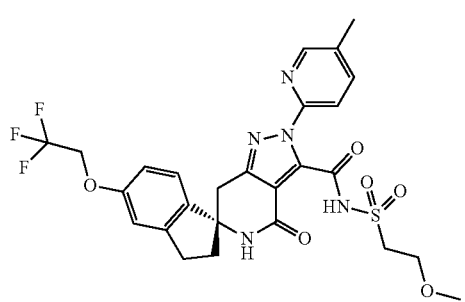 [SMILES: COCCS(=O)(=O)NC(=O)c1c2c(nn1-c1ccc(C)cn1)C[C@]1(CCc3cc(OCC(F)(F)F)ccc31)NC2=O]
II-212
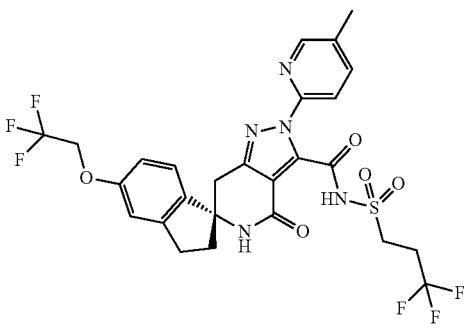 [SMILES: Cc1ccc(-n2nc3c(c2C(=O)NS(=O)(=O)CCC(F)(F)F)C(=O)N[C@@]2(CCc4cc(OCC(F)(F)F)ccc42)C3)nc1]
TABLE 40
II-213
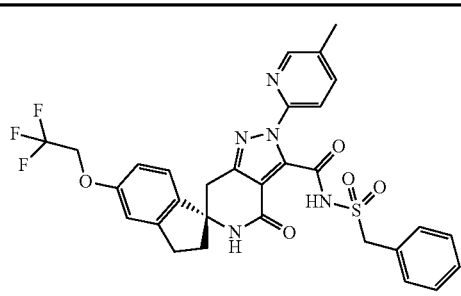

TABLE 40-continued
II-214
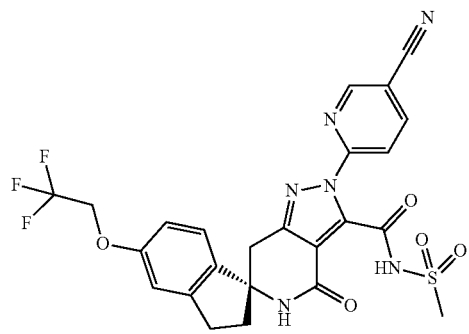 [SMILES: CS(=O)(=O)NC(=O)c1c2c(nn1-c1ccc(C#N)cn1)C[C@]1(CCc3cc(OCC(F)(F)F)ccc31)NC2=O]
II-215
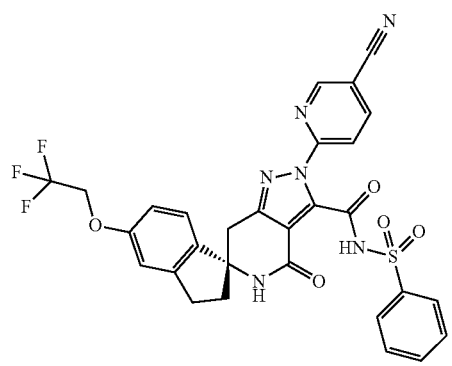 [SMILES: N#Cc1ccc(-n2nc3c(c2C(=O)NS(=O)(=O)c2ccccc2)C(=O)N[C@@]2(CCc4cc(OCC(F)(F)F)ccc42)C3)nc1]
II-216
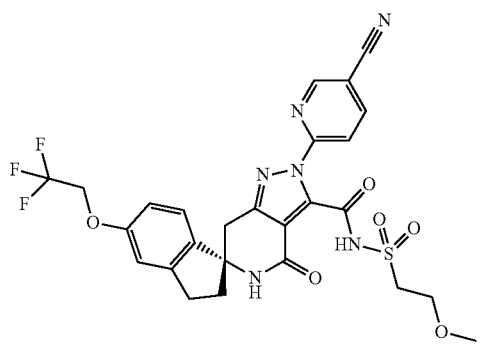 [SMILES: COCCS(=O)(=O)NC(=O)c1c2c(nn1-c1ccc(C#N)cn1)C[C@]1(CCc3cc(OCC(F)(F)F)ccc31)NC2=O]
II-217
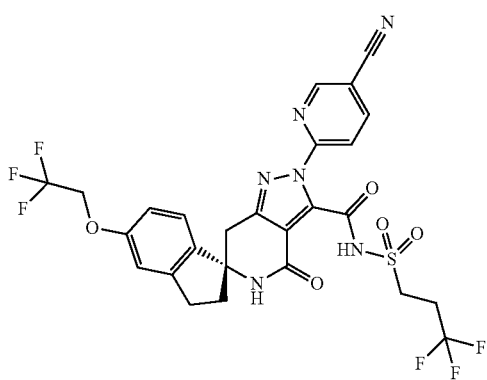 [SMILES: N#Cc1ccc(-n2nc3c(c2C(=O)NS(=O)(=O)CCC(F)(F)F)C(=O)N[C@@]2(CCc4cc(OCC(F)(F)F)ccc42)C3)nc1]
II-218
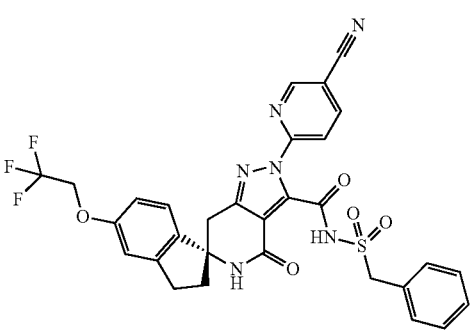 [SMILES: N#Cc1ccc(-n2nc3c(c2C(=O)NS(=O)(=O)Cc2ccccc2)C(=O)N[C@@]2(CCc4cc(OCC(F)(F)F)ccc42)C3)nc1]
II-219
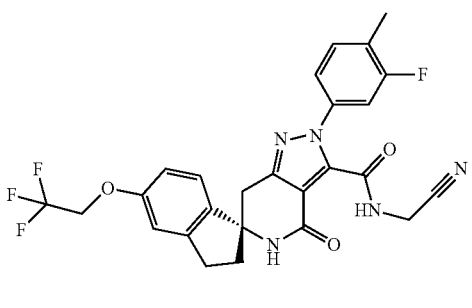 [SMILES: Cc1ccc(-n2nc3c(c2C(=O)NCC#N)C(=O)N[C@@]2(CCc4cc(OCC(F)(F)F)ccc42)C3)cc1F]
II-220
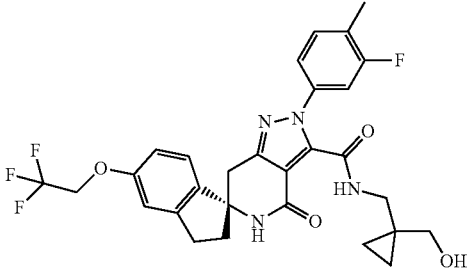 [SMILES: Cc1ccc(-n2nc3c(c2C(=O)NCC2(CO)CC2)C(=O)N[C@@]2(CCc4cc(OCC(F)(F)F)ccc42)C3)cc1F]
II-221
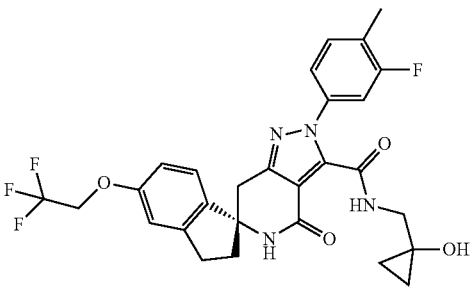 [SMILES: Cc1ccc(-n2nc3c(c2C(=O)NCC2(O)CC2)C(=O)N[C@@]2(CCc4cc(OCC(F)(F)F)ccc42)C3)cc1F]
II-222
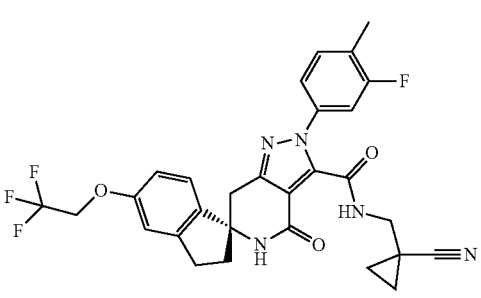 [SMILES: Cc1ccc(-n2nc3c(c2C(=O)NCC2(C#N)CC2)C(=O)N[C@@]2(CCc4cc(OCC(F)(F)F)ccc42)C3)cc1F]

TABLE 41
II-223
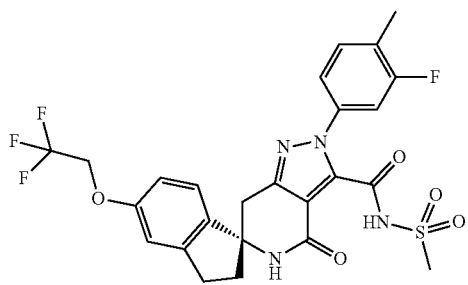 [SMILES: Cc1ccc(-n2nc3c(c2C(=O)NS(C)(=O)=O)C(=O)N[C@@]2(CCc4cc(OCC(F)(F)F)ccc42)C3)cc1F]
II-224
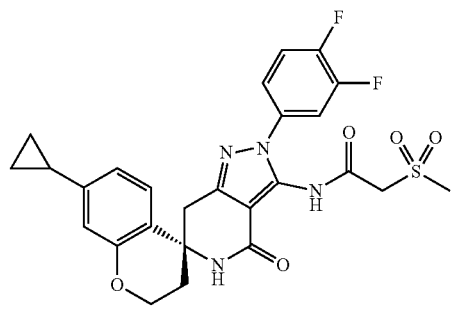 [SMILES: CS(=O)(=O)CC(=O)Nc1c2c(nn1-c1ccc(F)c(F)c1)C[C@]1(CCOc3cc(C4CC4)ccc31)NC2=O]
II-225
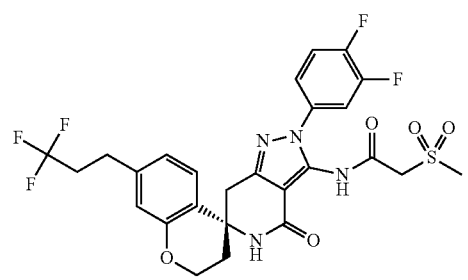 [SMILES: CS(=O)(=O)CC(=O)Nc1c2c(nn1-c1ccc(F)c(F)c1)C[C@]1(CCOc3cc(CCC(F)(F)F)ccc31)NC2=O]
II-226
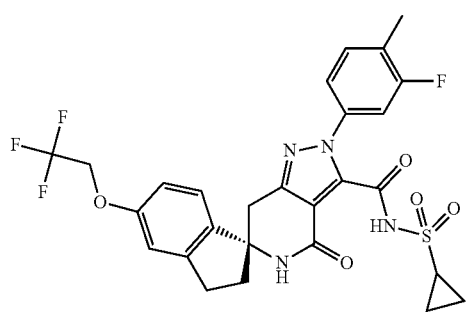 [SMILES: Cc1ccc(-n2nc3c(c2C(=O)NS(=O)(=O)C2CC2)C(=O)N[C@@]2(CCc4cc(OCC(F)(F)F)ccc42)C3)cc1F]
II-227
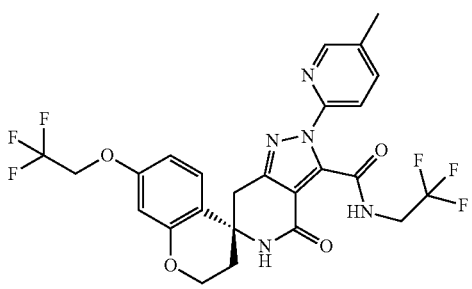 [SMILES: Cc1ccc(-n2nc3c(c2C(=O)NCC(F)(F)F)C(=O)N[C@@]2(CCOc4cc(OCC(F)(F)F)ccc42)C3)nc1]
TABLE 41-continued
II-228
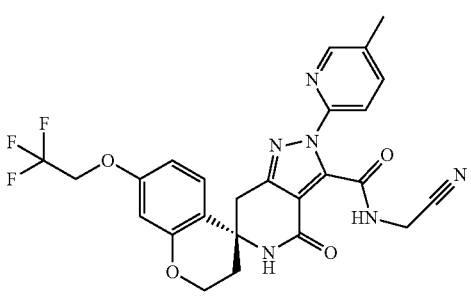 [SMILES: Cc1ccc(-n2nc3c(c2C(=O)NCC#N)C(=O)N[C@@]2(CCOc4cc(OCC(F)(F)F)ccc42)C3)nc1]
II-229
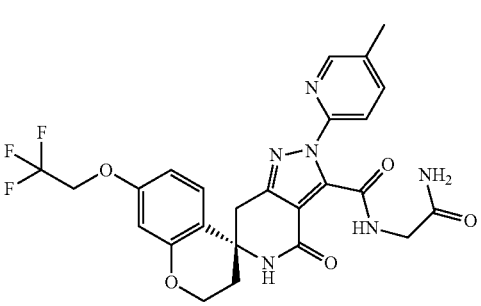 [SMILES: Cc1ccc(-n2nc3c(c2C(=O)NCC(N)=O)C(=O)N[C@@]2(CCOc4cc(OCC(F)(F)F)ccc42)C3)nc1]
II-230
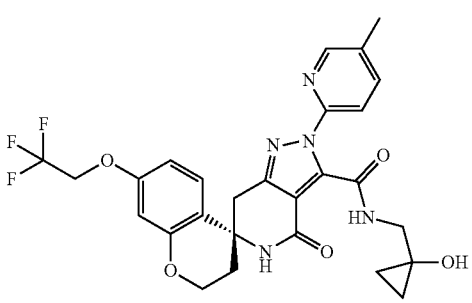 [SMILES: Cc1ccc(-n2nc3c(c2C(=O)NCC2(O)CC2)C(=O)N[C@@]2(CCOc4cc(OCC(F)(F)F)ccc42)C3)nc1]
II-231
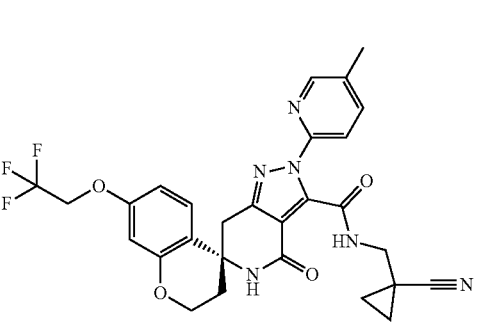 [SMILES: Cc1ccc(-n2nc3c(c2C(=O)NCC2(C#N)CC2)C(=O)N[C@@]2(CCOc4cc(OCC(F)(F)F)ccc42)C3)nc1]
II-232
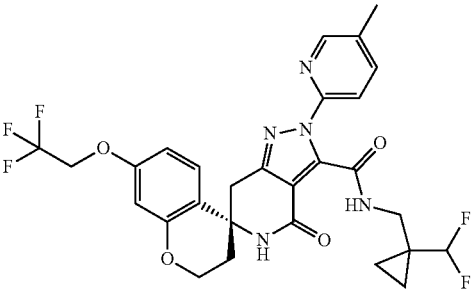 [SMILES: Cc1ccc(-n2nc3c(c2C(=O)NCC2(C(F)F)CC2)C(=O)N[C@@]2(CCOc4cc(OCC(F)(F)F)ccc42)C3)nc1]

US 11,198,695 B2
TABLE 41-continued
II-233
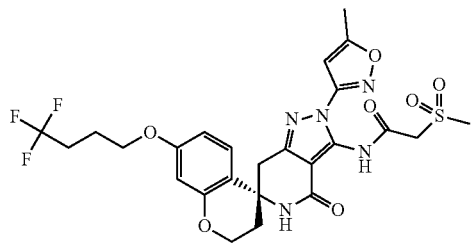 [SMILES: Cc1cc(-n2nc3c(c2NC(=O)CS(C)(=O)=O)C(=O)N[C@@]2(CCOc4cc(OCCCC(F)(F)F)ccc42)C3)no1]
II-234
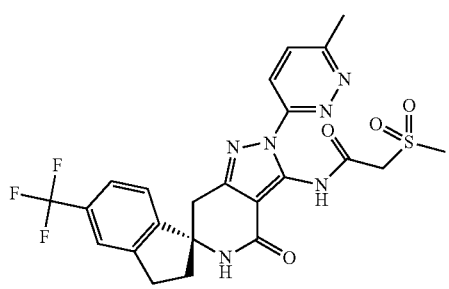 [SMILES: Cc1ccc(-n2nc3c(c2NC(=O)CS(C)(=O)=O)C(=O)N[C@@]2(CCc4cc(C(F)(F)F)ccc42)C3)nn1]
TABLE 42
II-235
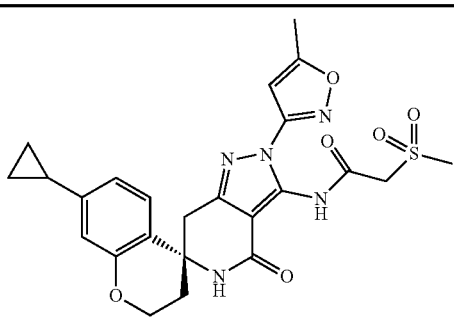
II-236
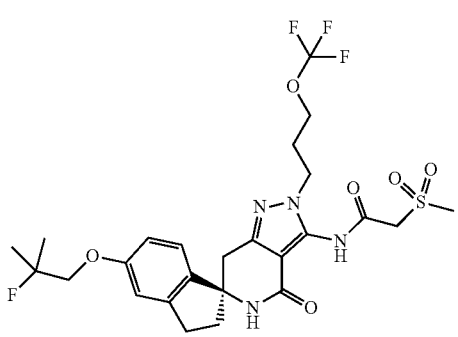 [SMILES: CC(C)(F)COc1ccc2c(c1)CC[C@@]21Cc2nn(CCCOC(F)(F)F)c(NC(=O)CS(C)(=O)=O)c2C(=O)N1]
II-237
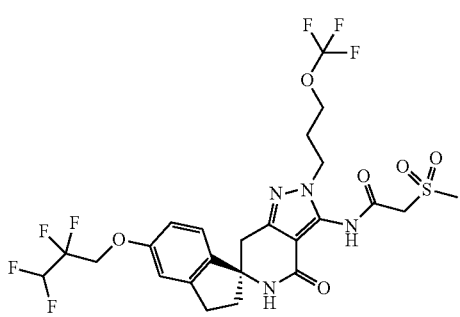 [SMILES: CS(=O)(=O)CC(=O)Nc1c2c(nn1CCCOC(F)(F)F)C[C@@]1(CCc3cc(OCC(F)(F)C(F)F)ccc31)NC2=O]
TABLE 42-continued
II-238
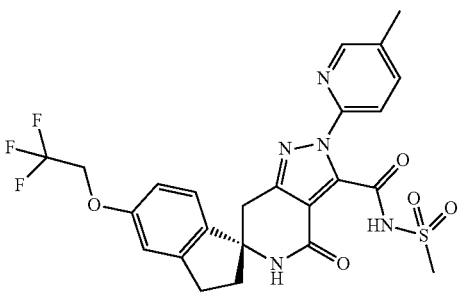 [SMILES: Cc1ccc(-n2nc3c(c2C(=O)NS(C)(=O)=O)C(=O)N[C@@]2(CCc4cc(OCC(F)(F)F)ccc42)C3)nc1]
II-239
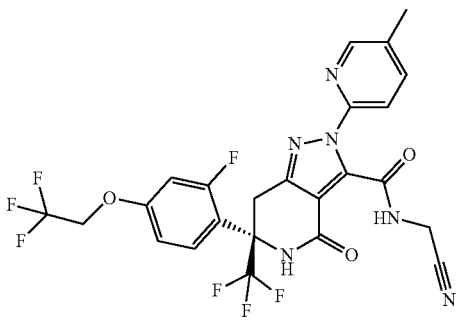 [SMILES: Cc1ccc(-n2nc3c(c2C(=O)NCC#N)C(=O)N[C@@](c2ccc(OCC(F)(F)F)cc2F)(C(F)(F)F)C3)nc1]
II-240
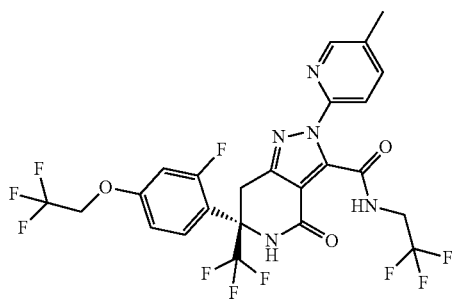 [SMILES: Cc1ccc(-n2nc3c(c2C(=O)NCC(F)(F)F)C(=O)N[C@@](c2ccc(OCC(F)(F)F)cc2F)(C(F)(F)F)C3)nc1]
II-241
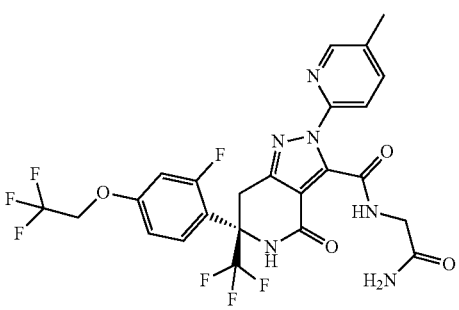 [SMILES: Cc1ccc(-n2nc3c(c2C(=O)NCC(N)=O)C(=O)N[C@@](c2ccc(OCC(F)(F)F)cc2F)(C(F)(F)F)C3)nc1]
II-242
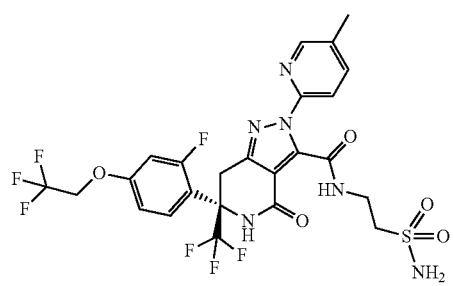 [SMILES: Cc1ccc(-n2nc3c(c2C(=O)NCCS(N)(=O)=O)C(=O)N[C@@](c2ccc(OCC(F)(F)F)cc2F)(C(F)(F)F)C3)nc1]

TABLE 42-continued
II-243
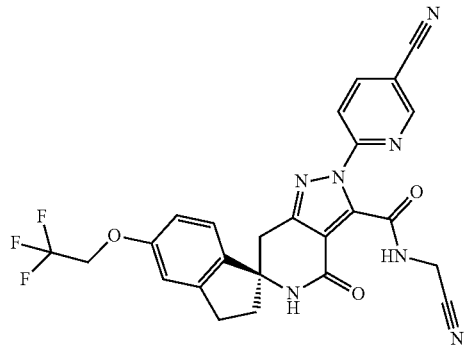 [SMILES: N#CCNC(=O)c1c2c(nn1-c1ccc(C#N)cn1)C[C@@]1(CCc3cc(OCC(F)(F)F)ccc31)NC2=O]
II-244
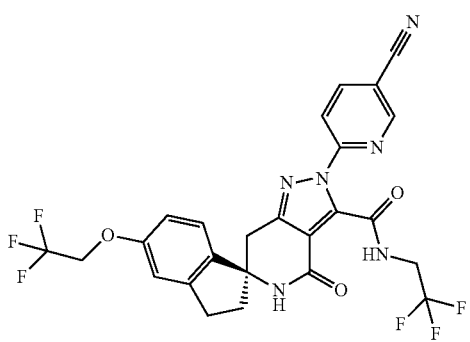 [SMILES: N#Cc1ccc(-n2nc3c(c2C(=O)NCC(F)(F)F)C(=O)N[C@]2(CCc4cc(OCC(F)(F)F)ccc42)C3)nc1]
II-245
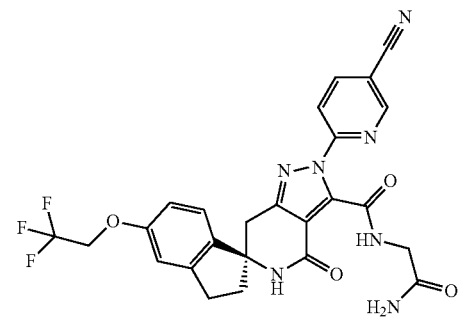 [SMILES: N#Cc1ccc(-n2nc3c(c2C(=O)NCC(N)=O)C(=O)N[C@]2(CCc4cc(OCC(F)(F)F)ccc42)C3)nc1]
II-246
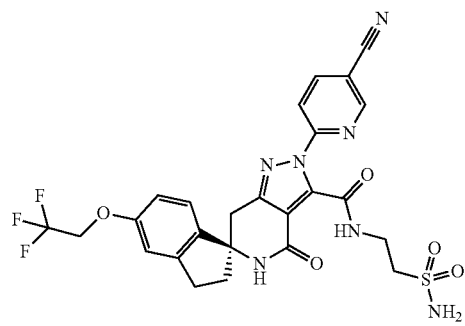 [SMILES: N#Cc1ccc(-n2nc3c(c2C(=O)NCCS(N)(=O)=O)C(=O)N[C@]2(CCc4cc(OCC(F)(F)F)ccc42)C3)nc1]
TABLE 43
II-247
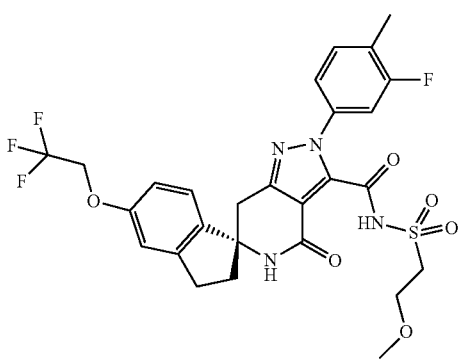 [SMILES: COCCS(=O)(=O)NC(=O)c1c2c(nn1-c1ccc(C)c(F)c1)C[C@]1(CCc3cc(OCC(F)(F)F)ccc31)NC2=O]
II-248
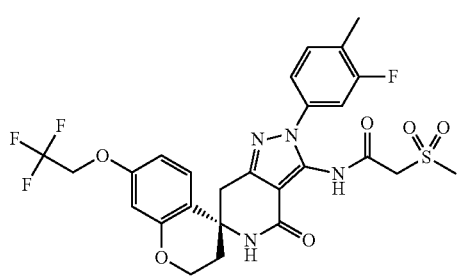 [SMILES: Cc1ccc(-n2nc3c(c2NC(=O)CS(C)(=O)=O)C(=O)N[C@@]2(CCOc4cc(OCC(F)(F)F)ccc42)C3)cc1F]
II-249
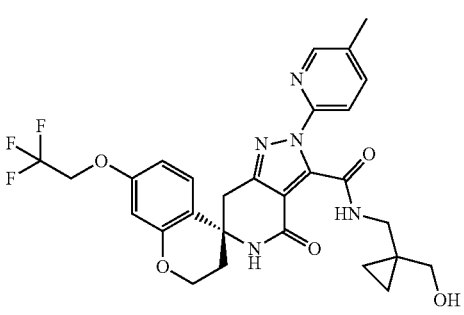 [SMILES: Cc1ccc(-n2nc3c(c2C(=O)NCC2(CO)CC2)C(=O)N[C@@]2(CCOc4cc(OCC(F)(F)F)ccc42)C3)nc1]
II-250
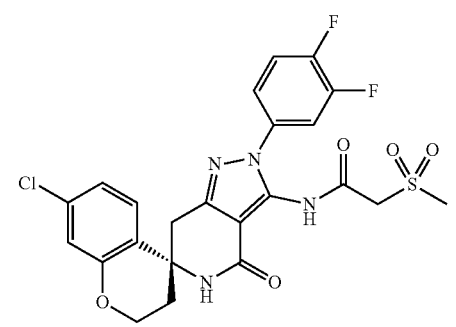 [SMILES: CS(=O)(=O)CC(=O)Nc1c2c(nn1-c1ccc(F)c(F)c1)C[C@]1(CCOc3cc(Cl)ccc31)NC2=O]
II-251
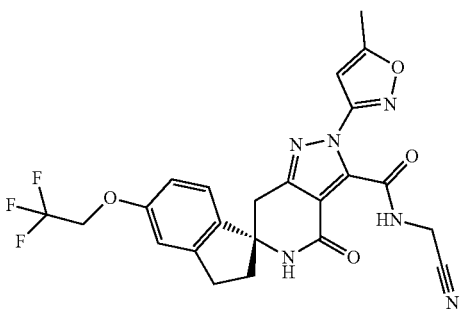 [SMILES: Cc1cc(-n2nc3c(c2C(=O)NCC#N)C(=O)N[C@@]2(CCc4cc(OCC(F)(F)F)ccc42)C3)no1]

TABLE 43-continued
II-252
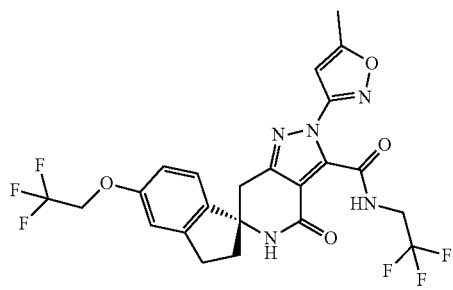 [SMILES: Cc1cc(-n2nc3c(c2C(=O)NCC(F)(F)F)C(=O)N[C@@]2(CCc4cc(OCC(F)(F)F)ccc42)C3)no1]
II-253
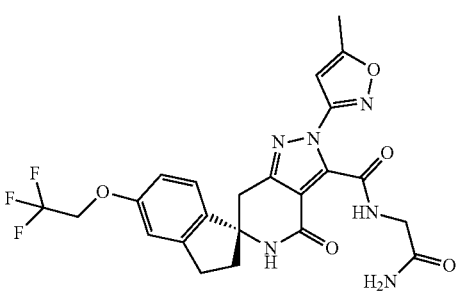 [SMILES: Cc1cc(-n2nc3c(c2C(=O)NCC(N)=O)C(=O)N[C@@]2(CCc4cc(OCC(F)(F)F)ccc42)C3)no1]
II-254
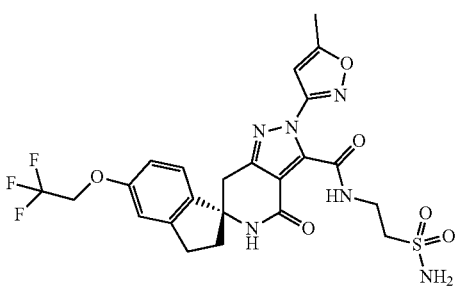 [SMILES: Cc1cc(-n2nc3c(c2C(=O)NCCS(N)(=O)=O)C(=O)N[C@@]2(CCc4cc(OCC(F)(F)F)ccc42)C3)no1]
II-255
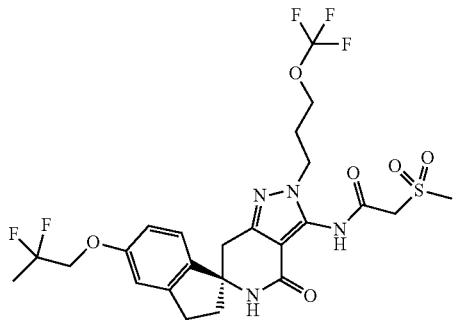 [SMILES: CC(F)(F)COc1ccc2c(c1)CC[C@@]21Cc2nn(CCCOC(F)(F)F)c(NC(=O)CS(C)(=O)=O)c2C(=O)N1]
II-256
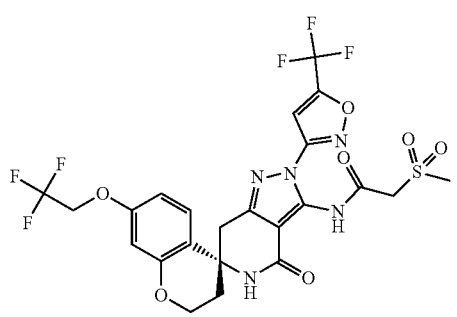 [SMILES: CS(=O)(=O)CC(=O)Nc1c2c(nn1-c1cc(C(F)(F)F)on1)C[C@]1(CCOc3cc(OCC(F)(F)F)ccc31)NC2=O]
II-257
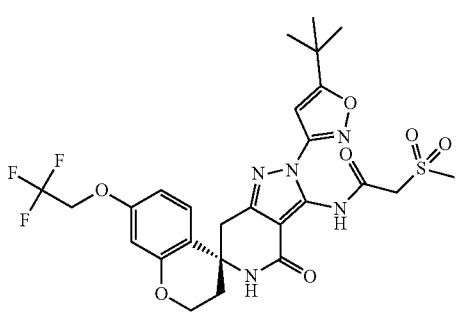 [SMILES: CC(C)(C)c1cc(-n2nc3c(c2NC(=O)CS(C)(=O)=O)C(=O)N[C@@]2(CCOc4cc(OCC(F)(F)F)ccc42)C3)no1]
II-258
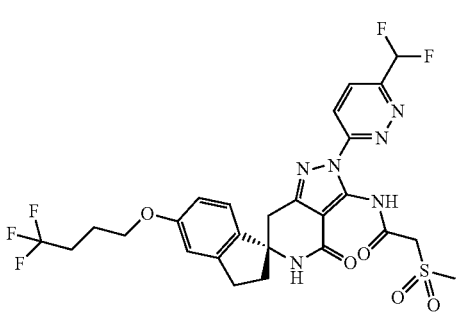 [SMILES: CS(=O)(=O)CC(=O)Nc1c2c(nn1-c1ccc(C(F)F)nn1)C[C@]1(CCc3cc(OCCCC(F)(F)F)ccc31)NC2=O]
TABLE 44
II-259
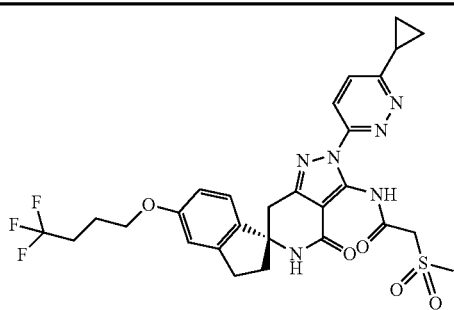
II-260
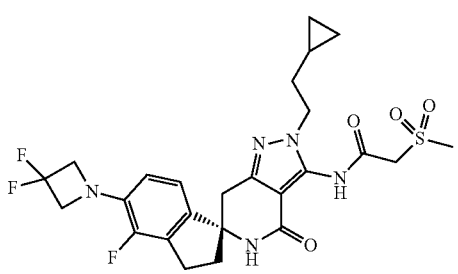 [SMILES: CS(=O)(=O)CC(=O)Nc1c2c(nn1CCC1CC1)C[C@]1(CCc3c1ccc(N1CC(F)(F)C1)c3F)NC2=O]
II-261
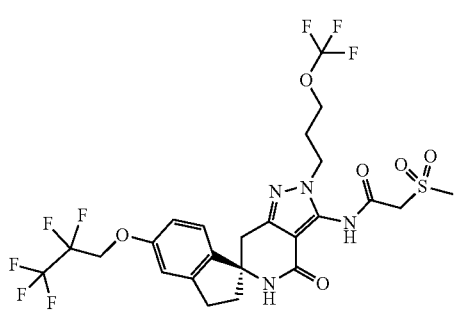 [SMILES: CS(=O)(=O)CC(=O)Nc1c2c(nn1CCCOC(F)(F)F)C[C@@]1(CCc3cc(OCC(F)(F)C(F)(F)F)ccc31)NC2=O]

TABLE 44-continued
II-262
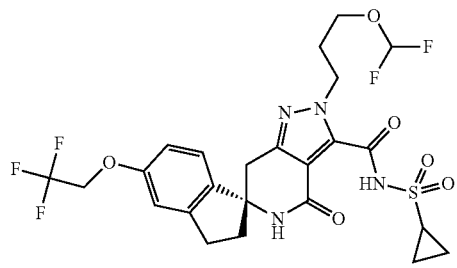 [SMILES: O=C1N[C@@]2(CCc3cc(OCC(F)(F)F)ccc32)Cc2nn(CCCOC(F)F)c(C(=O)NS(=O)(=O)C3CC3)c21]
II-263
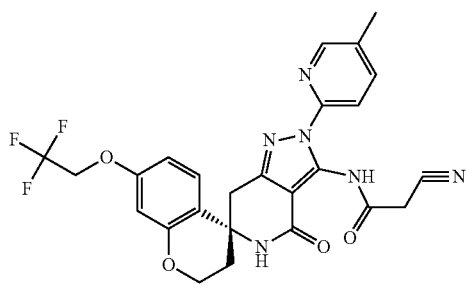 [SMILES: Cc1ccc(-n2nc3c(c2NC(=O)CC#N)C(=O)N[C@@]2(CCOc4cc(OCC(F)(F)F)ccc42)C3)nc1]
II-264
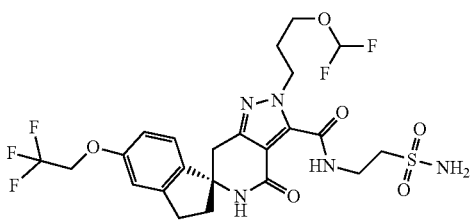 [SMILES: NS(=O)(=O)CCNC(=O)c1c2c(nn1CCCOC(F)F)C[C@]1(CCc3cc(OCC(F)(F)F)ccc31)NC2=O]
II-265
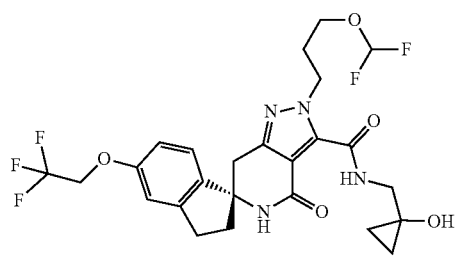 [SMILES: O=C1N[C@@]2(CCc3cc(OCC(F)(F)F)ccc32)Cc2nn(CCCOC(F)F)c(C(=O)NCC3(O)CC3)c21]
II-266
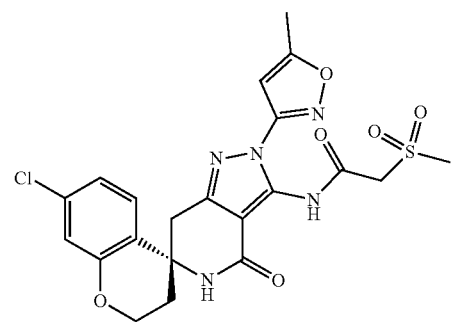 [SMILES: Cc1cc(-n2nc3c(c2NC(=O)CS(C)(=O)=O)C(=O)N[C@@]2(CCOc4cc(Cl)ccc42)C3)no1]
II-267
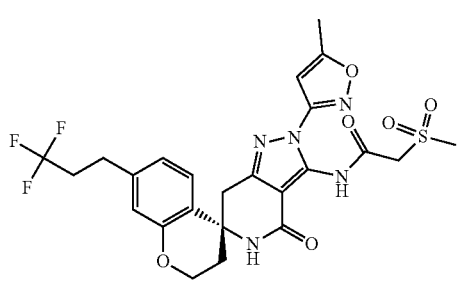 [SMILES: Cc1cc(-n2nc3c(c2NC(=O)CS(C)(=O)=O)C(=O)N[C@@]2(CCOc4cc(CCC(F)(F)F)ccc42)C3)no1]
TABLE 44-continued
II-268
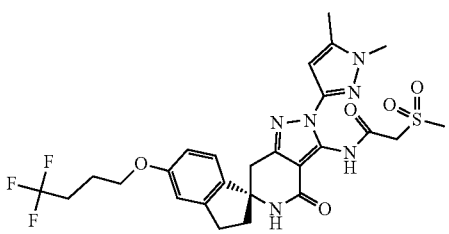 [SMILES: Cc1cc(-n2nc3c(c2NC(=O)CS(C)(=O)=O)C(=O)N[C@@]2(CCc4cc(OCCCC(F)(F)F)ccc42)C3)nn1C]
II-269
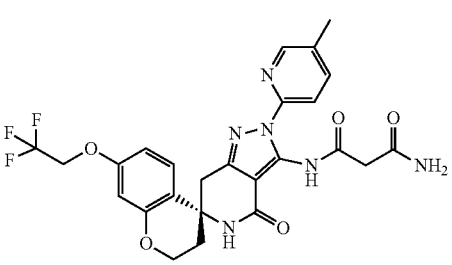 [SMILES: Cc1ccc(-n2nc3c(c2NC(=O)CC(N)=O)C(=O)N[C@@]2(CCOc4cc(OCC(F)(F)F)ccc42)C3)nc1]
II-270
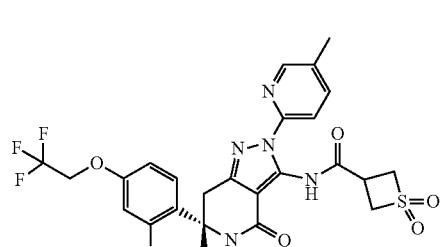
TABLE 45
II-271
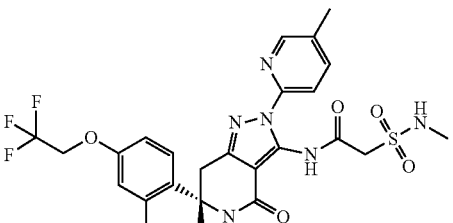
II-272
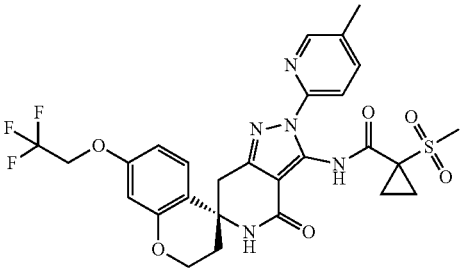 [SMILES: Cc1ccc(-n2nc3c(c2NC(=O)C2(S(C)(=O)=O)CC2)C(=O)N[C@@]2(CCOc4cc(OCC(F)(F)F)ccc42)C3)nc1]

TABLE 45-continued
II-273
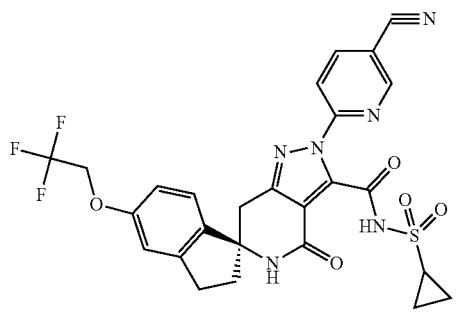 [SMILES: N#Cc1ccc(-n2nc3c(c2C(=O)NS(=O)(=O)C2CC2)C(=O)N[C@]2(CCc4cc(OCC(F)(F)F)ccc42)C3)nc1]
II-274
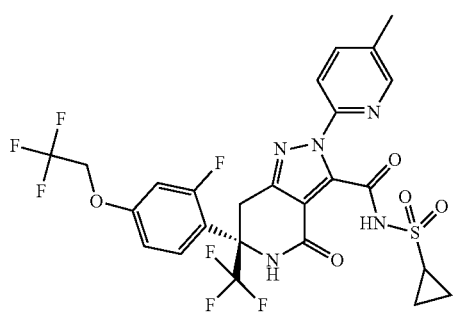 [SMILES: Cc1ccc(-n2nc3c(c2C(=O)NS(=O)(=O)C2CC2)C(=O)N[C@@](c2ccc(OCC(F)(F)F)cc2F)(C(F)(F)F)C3)nc1]
II-275
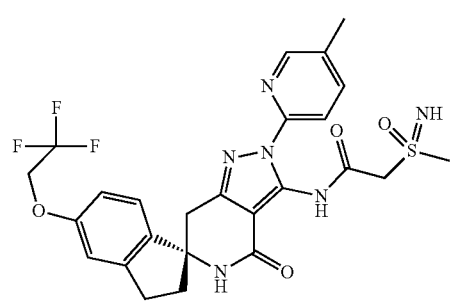 [SMILES: Cc1ccc(-n2nc3c(c2NC(=O)CS(C)(=N)=O)C(=O)N[C@@]2(CCc4cc(OCC(F)(F)F)ccc42)C3)nc1]
II-276
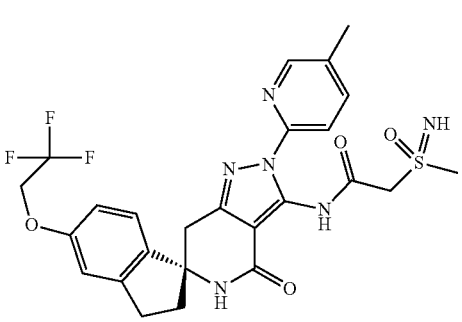 [SMILES: Cc1ccc(-n2nc3c(c2NC(=O)CS(C)(=N)=O)C(=O)N[C@@]2(CCc4cc(OCC(F)(F)F)ccc42)C3)nc1]
II-277
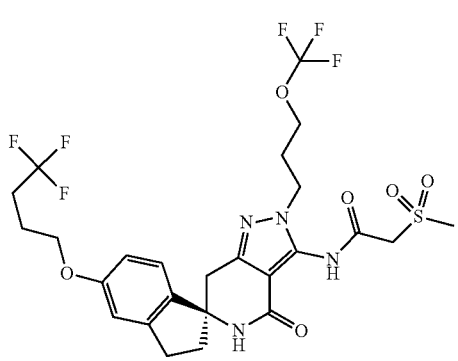 [SMILES: CS(=O)(=O)CC(=O)Nc1c2c(nn1CCCOC(F)(F)F)C[C@@]1(CCc3cc(OCCCC(F)(F)F)ccc31)NC2=O]
TABLE 45-continued
II-278
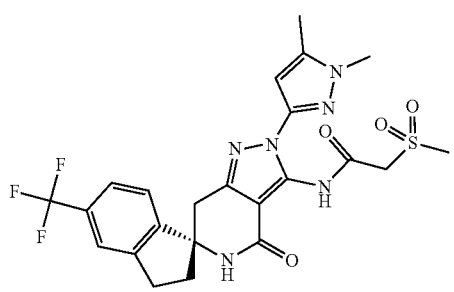 [SMILES: Cc1cc(-n2nc3c(c2NC(=O)CS(C)(=O)=O)C(=O)N[C@@]2(CCc4cc(C(F)(F)F)ccc42)C3)nn1C]
II-279
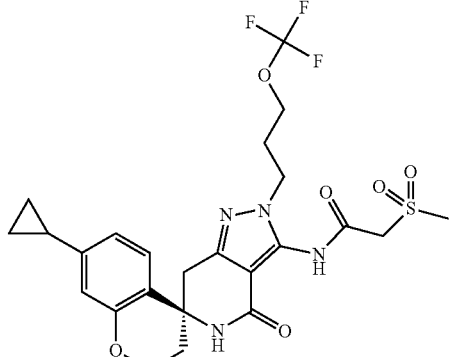
II-280
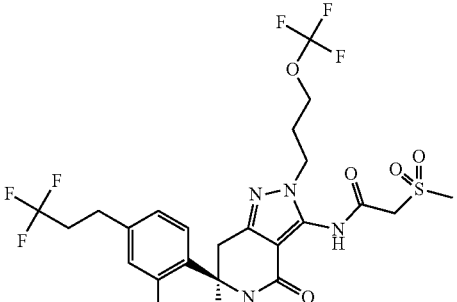
II-281
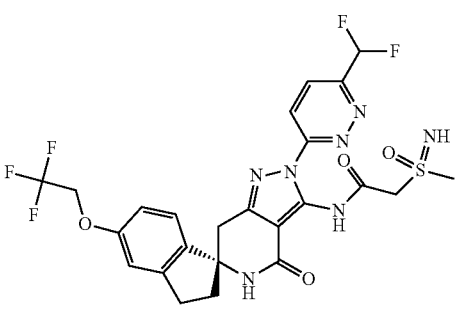 [SMILES: CS(=N)(=O)CC(=O)Nc1c2c(nn1-c1ccc(C(F)F)nn1)C[C@]1(CCc3cc(OCC(F)(F)F)ccc31)NC2=O]
II-282
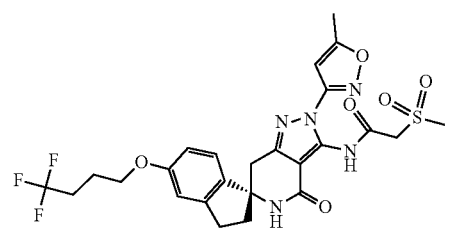 [SMILES: Cc1cc(-n2nc3c(c2NC(=O)CS(C)(=O)=O)C(=O)N[C@@]2(CCc4cc(OCCCC(F)(F)F)ccc42)C3)no1]

TABLE 46
II-283 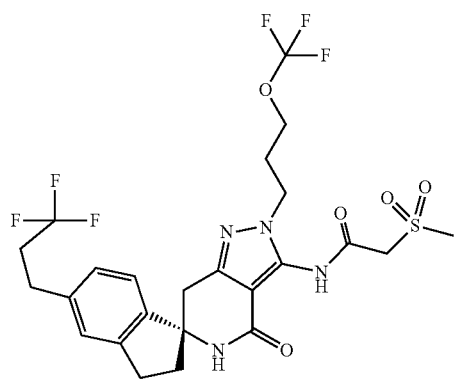 [SMILES: CS(=O)(=O)CC(=O)Nc1c2c(nn1CCCOC(F)(F)F)C[C@]1(CCc3cc(CCC(F)(F)F)ccc31)NC2=O]
II-284 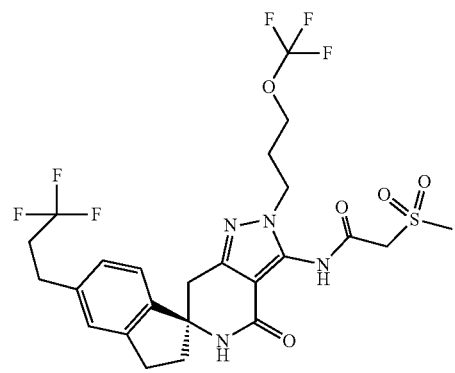 [SMILES: CS(=O)(=O)CC(=O)Nc1c2c(nn1CCCOC(F)(F)F)C[C@@]1(CCc3cc(CCC(F)(F)F)ccc31)NC2=O]
II-285 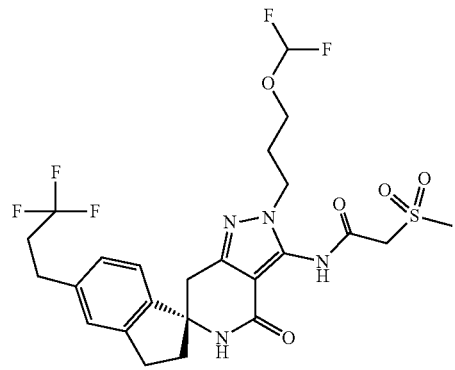 [SMILES: CS(=O)(=O)CC(=O)Nc1c2c(nn1CCCOC(F)F)C[C@]1(CCc3cc(CCC(F)(F)F)ccc31)NC2=O]
II-286 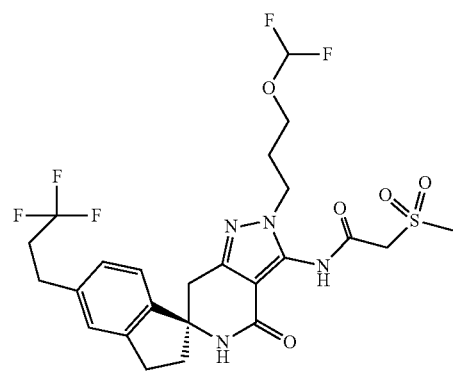 [SMILES: CS(=O)(=O)CC(=O)Nc1c2c(nn1CCCOC(F)F)C[C@@]1(CCc3cc(CCC(F)(F)F)ccc31)NC2=O]
TABLE 46-continued
II-287 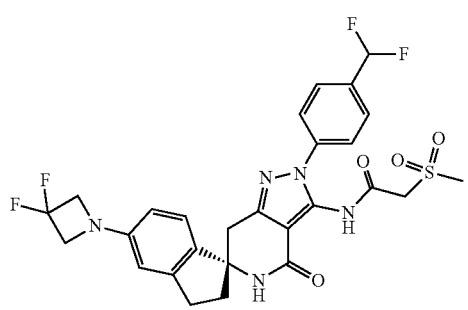 [SMILES: CS(=O)(=O)CC(=O)Nc1c2c(nn1-c1ccc(C(F)F)cc1)C[C@]1(CCc3cc(N4CC(F)(F)C4)ccc31)NC2=O]
II-288 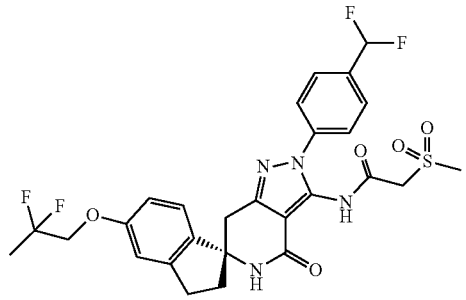 [SMILES: CC(F)(F)COc1ccc2c(c1)CC[C@]21Cc2nn(-c3ccc(C(F)F)cc3)c(NC(=O)CS(C)(=O)=O)c2C(=O)N1]
II-289 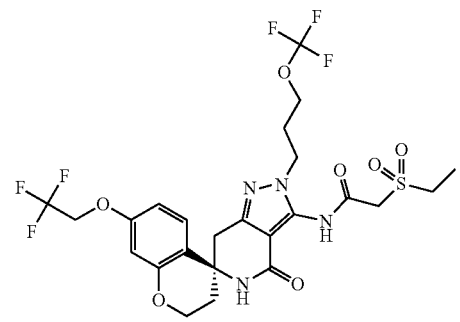 [SMILES: CCS(=O)(=O)CC(=O)Nc1c2c(nn1CCCOC(F)(F)F)C[C@@]1(CCOc3cc(OCC(F)(F)F)ccc31)NC2=O]
II-290 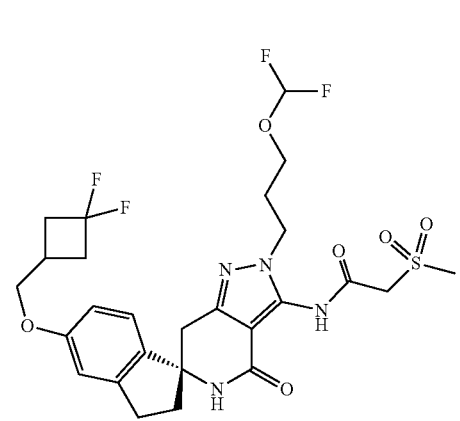 [SMILES: CS(=O)(=O)CC(=O)Nc1c2c(nn1CCCOC(F)F)C[C@]1(CCc3cc(OCC4CC(F)(F)C4)ccc31)NC2=O]

TABLE 46-continued
II-291
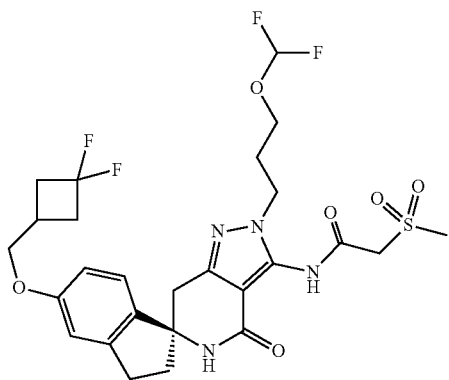 [SMILES: CS(=O)(=O)CC(=O)Nc1c2c(nn1CCCOC(F)F)C[C@@]1(CCc3cc(OCC4CC(F)(F)C4)ccc31)NC2=O]
II-292
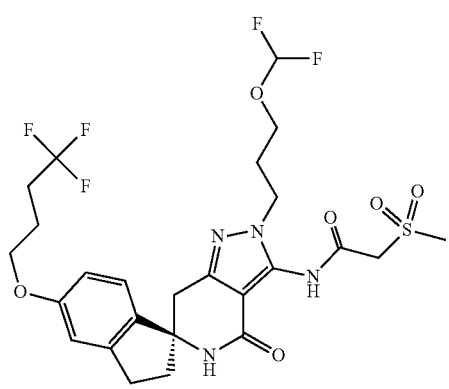 [SMILES: CS(=O)(=O)CC(=O)Nc1c2c(nn1CCCOC(F)F)C[C@@]1(CCc3cc(OCCCC(F)(F)F)ccc31)NC2=O]
TABLE 47
II-293
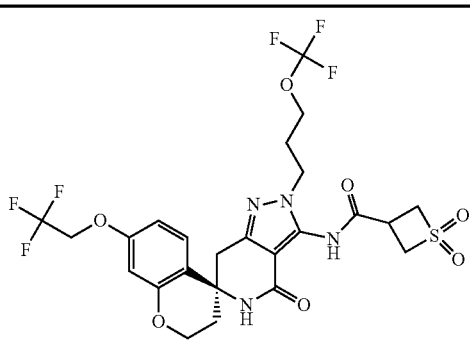
II-294
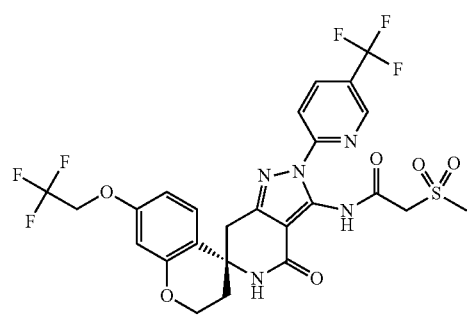 [SMILES: CS(=O)(=O)CC(=O)Nc1c2c(nn1-c1ccc(C(F)(F)F)cn1)C[C@]1(CCOc3cc(OCC(F)(F)F)ccc31)NC2=O]
TABLE 47-continued
II-295
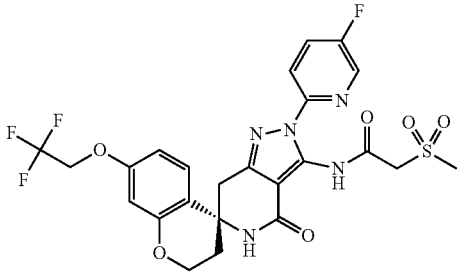 [SMILES: CS(=O)(=O)CC(=O)Nc1c2c(nn1-c1ccc(F)cn1)C[C@]1(CCOc3cc(OCC(F)(F)F)ccc31)NC2=O]
II-296
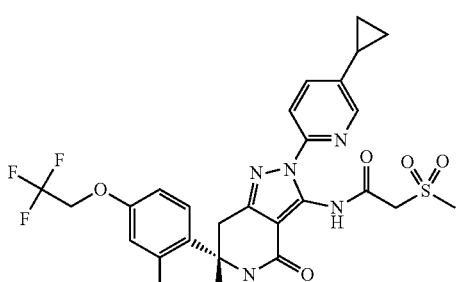
II-297
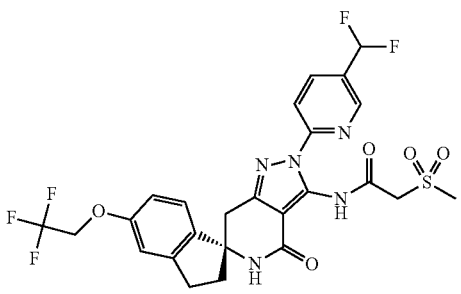 [SMILES: CS(=O)(=O)CC(=O)Nc1c2c(nn1-c1ccc(C(F)F)cn1)C[C@]1(CCc3cc(OCC(F)(F)F)ccc31)NC2=O]
II-298
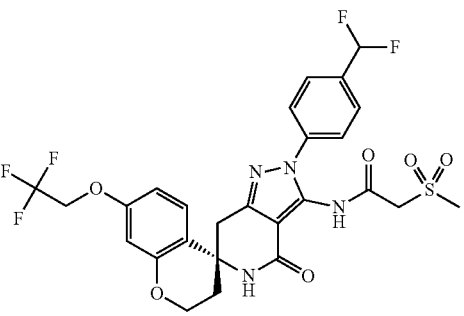 [SMILES: CS(=O)(=O)CC(=O)Nc1c2c(nn1-c1ccc(C(F)F)cc1)C[C@]1(CCOc3cc(OCC(F)(F)F)ccc31)NC2=O]
II-299
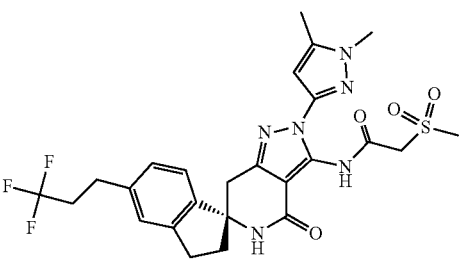 [SMILES: Cc1cc(-n2nc3c(c2NC(=O)CS(C)(=O)=O)C(=O)N[C@@]2(CCc4cc(CCC(F)(F)F)ccc42)C3)nn1C]

TABLE 47-continued

II-300
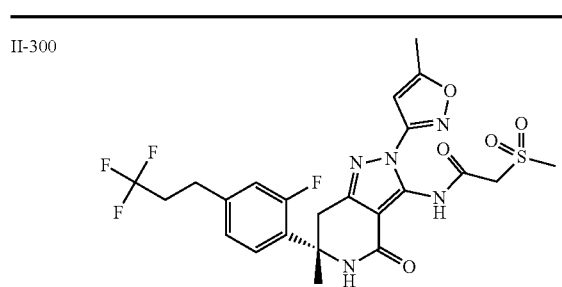

II-301
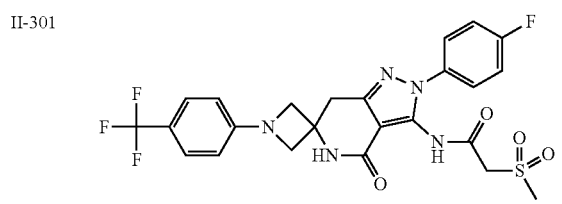

II-302
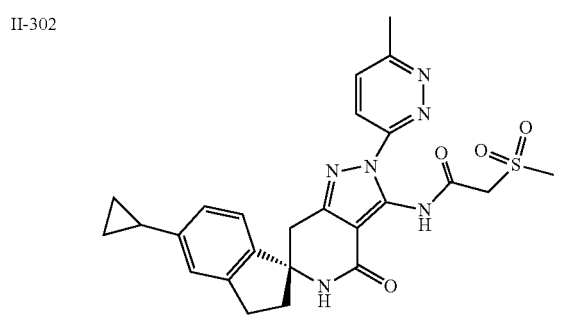

II-303
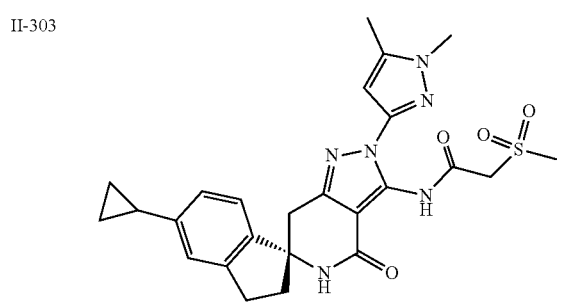

II-304
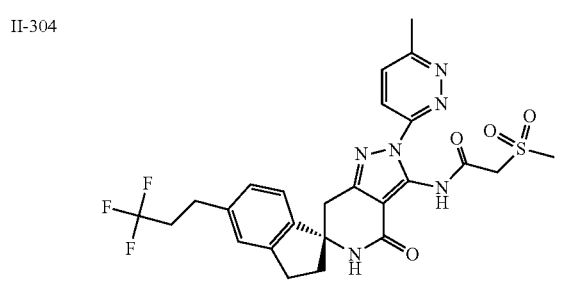

TABLE 48

II-305
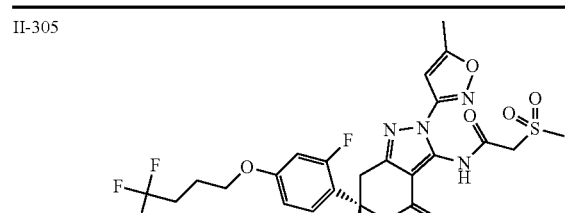

II-306
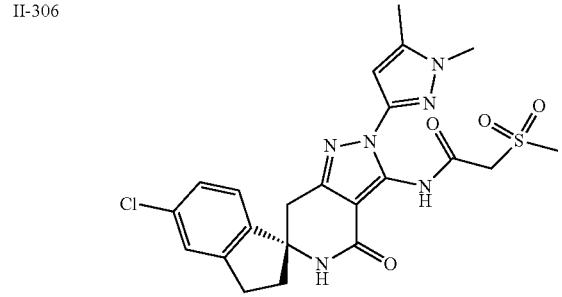

II-307
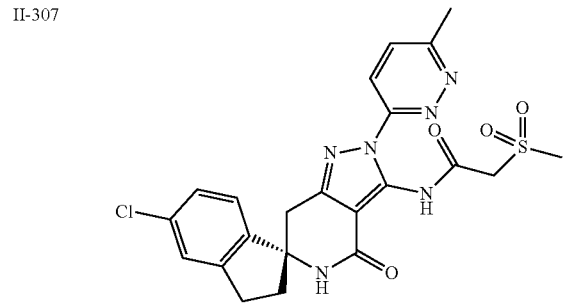

II-308
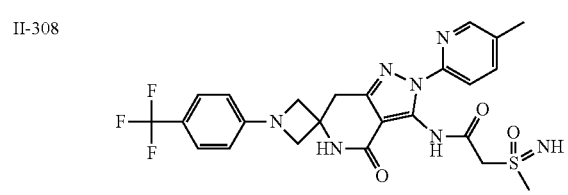

In II-275 and II-276, although the stereochemistry structure is not determined, II-275 and II-276 are optically active compounds having different stereochemistry of sulfoximine.

The physical data of the compounds are shown below.

In the tables, "RT" indicates retention time (minutes) in LC/MS (liquid chromatography/mass spectrometry), "MS" indicates mass (M+H) in LC/MS, and "LCMS Method" indicates any of the following measurement conditions for LC/MS.

[Measurement Condition A]

Column: ACQUITY UPLC (registered trademark) BEH C18 (1.7 μm i.d. 2.1×50 mm) (Waters)

Flow rate: 0.8 mL/min

UV detection wavelength: 254 nm

Mobile phase: [A] is 0.1% formic acid in aqueous solution, and [B] is 0.1% formic acid in acetonitrile solution.

Linear gradient of 5% to 100% solvent [B] for 3.5 minutes was performed, and 100% solvent [B] was maintained for 0.5 minute.

[Measurement Condition B]

Column: Shim-pack XR-ODS (2.2 μm, i.d. 50×3.0 mm) (Shimadzu)

Flow rate: 1.6 mL/min

UV detection wavelength: 254 nm;

Mobile phase: [A] is 0.1% formic acid in aqueous solution, and [B] is 0.1% formic acid in acetonitrile solution.

Gradient: linear gradient of 10% to 100% solvent [B] for 3 minutes was performed, and 100% solvent [B] was maintained for 0.5 minute.

[Measurement Condition C]

Column: ACQUITY UPLC (registered trademark) BEH C18 (1.7 μm i.d. 2.1×50 mm) (Waters)

Flow rate: 0.55 mL/min

UV detection wavelength: 254 nm

Mobile phase: [A] is 0.1% formic acid in aqueous solution, and [B] is 0.1% formic acid in acetonitrile solution.

Gradient: linear gradient of 5% to 100% solvent [B] for 3 minutes was performed, and then 100% solvent [B] was maintained for 0.5 minute.

[Measurement Condition D]

Column: Shim-pack XR-ODS (2.2 μm, i.d. 50×3.0 mm) (Shimadzu)

Flow rate: 1.6 mL/min

UV detection wavelength: 254 nm

Mobile phase: [A] is 0.1% formic acid in aqueous solution, and [B] is 0.1% formic acid in acetonitrile solution.

Gradient: linear gradient of 10% to 100% solvent [B] for 8 minutes was performed, and then 100% solvent [B] was maintained for 0.5 minute.

TABLE 49

| No. | LCMS method | MS |
| --- | --- | --- |
| I-1 | A | 544 |
| I-2 | A | 569 |
| I-3 | C | 483 |
| I-4 | A | 491 |
| I-5 | A | 569 |
| I-6 | C | 511 |
| I-7 | B | 523 |
| I-9 | C | 478 |
| I-11 | C | 491 |
| I-13 | B | 542 |
| I-14 | B | 534 |
| I-15 | B | 583 |
| I-16 | B | 571 |
| I-17 | B | 583 |
| I-18 | B | 544 |
| I-19 | B | 553 |
| I-20 | B | 541 |
| I-21 | C | 583 |
| I-22 | C | 541 |
| I-25 | B | 516 |
| I-26 | B | 559 |
| I-27 | B | 574 |
| I-28 | B | 548 |
| I-29 | B | 521 |
| I-30 | B | 571 |
| I-31 | B | 584 |
| I-32 | B | 575 |
| I-33 | B | 661 |
| I-35 | B | 539 |
| I-36 | B | 521 |
| I-37 | B | 595 |
| I-38 | B | 527 |
| I-39 | B | 627 |
| I-40 | B | 583 |
| I-41 | B | 617 |
| I-42 | B | 591 |
| I-43 | B | 655 |
| I-44 | B | 602 |

TABLE 49-continued

| No. | LCMS method | MS |
| --- | --- | --- |
| I-45 | B | 631 |
| I-46 | B | 572 |
| I-47 | B | 598 |
| I-48 | B | 591 |
| I-49 | C | 557 |
| I-50 | B | 619 |
| I-51 | B | 557 |
| I-52 | B | 605 |
| I-53 | B | 609 |
| I-54 | B | 543 |
| I-56 | B | 585 |
| I-57 | B | 611 |
| I-58 | B | 573 |
| I-59 | B | 595 |
| I-60 | B | 613 |
| I-61 | B | 665 |
| I-62 | B | 619 |
| I-63 | B | 557 |
| I-64 | B | 609 |
| I-65 | B | 611 |
| I-66 | B | 595 |
| I-67 | C | 568 |
| I-68 | B | 553 |
| I-69 | C | 587 |
| I-70 | C | 583 |
| I-71 | C | 541 |
| I-72 | C | 581 |
| I-73 | B | 665 |
| I-74 | B | 605 |
| I-75 | B | 605 |
| I-76 | C | 541 |
| I-77 | C | 584 |
| I-78 | B | 526 |
| I-79 | B | 526 |
| I-80 | B | 526 |
| I-81 | B | 527 |
| I-82 | C | 531 |
| I-83 | C | 533 |
| I-84 | B | 488 |
| I-85 | B | 493 |
| I-86 | B | 519 |
| I-87 | B | 555 |
| I-88 | B | 519 |
| I-89 | B | 549 |
| I-90 | B | 533 |
| I-91 | C | 628 |
| I-92 | B | 530 |
| I-93 | C | 468 |
| I-94 | C | 559 |
| I-96 | C | 555 |
| I-97 | C | 563 |
| I-98 | C | 563 |
| I-99 | C | 567 |
| I-100 | C | 579 |
| I-101 | C | 550 |
| I-103 | C | 592 |
| I-104 | C | 550 |
| I-105 | C | 566 |
| I-106 | C | 617 |
| I-107 | C | 501 |
| I-108 | B | 581 |
| I-109 | B | 563 |
| I-110 | B | 567 |
| I-111 | B | 589 |
| I-109 | B | 563 |
| I-110 | B | 567 |
| I-111 | B | 589 |
| I-112 | B | 571 |
| I-113 | B | 581 |
| I-114 | B | 585 |
| I-115 | B | 585 |
| I-116 | B | 567 |
| I-117 | B | 555 |
| I-118 | B | 569 |
| I-119 | B | 603 |
| I-120 | B | 541 |
| I-121 | B | 567 |

TABLE 49-continued

| No. | LCMS method | MS |
|---|---|---|
| I-122 | C | 600 |
| I-123 | B | 567 |
| I-124 | B | 583 |
| I-125 | B | 617 |
| I-126 | B | 633 |
| I-127 | B | 585 |
| I-128 | B | 617 |
| I-129 | B | 577 |
| I-130 | B | 685 |
| I-131 | B | 585 |
| I-132 | B | 577 |
| I-133 | B | 574 |
| I-134 | B | 564 |
| I-135 | B | 564 |
| I-136 | C | 601 |
| I-137 | C | 593 |
| I-138 | C | 513 |
| I-139 | C | 605 |
| I-140 | B | 567 |
| I-141 | B | 541 |
| I-142 | B | 583 |
| I-143 | B | 553 |
| I-144 | B | 543 |
| I-145 | B | 503 |
| I-146 | B | 553 |
| I-147 | B | 517 |
| I-148 | B | 545 |
| I-149 | B | 555 |
| I-150 | B | 530 |
| I-151 | B | 530 |
| I-152 | B | 530 |
| I-153 | B | 528 |
| I-154 | B | 530 |
| I-155 | B | 521 |
| I-156 | B | 519 |
| I-157 | B | 571 |
| I-158 | B | 585 |
| I-159 | B | 530 |
| I-160 | B | 530 |
| I-161 | B | 567 |
| I-162 | C | 593 |
| I-163 | C | 568 |
| I-164 | C | 512 |
| I-165 | C | 534 |
| I-166 | C | 566 |
| I-167 | B | 575 |
| I-168 | C | 600 |
| I-169 | C | 568 |
| I-170 | C | 635 |
| I-171 | C | 601 |
| I-172 | B | 530 |
| I-173 | B | 649 |
| I-174 | C | 583 |
| I-175 | C | 488 |
| I-176 | B | 530 |
| I-177 | B | 566 |
| I-178 | C | 479 |
| I-179 | C | 591 |
| I-180 | C | 591 |
| I-181 | C | 553 |
| I-182 | C | 583 |
| I-183 | B | 553 |
| I-184 | B | 539 |
| I-185 | C | 568 |
| I-186 | C | 490 |
| I-187 | C | 450 |
| I-188 | C | 551 |
| I-189 | C | 618 |
| I-191 | C | 577 |
| I-192 | C | 638 |
| I-193 | C | 583 |
| I-194 | B | 527 |
| I-195 | B | 539 |
| I-196 | B | 525 |
| I-197 | C | 635 |
| I-198 | C | 568 |
| I-199 | B | 527 |

TABLE 49-continued

| No. | LCMS method | MS |
|---|---|---|
| I-200 | C | 518 |
| I-202 | C | 552 |
| I-203 | C | 568 |
| I-204 | C | 534 |
| I-205 | B | 599 |
| I-206 | B | 611 |
| I-207 | B | 568 |
| I-208 | B | 611 |
| I-209 | B | 666 |
| I-210 | B | 666 |
| I-211 | C | 568 |
| I-212 | C | 583 |
| I-213 | C | 555 |
| I-214 | C | 543 |
| I-215 | B | 527 |
| I-216 | B | 527 |
| I-217 | B | 527 |
| I-218 | B | 515 |
| I-219 | B | 533 |
| I-220 | B | 515 |
| I-221 | B | 547 |
| I-222 | B | 532 |
| I-223 | B | 529 |
| I-224 | B | 530 |
| I-225 | B | 516 |
| I-226 | B | 530 |
| I-227 | B | 546 |
| I-228 | B | 532 |
| I-229 | B | 543 |
| I-230 | B | 546 |
| I-231 | B | 516 |
| I-232 | B | 529 |
| I-233 | C | 590 |
| I-234 | C | 566 |
| I-235 | C | 498 |
| I-236 | C | 564 |
| I-237 | C | 608 |
| I-238 | C | 592 |
| I-239 | B | 591 |
| I-240 | B | 607 |
| I-241 | B | 555 |
| I-242 | C | 517 |
| I-243 | B | 591 |
| I-244 | B | 579 |
| I-245 | B | 574 |
| I-246 | B | 589 |
| I-247 | B | 629 |
| I-248 | B | 589 |
| I-249 | C | 559 |
| I-250 | B | 545 |
| I-251 | B | 559 |
| I-252 | B | 545 |
| I-253 | B | 599 |
| I-254 | B | 540 |
| I-255 | B | 597 |
| I-256 | B | 569 |
| I-257 | B | 557 |
| I-258 | B | 585 |
| I-259 | B | 585 |
| I-260 | B | 554 |
| I-261 | B | 595 |
| I-262 | B | 580 |
| I-263 | B | 565 |
| I-256 | B | 569 |
| I-257 | B | 557 |
| I-258 | B | 585 |
| I-259 | B | 585 |
| I-260 | B | 554 |
| I-261 | B | 595 |
| I-262 | B | 580 |
| I-263 | B | 565 |
| I-264 | B | 565 |
| I-265 | B | 551 |
| I-266 | B | 563 |
| I-267 | B | 563 |
| I-268 | B | 580 |
| I-269 | B | 567 |

TABLE 49-continued

| No. | LCMS method | MS |
|---|---|---|
| I-270 | B | 564 |
| I-271 | A | 551 |
| I-272 | A | 551 |
| I-273 | B | 555 |
| I-274 | B | 579 |
| I-275 | B | 580 |
| I-276 | C | 599 |
| I-278 | C | 492 |
| I-279 | C | 527 |
| I-280 | C | 474 |
| I-281 | C | 548 |
| I-284 | C | 513 |
| I-285 | C | 556 |
| II-1 | C | 527 |
| II-4 | C | 499 |
| II-5 | B | 579 |
| II-6 | B | 595 |
| II-7 | A | 567 |
| II-8 | C | 557 |
| II-9 | C | 579 |
| II-10 | C | 591 |
| II-11 | B | 569 |
| II-12 | B | 577 |
| II-13 | A | 595 |
| II-15 | B | 571 |
| II-16 | C | 574 |
| II-17 | C | 617 |
| II-18 | A | 581 |
| II-19 | A | 597 |
| II-20 | A | 599 |
| II-21 | A | 545 |
| II-22 | A | 567 |
| II-23 | A | 595 |
| II-24 | A | 597 |
| II-25 | A | 613 |
| II-26 | A | 561 |
| II-27 | A | 583 |

TABLE 50

| No | LCMS method | MS |
|---|---|---|
| II-28 | A | 611 |
| II-29 | C | 588 |
| II-30 | C | 557 |
| II-31 | C | 561 |
| II-32 | C | 548 |
| II-33 | A | 574 |
| II-34 | A | 516 |
| II-35 | A | 564 |
| II-36 | A | 568 |
| II-37 | A | 526 |
| II-38 | A | 509 |
| II-39 | A | 525 |
| II-40 | A | 548 |
| II-41 | A | 556 |
| II-42 | A | 542 |
| II-43 | A | 590 |
| II-44 | A | 542 |
| II-45 | A | 570 |
| II-46 | A | 576 |
| II-47 | A | 548 |
| II-48 | A | 554 |
| II-49 | A | 540 |
| II-50 | A | 540 |
| II-51 | A | 497 |
| II-52 | C | 477 |
| II-53 | C | 578 |
| II-54 | B | 554 |
| II-55 | C | 550 |
| II-56 | C | 506 |
| II-57 | C | 562 |
| II-58 | C | 526 |

TABLE 50-continued

| No | LCMS method | MS |
|---|---|---|
| II-59 | A | 550 |
| II-60 | A | 547 |
| II-61 | C | 562 |
| II-62 | C | 583 |
| II-63 | B | 556 |
| II-64 | C | 615 |
| II-65 | C | 599 |
| II-66 | C | 539 |
| II-67 | C | 601 |
| II-68 | A | 543 |
| II-69 | A | 529 |
| II-70 | A | 590 |
| II-71 | C | 524 |
| II-72 | A | 587 |
| II-73 | A | 540 |
| II-74 | C | 596 |
| II-75 | C | 511 |
| II-76 | C | 483 |
| II-77 | C | 523 |
| II-78 | C | 567 |
| II-79 | C | 551 |
| II-80 | C | 534 |
| II-81 | A | 567 |
| II-82 | C | 563 |
| II-83 | C | 577 |
| II-84 | C | 528 |
| II-85 | A | 619 |
| II-86 | C | 600 |
| II-87 | C | 611 |
| II-88 | C | 621 |
| II-89 | C | 560 |
| II-90 | C | 561 |
| II-91 | A | 601 |
| II-92 | A | 577 |
| II-93 | C | 617 |
| II-94 | C | 570 |
| II-95 | C | 581 |
| II-96 | C | 591 |
| II-97 | A | 635 |
| II-98 | C | 499 |
| II-99 | A | 567 |
| II-100 | A | 585 |
| II-101 | A | 569 |
| II-102 | C | 513 |
| II-103 | B | 593 |
| II-104 | B | 592 |
| II-105 | B | 591 |
| II-106 | B | 619 |
| II-107 | B | 540 |
| II-108 | A | 567 |
| II-109 | A | 595 |
| II-110 | A | 548 |
| II-111 | A | 589 |
| II-112 | A | 553 |
| II-113 | A | 590 |
| II-114 | A | 595 |
| II-115 | A | 582 |
| II-116 | A | 581 |
| II-117 | A | 553 |
| II-118 | A | 569 |
| II-119 | A | 583 |
| II-120 | A | 557 |
| II-122 | A | 534 |
| II-123 | A | 555 |
| II-124 | A | 565 |
| II-125 | A | 541 |
| II-126 | A | 579 |
| II-127 | A | 540 |
| II-128 | A | 522 |
| II-129 | A | 604 |
| II-130 | A | 581 |
| II-131 | A | 567 |
| II-132 | A | 566 |
| II-133 | A | 567 |
| II-134 | A | 590 |
| II-135 | A | 555 |
| II-136 | B | 581 |

TABLE 50-continued

| No | LCMS method | MS |
|---|---|---|
| II-137 | B | 601 |
| II-138 | B | 564 |
| II-139 | B | 579 |
| II-140 | B | 565 |
| II-141 | B | 615 |
| II-142 | C | 545 |
| II-143 | C | 573 |
| II-144 | C | 593 |
| II-145 | B | 526 |
| II-146 | C | 562 |
| II-147 | C | 516 |
| II-148 | A | 588 |
| II-149 | A | 581 |
| II-150 | A | 570 |
| II-151 | C | 576 |
| II-152 | C | 559 |
| II-153 | C | 540 |
| II-154 | C | 573 |
| II-155 | C | 572 |
| II-156 | A | 506 |
| II-157 | A | 560 |
| II-158 | A | 546 |
| II-159 | A | 510 |
| II-160 | A | 524 |
| II-161 | A | 556 |
| II-162 | A | 624 |
| II-163 | C | 593 |
| II-164 | A | 500 |
| II-165 | A | 466 |
| II-166 | A | 559 |
| II-167 | B | 560 |
| II-169 | B | 554 |
| II-170 | A | 497 |
| II-171 | A | 579 |
| II-172 | C | 517 |
| II-173 | A | 581 |
| II-174 | B | 599 |
| II-175 | B | 549 |
| II-176 | C | 506 |
| II-177 | C | 563 |
| II-178 | A | 529 |
| II-179 | A | 537 |
| II-180 | A | 527 |
| II-181 | A | 554 |
| II-182 | A | 602 |
| II-183 | A | 536 |
| II-184 | A | 561 |
| II-185 | A | 611 |
| II-186 | A | 567 |
| II-187 | A | 553 |
| II-188 | A | 573 |
| II-189 | A | 587 |
| II-190 | A | 562 |
| II-191 | A | 605 |
| II-192 | A | 587 |
| II-193 | A | 571 |
| II-194 | A | 581 |
| II-195 | A | 568 |
| II-196 | A | 529 |
| II-197 | A | 511 |
| II-198 | A | 556 |
| II-199 | A | 578 |
| II-200 | A | 542 |
| II-201 | A | 587 |
| II-202 | A | 576 |
| II-204 | A | 595 |
| II-205 | B | 567 |
| II-206 | C | 552 |
| II-207 | C | 516 |
| II-208 | C | 566 |
| II-209 | A | 596 |
| II-210 | A | 612 |
| II-211 | A | 594 |
| II-212 | A | 632 |
| II-213 | A | 626 |
| II-214 | A | 561 |
| II-215 | A | 623 |
| II-216 | A | 605 |
| II-217 | A | 643 |
| II-218 | A | 637 |
| II-219 | A | 528 |
| II-220 | A | 573 |
| II-221 | A | 559 |
| II-222 | A | 568 |
| II-223 | A | 567 |
| II-224 | C | 543 |
| II-225 | C | 599 |
| II-226 | A | 593 |
| II-227 | A | 570 |
| II-228 | A | 527 |
| II-229 | A | 545 |
| II-230 | A | 558 |
| II-231 | A | 567 |
| II-232 | A | 592 |
| II 233 | B | 598 |
| II-234 | B | 535 |
| II-235 | B | 512 |
| II-236 | A | 591 |
| II-237 | A | 631 |
| II-238 | A | 550 |
| II-239 | A | 571 |
| II-240 | A | 614 |
| II-241 | A | 589 |
| II-242 | A | 639 |
| II-243 | A | 522 |
| II-244 | A | 565 |
| II-245 | A | 540 |
| II-246 | A | 590 |
| II-247 | A | 611 |
| II-248 | C | 597 |
| II-249 | A | 572 |
| II-250 | A | 537 |
| II-251 | A | 500 |
| II-252 | A | 544 |
| II-253 | A | 519 |
| II-254 | A | 569 |
| II-255 | A | 595 |
| II-256 | B | 624 |
| II-257 | B | 612 |
| II-258 | B | 629 |
| II-259 | B | 619 |
| II-260 | C | 552 |
| II-261 | A | 649 |
| II-262 | A | 593 |
| II-263 | A | 527 |
| II-264 | A | 596 |
| II-265 | A | 559 |
| II-266 | B | 506 |
| II-267 | B | 568 |
| II-268 | B | 595 |
| II-269 | A | 545 |
| II-270 | A | 592 |
| II-271 | A | 595 |
| II-272 | A | 606 |
| II-273 | A | 587 |
| II-274 | A | 636 |
| II-275 | A | 563 |
| II-276 | A | 563 |
| II-277 | A | 627 |
| II-278 | B | 537 |
| II-279 | C | 557 |
| II-280 | C | 613 |
| II-281 | B | 601 |
| II-282 | B | 582 |
| II-283 | A | 597 |
| II-284 | A | 597 |
| II-285 | A | 579 |
| II-286 | A | 579 |
| II-287 | B | 592 |
| II-288 | B | 595 |
| II-289 | C | 629 |
| II-290 | A | 603 |
| II-291 | A | 603 |
| II-292 | A | 609 |

TABLE 50-continued

| No | LCMS method | MS |
|---|---|---|
| II-293 | C | 627 |
| II-294 | C | 634 |
| II-295 | C | 584 |
| II-296 | C | 606 |
| II-297 | C | 600 |
| II-298 | C | 615 |
| II-299 | B | 565 |
| II-300 | B | 558 |
| II-301 | C | 552 |
| II-302 | B | 507 |
| II-303 | B | 509 |
| II-304 | B | 563 |
| II-305 | B | 588 |
| II-306 | B | 503 |
| II-307 | B | 501 |
| II-308 | C | 548 |

NMR analysis of each Example was performed by 300 MHz using DMSO-$d_6$ or CDCl$_3$.

TABLE 51

| No. | NMR |
|---|---|
| I-8 | 1H-NMR (CDCl3) δ: 0.00-0.02 (m, 2H), 0.39-0.44 (m, 2H), 0.61-0.68 (m, 1H), 1.76 (q, J = 7.2 Hz, 2H), 2.10-2.17 (m, 1H), 2.38-2.44 (m, 1H), 2.86-3.07 (m, 5H), 3.24 (s, 3H), 4.09 (t, J = 7.3 Hz, 2H), 4.21 (d, J = 14.3 Hz, 1H), 4.28-4.34 (m, 3H), 5.97 (s, 1H), 6.78-6.83 (m, 2H), 7.19 (d, J = 8.3 Hz, 1H), 9.60 (s, 1H). |
| I-23 | 1H-NMR (CDCl3) δ: 2.02-2.09 (m, 2H), 2.21-2.47 (m, 4H), 2.88-3.01 (m, 2H), 3.05 (d, J = 15.6 Hz, 1H), 3.18 (d, J = 15.8 Hz, 1H), 3.24 (s, 3H), 4.01 (t, J = 5.9 Hz, 2H), 4.17 (s, 2H), 5.63 (s, 1H), 6.78-6.80 (m, 2H), 7.27-7.30 (m, 2H), 7.87-7.95 (dd, J = 13.1, 8.5 Hz, 2H), 8.48 (br-d, J = 5.0 Hz, 1H), 11.15 (s, 1H). |
| I-95 | 1H-NMR (CDCl3) δ: 2.27-2.34 (m, 1H), 2.48-2.54 (m, 1H), 2.81 (s, 3H), 2.94-3.20 (m, 4H), 4.08 (d, J = 13.8 Hz, 1H), 4.16-4.23 (m, 2H), 4.41 (d, J = 13.6 Hz, 1H), 6.56 (s, 1H), 6.65 (br-d, J = 8.4 Hz, 1H), 6.82 (br-s, 1H), 7.14 (d, J = 8.5 Hz, 1H), 7.60-7.67 (m, 4H), 10.31 (s, 1H). |
| I-102 | 1H-NMR (CDCl3) δ: 0.00-0.02 (m, 2H), 0.39-0.44 (m, 2H), 0.640-.067(m, 1H), 1.76 (q, J = 7.1 Hz, 2H), 2.07-2.14 (m, 1H), 2.32-2.38 (m, 1H)2.81-2.95 (m, 3H), 3.06 (d, J = 15.8 Hz, 1H), 3.25 (s, 3H), 3.69-3.78 (m, 2H), 3.99 (t, J = 7.0 Hz, 1H), 4.09 (t, J = 7.2 Hz, 1H), 4.20 (d, J = 14.2 Hz, 1H), 4.29 (d, J = 14.3 Hz, 1H), 5.90 (s, 1H), 6.52-6.56 (m, 2H), 7.10 (d, J = 8.3 Hz, 1H), 9.49 (s, 1H). |
| I-190 | 1H-NMR (CDCl3) δ: 2.22-2.30 (m, 1H), 2.41-2.47 (dd, J = 12.3, 8.3 Hz, 1H), 2.90-3.21 (m, 7H), 4.18 (s, 2H), 4.35 (q, J = 8.1 Hz, 2H), 5.69 (s, 1H), 6.83-6.87 (m, 2H), 7.31 (d, J = 8.3 Hz, 1H), 8.07-8.14 (m, 2H), 8.78 (m, 1H), 10.73 (s, 1H). |

Biological Test Examples for the compounds of the present invention are described below.

Preparation Example 1: Preparation of Recombinant Human MGAT2

A full-length human MGAT2 gene to which a Flag-tag had been added at the N-terminal was inserted into pFastBac (from Invitrogen). A recombinant baculovirus was produced in accordance with the protocol for a Bac-to-Bac baculovirus expression system (produced by Invitrogen), and Sf-9 cells were infected therewith. The cells were collected and sonicated, and then the membrane fraction was collected through centrifugation. Western blotting analysis with an anti-Flag antibody was performed for the membrane fraction to confirm expression, and the membrane fraction was used as a recombinant human MGAT2 enzyme solution.

Test Example 1: Measurement of Human MGAT2 Inhibitory Activity

Solutions of the compounds of the present invention in DMSO were each aliquoted into 0.2-μL portions in a 384-well polystyrene microplate produced by Corning Incorporated, and 5 μL of an enzyme solution prepared with an assay buffer (100 mmol/L phosphate buffer (pH 7.4) containing 2 mmol/L DTT) and 5 μL of a substrate solution (100 mmol/L phosphate buffer (pH 7.4), 30 μmol/L 2-Oleoylglycerol, 10 μmol/L Oleoyl-CoA) were added thereto, and the resultant was stirred and centrifuged, and incubated in a moist chamber at room temperature for 1 hour. After enzymatic reaction, 50 μL of a quenching solution (containing 0.2 μmol/L Diolein-d5, 0.4% formic acid, and 50% isopropanol) containing Internal Standard (IS) was added to terminate the reaction, and the resultant was sealed in a plate produced by Shimadzu GLC Ltd., and then stirred and centrifuged, and measurement was performed by using an electrospray ionization method with a RapidFire360 and Agilent 6550 Q-TOF mass spectrometer. Diolein as a reaction product (P) of 2-Oleoylglycerol as the substrate and an ammonium adduct ion of the IS were detected, and the peak intensity ratio, P/IS, was calculated from the peak heights to evaluate the inhibitory activity. Inhibitory activities with/without addition of enzyme were defined as Control (+)/Control (−), respectively, and the respective % inhibitions were defined as 0% inhibition and 100% inhibition. The inhibitory activity was calculated from formula below with TIBCO Spotfire (produced by TIBCO Software Inc.):

Inhibitory activity (%)=[1−{Sample−Control(−)}/{Control(+)−Control(−)}]*100 where Sample indicates a peak intensity ratio: P/IS, when the compound of the present invention was added.

The inhibitory activity results of the compounds of the present invention are shown in the following table. IC$_{50}$ (nM) in the tables indicates a concentration exhibiting 50% enzyme inhibition.

TABLE 52

| No. | IC50 (nM) |
|---|---|
| I-1 | 540 |
| I-2 | 1.35 |
| I-3 | 9.22 |
| I-4 | 330 |
| I-5 | 500 |
| I-6 | 11.9 |
| I-7 | 15 |
| I-8 | 2.78 |
| I-9 | 70 |
| I-10 | 59 |
| I-11 | 500 |
| I-12 | 21 |
| I-13 | 90 |
| I-14 | 380 |
| I-15 | 280 |
| I-16 | 150 |
| I-17 | 160 |
| I-18 | 9.1 |
| I-19 | 38 |
| I-20 | 21 |
| I-21 | 17 |
| I-22 | 190 |
| I-23 | 6.5 |
| I-24 | 8.82 |
| I-25 | 49 |
| I-26 | 15 |
| I-27 | 600 |

TABLE 52-continued

| No. | IC50 (nM) |
|---|---|
| I-28 | 435 |
| I-29 | 113 |
| I-30 | 175 |
| I-31 | 3.2 |
| I-32 | 17 |
| I-33 | 14.7 |
| I-34 | 18 |
| I-35 | 6.8 |
| I-36 | 27 |
| I-37 | 145 |
| I-38 | 625 |
| I-39 | 930 |
| I-40 | 18 |
| I-41 | 79 |
| I-42 | 2.5 |
| I-43 | 340 |
| I-44 | 3.9 |
| I-45 | 41.5 |
| I-46 | 440 |
| I-47 | 265 |
| I-48 | 195 |
| I-49 | 1.9 |
| I-50 | 190 |
| I-51 | 16 |
| I-52 | 24 |
| I-53 | 13 |
| I-54 | 48 |
| I-55 | 120 |
| I-56 | 25 |
| I-57 | 10 |
| I-58 | 5.5 |
| I-59 | 14 |
| I-60 | 94 |
| I-61 | 340 |
| I-62 | 250 |
| I-63 | 400 |
| I-64 | 410 |
| I-65 | 660 |
| I-66 | 970 |
| I-67 | 7 |
| I-68 | 760 |
| I-69 | 55 |
| I-70 | 54 |
| I-71 | 3.9 |
| I-72 | 8.3 |
| I-73 | 290 |
| I-74 | 520 |
| I-75 | 580 |
| I-76 | 95.5 |
| I-77 | 1 |
| I-78 | 37.5 |
| I-79 | 860 |
| I-80 | 16 |
| I-81 | 240 |
| I-82 | 230 |
| I-83 | 110 |
| I-84 | 430 |
| I-85 | 570 |
| I-86 | 960 |
| I-87 | 440 |
| I-88 | 270 |
| I-89 | 55 |
| I-90 | 33 |
| I-91 | 1.2 |
| I-92 | 73 |
| I-93 | 160 |
| I-94 | 3.7 |
| I-95 | 5.1 |
| I-96 | 54 |
| I-97 | 6.9 |
| I-98 | 8.5 |
| I-99 | 6.2 |
| I-100 | 32 |
| I-101 | 17 |
| I-102 | 25 |
| I-103 | 320 |
| I-104 | 12 |
| I-105 | 6.8 |
| I-106 | 11 |
| I-107 | 760 |
| I-108 | 2.9 |
| I-109 | 6.1 |
| I-110 | 10 |
| I-111 | 190 |
| I-112 | 44.5 |
| I-113 | 810 |
| I-114 | 110 |
| I-115 | 64 |
| I-116 | 260 |
| I-117 | 51 |
| I-118 | 370 |
| I-119 | 150 |
| I-120 | 46 |
| I-121 | 47 |
| I-122 | 1.8 |
| I-123 | 55.5 |
| I-124 | 22 |
| I-125 | 525 |
| I-126 | 710 |
| I-127 | 105 |
| I-128 | 40.5 |
| I-129 | 26.5 |
| I-130 | 505 |
| I-131 | 5.2 |
| I-132 | 9.65 |
| I-133 | 14 |
| I-134 | 340 |
| I-135 | 3.1 |
| I-136 | 4.1 |
| I-137 | 1.7 |
| I-138 | 550 |
| I-139 | 4.1 |
| I-140 | 730 |
| I-141 | 430 |
| I-142 | 270 |
| I-143 | 510 |
| I-144 | 400 |
| I-145 | 83 |
| I-146 | 420 |
| I-147 | 39 |
| I-148 | 5.6 |
| I-149 | 690 |
| I-150 | 100 |
| I-151 | 180 |
| I-152 | 300 |
| I-153 | 240 |
| I-154 | 530 |
| I-155 | 180 |
| I-156 | 920 |
| I-157 | 38 |
| I-158 | 130 |
| I-159 | 600 |
| I-160 | 78 |
| I-161 | 430 |
| I-162 | 1.9 |
| I-163 | 3.6 |
| I-164 | 86 |
| I-165 | 5.2 |
| I-166 | 7.1 |
| I-167 | 3.3 |
| I-168 | 5.9 |
| I-169 | 9.8 |
| I-170 | 5.1 |
| I-171 | 12 |
| I-172 | 480 |
| I-173 | 78 |
| I-174 | 63.7 |
| I-175 | 86 |
| I-176 | 180 |
| I-177 | 610 |
| I-178 | 39 |
| I-179 | 6.1 |
| I-180 | 150 |
| I-181 | 15 |

TABLE 52-continued

| No. | IC50 (nM) |
|---|---|
| I-182 | 2.5 |
| I-183 | 18 |
| I-184 | 68 |
| I-185 | 6.3 |
| I-186 | 7.6 |
| I-187 | 190 |
| I-188 | 52 |
| I-189 | 1.2 |
| I-190 | 2.9 |
| I-191 | 28 |
| I-192 | 6.5 |
| I-193 | 6.1 |
| I-194 | 460 |
| I-195 | 450 |
| I-196 | 1000 |
| I-197 | 24 |
| I-198 | 67 |
| I-199 | 400 |
| I-200 | 5.6 |
| I-201 | 330 |
| I-202 | 6.2 |
| I-203 | 2.6 |
| I-204 | 11.3 |
| I-205 | 270 |
| I-206 | 2.4 |
| I-207 | 17.5 |
| I-208 | 250 |
| I-209 | 3.2 |
| I-210 | 550 |
| I-211 | 2.1 |
| I-212 | 6.9 |
| I-213 | 43 |
| I-214 | 460 |
| I-215 | 420 |
| I-216 | 35 |
| I-217 | 89.5 |
| I-218 | 48 |
| I-219 | 110 |
| I-220 | 35 |
| I-221 | 60 |
| I-222 | 88 |
| I-223 | 140 |
| I-224 | 310 |
| I-225 | 40 |
| I-226 | 90 |
| I-227 | 370 |
| I-228 | 28 |
| I-229 | 620 |
| I-230 | 210 |
| I-231 | 47.5 |
| I-232 | 270 |
| I-233 | 11 |
| I-234 | 9.8 |
| I-235 | 85 |
| I-236 | 2.8 |
| I-237 | 16 |
| I-238 | 10 |
| I-239 | 380 |
| I-240 | 1000 |
| I-241 | 380 |
| I-242 | 3.6 |
| I-243 | 3.5 |
| I-244 | 110 |
| I-245 | 530 |
| I-246 | 24 |
| I-247 | 84 |
| I-248 | 240 |
| I-249 | 3.5 |
| I-250 | 150 |
| I-251 | 490 |
| I-252 | 13 |
| I-253 | 1.4 |
| I-254 | 95 |
| I-255 | 17 |
| I-256 | 160 |
| I-257 | 80 |
| I-258 | 120 |
| I-259 | 59 |
| I-260 | 490 |
| I-261 | 16 |
| I-262 | 34 |
| I-263 | 4.7 |
| I-264 | 86 |
| I-265 | 36 |
| I-266 | 4.6 |
| I-267 | 9.8 |
| I-268 | 26 |
| I-269 | 5.5 |
| I-270 | 2.8 |
| I-271 | 780 |
| I-272 | 20 |
| I-273 | 20 |
| I-274 | 3.9 |
| I-275 | 2 |
| I-276 | 4.4 |
| I-277 | 99 |
| I-278 | 29 |
| I-279 | 50.5 |
| I-280 | 48 |
| I-281 | 72 |
| I-282 | 86 |
| I-283 | 91 |
| I-284 | 9.35 |
| I-285 | 3.5 |

TABLE 53

| No. | IC50 (nM) |
|---|---|
| II-1 | 46 |
| II-2 | 84 |
| II-3 | 210 |
| II-4 | 32 |
| II-5 | 4.6 |
| II-6 | 19 |
| II-7 | 20 |
| II-8 | 7 |
| II-9 | 9.5 |
| II-10 | 9.8 |
| II-11 | 64 |
| II-12 | 35 |
| II-13 | 27 |
| II-14 | 5.1 |
| II-15 | 12 |
| II-16 | 28 |
| II-17 | 38 |
| II-18 | 47 |
| II-19 | 12 |
| II-20 | 1.56 |
| II-21 | 17 |
| II-22 | 32 |
| II-23 | 18 |
| II-24 | 32 |
| II-25 | 7 |
| II-26 | 9.5 |
| II-27 | 21 |
| II-28 | 8.7 |
| II-29 | 220 |
| II-30 | 8.7 |
| II-31 | 14 |
| II-32 | 17 |
| II-33 | 3.3 |
| II-34 | 41 |
| II-35 | 48 |
| II-36 | 53 |
| II-37 | 12 |
| II-38 | 30 |
| II-39 | 42 |
| II-40 | 22 |
| II-41 | 40 |

TABLE 53-continued

| No. | IC50 (nM) |
|---|---|
| II-42 | 46 |
| II-43 | 3 |
| II-44 | 51 |
| II-45 | 98 |
| II-46 | 340 |
| II-47 | 320 |
| II-48 | 6.2 |
| II-49 | 59 |
| II-50 | 200 |
| II-51 | 440 |
| II-52 | 37 |
| II-53 | 14 |
| II-54 | 2.64 |
| II-55 | 44 |
| II-56 | 47 |
| II-57 | 66 |
| II-58 | 16 |
| II-59 | 33 |
| II-60 | 93 |
| II-61 | 16.7 |
| II-62 | 15.3 |
| II-63 | 300 |
| II-64 | 2.9 |
| II-65 | 1.9 |
| II-66 | 2.5 |
| II-67 | 2.64 |
| II-68 | 420 |
| II-69 | 43.9 |
| II-70 | 3.94 |
| II-71 | 12.6 |
| II-72 | 3.69 |
| II-73 | 8 |
| II-74 | 2.3 |
| II-75 | 3.69 |
| II-76 | 6 |
| II-77 | 5.5 |
| II-78 | 45 |
| II-79 | 110 |
| II-80 | 9.1 |
| II-81 | 46.6 |
| II-82 | 2.49 |
| II-83 | 1.99 |
| II-84 | 25.2 |
| II-85 | 45.5 |
| II-86 | 3.37 |
| II-87 | 2.63 |
| II-88 | 3.67 |
| II-89 | 10.8 |
| II-90 | 40 |
| II-91 | 2.79 |
| II-92 | 44.3 |
| II-93 | 1.21 |
| II-94 | 3.81 |
| II-95 | 4.29 |
| II-96 | 8.88 |
| II-97 | 3.97 |
| II-98 | 7.1 |
| II-99 | 9.59 |
| II-100 | 4.76 |
| II-101 | 1.25 |
| II-102 | 56.3 |
| II-103 | 1.61 |
| II-104 | 11.5 |
| II-105 | 2.68 |
| II-106 | 1.72 |
| II-107 | 40.7 |
| II-108 | 2.51 |
| II-109 | 23.1 |
| II-110 | 30.4 |
| II-111 | 50.8 |
| II-112 | 5.28 |
| II-113 | 8.23 |
| II-114 | 60.3 |
| II-115 | 204 |
| II-116 | 3.96 |
| II-117 | 37.9 |
| II-118 | 6.26 |
| II-119 | 26.8 |
| II-120 | 9.29 |
| II-121 | 2.91 |
| II-122 | 5.68 |
| II-123 | 21.7 |
| II-124 | 19.6 |
| II-125 | 63.5 |
| II-126 | 12.7 |
| II-127 | 39.2 |
| II-128 | 10.2 |
| II-129 | 202 |
| II-130 | 130 |
| II-131 | 5.79 |
| II-132 | 193 |
| II-133 | 188 |
| II-134 | 17.2 |
| II-135 | 60.6 |
| II-136 | 7.42 |
| II-137 | 4.79 |
| II-138 | 45.7 |
| II-139 | 3.15 |
| II-140 | 6.4 |
| II-141 | 12.8 |
| II-142 | 4.03 |
| II-143 | 0.706 |
| II-144 | 1.05 |
| II-145 | 6.43 |
| II-146 | 2.55 |
| II-147 | 4.92 |
| II-148 | 12.3 |
| II-149 | 9.01 |
| II-150 | 1.33 |
| II-151 | 2.05 |
| II-152 | 1.96 |
| II-153 | 4.94 |
| II-154 | 5.58 |
| II-155 | 1.85 |
| II-156 | 3.6 |
| II-157 | 3.83 |
| II-158 | 8.06 |
| II-159 | 7.02 |
| II-160 | 7.69 |
| II-161 | 4.67 |
| II-162 | 5.67 |
| II-163 | 6.1 |
| II-164 | 7.55 |
| II-165 | 26.9 |
| II-166 | 20.8 |
| II-167 | 3.63 |
| II-168 | 1.88 |
| II-169 | 7.38 |
| II-170 | 46.7 |
| II-171 | 9.64 |
| II-172 | 1.46 |
| II-173 | 1.34 |
| II-174 | 2.16 |
| II-175 | 25.4 |
| II-176 | 8.32 |
| II-177 | 5.86 |
| II-178 | 59.7 |
| II-179 | 10.1 |
| II-180 | 58.5 |
| II-181 | 28.7 |
| II-182 | 477 |
| II-183 | 35.5 |
| II-184 | 4.06 |
| II-185 | 28.2 |
| II-186 | 2.92 |
| II-187 | 24.5 |
| II-188 | 5.01 |
| II-189 | 3.06 |
| II-190 | 6.35 |
| II-191 | 91.2 |
| II-192 | 3.48 |
| II-193 | 33.7 |
| II-194 | 1.55 |
| II-195 | 29.8 |

TABLE 53-continued

| No. | IC50 (nM) |
|---|---|
| II-196 | 18.7 |
| II-197 | 6.79 |
| II-198 | 4.18 |
| II-199 | 73.6 |
| II-200 | 2.29 |
| II-201 | 12.1 |
| II-202 | 9.13 |
| II-203 | 2.98 |
| II-204 | 22.3 |
| II-205 | 3.78 |
| II-206 | 5.72 |
| II-207 | 5.86 |
| II-208 | 3.09 |
| II-209 | 95.3 |
| II-210 | 89.2 |
| II-211 | 33.1 |
| II-212 | 46.7 |
| II-213 | 59.5 |
| II-214 | 26.3 |
| II-215 | 77 |
| II-216 | 428 |
| II-217 | 68.9 |
| II-218 | 67.8 |
| II-219 | 82.5 |
| II-220 | 8.19 |
| II-221 | 6.87 |
| II-222 | 53.4 |
| II-223 | 52.4 |
| II-224 | 2.21 |
| II-225 | 1.14 |
| II-226 | 15.8 |
| II-227 | 96.4 |
| II-228 | 37 |
| II-229 | 64.8 |
| II-230 | 14.2 |
| II-231 | 97.8 |
| II-232 | 67.3 |
| II-233 | 0.224 |
| II-234 | 5.49 |
| II-235 | 1.17 |
| II-236 | 5.34 |
| II-237 | 3.43 |
| II-238 | 15 |
| II-239 | 4.62 |
| II-240 | 14.3 |
| II-241 | 24.6 |
| II-242 | 25.6 |
| II-243 | 1.74 |
| II-244 | 4.81 |
| II-245 | 11.3 |
| II-246 | 3.73 |
| II-247 | 48.4 |
| II-248 | 1.8 |
| II-249 | 13.4 |
| II-250 | 3.91 |
| II-251 | 10.1 |
| II-252 | 22.6 |
| II-253 | 4.28 |
| II-254 | 45.7 |
| II-255 | 2.74 |
| II-256 | 5.26 |
| II-257 | 0.409 |
| II-258 | 0.285 |
| II-259 | 0.439 |
| II-260 | 14 |
| II-261 | 1 |
| II-262 | 8.83 |
| II-263 | 40 |
| II-264 | 16.1 |
| II-265 | 54.4 |
| II-266 | 1.81 |
| II-267 | 1 |
| II-268 | 1.24 |
| II-269 | 11.7 |
| II-270 | 1.26 |
| II-271 | 1.34 |
| II-272 | 210 |
| II-273 | 14 |
| II-274 | 6.67 |
| II-275 | 6.15 |
| II-276 | 2.2 |
| II-277 | 1 |
| II-278 | 5.92 |
| II-279 | 1.12 |
| II-280 | <1 |
| II-281 | <1 |
| II-282 | <1 |
| II-283 | <1 |
| II-284 | <1 |
| II-285 | 1.04 |
| II-286 | 1.15 |
| II-287 | 5.26 |
| II-288 | 3.31 |
| II-289 | 1.06 |
| II-290 | <1 |
| II-291 | <1 |
| II-202 | <1 |
| II-293 | 2.76 |
| II-294 | <1 |
| II-295 | <1 |
| II-296 | <1 |
| II-297 | <1 |
| II-298 | <1 |
| II-299 | 1.98 |
| II-300 | <1 |
| II-301 | 15.9 |
| II-302 | 3.61 |
| II-303 | 4.42 |
| II-304 | 1.39 |
| II-305 | 1 |
| II-306 | 11.3 |
| II-307 | 6.19 |
| II-308 | 6.58 |

Test Example 2: Metabolism Stability Test

Using commercially available pooled human hepatic microsomes, the compound of the present invention was reacted for a constant time, a remaining rate was calculated by comparing a reacted sample and an unreacted sample, thereby, a degree of metabolism of the compound of the present invention in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v) solution, mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%. (Result) Remaining rate was shown at 0.5 µmol/L of test compound.

TABLE 54

| No. | Remaining rate (%) | No. | Remaining rate (%) | No. | Remaining rate (%) | No. | Remaining rate (%) | No. | Remaining rate (%) |
|---|---|---|---|---|---|---|---|---|---|
| II-94 | 98.4 | II-225 | 104 | I-8 | 102 | I-190 | 96.6 | I-170 | 100 |
| II-103 | 95.6 | II-233 | 94.7 | I-10 | 1.88 | I-253 | 76.8 | I-236 | 87.6 |
| II-121 | 89.7 | II-270 | 99.9 | I-12 | 96.8 | I-276 | 90.4 | I-67 | 89 |
| II-151 | 82.6 | II-276 | 98.2 | I-23 | 98.7 | I-275 | 91.8 | II-202 | 98.7 |
| II-168 | 91.6 | II-295 | 102 | I-24 | 78.2 | I-212 | 62.6 | I-167 | 89 |
| II-174 | 99.9 | II-203 | 104 | I-34 | 87.6 | II-93 | 103 | I-200 | 94 |

Test Example 3: Solubility Test

The solubility of the compound of the present invention was determined under 1% DMSO addition conditions. 10 mmol/L solution of the compound was prepared with DMSO, and 6 µL of the solution of the compound of the present invention was added to 594 µL of pH 6.8 artificial intestinal juice (118 mL of 0.2 mol/L NaOH test solution and water were added to 250 mL of 0.2 mol/L potassium dihydrogen phosphate test solution to reach 1000 mL). The mixture was left standing for 16 hours at 25° C., and the mixture was vacuum-filtered. The filtrate was two-fold diluted with methanol/water=1/1 (V/V), and the compound concentration in the filtrate was measured with HPLC or LC/MS/MS by the absolute calibration method.
(Result)

TABLE 55

| No. | Solubility (µmol/L) | No. | Solubility (µmol/L) | No. | Solubility (µmol/L) | No. | Solubility (µmol/L) | No. | Solubility (µmol/L) |
|---|---|---|---|---|---|---|---|---|---|
| II-94 | >50 | II-225 | 45.1 | I-8 | >50 | I-190 | >50 | I-170 | >50 |
| II-103 | >50 | II-233 | >50 | I-10 | 15.8 | I-253 | >50 | I-236 | >50 |
| II-121 | >50 | II-270 | >50 | I-12 | 25.9 | I-276 | >50 | I-67 | >50 |
| II-151 | >50 | II-276 | >50 | I-23 | 48.2 | I-275 | >50 | II-202 | >50 |
| II-168 | >50 | II-295 | >50 | I-24 | >50 | I-212 | >50 | I-167 | >50 |
| II-174 | 32.4 | II-203 | >50 | I-34 | 36.6 | II-93 | >50 | I-200 | >50 |

Test Example 4: Phototoxicity Test

An erythrocyte photohemolysis test (Wolfgang J. W. Pepe et al., ATLA29, 145-162, 2001), which was an evaluation method using effect to biomembranes and photoperoxidation as indexes, was conducted as an In vitro phototoxicity test. In this method, a solution of the compound of the present invention was prepared with dimethylsulfoxide as a medium, to which a sheep erythrocyte solution in a ratio of 2.5% (v/v) with respect to the prepared solution was added, and the thus-obtained mixed solution (concentration: 0.1 to 0.0008%) was used. The mixed solution was added to two microplates, and one of the prepared microplates was irradiated with light in UVA and UVB regions (10 J/cm$^2$, 290 to 400 nm) by using an ultraviolet fluorescence lamp (GL20SE lamp, SANKYO DENKI Co., Ltd., and, FL20S-BLB lamp, Panasonic Corporation), and subjected to centrifugation together with the microplate without irradiation with light, and then the absorbance (540 nm or 630 nm) of the supernatant was measured. To determine two indexes (effect to biomembranes and photoperoxidation) for evaluation of phototoxicity, the absorbance of the medium was subtracted from the absorbance obtained from the compound of the present invention for each of the cases with and without irradiation with light, and the thus-calculated values were used for the subsequent calculations. With respect to effect to biomembranes, a photohemolysis rate was determined from the difference in absorbance (540 nm) between the case with irradiation with light and the case without irradiation with light, and, with respect to photoperoxidation, change in absorbance (630 nm) between the case with irradiation with light and the case without irradiation with light was determined. In calculation of a photohemolysis rate, the absorbance (540 nm) obtained from a 2.5% (v/v) sheep erythrocyte solution which had been subjected to forced hemolysis with distilled water was defined as the 100% photohemolysis rate and used as a reference. It was judged to be (−) when the photohemolysis rate was less than 10% and the change in the absorbance at 630 nm was less than 0.05. It was judged to be (+) when the photohemolysis rate was 10% or more and the change in the absorbance at 630 nm was 0.05 or more.

(Result)
Compound I-34: (−)

Test Example 5: Cytotoxicity Test

Cells after being exposed to the compound were automatically counted by using the cell image analyzer Toxinsight (Thermo Fisher Scientific) to evaluate the cytotoxicity of the compound of the present invention.

HepG2 cells (derived from human liver cancer cells) were seeded in a 384-well plate at 60000 cells/mL, and a solution of the compound was added to each well after 24 hours. The solution of the compound was a solution of the compound of the present invention in DMSO (five stage dilution from maximum concentration of 50 µmol/L to minimum concentration of about 3.1 µmol/L at 2 fold ratio), and a solution consisting only of DMSO was used as a negative control, and a solution of camptothecin was used as a positive control. The solution of the compound of the present invention in DMSO, the negative control solution, or the positive control solution was added to each well. After 71 hours, a solution of Hoechst 33342 diluted with Dulbecco's phosphate buffer solution (D-PBS) to a final concentration of 1 µg/mL was added to each well, and nuclear staining was performed in an incubator at 37° C. and 5% CO$_2$ for 1 hour. After the staining, the resultant was fixed with 4% paraformaldehyde in a CO$_2$ incubator at 37° C. for 20 minutes. Finally, the wells were washed by D-PBS three times, and nuclei with development of fluorescence were counted for each well by using a Toxinsight (Thermo Fisher Scientific). Four wells were assigned for one concentration, and the mean value and variation (SD) of nucleus counts (counts of cells for which toxicity was not found) in the four wells were calculated. Comparison was made with the negative control group, and an exposure concentration to the compound ($IC_{50}$) at which the mean value was lowered to less than 50% of the mean value for the negative control was calculated. A smaller $IC_{50}$ value was rated as a higher risk of cytotoxicity.

Test Example 6: Anti-Obesity Effect Test

The anti-obesity effect of the compound of the present invention was examined by using C57BL/6j mice (DIO mice) provided with a high-fat diet (TestDiet; 58Y1).

Five-week-old male C57BL/6j mice (CLEA Japan, Inc.) were purchased, and grown with feeding of a high-fat diet under 12-hour light-dark cycles for 4 weeks to produce DIO mice. A medium (0.5% HPMC) was administered twice per day from 3 weeks before administration of the compound. Randomization was performed for grouping (n=7) on the basis of body weight and change in food consumption during the period of administration for conditioning. Forced oral administration of Example Compound or a medium (0.5% HPMC) was performed twice per day from Day 1 to Day 28. Body weight and food consumption were measured every day. Dissection was performed on Day 28, and measurement of the weight of epididymal fat and a biochemical test for the blood collected were conducted.

Test Example 7: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by the compound of the present invention was assessed.

The reaction conditions are as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human liver microsomes 0.2 mg protein/mL; concentrations of the compound of the present invention, 1, 5, 10, 20 μmol/L (four points).

As a reaction solution, each five kinds of substrates, human liver microsomes, or compound of the present invention in 50 mmol/L Hepes buffer were added to a 96-well plate at the composition as described above, and NADPH, as a cofactor was added to initiate metabolism reactions. After the incubation at 37° C. for 15 minutes, a methanol/acetonitrile=1/1 (V/V) solution was added to stop the reaction. After the centrifugation at 3000 rpm for 15 minutes, resorufin (CYP1A2 metabolite) in the supernatant was quantified by a fluorescent multilabel counter or LC/MS/MS, and tolbutamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%). Remaining activity (%) was calculated. $IC_{50}$ was calculated by reverse presumption by a logistic model using the concentration and an inhibition rate.
(Result)
Compound II-103: Five Kinds >20 μmol/L Test Example 8: BA Test Materials and Methods for Experiments to Evaluate Oral Absorption
(1) Animals: the mice or SD rats were used.
(2) Breeding conditions: the mice or SD rats were allowed to freely take solid food and sterilized tap water.
(3) Setting of dosage and grouping: Oral administration and intravenous administration were performed with a predetermined dosage. Grouping was set as below. (dosage changed per compound)
Oral administration: 1 to 30 mg/kg (n=2 to 3)
Intravenous administration: 0.5 to 10 mg/kg (n=2 to 3)
(4) Preparation of administration solution: Oral administration was performed in the form of a suspension or a solution. Intravenous administration was performed after solubilization.
(5) Routes of administration: Oral administration was performed mandatory into the stomach by oral sonde. Intravenous administration was performed from caudal vein or femoral vein by syringes with needle.
(6) Evaluation items: blood was collected over time, and the plasma concentration of the compound of the present invention was measured by LC/MS/MS.
(7) Statistical analysis: regarding the transition of the plasma concentration of the compound of the present invention, the area under the plasma concentration-time curve (AUC) was calculated by non-linear least squares program WinNonlin (registered trademark), and the bioavailability (BA) of the compound of the present invention was calculated from the AUCs of the oral administration group and intravenous administration group.
(Result)
Compound II-94: 73%

Test Example 9: CYP3A4 (MDZ) MBI Test

CYP3A4 (MDZ) MBI test is a test of investigating mechanism based inhibition (MBI) potential on CYP3A4 by the enhancement of inhibitory degree of a metabolic reaction caused by the compound of the present invention. CYP3A4 inhibition was evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, at pre-reaction time 1, 5, 10, 20 μmol/L (four points).

Pooled human liver microsomes and a solution of the compound of the present invention in K-Pi buffer (pH 7.4) as a pre-reaction solution were added to a 96-well plate at the composition of the pre-reaction. A part of pre-reaction solution was transferred to another 96-well plate, and 1/10 diluted by K-Pi buffer containing a substrate. NADPH as a co-factor was added to initiate a reaction as a marker reaction (without pre-reaction). After a predetermined time of a reaction, methanol/acetonitrile=1/1 (V/V) solution was added to stop the reaction. In addition, NADPH was added to a remaining pre-reaction solution to initiate a pre-reaction (with pre-reaction). After a predetermined time of a pre-reaction, a part was transferred to another plate, and 1/10 diluted by K-Pi buffer containing a substrate to initiate a reaction as a marker reaction. After a predetermined time of a reaction, methanol/acetonitrile=1/1 (V/V) solution was added in order to stop the reaction. The plate on which each index reaction had been performed was centrifuged at 3000 rpm for 15 minutes, and thereafter 1-hydroxylated midazolam in the supernatant was quantified by LC/MS/MS.

The sample adding DMSO as a solvent to a reaction system instead of a solution dissolving the compound of the present invention was adopted as a control (100%). Remaining activity (%) was calculated at each concentration of the compound of the present invention compared to a control, and IC value was calculated by reverse-presumption by a logistic model using a concentration and an inhibition rate. IC at Preincubation 0 min/IC at Preincubation 30 min was defined as a value of Shifted IC, and a case that Shifted IC was 1.5 or more was regarded as Positive, and a case that Shifted IC was 1.0 or less was regarded as Negative.
(Result)
Compound II-103: Negative Test Example 10: Powder Solubility Test Appropriate quantity of the compound of the present invention was put in suitable containers. 200 µL of JP-1 solution (water was added to 2.0 g of sodium chloride and 7.0 mL of hydrochloric acid to reach 1000 mL), 200 µL of JP-2 solution (500 mL of water was added to 500 mL of phosphate buffer (pH 6.8)) or 20 mmol/L sodium taurocholate (TCA)/JP-2 solution (JP-2 solution was added to 1.08 g of TCA to reach 100 mL) was independently added to each container. When total amount was dissolved after adding the test reagent, the compound of the present invention was added appropriately. After sealing and shaking at 37° C. for 1 hour, solution is filtrated and 100 µL of methanol is added to 100 µL of each filtrate to dilute two-fold. The dilution rate is changed as necessary. After checking that there was no bubble and deposit, the container was sealed and shaken. The compound of the present invention was measured using HPLC by absolute calibration curve method.
(Result)
Compound II-94: JP-2 solution: 3.4 µmol/L Test Example 11: Fluctuation Ames Test Mutagenicity of the compound of the present invention was evaluated. 20 µL of freezing-stored rat typhoid bacillus (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 8.0 mL of a bacterial solution of the TA98 strain was centrifuged (2000×g, 10 minutes) to remove a culturing solution. The bacteria was suspended in 8.0 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4$·$7H_2O$: 0.1 g/L), the suspension was added to 120 mL of an Exposure medium (Micro F buffer containing Biotin: 8 µg/mL, histidine: 0.2 µg/mL, glucose: 8 mg/mL). The TA100 strain was added to 120 mL of the Exposure medium relative to 3.1 mL of the bacterial solution to prepare a test bacterial solution. Each 12 µL of DMSO solution of the compound of the present invention (several stage dilution from maximum dose 50 mg/mL at 2 to 3 fold ratio), DMSO as a negative control, and 50 µg/mL of 4-nitroquinoline-1-oxide DMSO solution for the TA98 strain, 0.25 µg/mL of 2-(2-furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µL of the test bacterial solution and 90 µL of S9 mix under the metabolism activating condition) were mixed, and this was shaking-cultured at 37° C. for 90 minutes. 230 µL of the bacterial solution exposed to the compound of the present invention was mixed with 1150 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL was dispensed into microplate 48 wells/dose, and this was subjected to stationary culturing at 37° C. for 3 days. Since a well containing a bacterium which had obtained the proliferation ability by mutation of an amino acid (histidine) synthesizing enzyme gene turns from purple to yellow due to a pH change, the bacterium proliferation well which had turned to yellow in 48 wells per dose was counted, and was assessed by comparing with a negative control group. (−) and (+) means negative and positive in mutagenicity respectively.
(Result)
Compound I-24: (−)

Test Example 12: hERG Test

For the purpose of assessing risk of an electrocardiogram QT interval prolongation of the compound of the present invention, effects of the compound of the present invention on delayed rectifier $K^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion BIoscience A/S), $I_{Kr}$ induced by application of a leak potential of −50 mV followed by depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition of tail peak current for the compound of the present invention relative to the tail peak current after application of the vehicle is calculated to assess influence of the compound of the present invention on $I_{Kr}$.
(Result) % inhibition was shown at 10 µmol/L of test compound.
Compound I-253: 6.9%

Formulation Example

The compound of the present invention can be administered as a pharmaceutical composition by any conventional route, in particular enterally, for example, orally, for example, in the form of tablets or capsules, or parenterally, for example, in the form of injectable solutions or suspensions, topically, for example, in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets, granules, or capsules containing excipients, disintegrants, binders, lubricants and the like and active ingredients. Compositions for injection can be solutions or suspension, may be sterilized, and may contain preservatives, stabilizers, buffering agents, and the like.

INDUSTRIAL APPLICABILITY

Since the compounds of the present invention have MGAT2 inhibitory activity, they are useful as a medicine for MGAT2-associated diseases including obesity, metabolic syndrome, hyperlipidemia, hypertriglyceridemia, hyper-VLDL-triglyceridemia, hyperfattyacidemia, diabetes mellitus, and arteriosclerosis.

The invention claimed is:

1. A compound represented by the formula:

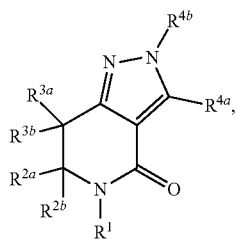

wherein:
R$^1$ is hydrogen;
R$^{2a}$ is represented by formula:

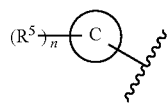

wherein ring C is benzene or pyridine;
R$^5$ is each independently halogen, haloalkyl, haloalkyloxy, non-aromatic carbocyclyl optionally substituted with halogen or haloalkyl, or non-aromatic heterocyclyl optionally substituted with halogen or haloalkyl, and
n is an integer of 1 to 3,
R$^{2b}$ is alkyl or haloalkyl, or
optionally, R$^{2a}$ and R$^{2b}$ are taken together with an adjacent carbon atom to form ring B, ring B is represented by formula:

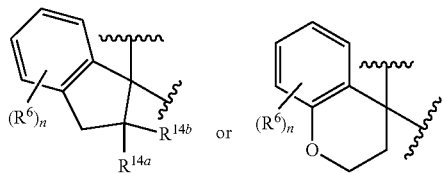

wherein R$^6$ is each independently halogen, haloalkyl, haloalkyloxy, non-aromatic carbocyclyl optionally substituted with halogen or haloalkyl, or non-aromatic heterocyclyl optionally substituted with halogen or haloalkyl,
R$^{14a}$ and R$^{14b}$ are each independently hydrogen or halogen, and
n is an integer of 1 to 3;
R$^{3a}$ is hydrogen,
R$^{3b}$ is hydrogen;
R$^{4a}$ is carboxy or represented by formula:

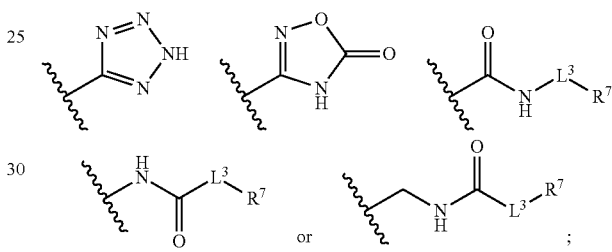

L$^3$ is a single bond or alkylene,
R$^7$ is hydrogen, halogen, alkylsulfonyl, non-aromatic heterocyclyl optionally substituted with oxo, or non-aromatic carbocyclylsulfonyl optionally substituted with alkyl, or is represented by formula: —S(=O)(=N—H)—R$^{S1}$,
R$^{4b}$ is alkyl optionally substituted with a substituent group α, aromatic carbocyclyl optionally substituted with a substituent group β, or aromatic heterocyclyl optionally substituted with the substituent group β,
R$^{S1}$ is alkyl,
the substituent group α is selected from the group consisting of halogen, haloalkyloxy, and non-aromatic carbocyclyl, and
the substituent group β is selected from the group consisting of halogen, cyano, alkyl, haloalkyl, and alkyloxy,
or its pharmaceutically acceptable salt.

2. The compound or its pharmaceutically acceptable salt according to claim 1, wherein R$^{2a}$ and R$^{2b}$ are taken together with an adjacent carbon atom to form ring B, and ring B is represented by any one of formulas:

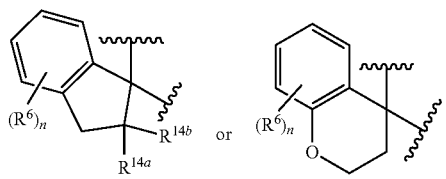

wherein each symbol is as defined in claim 1.

3. The compound or its pharmaceutically acceptable salt according to claim 1, wherein $R^{2a}$ is represented by formula:

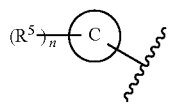

wherein each symbol is as defined in claim 1, and $R^{2b}$ is alkyl or haloalkyl.

4. The compound or its pharmaceutically acceptable salt according to claim 1, wherein $R^{2a}$ and $R^{2b}$ are taken together with an adjacent carbon atom to form ring B, and ring B is represented by any one of formulas:

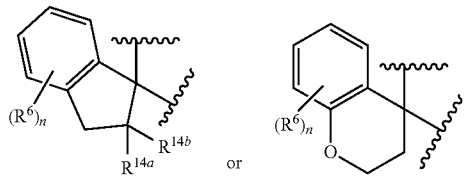

wherein $R^6$ is each independently halogen, haloalkyl or haloalkyloxy,
$R^{14a}$ and $R^{14b}$ are each independently hydrogen, and
n is an integer of 1 to 2;
$R^{4a}$ is represented by formula:

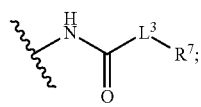

$L^3$ is alkylene,
$R^7$ is alkylsulfonyl,
$R^{4b}$ is alkyl optionally substituted with a substituent group α, aromatic carbocyclyl optionally substituted with a substituent group β, or aromatic heterocyclyl optionally substituted with the substituent group β,
the substituent group α is haloalkyloxy, and
the substituent group β is halogen or alkyl.

5. The compound or its pharmaceutically acceptable salt according to claim 1, wherein the compound is selected from the group consisting of:

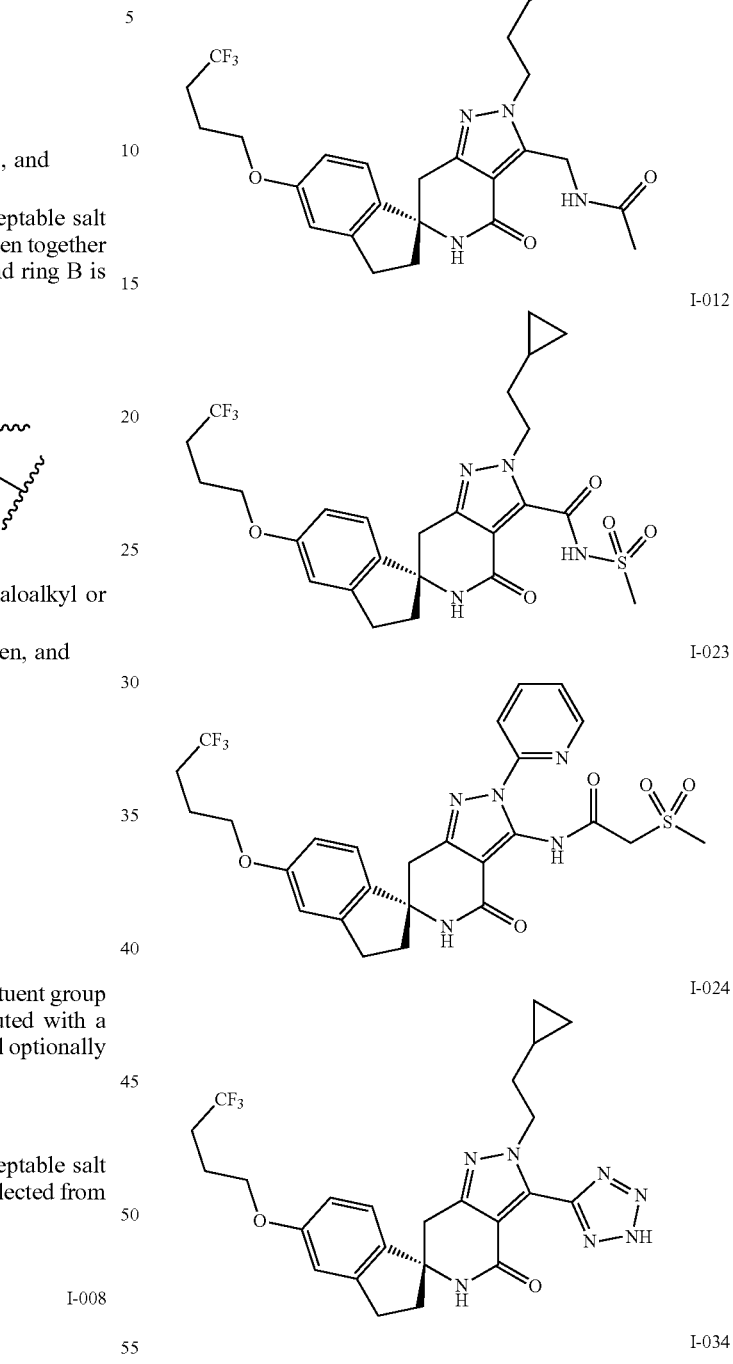

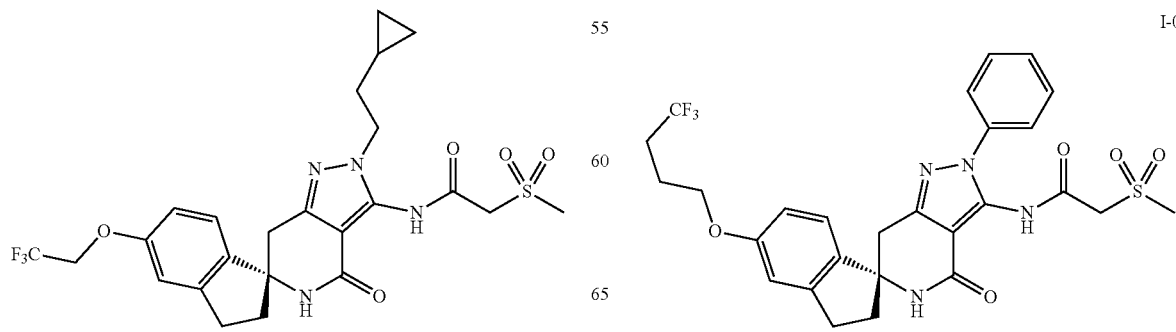

I-067
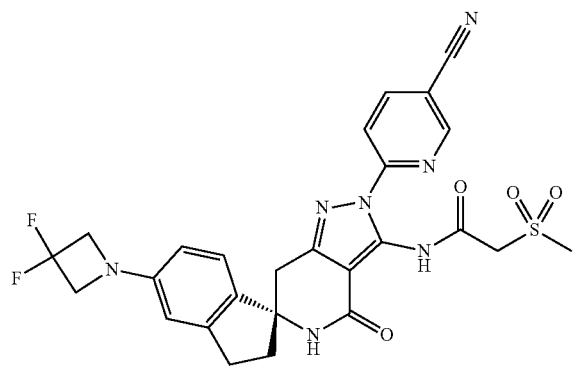
I-236
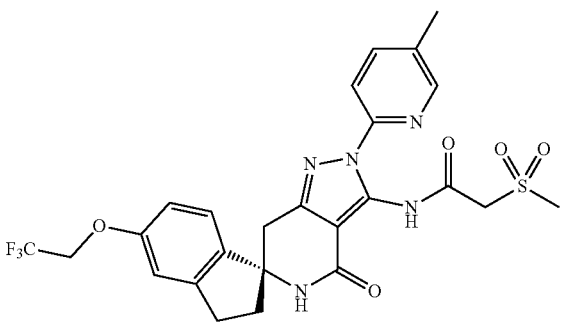
I-170
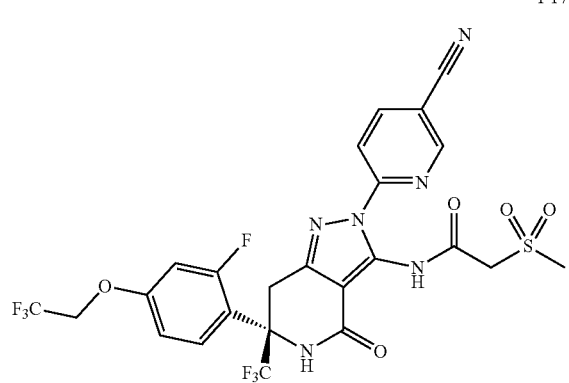
I-253
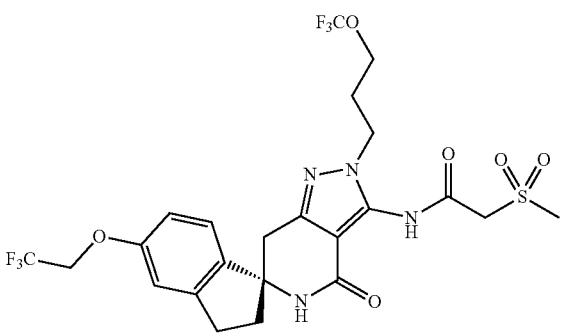
I-190
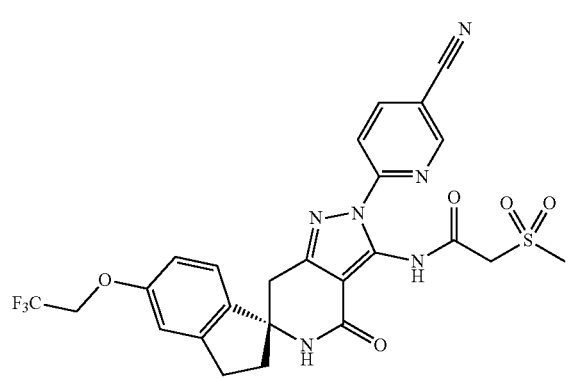
I-275
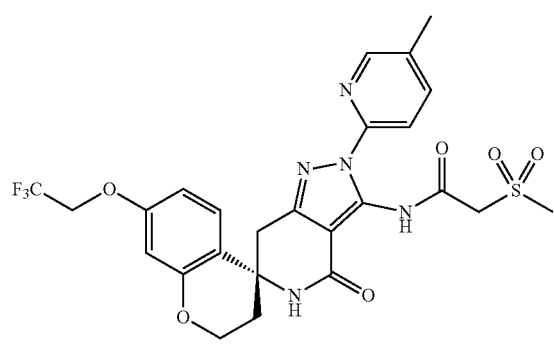
I-212
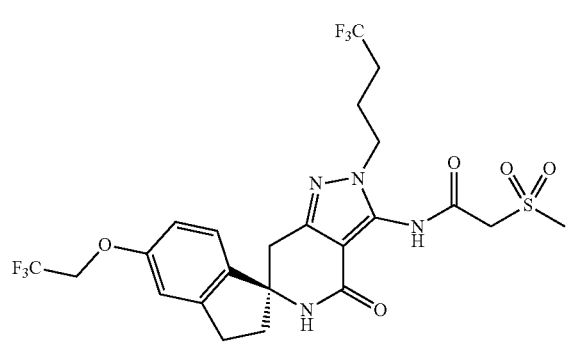
I-276
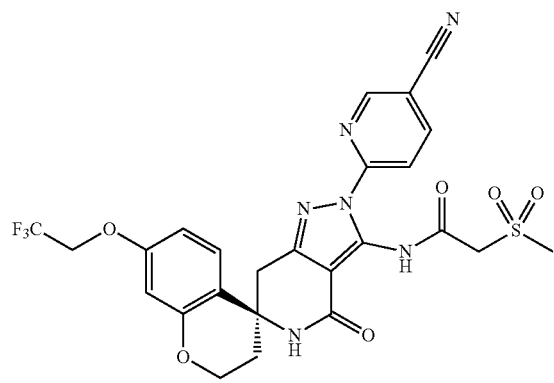

II-093
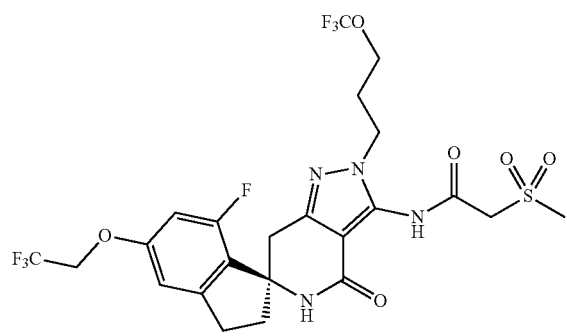
II-094
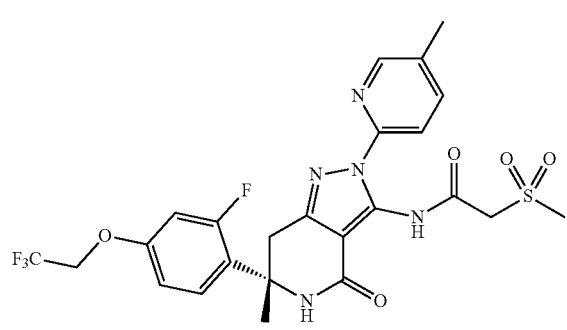
II-103
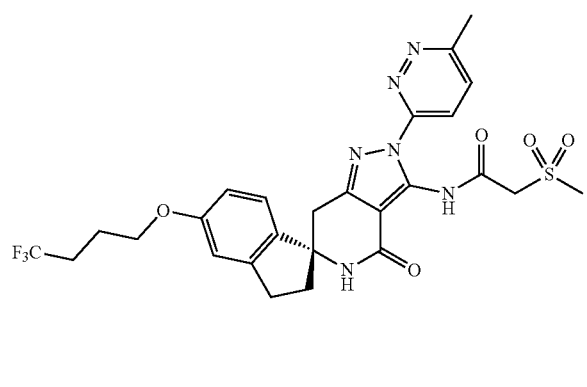
II-121
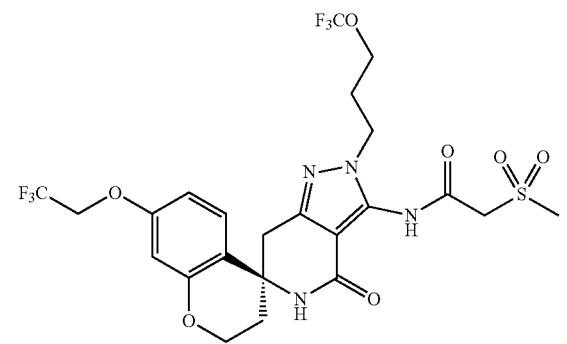
II-151
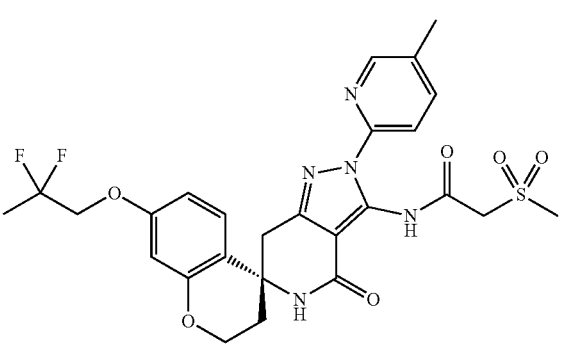
II-168
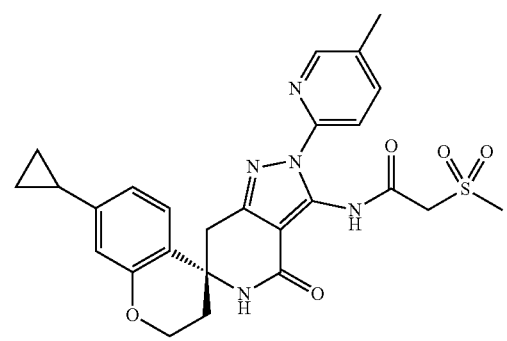
II-174
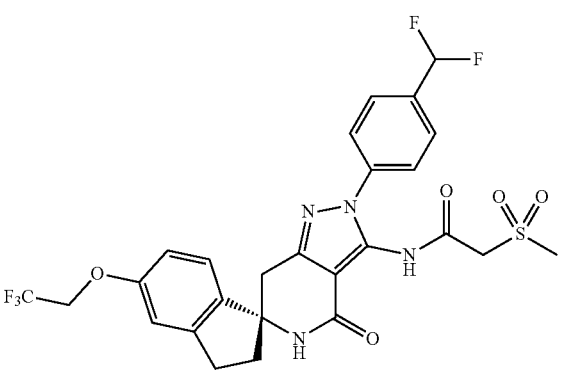
II-203
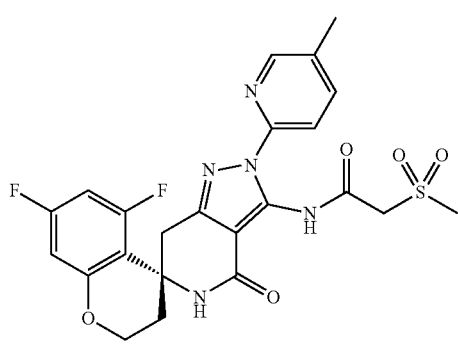

II-225
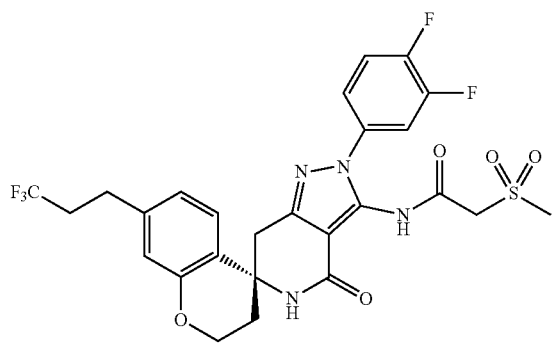

II-295
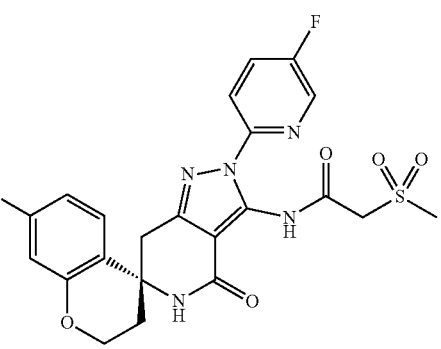

II-233
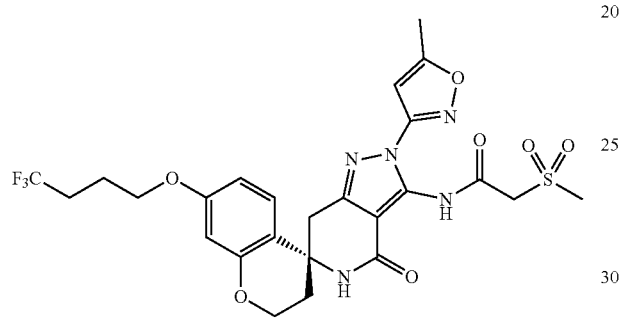

6. The compound or its pharmaceutically acceptable salt according to claim 1, wherein the compound is a compound of formula (I-253):

I-253

II-270
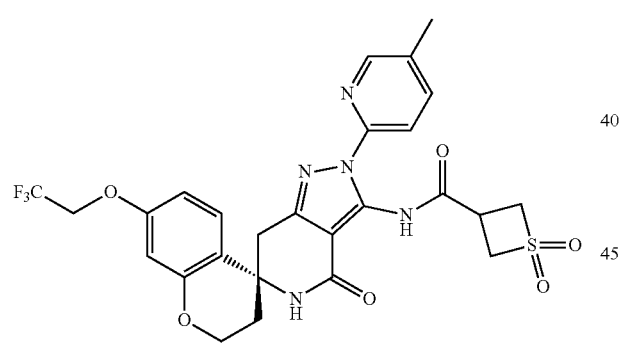

7. The compound or its pharmaceutically acceptable salt according to claim 1, wherein the compound is a compound of formula (I-275):

I-275
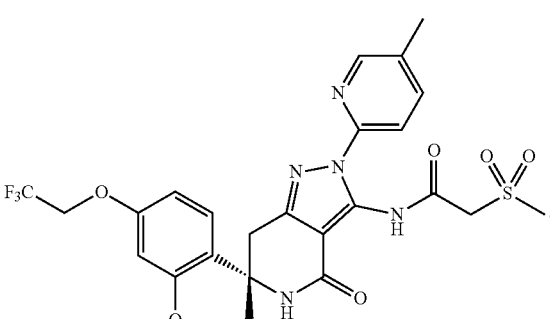

II-276
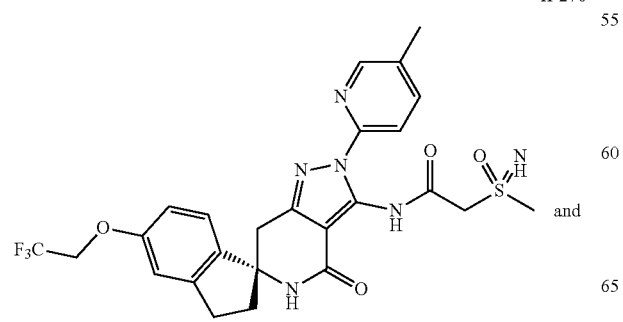
and

8. The compound or its pharmaceutically acceptable salt according to claim 1, wherein the compound is a compound of formula (II-103):

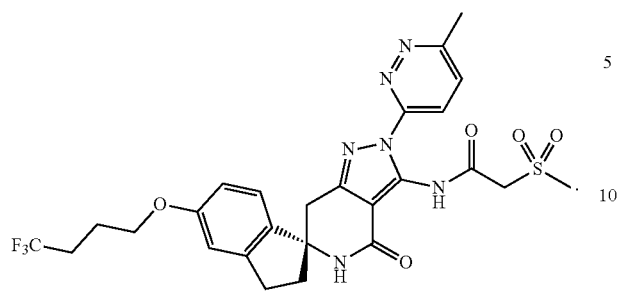

II-103

9. The compound or its pharmaceutically acceptable salt according to claim 1, wherein the compound is a compound of formula (II-121):

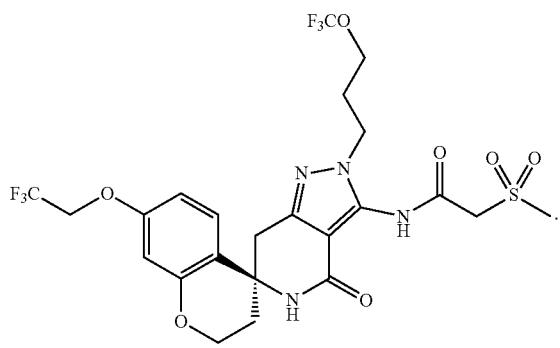

II-121

10. The compound or its pharmaceutically acceptable salt according to claim 1, wherein the compound is a compound of formula (II-203):

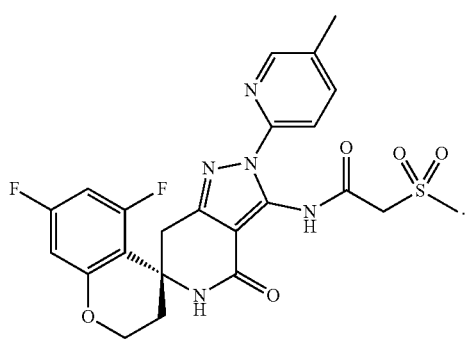

II-203

11. The compound or its pharmaceutically acceptable salt according to claim 1, wherein the compound is a compound of formula (II-225):

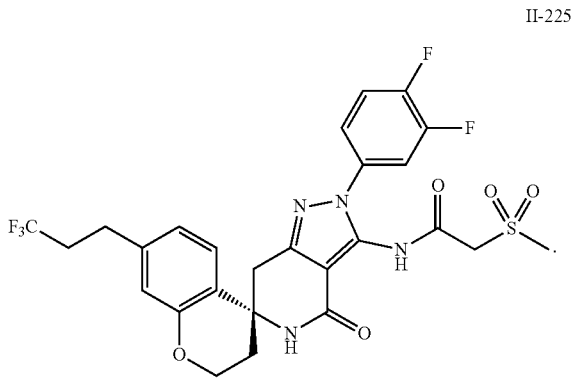 [SMILES: CS(=O)(=O)CC(=O)Nc1c2c(nn1-c1ccc(F)c(F)c1)C[C@]1(CCOc3cc(CCC(F)(F)F)ccc31)NC2=O]

II-225

12. The compound or its pharmaceutically acceptable salt according to claim 1, wherein the compound is a compound of formula (II-233):

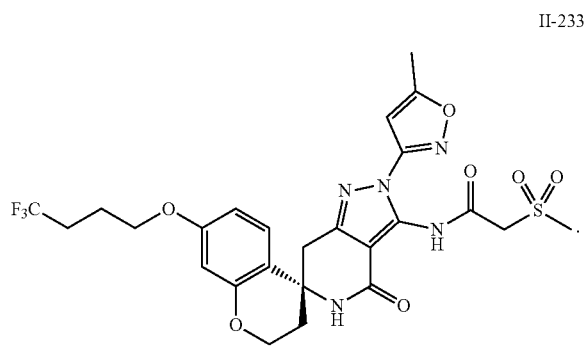 [SMILES: Cc1cc(-n2nc3c(c2NC(=O)CS(C)(=O)=O)C(=O)N[C@@]2(CCOc4cc(OCCCC(F)(F)F)ccc42)C3)no1]

II-233

13. A pharmaceutical composition comprising the compound or its pharmaceutically acceptable salt according to claim 1 and a pharmaceutically acceptable carrier or diluent.

* * * * *